United States Patent
Kaieda et al.

(10) Patent No.: US 10,308,643 B2
(45) Date of Patent: Jun. 4, 2019

(54) HETEROCYCLIC COMPOUND

(71) Applicant: Takeda Pharmaceutical Company Limited, Osaka-shi, Osaka (JP)

(72) Inventors: Akira Kaieda, Kanagawa (JP); Masashi Toyofuku, Kanagawa (JP); Masaki Daini, Kanagawa (JP); Hiroshi Nara, Kanagawa (JP); Masato Yoshikawa, Kanagawa (JP); Naoki Ishii, Kanagawa (JP); Kousuke Hidaka, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/210,965

(22) Filed: Jul. 15, 2016

(65) Prior Publication Data
US 2017/0015655 A1    Jan. 19, 2017

(30) Foreign Application Priority Data

Jul. 17, 2015  (JP) .................................. 2015-143354
Feb. 18, 2016  (JP) .................................. 2016-029020

(51) Int. Cl.
| | |
|---|---|
| C07D 413/14 | (2006.01) |
| C07D 413/04 | (2006.01) |
| C07D 471/04 | (2006.01) |
| C07D 491/08 | (2006.01) |
| C07D 491/107 | (2006.01) |
| C07D 417/14 | (2006.01) |
| C07D 498/08 | (2006.01) |

(52) U.S. Cl.
CPC ......... *C07D 413/14* (2013.01); *C07D 413/04* (2013.01); *C07D 417/14* (2013.01); *C07D 471/04* (2013.01); *C07D 491/08* (2013.01); *C07D 491/107* (2013.01); *C07D 498/08* (2013.01)

(58) Field of Classification Search
CPC .. C07D 413/14; C07D 413/04; C07D 417/14; C07D 471/04; C07D 491/08; C07D 491/107; C07D 498/08
See application file for complete search history.

(56) References Cited

U.S. PATENT DOCUMENTS

| | | |
|---|---|---|
| 10,081,624 B2 | 9/2018 | Kaieda |
| 2010/0267740 A1 | 10/2010 | Clayton |
| 2011/0166155 A1 | 7/2011 | Van Wagenen |
| 2012/0289495 A1 | 11/2012 | Baloglu et al. |
| 2013/0059883 A1 | 3/2013 | Baloglu et al. |
| 2014/0142105 A1 | 5/2014 | Hebach et al. |
| 2014/0329825 A1 | 11/2014 | Hebach et al. |
| 2014/0378385 A1 | 12/2014 | Raje et al. |
| 2015/0038534 A1 | 2/2015 | Baloglu et al. |
| 2017/0305866 A1 | 10/2017 | Raje et al. |
| 2018/0222896 A1 | 8/2018 | Kaieda |
| 2018/0263967 A1 | 9/2018 | Kaieda |

FOREIGN PATENT DOCUMENTS

| | | |
|---|---|---|
| JP | 2009-514858 | 4/2009 |
| JP | 2010-531359 | 9/2010 |
| JP | 2013-517278 | 5/2013 |
| JP | 2013-517281 | 5/2013 |
| JP | 2014-520794 | 8/2014 |
| JP | 2014-523857 | 9/2014 |
| JP | 2014-524992 | 9/2014 |
| JP | 2014-533721 | 12/2014 |
| WO | 2011/088181 | 7/2011 |
| WO | 2011/088192 | 7/2011 |
| WO | 2013/006408 | 1/2013 |
| WO | 2013/008162 | 1/2013 |
| WO | 2013/009810 | 1/2013 |
| WO | 2013/009827 | 1/2013 |
| WO | 2013/009830 | 1/2013 |
| WO | 2013/066831 | 5/2013 |
| WO | 2013/066833 | 5/2013 |

(Continued)

OTHER PUBLICATIONS

Jin et al. (Bioorg. Med. Chem. 23 (2015) 4728-4736).*
Kubinyi (3D QSAR in Drug Design: Ligand-Protein Interactions and Molecular Similarity, vol. 2-3, Springer, 1998, 800 pages). pp. 243-44 provided.*
Wermuth, The Practice of Medicinal Chemsitry, 2d ed. (2003), 768 pages. Chs. 9-10 provided.*
International Search Report issued for corresponding International Application No. PCT/JP2016/071655, dated Oct. 20, 2016, 4 pages.
Azad, et al., "The furture of epigenetic therapy in salad tumours-lessons from the past", Nature Reviews Clinical Oncology, vol. 10, May 2013, pp. 256-266.

(Continued)

*Primary Examiner* — Robert H Havlin
(74) *Attorney, Agent, or Firm* — Hamre, Schumann, Mueller & Larson, P.C.

(57) ABSTRACT

The present invention provide a heterocyclic compound having a HDAC inhibitory action, and useful for the treatment of autoimmune diseases and/or inflammatory diseases, graft versus host disease, cancers, central nervous diseases including neurodegenerative diseases, Charcot-Marie-Tooth disease and the like, and a pharmaceutical composition comprising the compound.

The present invention relates to a compound represented by the formula (I):

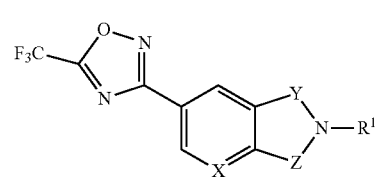

(I)

wherein each symbol is as defined in the specification, or a salt thereof.

12 Claims, 2 Drawing Sheets

(56) References Cited

FOREIGN PATENT DOCUMENTS

| WO | 2013/066838 | 5/2013 |
|---|---|---|
| WO | 2013/066839 | 5/2013 |
| WO | 2013066835 | 5/2013 |
| WO | 2013/080120 | 6/2013 |
| WO | 2016/031815 | 3/2016 |
| WO | 2016/039398 | 3/2016 |
| WO | 2017/014170 | 1/2017 |
| WO | 2017/014321 | 1/2017 |
| WO | 2017-033946 | 3/2017 |
| WO | 2017/110863 | 6/2017 |
| WO | 2017/222950 | 12/2017 |
| WO | 2017/222951 | 12/2017 |
| WO | 2017/222952 | 12/2017 |

OTHER PUBLICATIONS

Santo, et al., "Preclinical activity, pharmacodynamic, and pharmacokinetic properties of a selective HDAC6 inhibitor, ACY-1215, in combination with bortezomib in multiple myeloma", Blood, vol. 119, No. 11, Mar. 2012, pp. 2579-2589.

Chuang, et al., Multiple roles of HDAC inhibition in neurodegenerative conditions, Trends in Neurosciences, vol. 32, No. 11, 2009, pp. 591-601.

Jochems, et al., "Antidepressant-Like Properties of Novel HDAC6-Selective Inhibitors with Improved Brain Bioavailability", Neuropsychopharmacology, vol. 39, 2014, pp. 389-400.

Govindarajan, et al., "Reducing HDAC6 ameliorates congitive deficits in a mouse model for Alzheimer's disease", EMBO Mol Med, vol. 5, 2013, pp. 52-63.

Kalin, et al., "Development and Therapeutic Implications of Selective Histone Deacetylase 6 Inhibitors", Journal of Medicinal Chemistry, vol. 56, 2013, pp. 6297-6313.

Haberland, et al., The many roles of histone deacetylases in development and physiology: implications for disease and therapy Nature Reviews Genetics, vol. 10, Jan. 2009, pp. 32-42.

Shakespear, et al., "Histone deacetylases as regulators of inflammation and immunity", Trends in Immunology, vol. 32, No. 7, Jul. 2011, pp. 335-343.

West, et al., "New and emerging HDAC inhibitors for cancer treatment", The Journal of Clinical Investigation, vol. 124, No. 1, Jan. 2014, pp. 30-39.

Chung, et al., "A Therapeutic Strategy Uses Histone Deacetylase Inhibitors to Modulate the Expression of Genes Involved in the Pathogenesis of Rheumatoid Arthritis", Molecular Therapy, vol. 8, No. 5, Nov. 2003, pp. 707-717.

Glauben, et al., "Histone Hyperacetylation is Associated with Amelioration of Experimental Colitis in Mice", The Journal of Immunology, vol. 176, 2006, pp. 5015-5022.

Lin, et al., "Anti-rheumatic activities of histone deacetylase (HDAC) inhibitors in vivo in collagen-induced arthritis in rodents", British Journal of Pharmacology, vol. 150, 2007, pp. 862-872.

Li, et al., "HDAC inhibitor reduces cytokine storm and facilitates indcution of chimerism that reverses lupus in anti-CD3 conditioning regiment", Proc Natl Acad Sci USA, vol. 105, Mar. 2008, pp. 4796-4801.

Zoeten, et al., "Histone Deacetylase 6 and Heat Shock Protein 90 Control the Functions of Foxp3+ T-Regulatory Cells", Molecular and Cellular Biology, vol. 31, No. 10, May 2011, pp. 2066-2078.

Hancock, et al., "HDAC inhibitor therapy in autoimmunity and transplantation", Ann Rheum Dis, vol. 71 (Supp II): i46-i54, 2011.

International Search Report issued in International Application No. PCT/JP2016/074573, dated Nov. 1, 2016, 11 pages.

International Search Report issued in International Application No. PCT/JP2016/070936, dated Oct. 18, 2016, 10 pages.

Van Helleputte; Research and Reports in Biology 2014, 5, 1-13. (Year: 2014).

Simoes-Peres; Molecular Neurodegeneration 2013, 8(7), 16 pages. (Year: 2013).

Schafer; ChemMedChem 2009, 4, 283-290. (Year: 2009).

* cited by examiner

HETEROCYCLIC COMPOUND

TECHNICAL FIELD

The present invention relates to a heterocyclic compound having a histone deacetylase (in the present specification, sometimes to be referred to as "HDAC") inhibitory action, preferably a class II HDAC inhibitory action, more preferably a HDAC6 inhibitory action, and may be useful for the treatment of autoimmune diseases and/or inflammatory diseases (inflammatory bowel disease, rheumatoid arthritis, psoriasis, multiple sclerosis, Sjogren's syndrome, Behcet's disease, systemic lupus erythematosus, etc.), graft versus host disease (GvHD), cancers (multiple myeloma, leukemia, uterine leiomyosarcoma, prostate cancer, cachexia, myelofibrosis, etc.), central nervous diseases including neurodegenerative diseases (Alzheimer's disease, frontotemporal lobar degeneration, progressive supranuclea palsy, Parkinson's disease, Huntington's disease, etc.), Charcot-Marie-Tooth disease and the like, and a pharmaceutical composition comprising the compound and the like.

BACKGROUND OF THE INVENTION

HDAC is a generic term for proteins deacetylating histone, and mainly controls gene expression in the nucleus of cells. HDAC has various types, and is reported to be deeply related to pathological conditions such as immune, inflammation, cancer, nervous disease and the like. The gene expression regulation by HDAC is dependent on kinds of cell, target protein to be acted on, or cellular environment (Non-Patent Document 1).

Acetylation of histone is one of important determinants for gene expression. It is known that acetylation of histone generally acts in the direction of acceleration of transcription, and deacetylation of histone generally acts in the direction of suppression of gene expression. HDAC is a generic term for enzymes removing an acetyl group from lysine residue of target protein including histone. HDAC family is classified into four kinds of HDACs (class I HDACs (HDAC1, 2, 3, 8), class II HDACs (HDAC4, 5, 6, 7, 9, 10), class III HDACs (SIRT1-7), class IV HDAC (HDAC11)). Among them, class I HDACs is ubiquitously expressed, and mainly localized in the nucleus. It shows high enzyme activity against histone, and its role as modification of histone and transcription repressor is widely studied. Class II HDAC is classified into IIa (HDAC4, 5, 7, 9) and IIb (HDAC6, 10) based on the domain structure. Class IIa HDACs have an N-terminal domain bonded to transcription factor and a C-terminal domain having a nuclear transport signal, and can move between nucleus and cytoplasm. Unlike the other HDACs, its expression pattern is comparatively localized. For example, HDAC5 and HDAC9 are expressed in muscle, heart and brain. On the other hand, class IIb HDACs has a tandem structure of deacetylating domain, unlike class IIa HDACs, and HDAC6 is mainly expressed in cytoplasm. As the target molecule of HDAC6, α-tubulin and cortactin and the like, which are cytoskeleton proteins, are reported. It is known that low molecular HDAC inhibitors cause various cellular reactions such as cell-growth inhibition, cellular differentiation and cellular apoptosis, and HDAC inhibitors such as SAHA (vorinostat) and FK228 (romidepsin) are presently clinically used for T-cell malignant lymphoma as indication. In addition, effects of HDAC inhibitor on animal models of some inflammatory diseases, for example, models of arthritis, inflammatory bowel disease, GvHD, sepsis and the like are also reported (Non-Patent Documents 1, 2 and 3).

It is reported that vorinostat and trichostatin, which are HDAC inhibitors, show symptom improvement of pathological condition and actions such as protection action and the like in various animal models of autoimmune disease or inflammatory disease including arthritis model, enteritis model, GvHD model and the like (see Non-Patent Documents 4 to 7). In addition, it is reported that tubacin, which is a HDAC6 inhibitor, enhances regulatory T cell inhibitory action, and suppresses T-cell-dependent immune response in experimental enteritis model (Non-Patent Document 8). Therefore, HDAC inhibitor and/or HDAC6 inhibitor can be therapeutic drugs for various autoimmune diseases and/or inflammatory diseases such as inflammatory bowel disease, rheumatoid arthritis, psoriasis, Sjogren's syndrome, Behcet's disease, multiple sclerosis, systemic lupus erythematosus and the like, GvHD and the like (Non-Patent Documents 2 and 9).

In addition, HDAC has an important role in tumor formation because it regulates activities of tumor suppressor gene and oncogene. For example, it is reported that overexpression of HDAC in prostate cancer, colorectal cancer, breast cancer, lung cancer, liver cancer, stomach cancer and the like correlates with decrease in disease-free survival and overall survival (Non-Patent Document 3). Therefore, HDAC inhibitor targeting solid cancer and blood tumor is developed. Vorinostat and romidepsin, which are HDAC inhibitors, have been approved by FDA as a therapeutic drug for T-cell malignant lymphoma, and plural HDAC inhibitors are preclinical or in clinical trials (Non-Patent Document 10). In addition, it is reported that ACY-1215, which is a HDAC6 inhibitor, has a tumor growth inhibitory action or an extended survival action in multiple myeloma model, when used in combination with bortezomib (Non-Patent Document 11). Therefore, HDAC inhibitor and/or HDAC6 inhibitor can be therapeutic drugs for cancers such as multiple myeloma, leukemia, uterine leiomyosarcoma, prostate cancer, cachexia, myelofibrosis and the like.

On the other hand, it is reported that vorinostat and valproic acid, which are HDAC inhibitors, show actions such as improvement of spatial memory, increased motor function and the like in animal models such as Alzheimer's disease model, Huntington's disease model and the like (Non-Patent Document 12). In addition, it is reported that ACY-738 and ACY-775, which are HDAC6 inhibitors, show a significant antidepressant action in ethopharmacological experiments such as tail suspension test and the like (Non-Patent Document 13). Moreover, it is reported that HDAC6 also has an important role in regulation of amyloid β involved in maintenance of homeostasis of tau and stability of microtubule which are deeply related to Alzheimer's disease, and that inhibition of HDAC6 improves memory in neurodegeneration mouse model in water maze test using HDAC6 knockout mouse and APPPS1-21 mouse which is a Alzheimer's disease mouse model (Non-Patent Documents 14 and 15). Therefore, HDAC inhibitor and/or HDAC6 inhibitor can be therapeutic drugs for central nervous system diseases including neurodegenerative diseases.

The compounds having a structure similar to that of the compound described in the present specification are, for example, the following compounds.

(1) Patent Document 1 discloses a compound represented by the following formula:

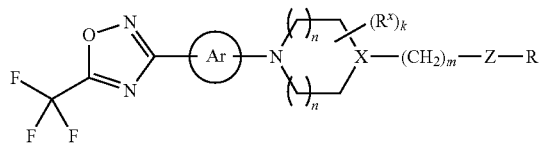

wherein each symbol is as defined in the document, which is a class II HDAC (HDAC4, HDAC5, HDAC6, HDAC7, HDAC9) inhibitor, and useful for the treatment of autoimmune disease, immune disease, inflammatory disease and the like.

(2) Patent Document 2 discloses a compound represented by the following formula:

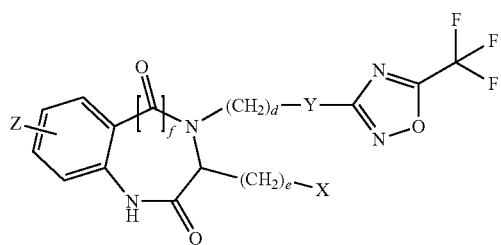

wherein each symbol is as defined in the document, which is a class II HDAC (HDAC4, HDAC5, HDAC6, HDAC7, HDAC9) inhibitor, and useful for the treatment of autoimmune disease, immune disease, inflammatory disease and the like.

DOCUMENT LIST

Patent Document

Patent Document 1: WO 2013/066831
Patent Document 2: WO 2013/066838

Non-Patent Document

Non-Patent Document 1: Nature Reviews Genetics 10, 32-42 (2009).
Non-Patent Document 2: Trend in Immunology 32, 335-343 (2011).
Non-Patent Document 3: J Clin Invest 124, 30-39 (2014).
Non-Patent Document 4: Mol Ther 8, 707-717 (2003).
Non-Patent Document 5: J Immunol 176, 5015-5022 (2006).
Non-Patent Document 6: Br J Pharmacol 150, 862-872 (2007).
Non-Patent Document 7: Proc Natl Acad Sci USA 105, 4796-4801 (2008).
Non-Patent Document 8: Mol Cell Biol 31, 2066-2078 (2011).
Non-Patent Document 9: Ann Rheum Dis 71, i46-i54 (2011).
Non-Patent Document 10: Nature Review Clinical Oncology 10, 256-266 (2013).
Non-Patent Document 11: Blood 119, 2579-2589 (2012).
Non-Patent Document 12: Trend in Neuroscience 32, 591-601 (2009)
Non-Patent Document 13: Neuropsychopharmacology 39, 389-400 (2014).
Non-Patent Document 14: EMBO Mol Med 5, 52-63 (2013)
Non-Patent Document 15: Journal of Medicinal Chemistry 56, 6297-6313 (2013).

SUMMARY OF THE INVENTION

Problems to be Solved by the Invention

The present invention aims to provide a heterocyclic compound having a HDAC inhibitory action, and useful for the treatment of autoimmune diseases and/or inflammatory diseases (inflammatory bowel disease, rheumatoid arthritis, psoriasis, multiple sclerosis, Sjogren's syndrome, Behcet's disease, systemic lupus erythematosus, etc.), graft versus host disease (GvHD), cancers (multiple myeloma, leukemia, uterine leiomyosarcoma, prostate cancer, cachexia, myelofibrosis, etc.), central nervous diseases including neurodegenerative diseases (Alzheimer's disease, frontotemporal lobar degeneration, progressive supranuclea palsy, Parkinson's disease, Huntington's disease, etc.), Charcot-Marie-Tooth disease and the like, and a pharmaceutical composition comprising the compound.

Means of Solving the Problems

The present inventors have conducted intensive studies to solve the above-mentioned problems, and have found that a compound represented by the following formula (I) has a superior HDAC inhibitory action, and completed the present invention based on these findings.

Accordingly, the present invention provides the following.

[1] A compound represented by the formula:

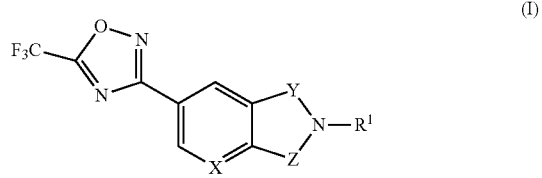

wherein
X is CH or N,
one of Y and Z is C(O), and the other is C(R$^2$)(R$^3$),
R$^2$ and R$^3$ are independently a hydrogen atom or a substituent, and
R$^1$ is an optionally substituted cyclic group,
or a salt thereof (hereinafter sometimes to be referred to as compound (I)).
[2] The compound or salt of the above-mentioned [1], wherein R$^2$ and R$^3$ are both hydrogen atoms;
the atom on R$^1$ bonded to N of the Y—N—Z is C; and
R$^1$ is an optionally substituted C$_{6-14}$ aryl group, an optionally substituted C$_{3-10}$ cycloalkyl group which is optionally fused with an optionally substituted benzene ring, or an optionally substituted non-aromatic heterocyclic group.
[3] The compound or salt of the above-mentioned [1], wherein R$^2$ and R$^3$ are both hydrogen atoms;
the atom on R$^1$ bonded to N of the Y—N—Z is C; and
R$^1$ is
(1) a C$_{6-14}$ aryl group optionally substituted by 1 to 3 substituents selected from
(a) a halogen atom,
(b) a mono- or di-C$_{1-6}$ alkyl-carbamoyl group, and (c) a 3- to 14-membered non-aromatic heterocyclic group optionally substituted by 1 to 3 oxo groups,
(2) a $C_{3-10}$ cycloalkyl group optionally fused with a benzene ring and optionally substituted by 1 to 3 substituents selected from
   (a) a halogen atom,
   (b) an amino group,
   (c) a $C_{6-14}$ aryl group,
   (d) a $C_{7-16}$ aralkyl group,
   (e) a 3- to 14-membered non-aromatic heterocyclic group optionally substituted by 1 to 3 oxo groups,
   (f) a $C_{1-6}$ alkyl-carbonylamino group optionally substituted by 1 to 3 substituents selected from
      (i) a hydroxy group,
      (ii) a halogen atom,
      (iii) a cyano group,
      (iv) a $C_{3-10}$ cycloalkyl group optionally substituted by 1 to 3 hydroxy groups, and
      (v) a 3- to 14-membered non-aromatic heterocyclic group optionally substituted by 1 to 3 oxo groups,
   (g) a $C_{1-6}$ alkoxy-carbonylamino group,
   (h) a $C_{3-10}$ cycloalkyl-carbonylamino group optionally substituted by 1 to 4 substituents selected from
      (i) a halogen atom,
      (ii) a cyano group,
      (iii) a hydroxy group,
      (iv) a $C_{1-6}$ alkyl group optionally substituted by 1 to 3 hydroxy groups, and
      (v) a $C_{1-6}$ alkoxy group,
   (i) a $C_{6-14}$ aryl-carbonylamino group optionally substituted by 1 to 3 cyano groups,
   (j) a 5- to 14-membered aromatic heterocyclylcarbonylamino group optionally substituted by 1 to 3 $C_{1-6}$ alkyl groups,
   (k) a 3- to 14-membered non-aromatic heterocyclylcarbonylamino group optionally substituted by 1 to 3 substituents selected from
      (i) an oxo group,
      (ii) a halogen atom,
      (iii) a $C_{1-6}$ alkyl group optionally substituted by 1 to 3 hydroxy groups,
      (iv) a $C_{1-6}$ alkoxy group,
      (v) a $C_{6-14}$ aryl group,
      (vi) a $C_{1-6}$ alkyl-carbonyl group, and
      (vii) a $C_{1-6}$ alkoxy-carbonyl group,
   (l) a mono- or di-$C_{1-6}$ alkyl-carbamoylamino group,
   (m) a $C_{3-10}$ cycloalkyl-carbamoylamino group,
   (n) a ($C_{1-6}$ alkyl)($C_{3-10}$ cycloalkyl)carbamoylamino group,
   (o) a 3- to 14-membered non-aromatic heterocyclylcarbamoylamino group, and
   (p) a $C_{3-10}$ cycloalkylsulfonylamino group, or
(3) a 3- to 14-membered non-aromatic heterocyclic group optionally substituted by 1 to 3 substituents selected from
   (a) an oxo group,
   (b) a $C_{6-14}$ aryl group optionally substituted by 1 to 3 substituents selected from
      (i) a halogen atom,
      (ii) a $C_{1-6}$ alkyl group, and
      (iii) a $C_{1-6}$ alkoxy group,
   (c) a $C_{7-16}$ aralkyl group,
   (d) a $C_{1-6}$ alkyl-carbonyl group optionally substituted by 3- to 14-membered non-aromatic heterocyclic group(s) optionally substituted by 1 to 3 oxo groups,
   (e) a $C_{1-6}$ alkoxy-carbonyl group,
   (f) a $C_{3-10}$ cycloalkyl-carbonyl group,
   (g) a $C_{6-14}$ aryl-carbonyl group,
   (h) a $C_{7-16}$ aralkyl-carbonyl group optionally substituted by 1 to 3 halogen atoms,
   (i) a carbamoyl group,
   (j) a $C_{1-6}$ alkyl-carbamoyl group,
   (k) a $C_{1-6}$ alkoxy-carbonylamino group,
   (l) a $C_{3-10}$ cycloalkyl-carbonylamino group optionally substituted by 1 to 3 halogen atoms,
   (m) a 3- to 14-membered non-aromatic heterocyclylcarbonylamino group optionally substituted by 1 to 3 $C_{1-6}$ alkyl groups,
   (n) a 3- to 14-membered non-aromatic heterocyclic group optionally substituted by 1 to 3 oxo groups,
   (o) a hydroxy group,
   (p) an amino group, and
   (q) a $C_{1-6}$ alkyl-carbonylamino group optionally substituted by 1 to 3 halogen atoms.

[4] The compound or salt of the above-mentioned [1], wherein $R^2$ and $R^3$ are both hydrogen atoms; the atom on $R^1$ bonded to N of the Y—N—Z is C; and $R^1$ is
(1) a $C_{3-10}$ cycloalkyl group optionally substituted by 1 to 3 substituents selected from
   (a) a halogen atom,
   (b) a $C_{6-14}$ aryl group,
   (c) a 3- to 14-membered non-aromatic heterocyclic group optionally substituted by 1 to 3 oxo groups,
   (d) a $C_{1-6}$ alkyl-carbonylamino group optionally substituted by 1 to 3 hydroxy groups,
   (e) a $C_{1-6}$ alkoxy-carbonylamino group,
   (f) a $C_{3-10}$ cycloalkyl-carbonylamino group optionally substituted by 1 to 3 substituents selected from
      (i) a halogen atom,
      (ii) a cyano group,
      (iii) a hydroxy group,
      (iv) a $C_{1-6}$ alkyl group optionally substituted by 1 to 3 hydroxy groups, and
      (v) a $C_{1-6}$ alkoxy group,
   (g) a $C_{6-14}$ aryl-carbonylamino group,
   (h) a 3- to 14-membered non-aromatic heterocyclylcarbonylamino group optionally substituted by 1 to 3 substituents selected from
      (i) a halogen atom,
      (ii) a $C_{1-6}$ alkyl group, and
      (iii) a $C_{6-14}$ aryl group,
   (i) a mono- or di-$C_{1-6}$ alkyl-carbamoylamino group,
   (j) a $C_{3-10}$ cycloalkyl-carbamoylamino group,
   (k) a ($C_{1-6}$ alkyl)($C_{3-10}$ cycloalkyl)carbamoylamino group,
   (l) a 3- to 14-membered non-aromatic heterocyclylcarbamoylamino group, and
   (m) a $C_{3-10}$ cycloalkylsulfonylamino group, or
(2) a 3- to 14-membered non-aromatic heterocyclic group optionally substituted by 1 to 3 substituents selected from
   (a) a $C_{6-14}$ aryl group,
   (b) a $C_{1-6}$ alkyl-carbonyl group,
   (c) a $C_{1-6}$ alkoxy-carbonyl group,
   (d) a $C_{3-10}$ cycloalkyl-carbonyl group,
   (e) a $C_{6-14}$ aryl-carbonyl group,
   (f) a carbamoyl group,
   (g) a $C_{1-6}$ alkyl-carbamoyl group,
   (h) a $C_{1-6}$ alkoxy-carbonylamino group,
   (i) a $C_{3-10}$ cycloalkyl-carbonylamino group optionally substituted by 1 to 3 halogen atoms,
   (j) a 3- to 14-membered non-aromatic heterocyclylcarbonylamino group optionally substituted by 1 to 3 $C_{1-6}$ alkyl groups, and (k) a 3- to 14-membered non-aromatic heterocyclic group optionally substituted by 1 to 3 oxo groups.

[5] The compound or salt of the above-mentioned [1], wherein $R^2$ and $R^3$ are both hydrogen atoms; and
$R^1$ is an optionally substituted cyclohexyl group or an optionally substituted tetrahydropyranyl group.

[6] The compound or salt of the above-mentioned [1], wherein
Y is C(O);
Z is $C(R^2)(R^3)$;
$R^2$ and $R^3$ are both hydrogen atoms;
the atom on $R^1$ bonded to N of the Y—N—Z is C; and
$R^1$ is an optionally substituted $C_{6-14}$ aryl group, an optionally substituted $C_{3-10}$ cycloalkyl group which is optionally fused with an optionally substituted benzene ring, or an optionally substituted non-aromatic heterocyclic group.

[7] The compound or salt of the above-mentioned [1], wherein
X is CH;
Y is C(O);
Z is $C(R^2)(R^3)$;
$R^2$ and $R^3$ are both hydrogen atoms; and
$R^1$ is an optionally substituted cyclohexyl group or an optionally substituted tetrahydropyranyl group.

[8] 3-Methyl-N-((1R,2R)-2-(1-oxo-6-(5-(trifluoromethyl)-1,2,4-oxadiazol-3-yl)-1,3-dihydro-2H-isoindol-2-yl)cyclohexyl)oxetane-3-carboxamide, or a salt thereof.

[9] (2S)—N-((1R,2R)-2-(1-Oxo-6-(5-(trifluoromethyl)-1,2,4-oxadiazol-3-yl)-1,3-dihydro-2H-isoindol-2-yl)cyclohexyl)tetrahydrofuran-2-carboxamide, or a salt thereof.

[10] 2-Hydroxy-2-methyl-N-((1R,2R)-2-(1-oxo-6-(5-(trifluoromethyl)-1,2,4-oxadiazol-3-yl)-1,3-dihydro-2H-isoindol-2-yl)cyclohexyl)propanamide, or a salt thereof.

[11] (1S)-2,2-Difluoro-N-((3S,4R)-4-(1-oxo-6-(5-(trifluoromethyl)-1,2,4-oxadiazol-3-yl)-1,3-dihydro-2H-isoindol-2-yl)tetrahydro-2H-pyran-3-yl)cyclopropanecarboxamide, or a salt thereof.

[12] (1S)-2,2-Difluoro-N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide, or a salt thereof.

[13] A medicament comprising the compound or salt of the above-mentioned [1].

[14] The medicament of the above-mentioned [13], which is histone deacetylase inhibitor.

[15] The medicament of the above-mentioned [13], which is an agent for the prophylaxis or treatment of neurodegenerative diseases.

[16] The medicament of the above-mentioned [13], which is an agent for the prophylaxis or treatment of Charcot-Marie-Tooth disease.

[17] The compound or salt of the above-mentioned [1] for use in the prophylaxis or treatment of neurodegenerative diseases.

[18] The compound or salt of the above-mentioned [1] for use in the prophylaxis or treatment of Charcot-Marie-Tooth disease.

[19] A method of inhibiting histone deacetylase in a mammal, which comprises administering an effective amount of the compound or salt of the above-mentioned [1] to the mammal.

[20] A method for the prophylaxis or treatment of neurodegenerative diseases in a mammal, which comprises administering an effective amount of the compound or salt of the above-mentioned [1] to the mammal.

[21] A method for the prophylaxis or treatment of Charcot-Marie-Tooth disease in a mammal, which comprises administering an effective amount of the compound or salt of the above-mentioned [1] to the mammal.

[22] Use of the compound or salt of the above-mentioned [1] for the production of an agent for the prophylaxis or treatment of neurodegenerative diseases.

[23] Use of the compound or salt of the above-mentioned [1] for the production of an agent for the prophylaxis or treatment of Charcot-Marie-Tooth disease.

Effect of the Invention

Compound (I) has a HDAC inhibitory action, and may be useful for the treatment of autoimmune diseases and/or inflammatory diseases (inflammatory bowel disease, rheumatoid arthritis, psoriasis, multiple sclerosis, Sjogren's syndrome, Behcet's disease, systemic lupus erythematosus, etc.), graft versus host disease (GvHD), cancers (multiple myeloma, leukemia, uterine leiomyosarcoma, prostate cancer, cachexia, myelofibrosis, etc.), central nervous diseases including neurodegenerative diseases (Alzheimer's disease, frontotemporal lobar degeneration, progressive supranuclea palsy, Parkinson's disease, Huntington's disease, etc.), Charcot-Marie-Tooth disease and the like.

DETAILED DESCRIPTION OF THE INVENTION

Figure 1:
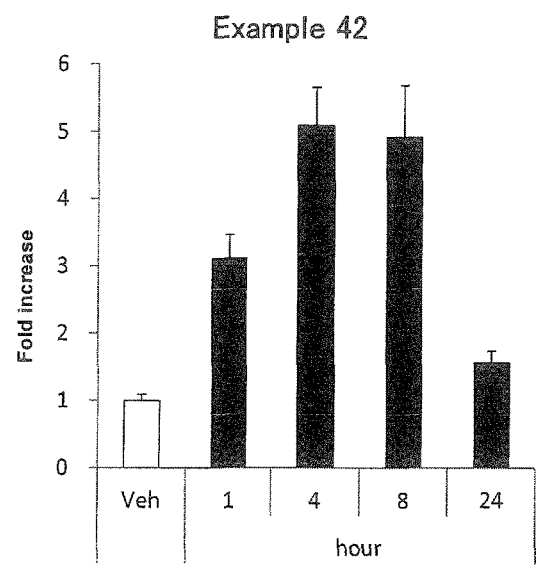
FIG. 1 shows increase in acetylated tubulin in mice in vivo in Experimental Example 2.

The present invention is explained in detail in the following.
The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ arylcarbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),

(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl) amino group (e.g., N-acetyl-N-methylamino) and a ($C_{1-6}$ alkyl)($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "$C_{1-6}$ alkylene group" include —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$CH(C_2H_5)$—, —$CH(C_3H_7)$—, —$CH(CH(CH_3)_2)$—, —$(CH(CH_3))_2$—, —$CH_2$—$CH(CH_3)$—, —$CH(CH_3)$—$CH_2$—, —$CH_2$—$CH_2$—$C(CH_3)_2$—, —$C(CH_3)_2$—$CH_2$—$CH_2$—, —$CH_2$—$CH_2$—$CH_2$—$C(CH_3)_2$— and —$C(CH_3)_2$—$CH_2$—$CH_2$—$CH_2$—.

In the present specification, examples of the "$C_{2-6}$ alkenylene group" include —CH=CH—, —$CH_2$—CH=CH—, —CH=CH—$CH_2$—, —C($CH_3$)$_2$—CH=CH—, —CH=CH—C($CH_3$)$_2$—, —$CH_2$—CH=CH—$CH_2$—, —$CH_2$—$CH_2$—CH=CH—, —CH=CH—$CH_2$—$CH_2$—, —CH=CH—CH=CH—, —CH=CH—$CH_2$—$CH_2$—$CH_2$— and —$CH_2$—$CH_2$—$CH_2$—CH=CH—.

In the present specification, examples of the "$C_{2-6}$ alkynylene group" include —C≡C—, —$CH_2$—C≡C—, —C≡C—$CH_2$—, —C($CH_3$)$_2$—C≡C—, —C≡C—C($CH_3$)$_2$—, —$CH_2$—C≡C—$CH_2$—, —$CH_2$—$CH_2$—C≡C—, —C≡C—$CH_2$—$CH_2$—, —C≡C—C≡C—, —C≡C—$CH_2$—$CH_2$—$CH_2$— and —$CH_2$—$CH_2$—$CH_2$—C≡C—.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

The definition of each symbol in the formula (I) is explained in detail in the following.

X is CH or N.

X is preferably CH.

One of Y and Z is C(O), and the other is C(R$^2$)(R$^3$).

Preferably, Y is C(O), and Z is C(R$^2$)(R$^3$)

R$^2$ and R$^3$ are independently a hydrogen atom or a substituent.

R$^2$ and R$^3$ are preferably both hydrogen atoms.

R$^1$ is an optionally substituted cyclic group.

Examples of the "cyclic group" of the "optionally substituted cyclic group" represented by R$^1$ include a C$_{6-14}$ aryl group, a C$_{3-10}$ cycloalkyl group, a C$_{3-10}$ cycloalkenyl group, and a heterocyclic group.

The "cyclic group" of the "optionally substituted cyclic group" represented by R$^1$ is preferably a C$_{6-14}$ aryl group, a C$_{3-10}$ cycloalkyl group optionally fused with an optionally substituted benzene ring, or a non-aromatic heterocyclic group (preferably a 3- to 14-membered (preferably 4- to 10-membered) non-aromatic heterocyclic group), more preferably a C$_{3-10}$ cycloalkyl group or a non-aromatic heterocyclic group (preferably a 3- to 14-membered (preferably 4- to 10-membered) non-aromatic heterocyclic group).

The "cyclic group" of the "optionally substituted cyclic group" represented by R$^1$ is optionally substituted, for example, by substituent(s) selected from the above-mentioned Substituent Group A. The number of the substituents is, for example, 1 to 3. When the number of the substituents is 2 or more, the respective substituents may be the same or different. In addition, the Substituent Group A is optionally substituted by substituent(s) selected from Substituent Group A. The number of the substituents is, for example, 1 to 3. When the number of the substituents is 2 or more, the respective substituents may be the same or different.

In R$^1$, the atom on R$^1$ bonded to N of the Y—N—Z is preferably C.

R$^1$ is preferably an optionally substituted C$_{6-14}$ aryl group, an optionally substituted C$_{3-10}$ cycloalkyl group which is optionally fused with an optionally substituted benzene ring, or an optionally substituted non-aromatic heterocyclic group (preferably a 3- to 14-membered (preferably 4- to 10-membered) non-aromatic heterocyclic group).

R$^1$ is more preferably (1) a C$_{6-14}$ aryl group (e.g., phenyl), (2) a C$_{3-10}$ cycloalkyl group optionally fused with a benzene ring (e.g., cyclopropyl, cyclobutyl, cyclopentyl, cyclohexyl, indanyl) and optionally substituted by 1 to 3 substituents selected from
   (a) a halogen atom (e.g., a fluorine atom),
   (b) an amino group,
   (c) a C$_{6-14}$ aryl group (e.g., phenyl),
   (d) a C$_{7-16}$ aralkyl group (e.g., benzyl),
   (e) a 3- to 14-membered (preferably 4- to 10-membered) non-aromatic heterocyclic group (preferably a 3- to 8-membered monocyclic non-aromatic heterocyclic group (e.g., pyrrolidinyl, morpholinyl)) optionally substituted by 1 to 3 oxo groups,
   (f) a C$_{1-6}$ alkyl-carbonylamino group (e.g., acetylamino, 2-methylpropanoylamino, butanoylamino, 3-methylbutanoylamino) optionally substituted by 1 to 3 substituents selected from
      (i) a hydroxy group,
      (ii) a halogen atom (e.g., a fluorine atom),
      (iii) a cyano group,
      (iv) a C$_{3-10}$ cycloalkyl group (e.g., cyclopentyl) optionally substituted by 1 to 3 hydroxy groups, and
      (v) a 3- to 14-membered (preferably 4- to 10-membered) non-aromatic heterocyclic group (preferably a 3- to 8-membered monocyclic non-aromatic heterocyclic group (e.g., pyrazolidinyl, pyrrolidinyl)) optionally substituted by 1 to 3 oxo groups,
   (g) a C$_{1-6}$ alkoxy-carbonylamino group (e.g., tert-butoxycarbonylamino),
   (h) a C$_{3-10}$ cycloalkyl-carbonylamino group (e.g., cyclopropylcarbonylamino, cyclobutylcarbonylamino, bicyclo[1.1.1]pentylcarbonylamino) optionally substituted by 1 to 4 substituents selected from
      (i) a halogen atom (e.g., a fluorine atom),
      (ii) a cyano group,
      (iii) a hydroxy group,
      (iv) a C$_{1-6}$ alkyl group (e.g., methyl) optionally substituted by 1 to 3 hydroxy groups, and
      (v) a C$_{1-6}$ alkoxy group (e.g., methoxy),
   (i) a C$_{6-14}$ aryl-carbonylamino group (e.g., phenylcarbonylamino) optionally substituted by 1 to 3 cyano groups,
   (j) a 5- to 14-membered (preferably 5- to 10-membered) aromatic heterocyclylcarbonylamino group (preferably a 5- or 6-membered monocyclic aromatic heterocyclylcarbonylamino group (e.g., imidazolylcarbonylamino, pyrazolylcarbonylamino, oxazolylcarbonylamino, pyrimidinylcarbonylamino)) optionally substituted by 1 to 3 C$_{1-6}$ alkyl groups (e.g., methyl),
   (k) a 3- to 14-membered (preferably 4- to 10-membered) non-aromatic heterocyclylcarbonylamino group (e.g., oxetanylcarbonylamino, tetrahydrofurylcarbonylamino, tetrahydropyranylcarbonylamino, azetidinylcarbonylamino, pyrrolidinylcarbonylamino, piperidylcarbonylamino, imidazolidinylcarbonylamino, tetrahydropyridazinylcarbonylamino, oxepanylcarbonylamino, morpholinylcarbonylamino, 1,1-dioxidothiomorpholinylcarbonylamino, 3-oxa-6-azabicyclo[3.1.1]heptylcarbonylamino, 3-oxa-8-azabicyclo[3.2.1]octylcarbonylamino, 8-oxa-3-azabicyclo[3.2.1]octylcarbonylamino, 2-oxa-5-azabicyclo[2.2.1]heptylcarbonylamino, 6-oxa-3-azabicyclo[3.1.1]heptylcarbonylamino, 3-oxa-9-azabicyclo[3.3.1]nonylcarbonylamino, 2-oxa-6-azaspiro[3.3]heptylcarbonylamino) optionally substituted by 1 to 3 substituents selected from
      (i) an oxo group,
      (ii) a halogen atom (e.g., a fluorine atom),
      (iii) a C$_{1-6}$ alkyl group (e.g., methyl, ethyl, tert-butyl) optionally substituted by 1 to 3 hydroxy groups, (iv) a C$_{1-6}$ alkoxy group (e.g., methoxy), and
      (v) a C$_{6-14}$ aryl group (e.g., phenyl),
   (l) a mono- or di-C$_{1-6}$ alkyl-carbamoylamino group (e.g., diisopropylcarbamoylamino),
   (m) a C$_{3-10}$ cycloalkyl-carbamoylamino group (e.g., cyclopropylcarbamoylamino),
   (n) a (C$_{1-6}$ alkyl)(C$_{3-10}$ cycloalkyl)carbamoylamino group (e.g., N-methyl-N-cyclopropylcarbamoylamino),
   (o) a 3- to 14-membered (preferably 4- to 10-membered) non-aromatic heterocyclylcarbamoylamino group (preferably a 3- to 8-membered monocyclic non-aromatic heterocyclylcarbamoylamino group (e.g., oxetanylcarbamoylamino)), and
   (p) a C$_{3-10}$ cycloalkylsulfonylamino group (e.g., cyclopropylsulfonylamino), or (3) a 3- to 14-membered (preferably 4- to 10-membered) non-aromatic heterocyclic group (e.g., azetidinyl, pyrrolidinyl, piperidyl, tetrahydropyranyl, octahydrocyclopentapyrrolyl, 1-azaspiro[4.5]decyl) optionally substituted by 1 to 3 substituents selected from
(a) an oxo group,
(b) a $C_{6-14}$ aryl group (e.g., phenyl) optionally substituted by 1 to 3 substituents selected from
   (i) a halogen atom (e.g., a fluorine atom, a chlorine atom),
   (ii) a $C_{1-6}$ alkyl group (e.g., methyl), and
   (iii) a $C_{1-6}$ alkoxy group (e.g., methoxy),
(c) a $C_{7-16}$ aralkyl group (e.g., benzyl, 1-phenylethyl),
(d) a $C_{1-6}$ alkyl-carbonyl group (e.g., acetyl) optionally substituted by 3- to 14-membered non-aromatic heterocyclic group(s) (preferably a 9- to 14-membered fused polycyclic (preferably bicyclic or tricyclic) non-aromatic heterocyclic group (e.g., dihydrobenzoxazolyl)) optionally substituted by 1 to 3 oxo groups,
(e) a $C_{1-6}$ alkoxy-carbonyl group (e.g., tert-butoxycarbonyl),
(f) a $C_{3-10}$ cycloalkyl-carbonyl group (e.g., cyclopropylcarbonyl),
(g) a $C_{6-14}$ aryl-carbonyl group (e.g., benzoyl),
(h) a $C_{7-16}$ aralkyl-carbonyl group (e.g., benzylcarbonyl) optionally substituted by 1 to 3 halogen atoms (e.g., a fluorine atom),
(i) a carbamoyl group,
(j) a $C_{1-6}$ alkyl-carbamoyl group (e.g., ethylcarbamoyl),
(k) a $C_{1-6}$ alkoxy-carbonylamino group (e.g., tert-butoxycarbonylamino),
(l) a $C_{3-10}$ cycloalkyl-carbonylamino group (e.g., cyclopropylcarbonylamino) optionally substituted by 1 to 3 halogen atoms (e.g., a fluorine atom), and
(m) a 3- to 14-membered (preferably 4- to 10-membered) non-aromatic heterocyclylcarbonylamino group (preferably a 3- to 8-membered monocyclic non-aromatic heterocyclylcarbonylamino group (e.g., oxetanylcarbonylamino)) optionally substituted by 1 to 3 $C_{1-6}$ alkyl groups (e.g., methyl).

$R^1$ is further more preferably
(1) a $C_{3-10}$ cycloalkyl group (e.g., cyclohexyl) optionally substituted by 1 to 3 substituents selected from
   (a) a halogen atom (e.g., a fluorine atom),
   (b) a $C_{6-14}$ aryl group (e.g., phenyl),
   (c) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups,
   (d) a $C_{1-6}$ alkyl-carbonylamino group (e.g., acetylamino, 2-methylpropanoylamino, 3-methylbutanoylamino) optionally substituted by 1 to 3 hydroxy groups,
   (e) a $C_{1-6}$ alkoxy-carbonylamino group (e.g., tert-butoxycarbonylamino),
   (f) a $C_{3-10}$ cycloalkyl-carbonylamino group (e.g., cyclopropylcarbonylamino, cyclobutylcarbonylamino, bicyclo[1.1.1]pentylcarbonylamino) optionally substituted by 1 to 3 substituents selected from
      (i) a halogen atom (e.g., a fluorine atom),
      (ii) a cyano group,
      (iii) a hydroxy group,
      (iv) a $C_{1-6}$ alkyl group (e.g., methyl) optionally substituted by 1 to 3 hydroxy groups, and
      (v) a $C_{1-6}$ alkoxy group (e.g., methoxy),
   (g) a $C_{6-14}$ aryl-carbonylamino group (e.g., phenylcarbonylamino),
   (h) a 3- to 14-membered (preferably 4- to 10-membered) non-aromatic heterocyclylcarbonylamino group (e.g., oxetanylcarbonylamino, tetrahydropyranylcarbonylamino, azetidinylcarbonylamino, pyrrolidinylcarbonylamino, morpholinylcarbonylamino, 1,1-dioxidothiomorpholinylcarbonylamino, 3-oxa-6-azabicyclo[3.1.1]heptylcarbonylamino, 3-oxa-8-azabicyclo[3.2.1]octylcarbonylamino, 8-oxa-3-azabicyclo[3.2.1]octylcarbonylamino, 2-oxa-5-azabicyclo[2.2.1]heptylcarbonylamino, 6-oxa-3-azabicyclo[3.1.1]heptylcarbonylamino, 3-oxa-9-azabicyclo[3.3.1]nonylcarbonylamino) optionally substituted by 1 to 3 substituents selected from
      (i) a halogen atom (e.g., a fluorine atom),
      (ii) a $C_{1-6}$ alkyl group (e.g., methyl, ethyl), and
      (iii) a $C_{6-14}$ aryl group (e.g., phenyl),
   (i) a mono- or di-$C_{1-6}$ alkyl-carbamoylamino group (e.g., diisopropylcarbamoylamino),
   (j) a $C_{3-10}$ cycloalkyl-carbamoylamino group (e.g., cyclopropylcarbamoylamino),
   (k) a ($C_{1-6}$ alkyl)($C_{3-10}$ cycloalkyl)carbamoylamino group (e.g., N-methyl-N-cyclopropylcarbamoylamino),
   (l) a 3- to 14-membered (preferably 4- to 10-membered) non-aromatic heterocyclylcarbamoylamino group (preferably a 3- to 8-membered monocyclic non-aromatic heterocyclylcarbamoylamino group (e.g., oxetanylcarbamoylamino)), and
   (m) a $C_{3-10}$ cycloalkylsulfonylamino group (e.g., cyclopropylsulfonylamino), or
(2) a 3- to 14-membered (preferably 4- to 10-membered) non-aromatic heterocyclic group (preferably a 3- to 8-membered monocyclic non-aromatic heterocyclic group (e.g., pyrrolidinyl, piperidyl, tetrahydropyranyl)) optionally substituted by 1 to 3 substituents selected from
   (a) a $C_{6-14}$ aryl group (e.g., phenyl),
   (b) a $C_{1-6}$ alkyl-carbonyl group (e.g., acetyl),
   (c) a $C_{1-6}$ alkoxy-carbonyl group (e.g., tert-butoxycarbonyl),
   (d) a $C_{3-10}$ cycloalkyl-carbonyl group (e.g., cyclopropylcarbonyl),
   (e) a $C_{6-14}$ aryl-carbonyl group (e.g., benzoyl),
   (f) a carbamoyl group,
   (g) a $C_{1-6}$ alkyl-carbamoyl group (e.g., ethylcarbamoyl),
   (h) a $C_{1-6}$ alkoxy-carbonylamino group (e.g., tert-butoxycarbonylamino),
   (i) a $C_{3-10}$ cycloalkyl-carbonylamino group (e.g., cyclopropylcarbonylamino) optionally substituted by 1 to 3 halogen atoms (e.g., a fluorine atom), and
   (j) a 3- to 14-membered (preferably 4- to 10-membered) non-aromatic heterocyclylcarbonylamino group (preferably a 3- to 8-membered monocyclic non-aromatic heterocyclylcarbonylamino group (e.g., oxetanylcarbonylamino)) optionally substituted by 1 to 3 $C_{1-6}$ alkyl groups (e.g., methyl).

$R^1$ is still more preferably
(1) a $C_{3-10}$ cycloalkyl group (e.g., cyclohexyl) optionally substituted by 1 to 3 of 3- to 14-membered (preferably 4- to 10-membered) non-aromatic heterocyclylcarbonylamino groups (preferably a 3- to 8-membered monocyclic non-aromatic heterocyclylcarbonylamino group (e.g., oxetanylcarbonylamino)) optionally substituted by 1 to 3 $C_{1-6}$ alkyl groups (e.g., methyl), or
(2) a 3- to 14-membered (preferably 4- to 10-membered) non-aromatic heterocyclic group (preferably a 3- to 8-membered monocyclic non-aromatic heterocyclic group (e.g., pyrrolidinyl, piperidyl, tetrahydropyranyl)) optionally substituted by 1 to 3 $C_{3-10}$ cycloalkyl-carbonylamino groups (e.g., cyclopropylcarbonylamino) optionally substituted by 1 to 3 halogen atoms (e.g., a fluorine atom).

In another embodiment, $R^1$ is more preferably (1) a $C_{6-14}$ aryl group (e.g., phenyl) optionally substituted by 1 to 3 substituents selected from
  (a) a halogen atom (e.g., a chlorine atom),
  (b) a mono- or di-$C_{1-6}$ alkyl-carbamoyl group (e.g., dimethylcarbamoyl), and
  (c) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups, (2) a $C_{3-10}$ cycloalkyl group optionally fused with a benzene ring (e.g., cyclopropyl, cyclobutyl, cyclopentyl, cyclohexyl, indanyl) and optionally substituted by 1 to 3 substituents selected from
  (a) a halogen atom (e.g., a fluorine atom),
  (b) an amino group,
  (c) a $C_{6-14}$ aryl group (e.g., phenyl),
  (d) a $C_{7-16}$ aralkyl group (e.g., benzyl),
  (e) a 3- to 14-membered (preferably 4- to 10-membered) non-aromatic heterocyclic group (preferably a 3- to 8-membered monocyclic non-aromatic heterocyclic group (e.g., pyrrolidinyl, morpholinyl)) optionally substituted by 1 to 3 oxo groups,
  (f) a $C_{1-6}$ alkyl-carbonylamino group (e.g., acetylamino, 2-methylpropanoylamino, butanoylamino, 3-methylbutanoylamino) optionally substituted by 1 to 3 substituents selected from
    (i) a hydroxy group,
    (ii) a halogen atom (e.g., a fluorine atom),
    (iii) a cyano group,
    (iv) a $C_{3-10}$ cycloalkyl group (e.g., cyclopentyl) optionally substituted by 1 to 3 hydroxy groups, and
    (v) a 3- to 14-membered (preferably 4- to 10-membered) non-aromatic heterocyclic group (preferably a 3- to 8-membered monocyclic non-aromatic heterocyclic group (e.g., pyrazolidinyl, pyrrolidinyl)) optionally substituted by 1 to 3 oxo groups,
  (g) a $C_{1-6}$ alkoxy-carbonylamino group (e.g., tert-butoxycarbonylamino),
  (h) a $C_{3-10}$ cycloalkyl-carbonylamino group (e.g., cyclopropylcarbonylamino, cyclobutylcarbonylamino, bicyclo[1.1.1]pentylcarbonylamino) optionally substituted by 1 to 4 substituents selected from
    (i) a halogen atom (e.g., a fluorine atom),
    (ii) a cyano group,
    (iii) a hydroxy group,
    (iv) a $C_{1-6}$ alkyl group (e.g., methyl) optionally substituted by 1 to 3 hydroxy groups, and
    (v) a $C_{1-6}$ alkoxy group (e.g., methoxy),
  (i) a $C_{6-14}$ aryl-carbonylamino group (e.g., phenylcarbonylamino) optionally substituted by 1 to 3 cyano groups,
  (j) a 5- to 14-membered (preferably 5- to 10-membered) aromatic heterocyclylcarbonylamino group (preferably a 5- or 6-membered monocyclic aromatic heterocyclylcarbonylamino group (e.g., imidazolylcarbonylamino, pyrazolylcarbonylamino, oxazolylcarbonylamino, pyrimidinylcarbonylamino)) optionally substituted by 1 to 3 $C_{1-6}$ alkyl groups (e.g., methyl),
  (k) a 3- to 14-membered (preferably 4- to 10-membered) non-aromatic heterocyclylcarbonylamino group (e.g., oxetanylcarbonylamino, tetrahydrofurylcarbonylamino, tetrahydropyranylcarbonylamino, azetidinylcarbonylamino, pyrrolidinylcarbonylamino, piperidylcarbonylamino, imidazolidinylcarbonylamino, tetrahydropyridazinylcarbonylamino, oxepanylcarbonylamino, morpholinylcarbonylamino, 1,1-dioxidothiomorpholinylcarbonylamino, 3-oxa-6-azabicyclo[3.1.1]heptylcarbonylamino, 3-oxa-8-azabicyclo[3.2.1]octylcarbonylamino, 8-oxa-3-azabicyclo[3.2.1]octylcarbonylamino, 2-oxa-5-azabicyclo[2.2.1]heptylcarbonylamino, 6-oxa-3-azabicyclo[3.1.1]heptylcarbonylamino, 3-oxa-9-azabicyclo[3.3.1]nonylcarbonylamino, 2-oxa-6-azaspiro[3.3]heptylcarbonylamino) optionally substituted by 1 to 3 substituents selected from
    (i) an oxo group,
    (ii) a halogen atom (e.g., a fluorine atom),
    (iii) a $C_{1-6}$ alkyl group (e.g., methyl, ethyl, tert-butyl) optionally substituted by 1 to 3 hydroxy groups,
    (iv) a $C_{1-6}$ alkoxy group (e.g., methoxy), and
    (v) a $C_{6-14}$ aryl group (e.g., phenyl),
  (l) a mono- or di-$C_{1-6}$ alkyl-carbamoylamino group (e.g., diisopropylcarbamoylamino),
  (m) a $C_{3-10}$ cycloalkyl-carbamoylamino group (e.g., cyclopropylcarbamoylamino),
  (n) a ($C_{1-6}$ alkyl)($C_{3-10}$ cycloalkyl)carbamoylamino group (e.g., N-methyl-N-cyclopropylcarbamoylamino),
  (o) a 3- to 14-membered (preferably 4- to 10-membered) non-aromatic heterocyclylcarbamoylamino group (preferably a 3- to 8-membered monocyclic non-aromatic heterocyclylcarbamoylamino group (e.g., oxetanylcarbamoylamino)), and
  (p) a $C_{3-10}$ cycloalkylsulfonylamino group (e.g., cyclopropylsulfonylamino), or (3) a 3- to 14-membered (preferably 4- to 10-membered) non-aromatic heterocyclic group (e.g., azetidinyl, pyrrolidinyl, piperidyl, tetrahydropyranyl, octahydrocyclopentapyrrolyl, 1-azaspiro[4.5]decyl) optionally substituted by 1 to 3 substituents selected from
  (a) an oxo group,
  (b) a $C_{6-14}$ aryl group (e.g., phenyl) optionally substituted by 1 to 3 substituents selected from
    (i) a halogen atom (e.g., a fluorine atom, a chlorine atom),
    (ii) a $C_{1-6}$ alkyl group (e.g., methyl), and
    (iii) a $C_{1-6}$ alkoxy group (e.g., methoxy),
  (c) a $C_{7-16}$ aralkyl group (e.g., benzyl, 1-phenylethyl),
  (d) a $C_{1-6}$ alkyl-carbonyl group (e.g., acetyl) optionally substituted by 3- to 14-membered non-aromatic heterocyclic group(s) (preferably a 9- to 14-membered fused polycyclic (preferably bicyclic or tricyclic) non-aromatic heterocyclic group (e.g., dihydrobenzoxazolyl)) optionally substituted by 1 to 3 oxo groups,
  (e) a $C_{1-6}$ alkoxy-carbonyl group (e.g., tert-butoxycarbonyl),
  (f) a $C_{3-10}$ cycloalkyl-carbonyl group (e.g., cyclopropylcarbonyl),
  (g) a $C_{6-14}$ aryl-carbonyl group (e.g., benzoyl),
  (h) a $C_{7-16}$ aralkyl-carbonyl group (e.g., benzylcarbonyl) optionally substituted by 1 to 3 halogen atoms (e.g., a fluorine atom),
  (i) a carbamoyl group,
  (j) a $C_{1-6}$ alkyl-carbamoyl group (e.g., ethylcarbamoyl),
  (k) a $C_{1-6}$ alkoxy-carbonylamino group (e.g., tert-butoxycarbonylamino),
  (l) a $C_{3-10}$ cycloalkyl-carbonylamino group (e.g., cyclopropylcarbonylamino) optionally substituted by 1 to 3 halogen atoms (e.g., a fluorine atom),
  (m) a 3- to 14-membered (preferably 4- to 10-membered) non-aromatic heterocyclylcarbonylamino group (preferably a 3- to 8-membered monocyclic non-aromatic heterocyclylcarbonylamino group (e.g., oxetanylcarbonylamino)) optionally substituted by 1 to 3 $C_{1-6}$ alkyl groups (e.g., methyl),
  (n) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups, and
  (o) a hydroxy group.

In this embodiment, $R^1$ is further more preferably
(1) a $C_{3-10}$ cycloalkyl group (e.g., cyclohexyl) optionally substituted by 1 to 3 substituents selected from
  (a) a halogen atom (e.g., a fluorine atom),
  (b) a $C_{6-14}$ aryl group (e.g., phenyl),
  (c) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups,
  (d) a $C_{1-6}$ alkyl-carbonylamino group (e.g., acetylamino, 2-methylpropanoylamino, 3-methylbutanoylamino) optionally substituted by 1 to 3 hydroxy groups,
  (e) a $C_{1-6}$ alkoxy-carbonylamino group (e.g., tert-butoxycarbonylamino),
  (f) a $C_{3-10}$ cycloalkyl-carbonylamino group (e.g., cyclopropylcarbonylamino, cyclobutylcarbonylamino, bicyclo[1.1.1]pentylcarbonylamino) optionally substituted by 1 to 3 substituents selected from
    (i) a halogen atom (e.g., a fluorine atom),
    (ii) a cyano group,
    (iii) a hydroxy group,
    (iv) a $C_{1-6}$ alkyl group (e.g., methyl) optionally substituted by 1 to 3 hydroxy groups, and
    (v) a $C_{1-6}$ alkoxy group (e.g., methoxy),
  (g) a $C_{6-14}$ aryl-carbonylamino group (e.g., phenylcarbonylamino),
  (h) a 3- to 14-membered (preferably 4- to 10-membered) non-aromatic heterocyclylcarbonylamino group (e.g., oxetanylcarbonylamino, tetrahydropyranylcarbonylamino, azetidinylcarbonylamino, pyrrolidinylcarbonylamino, morpholinylcarbonylamino, 1,1-dioxidothiomorpholinylcarbonylamino, 3-oxa-6-azabicyclo[3.1.1]heptylcarbonylamino, 3-oxa-8-azabicyclo[3.2.1]octylcarbonylamino, 8-oxa-3-azabicyclo[3.2.1]octylcarbonylamino, 2-oxa-5-azabicyclo[2.2.1]heptylcarbonylamino, 6-oxa-3-azabicyclo[3.1.1]heptylcarbonylamino, 3-oxa-9-azabicyclo[3.3.1]nonylcarbonylamino) optionally substituted by 1 to 3 substituents selected from
    (i) a halogen atom (e.g., a fluorine atom),
    (ii) a $C_{1-6}$ alkyl group (e.g., methyl, ethyl), and
    (iii) a $C_{6-14}$ aryl group (e.g., phenyl),
  (i) a mono- or di-$C_{1-6}$ alkyl-carbamoylamino group (e.g., diisopropylcarbamoylamino),
  (j) a $C_{3-10}$ cycloalkyl-carbamoylamino group (e.g., cyclopropylcarbamoylamino),
  (k) a ($C_{1-6}$ alkyl)($C_{3-10}$ cycloalkyl)carbamoylamino group (e.g., N-methyl-N-cyclopropylcarbamoylamino),
  (l) a 3- to 14-membered (preferably 4- to 10-membered) non-aromatic heterocyclylcarbamoylamino group (preferably a 3- to 8-membered monocyclic non-aromatic heterocyclylcarbamoylamino group (e.g., oxetanylcarbamoylamino)), and
  (m) a $C_{3-10}$ cycloalkylsulfonylamino group (e.g., cyclopropylsulfonylamino), or
(2) a 3- to 14-membered (preferably 4- to 10-membered) non-aromatic heterocyclic group (preferably a 3- to 8-membered monocyclic non-aromatic heterocyclic group (e.g., pyrrolidinyl, piperidyl, tetrahydropyranyl)) optionally substituted by 1 to 3 substituents selected from
  (a) a $C_{6-14}$ aryl group (e.g., phenyl),
  (b) a $C_{1-6}$ alkyl-carbonyl group (e.g., acetyl),
  (c) a $C_{1-6}$ alkoxy-carbonyl group (e.g., tert-butoxycarbonyl),
  (d) a $C_{3-10}$ cycloalkyl-carbonyl group (e.g., cyclopropylcarbonyl),
  (e) a $C_{6-14}$ aryl-carbonyl group (e.g., benzoyl),
  (f) a carbamoyl group,
  (g) a $C_{1-6}$ alkyl-carbamoyl group (e.g., ethylcarbamoyl),
  (h) a $C_{1-6}$ alkoxy-carbonylamino group (e.g., tert-butoxycarbonylamino),
  (i) a $C_{3-10}$ cycloalkyl-carbonylamino group (e.g., cyclopropylcarbonylamino) optionally substituted by 1 to 3 halogen atoms (e.g., a fluorine atom),
  (j) a 3- to 14-membered (preferably 4- to 10-membered) non-aromatic heterocyclylcarbonylamino group (preferably a 3- to 8-membered monocyclic non-aromatic heterocyclylcarbonylamino group (e.g., oxetanylcarbonylamino)) optionally substituted by 1 to 3 $C_{1-6}$ alkyl groups (e.g., methyl), and
  (k) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups.

In this embodiment, $R^1$ is still more preferably
(1) a $C_{3-10}$ cycloalkyl group (e.g., cyclohexyl) optionally substituted by 1 to 3 of 3- to 14-membered (preferably 4- to 10-membered) non-aromatic heterocyclylcarbonylamino groups (preferably a 3- to 8-membered monocyclic non-aromatic heterocyclylcarbonylamino group (e.g., oxetanylcarbonylamino)) optionally substituted by 1 to 3 $C_{1-6}$ alkyl groups (e.g., methyl), or
(2) a 3- to 14-membered (preferably 4- to 10-membered) non-aromatic heterocyclic group (preferably a 3- to 8-membered monocyclic non-aromatic heterocyclic group (e.g., pyrrolidinyl, piperidyl, tetrahydropyranyl)) optionally substituted by 1 to 3 substituents selected from
  (a) a $C_{3-10}$ cycloalkyl-carbonylamino group (e.g., cyclopropylcarbonylamino) optionally substituted by 1 to 3 halogen atoms (e.g., a fluorine atom), and
  (b) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups.

In yet another embodiment, $R^1$ is more preferably
(1) a $C_{6-14}$ aryl group (e.g., phenyl) optionally substituted by 1 to 3 substituents selected from
  (a) a halogen atom (e.g., a chlorine atom),
  (b) a mono- or di-$C_{1-6}$ alkyl-carbamoyl group (e.g., dimethylcarbamoyl), and
  (c) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups,
(2) a $C_{3-10}$ cycloalkyl group optionally fused with a benzene ring (e.g., cyclopropyl, cyclobutyl, cyclopentyl, cyclohexyl, indanyl) and optionally substituted by 1 to 3 substituents selected from
  (a) a halogen atom (e.g., a fluorine atom),
  (b) an amino group,
  (c) a $C_{6-14}$ aryl group (e.g., phenyl), (d) a $C_{7-16}$ aralkyl group (e.g., benzyl),
(e) a 3- to 14-membered (preferably 4- to 10-membered) non-aromatic heterocyclic group (preferably a 3- to 8-membered monocyclic non-aromatic heterocyclic group (e.g., pyrrolidinyl, morpholinyl)) optionally substituted by 1 to 3 oxo groups,
(f) a $C_{1-6}$ alkyl-carbonylamino group (e.g., acetylamino, 2-methylpropanoylamino, butanoylamino, 3-methylbutanoylamino, 2,2-dimethylpropanoylamino) optionally substituted by 1 to 3 substituents selected from
  (i) a hydroxy group,
  (ii) a halogen atom (e.g., a fluorine atom, a chlorine atom),
  (iii) a cyano group,
  (iv) a $C_{3-10}$ cycloalkyl group (e.g., cyclopentyl) optionally substituted by 1 to 3 hydroxy groups, and
  (v) a 3- to 14-membered (preferably 4- to 10-membered) non-aromatic heterocyclic group (preferably a 3- to 8-membered monocyclic non-aromatic heterocyclic group (e.g., pyrazolidinyl, pyrrolidinyl)) optionally substituted by 1 to 3 oxo groups,
(g) a $C_{1-6}$ alkoxy-carbonylamino group (e.g., tert-butoxycarbonylamino),
(h) a $C_{3-10}$ cycloalkyl-carbonylamino group (e.g., cyclopropylcarbonylamino, cyclobutylcarbonylamino, bicyclo[1.1.1]pentylcarbonylamino) optionally substituted by 1 to 4 substituents selected from
  (i) a halogen atom (e.g., a fluorine atom),
  (ii) a cyano group,
  (iii) a hydroxy group,
  (iv) a $C_{1-6}$ alkyl group (e.g., methyl) optionally substituted by 1 to 3 hydroxy groups, and
  (v) a $C_{1-6}$ alkoxy group (e.g., methoxy),
(i) a $C_{6-14}$ aryl-carbonylamino group (e.g., phenylcarbonylamino) optionally substituted by 1 to 3 cyano groups,
(j) a 5- to 14-membered (preferably 5- to 10-membered) aromatic heterocyclylcarbonylamino group (preferably a 5- or 6-membered monocyclic aromatic heterocyclylcarbonylamino group (e.g., imidazolylcarbonylamino, pyrazolylcarbonylamino, oxazolylcarbonylamino, pyrimidinylcarbonylamino)) optionally substituted by 1 to 3 $C_{1-6}$ alkyl groups (e.g., methyl),
(k) a 3- to 14-membered (preferably 4- to 10-membered) non-aromatic heterocyclylcarbonylamino group (e.g., oxetanylcarbonylamino, tetrahydrofurylcarbonylamino, tetrahydropyranylcarbonylamino, azetidinylcarbonylamino, pyrrolidinylcarbonylamino, piperidylcarbonylamino, imidazolidinylcarbonylamino, tetrahydropyridazinylcarbonylamino, oxepanylcarbonylamino, morpholinylcarbonylamino, 1,1-dioxidothiomorpholinylcarbonylamino, 3-oxa-6-azabicyclo[3.1.1]heptylcarbonylamino, 3-oxa-8-azabicyclo[3.2.1]octylcarbonylamino, 8-oxa-3-azabicyclo[3.2.1]octylcarbonylamino, 2-oxa-5-azabicyclo[2.2.1]heptylcarbonylamino, 6-oxa-3-azabicyclo[3.1.1]heptylcarbonylamino, 3-oxa-9-azabicyclo[3.3.1]nonylcarbonylamino, 2-oxa-6-azaspiro[3.3]heptylcarbonylamino) optionally substituted by 1 to 3 substituents selected from
  (i) an oxo group,
  (ii) a halogen atom (e.g., a fluorine atom),
  (iii) a $C_{1-6}$ alkyl group (e.g., methyl, ethyl, tert-butyl) optionally substituted by 1 to 3 hydroxy groups,
  (iv) a $C_{1-6}$ alkoxy group (e.g., methoxy),
  (v) a $C_{6-14}$ aryl group (e.g., phenyl),
  (vi) a $C_{1-6}$ alkyl-carbonyl group (e.g., acetyl), and
  (vii) a $C_{1-6}$ alkoxy-carbonyl group (e.g., tert-butoxycarbonyl),
(l) a mono- or di-$C_{1-6}$ alkyl-carbamoylamino group (e.g., diisopropylcarbamoylamino),
(m) a $C_{3-10}$ cycloalkyl-carbamoylamino group (e.g., cyclopropylcarbamoylamino),
(n) a ($C_{1-6}$ alkyl)($C_{3-10}$ cycloalkyl)carbamoylamino group (e.g., N-methyl-N-cyclopropylcarbamoylamino),
(o) a 3- to 14-membered (preferably 4- to 10-membered) non-aromatic heterocyclylcarbamoylamino group (preferably a 3- to 8-membered monocyclic non-aromatic heterocyclylcarbamoylamino group (e.g., oxetanylcarbamoylamino)), and
(p) a $C_{3-10}$ cycloalkylsulfonylamino group (e.g., cyclopropylsulfonylamino), or
(3) a 3- to 14-membered (preferably 4- to 10-membered) non-aromatic heterocyclic group (e.g., azetidinyl, pyrrolidinyl, piperidyl, tetrahydropyranyl, octahydrocyclopentapyrrolyl, 1-azaspiro[4.5]decyl) optionally substituted by 1 to 3 substituents selected from
(a) an oxo group,
(b) a $C_{6-14}$ aryl group (e.g., phenyl) optionally substituted by 1 to 3 substituents selected from
  (i) a halogen atom (e.g., a fluorine atom, a chlorine atom),
  (ii) a $C_{1-6}$ alkyl group (e.g., methyl), and
  (iii) a $C_{1-6}$ alkoxy group (e.g., methoxy),
(c) a $C_{7-16}$ aralkyl group (e.g., benzyl, 1-phenylethyl),
(d) a $C_{1-6}$ alkyl-carbonyl group (e.g., acetyl) optionally substituted by 3- to 14-membered non-aromatic heterocyclic group(s) (preferably a 9- to 14-membered fused polycyclic (preferably bicyclic or tricyclic) non-aromatic heterocyclic group (e.g., dihydrobenzoxazolyl)) optionally substituted by 1 to 3 oxo groups,
(e) a $C_{1-6}$ alkoxy-carbonyl group (e.g., tert-butoxycarbonyl),
(f) a $C_{3-10}$ cycloalkyl-carbonyl group (e.g., cyclopropylcarbonyl),
(g) a $C_{6-14}$ aryl-carbonyl group (e.g., benzoyl),
(h) a $C_{7-16}$ aralkyl-carbonyl group (e.g., benzylcarbonyl) optionally substituted by 1 to 3 halogen atoms (e.g., a fluorine atom),
(i) a carbamoyl group,
(j) a $C_{1-6}$ alkyl-carbamoyl group (e.g., ethylcarbamoyl),
(k) a $C_{1-6}$ alkoxy-carbonylamino group (e.g., tert-butoxycarbonylamino),
(l) a $C_{3-10}$ cycloalkyl-carbonylamino group (e.g., cyclopropylcarbonylamino) optionally substituted by 1 to 3 halogen atoms (e.g., a fluorine atom),
(m) a 3- to 14-membered (preferably 4- to 10-membered) non-aromatic heterocyclylcarbonylamino group (preferably a 3- to 8-membered monocyclic non-aromatic heterocyclylcarbonylamino group (e.g., oxetanylcarbonylamino, tetrahydrofurylcarbonylamino)) optionally substituted by 1 to 3 $C_{1-6}$ alkyl groups (e.g., methyl),
(n) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups,
(o) a hydroxy group,
(p) an amino group, and
(q) a $C_{1-6}$ alkyl-carbonylamino group (e.g., acetylamino) optionally substituted by 1 to 3 halogen atoms (e.g., a chlorine atom).

In this embodiment, $R^1$ is further more preferably
(1) a $C_{3-10}$ cycloalkyl group (e.g., cyclohexyl) optionally substituted by 1 to 3 substituents selected from
   (a) a halogen atom (e.g., a fluorine atom),
   (b) a $C_{6-14}$ aryl group (e.g., phenyl),
   (c) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups,
   (d) a $C_{1-6}$ alkyl-carbonylamino group (e.g., acetylamino, 2-methylpropanoylamino, 3-methylbutanoylamino) optionally substituted by 1 to 3 hydroxy groups,
   (e) a $C_{1-6}$ alkoxy-carbonylamino group (e.g., tert-butoxycarbonylamino),
   (f) a $C_{3-10}$ cycloalkyl-carbonylamino group (e.g., cyclopropylcarbonylamino, cyclobutylcarbonylamino, bicyclo[1.1.1]pentylcarbonylamino) optionally substituted by 1 to 3 substituents selected from
      (i) a halogen atom (e.g., a fluorine atom),
      (ii) a cyano group,
      (iii) a hydroxy group,
      (iv) a $C_{1-6}$ alkyl group (e.g., methyl) optionally substituted by 1 to 3 hydroxy groups, and
      (v) a $C_{1-6}$ alkoxy group (e.g., methoxy),
   (g) a $C_{6-14}$ aryl-carbonylamino group (e.g., phenylcarbonylamino),
   (h) a 3- to 14-membered (preferably 4- to 10-membered) non-aromatic heterocyclylcarbonylamino group (e.g., oxetanylcarbonylamino, tetrahydrofurylcarbonylamino, tetrahydropyranylcarbonylamino, azetidinylcarbonylamino, pyrrolidinylcarbonylamino, morpholinylcarbonylamino, 1,1-dioxidothiomorpholinylcarbonylamino, 3-oxa-6-azabicyclo[3.1.1]heptylcarbonylamino, 3-oxa-8-azabicyclo[3.2.1]octylcarbonylamino, 8-oxa-3-azabicyclo[3.2.1]octylcarbonylamino, 2-oxa-5-azabicyclo[2.2.1]heptylcarbonylamino, 6-oxa-3-azabicyclo[3.1.1]heptylcarbonylamino, 3-oxa-9-azabicyclo[3.3.1]nonylcarbonylamino) optionally substituted by 1 to 3 substituents selected from
      (i) a halogen atom (e.g., a fluorine atom),
      (ii) a $C_{1-6}$ alkyl group (e.g., methyl, ethyl), and
      (iii) a $C_{6-14}$ aryl group (e.g., phenyl),
   (i) a mono- or di-$C_{1-6}$ alkyl-carbamoylamino group (e.g., diisopropylcarbamoylamino),
   (j) a $C_{3-10}$ cycloalkyl-carbamoylamino group (e.g., cyclopropylcarbamoylamino),
   (k) a ($C_{1-6}$ alkyl)($C_{3-10}$ cycloalkyl)carbamoylamino group (e.g., N-methyl-N-cyclopropylcarbamoylamino),
   (l) a 3- to 14-membered (preferably 4- to 10-membered) non-aromatic heterocyclylcarbamoylamino group (preferably a 3- to 8-membered monocyclic non-aromatic heterocyclylcarbamoylamino group (e.g., oxetanylcarbamoylamino)), and
   (m) a $C_{3-10}$ cycloalkylsulfonylamino group (e.g., cyclopropylsulfonylamino), or
(2) a 3- to 14-membered (preferably 4- to 10-membered) non-aromatic heterocyclic group (preferably a 3- to 8-membered monocyclic non-aromatic heterocyclic group (e.g., pyrrolidinyl, piperidyl, tetrahydropyranyl)) optionally substituted by 1 to 3 substituents selected from
   (a) a $C_{6-14}$ aryl group (e.g., phenyl),
   (b) a $C_{1-6}$ alkyl-carbonyl group (e.g., acetyl),
   (c) a $C_{1-6}$ alkoxy-carbonyl group (e.g., tert-butoxycarbonyl),
   (d) a $C_{3-10}$ cycloalkyl-carbonyl group (e.g., cyclopropylcarbonyl),
   (e) a $C_{6-14}$ aryl-carbonyl group (e.g., benzoyl),
   (f) a carbamoyl group,
   (g) a $C_{1-6}$ alkyl-carbamoyl group (e.g., ethylcarbamoyl),
   (h) a $C_{1-6}$ alkoxy-carbonylamino group (e.g., tert-butoxycarbonylamino),
   (i) a $C_{3-10}$ cycloalkyl-carbonylamino group (e.g., cyclopropylcarbonylamino) optionally substituted by 1 to 3 halogen atoms (e.g., a fluorine atom),
   (j) a 3- to 14-membered (preferably 4- to 10-membered) non-aromatic heterocyclylcarbonylamino group (preferably a 3- to 8-membered monocyclic non-aromatic heterocyclylcarbonylamino group (e.g., oxetanylcarbonylamino)) optionally substituted by 1 to 3 $C_{1-6}$ alkyl groups (e.g., methyl), and
   (k) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups.

In this embodiment, $R^1$ is still more preferably
(1) a $C_{3-10}$ cycloalkyl group (e.g., cyclohexyl) optionally substituted by 1 to 3 substituents selected from
   (a) a 3- to 14-membered (preferably 4- to 10-membered) non-aromatic heterocyclylcarbonylamino group (preferably a 3- to 8-membered monocyclic non-aromatic heterocyclylcarbonylamino group (e.g., oxetanylcarbonylamino, tetrahydrofurylcarbonylamino)) optionally substituted by 1 to 3 $C_{1-6}$ alkyl groups (e.g., so methyl), and
   (b) a $C_{1-6}$ alkyl-carbonylamino group (e.g., 2-methylpropanoylamino) optionally substituted by 1 to 3 hydroxy groups, or
(2) a 3- to 14-membered (preferably 4- to 10-membered) non-aromatic heterocyclic group (preferably a 3- to 8-membered monocyclic non-aromatic heterocyclic group (e.g., tetrahydropyranyl)) optionally substituted by 1 to 3 substituents selected from
   (a) a $C_{3-10}$ cycloalkyl-carbonylamino group (e.g., cyclopropylcarbonylamino) optionally substituted by 1 to 3 halogen atoms (e.g., a fluorine atom).

In yet another embodiment, $R^1$ is more preferably an optionally substituted $C_{3-10}$ cycloalkyl group or an optionally substituted non-aromatic heterocyclic group (preferably a 3- to 14-membered (preferably 4- to 10-membered) non-aromatic heterocyclic group, more preferably a 3- to 8-membered monocyclic non-aromatic heterocyclic group).

In this embodiment, $R^1$ is further more preferably an optionally substituted cyclohexyl group or an optionally substituted tetrahydropyranyl group.

$R^1$ is particularly preferably
(1) a cyclohexyl group optionally substituted by 1 to 3 substituents selected from
   (a) a 3- to 14-membered (preferably 4- to 10-membered) non-aromatic heterocyclylcarbonylamino group (preferably a 3- to 8-membered monocyclic non-aromatic heterocyclylcarbonylamino group (e.g., oxetanylcarbonylamino, tetrahydrofurylcarbonylamino)) optionally substituted by 1 to 3 $C_{1-6}$ alkyl groups (e.g., methyl), and
   (b) a $C_{1-6}$ alkyl-carbonylamino group (e.g., 2-methylpropanoylamino) optionally substituted by 1 to 3 hydroxy groups, or (2) a tetrahydropyranyl group optionally substituted by 1 to 3 substituents selected from
(a) a $C_{3-10}$ cycloalkyl-carbonylamino group (e.g., cyclopropylcarbonylamino) optionally substituted by 1 to 3 halogen atoms (e.g., a fluorine atom).

Preferable examples of compound (I) include the following compounds.

[Compound A-1]
Compound (I) wherein
X is CH or N;
one of Y and Z is C(O), and the other is $C(R^2)(R^3)$;
$R^2$ and $R^3$ are both hydrogen atoms; and
$R^1$ is an optionally substituted $C_{6-14}$ aryl group, an optionally substituted $C_{3-10}$ cycloalkyl group (optionally fused with a benzene ring) or an optionally substituted non-aromatic heterocyclic group.

[Compound B-1]
Compound (I) wherein
X is CH or N;
one of Y and Z is C(O), and the other is $C(R^2)(R^3)$;
$R^2$ and $R^3$ are both hydrogen atoms; and
$R^1$ is
(1) a $C_{6-14}$ aryl group (e.g., phenyl),
(2) a $C_{3-10}$ cycloalkyl group optionally fused with a benzene ring (e.g., cyclopropyl, cyclobutyl, cyclopentyl, cyclohexyl, indanyl) and optionally substituted by 1 to 3 substituents selected from
  (a) a halogen atom (e.g., a fluorine atom),
  (b) an amino group,
  (c) a $C_{6-14}$ aryl group (e.g., phenyl),
  (d) a $C_{7-16}$ aralkyl group (e.g., benzyl),
  (e) a 3- to 14-membered (preferably 4- to 10-membered) non-aromatic heterocyclic group (preferably a 3- to 8-membered monocyclic non-aromatic heterocyclic group (e.g., pyrrolidinyl, morpholinyl)) optionally substituted by 1 to 3 oxo groups,
  (f) a $C_{1-6}$ alkyl-carbonylamino group (e.g., acetylamino, 2-methylpropanoylamino, butanoylamino, 3-methylbutanoylamino) optionally substituted by 1 to 3 substituents selected from
    (i) a hydroxy group,
    (ii) a halogen atom (e.g., a fluorine atom),
    (iii) a cyano group,
    (iv) a $C_{3-10}$ cycloalkyl group (e.g., cyclopentyl) optionally substituted by 1 to 3 hydroxy groups, and
    (v) a 3- to 14-membered (preferably 4- to 10-membered) non-aromatic heterocyclic group (preferably a 3- to 8-membered monocyclic non-aromatic heterocyclic group (e.g., pyrazolidinyl, pyrrolidinyl)) optionally substituted by 1 to 3 oxo groups,
  (g) a $C_{1-6}$ alkoxy-carbonylamino group (e.g., tert-butoxycarbonylamino),
  (h) a $C_{3-10}$ cycloalkyl-carbonylamino group (e.g., cyclopropylcarbonylamino, cyclobutylcarbonylamino, bicyclo[1.1.1]pentylcarbonylamino) optionally substituted by 1 to 4 substituents selected from
    (i) a halogen atom (e.g., a fluorine atom),
    (ii) a cyano group,
    (iii) a hydroxy group,
    (iv) a $C_{1-6}$ alkyl group (e.g., methyl) optionally substituted by 1 to 3 hydroxy groups, and
    (v) a $C_{1-6}$ alkoxy group (e.g., methoxy),
  (i) a $C_{6-14}$ aryl-carbonylamino group (e.g., phenylcarbonylamino) optionally substituted by 1 to 3 cyano groups,
  (j) a 5- to 14-membered (preferably 5- to 10-membered) aromatic heterocyclylcarbonylamino group (preferably a 5- or 6-membered monocyclic aromatic heterocyclylcarbonylamino group (e.g., imidazolylcarbonylamino, pyrazolylcarbonylamino, oxazolylcarbonylamino, pyrimidinylcarbonylamino)) optionally substituted by 1 to 3 $C_{1-6}$ alkyl groups (e.g., methyl),
  (k) a 3- to 14-membered (preferably 4- to 10-membered) non-aromatic heterocyclylcarbonylamino group (e.g., oxetanylcarbonylamino, tetrahydrofurylcarbonylamino, tetrahydropyranylcarbonylamino, azetidinylcarbonylamino, pyrrolidinylcarbonylamino, piperidylcarbonylamino, imidazolidinylcarbonylamino, tetrahydropyridazinylcarbonylamino, oxepanylcarbonylamino, morpholinylcarbonylamino, 1,1-dioxidothiomorpholinylcarbonylamino, 3-oxa-6-azabicyclo[3.1.1]heptylcarbonylamino, 3-oxa-8-azabicyclo[3.2.1]octylcarbonylamino, 8-oxa-3-azabicyclo[3.2.1]octylcarbonylamino, 2-oxa-5-azabicyclo[2.2.1]heptylcarbonylamino, 6-oxa-3-azabicyclo[3.1.1]heptylcarbonylamino, 3-oxa-9-azabicyclo[3.3.1]nonylcarbonylamino, 2-oxa-6-azaspiro[3.3]heptylcarbonylamino) optionally substituted by 1 to 3 substituents selected from
    (i) an oxo group,
    (ii) a halogen atom (e.g., a fluorine atom),
    (iii) a $C_{1-6}$ alkyl group (e.g., methyl, ethyl, tert-butyl) optionally substituted by 1 to 3 hydroxy groups,
    (iv) a $C_{1-6}$ alkoxy group (e.g., methoxy), and
    (v) a $C_{6-14}$ aryl group (e.g., phenyl),
  (l) a mono- or di-$C_{1-6}$ alkyl-carbamoylamino group (e.g., diisopropylcarbamoylamino),
  (m) a $C_{3-10}$ cycloalkyl-carbamoylamino group (e.g., cyclopropylcarbamoylamino),
  (n) a ($C_{1-6}$ alkyl)($C_{3-10}$ cycloalkyl)carbamoylamino group (e.g., N-methyl-N-cyclopropylcarbamoylamino),
  (o) a 3- to 14-membered (preferably 4- to 10-membered) non-aromatic heterocyclylcarbamoylamino group (preferably a 3- to 8-membered monocyclic non-aromatic heterocyclylcarbamoylamino group (e.g., oxetanylcarbamoylamino)), and
  (p) a $C_{3-10}$ cycloalkylsulfonylamino group (e.g., cyclopropylsulfonylamino), or
(3) a 3- to 14-membered (preferably 4- to 10-membered) non-aromatic heterocyclic group (e.g., azetidinyl, pyrrolidinyl, piperidyl, tetrahydropyranyl, octahydrocyclopentapyrrolyl, 1-azaspiro[4.5]decyl) optionally substituted by 1 to 3 substituents selected from
  (a) an oxo group,
  (b) a $C_{6-14}$ aryl group (e.g., phenyl) optionally substituted by 1 to 3 substituents selected from
    (i) a halogen atom (e.g., a fluorine atom, a chlorine atom),
    (ii) a $C_{1-6}$ alkyl group (e.g., methyl), and
    (iii) a $C_{1-6}$ alkoxy group (e.g., methoxy),
  (c) a $C_{7-16}$ aralkyl group (e.g., benzyl, 1-phenylethyl),
  (d) a $C_{1-6}$ alkyl-carbonyl group (e.g., acetyl) optionally substituted by 3- to 14-membered non-aromatic heterocyclic group(s) (preferably a 9- to 14-membered fused polycyclic (preferably bicyclic or tricyclic) non-aromatic heterocyclic group (e.g., dihydrobenzoxazolyl)) optionally substituted by 1 to 3 oxo groups,
  (e) a $C_{1-6}$ alkoxy-carbonyl group (e.g., tert-butoxycarbonyl),
  (f) a $C_{3-10}$ cycloalkyl-carbonyl group (e.g., cyclopropylcarbonyl),
  (g) a $C_{6-14}$ aryl-carbonyl group (e.g., benzoyl), (h) a $C_{7-16}$ aralkyl-carbonyl group (e.g., benzylcarbonyl) optionally substituted by 1 to 3 halogen atoms (e.g., a fluorine atom),
(i) a carbamoyl group,
(j) a $C_{1-6}$ alkyl-carbamoyl group (e.g., ethylcarbamoyl),
(k) a $C_{1-6}$ alkoxy-carbonylamino group (e.g., tert-butoxycarbonylamino),
(l) a $C_{3-10}$ cycloalkyl-carbonylamino group (e.g., cyclopropylcarbonylamino) optionally substituted by 1 to 3 halogen atoms (e.g., a fluorine atom), and
(m) a 3- to 14-membered (preferably 4- to 10-membered) non-aromatic heterocyclylcarbonylamino group (preferably a 3-to 8-membered monocyclic non-aromatic heterocyclylcarbonylamino group (e.g., oxetanylcarbonylamino)) optionally substituted by 1 to 3 $C_{1-6}$ alkyl groups (e.g., methyl).

[Compound C-1]

Compound (I) wherein

X is CH or N;
one of Y and Z is C(O), and the other is $C(R^2)(R^3)$ (preferably Y is C(O), and Z is $C(R^2)(R^3)$);
$R^2$ and $R^3$ are both hydrogen atoms; and
$R^1$ is
(1) a $C_{3-10}$ cycloalkyl group (e.g., cyclohexyl) optionally substituted by 1 to 3 substituents selected from
  (a) a halogen atom (e.g., a fluorine atom),
  (b) a $C_{6-14}$ aryl group (e.g., phenyl),
  (c) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups,
  (d) a $C_{1-6}$ alkyl-carbonylamino group (e.g., acetylamino, 2-methylpropanoylamino, 3-methylbutanoylamino) optionally substituted by 1 to 3 hydroxy groups,
  (e) a $C_{1-6}$ alkoxy-carbonylamino group (e.g., tert-butoxycarbonylamino),
  (f) a $C_{3-10}$ cycloalkyl-carbonylamino group (e.g., cyclopropylcarbonylamino, cyclobutylcarbonylamino, bicyclo[1.1.1]pentylcarbonylamino) optionally substituted by 1 to 3 substituents selected from
    (i) a halogen atom (e.g., a fluorine atom),
    (ii) a cyano group,
    (iii) a hydroxy group,
    (iv) a $C_{1-6}$ alkyl group (e.g., methyl) optionally substituted by 1 to 3 hydroxy groups, and
    (v) a $C_{1-6}$ alkoxy group (e.g., methoxy),
  (g) a $C_{6-14}$ aryl-carbonylamino group (e.g., phenylcarbonylamino),
  (h) a 3- to 14-membered (preferably 4- to 10-membered) non-aromatic heterocyclylcarbonylamino group (e.g., oxetanylcarbonylamino, tetrahydropyranylcarbonylamino, azetidinylcarbonylamino, pyrrolidinylcarbonylamino, morpholinylcarbonylamino, 1,1-dioxidothiomorpholinylcarbonylamino, 3-oxa-6-azabicyclo[3.1.1]heptylcarbonylamino, 3-oxa-8-azabicyclo[3.2.1]octylcarbonylamino, 8-oxa-3-azabicyclo[3.2.1]octylcarbonylamino, 2-oxa-5-azabicyclo[2.2.1]heptylcarbonylamino, 6-oxa-3-azabicyclo[3.1.1]heptylcarbonylamino, 3-oxa-9-azabicyclo[3.3.1]nonylcarbonylamino) optionally substituted by 1 to 3 substituents selected from
    (i) a halogen atom (e.g., a fluorine atom),
    (ii) a $C_{1-6}$ alkyl group (e.g., methyl, ethyl), and (iii) a $C_{6-14}$ aryl group (e.g., phenyl),
  (i) a mono- or di-$C_{1-6}$ alkyl-carbamoylamino group (e.g., diisopropylcarbamoylamino),
  (j) a $C_{3-10}$ cycloalkyl-carbamoylamino group (e.g., cyclopropylcarbamoylamino),
  (k) a ($C_{1-6}$ alkyl)($C_{3-10}$ cycloalkyl)carbamoylamino group (e.g., N-methyl-N-cyclopropylcarbamoylamino),
  (l) a 3- to 14-membered (preferably 4- to 10-membered) non-aromatic heterocyclylcarbamoylamino group (preferably a 3- to 8-membered monocyclic non-aromatic heterocyclylcarbamoylamino group (e.g., oxetanylcarbamoylamino)), and
  (m) a $C_{3-10}$ cycloalkylsulfonylamino group (e.g., cyclopropylsulfonylamino), or
(2) a 3- to 14-membered (preferably 4- to 10-membered) non-aromatic heterocyclic group (preferably a 3- to 8-membered monocyclic non-aromatic heterocyclic group (e.g., pyrrolidinyl, piperidyl, tetrahydropyranyl)) optionally substituted by 1 to 3 substituents selected from
  (a) a $C_{6-14}$ aryl group (e.g., phenyl),
  (b) a $C_{1-6}$ alkyl-carbonyl group (e.g., acetyl),
  (c) a $C_{1-6}$ alkoxy-carbonyl group (e.g., tert-butoxycarbonyl),
  (d) a $C_{3-10}$ cycloalkyl-carbonyl group (e.g., cyclopropylcarbonyl),
  (e) a $C_{6-14}$ aryl-carbonyl group (e.g., benzoyl),
  (f) a carbamoyl group,
  (g) a $C_{1-6}$ alkyl-carbamoyl group (e.g., ethylcarbamoyl),
  (h) a $C_{1-6}$ alkoxy-carbonylamino group (e.g., tert-butoxycarbonylamino),
  (i) a $C_{3-10}$ cycloalkyl-carbonylamino group (e.g., cyclopropylcarbonylamino) optionally substituted by 1 to 3 halogen atoms (e.g., a fluorine atom), and
  (j) a 3- to 14-membered (preferably 4- to 10-membered) non-aromatic heterocyclylcarbonylamino group (preferably a 3- to 8-membered monocyclic non-aromatic heterocyclylcarbonylamino group (e.g., oxetanylcarbonylamino)) optionally substituted by 1 to 3 $C_{1-6}$ alkyl groups (e.g., methyl).

[Compound D-1]

Compound (I) wherein

X is CH;
one of Y and Z is C(O), and the other is $C(R^2)(R^3)$ (preferably Y is C(O), and Z is $C(R^2)(R^3)$);
$R^2$ and $R^3$ are both hydrogen atoms; and
$R^1$ is
(1) a $C_{3-10}$ cycloalkyl group (e.g., cyclohexyl) optionally substituted by 1 to 3 of 3- to 14-membered (preferably 4- to 10-membered) non-aromatic heterocyclylcarbonylamino groups (preferably a 3- to 8-membered monocyclic non-aromatic heterocyclylcarbonylamino group (e.g., oxetanylcarbonylamino)) optionally substituted by 1 to 3 $C_{1-6}$ alkyl groups (e.g., methyl), or
(2) a 3- to 14-membered (preferably 4- to 10-membered) non-aromatic heterocyclic group (preferably a 3- to 8-membered monocyclic non-aromatic heterocyclic group (e.g., pyrrolidinyl, piperidyl, tetrahydropyranyl)) optionally substituted by 1 to 3 $C_{3-10}$ cycloalkyl-carbonylamino groups (e.g., cyclopropylcarbonylamino) optionally substituted by 1 to 3 halogen atoms (e.g., a fluorine atom).

[Compound B-2]

Compound (I) wherein

X is CH or N;
one of Y and Z is C(O), and the other is $C(R^2)(R^3)$;

$R^2$ and $R^3$ are both hydrogen atoms; and
$R^1$ is
(1) a $C_{6-14}$ aryl group (e.g., phenyl) optionally substituted by 1 to 3 substituents selected from
  (a) a halogen atom (e.g., a chlorine atom),
  (b) a mono- or di-$C_{1-6}$ alkyl-carbamoyl group (e.g., dimethylcarbamoyl), and
  (c) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups,
(2) a $C_{3-10}$ cycloalkyl group optionally fused with a benzene ring (e.g., cyclopropyl, cyclobutyl, cyclopentyl, cyclohexyl, indanyl) and optionally substituted by 1 to 3 substituents selected from
  (a) a halogen atom (e.g., a fluorine atom),
  (b) an amino group,
  (c) a $C_{6-14}$ aryl group (e.g., phenyl),
  (d) a $C_{7-16}$ aralkyl group (e.g., benzyl),
  (e) a 3- to 14-membered (preferably 4- to 10-membered) non-aromatic heterocyclic group (preferably a 3- to 8-membered monocyclic non-aromatic heterocyclic group (e.g., pyrrolidinyl, morpholinyl)) optionally substituted by 1 to 3 oxo groups,
  (f) a $C_{1-6}$ alkyl-carbonylamino group (e.g., acetylamino, 2-methylpropanoylamino, butanoylamino, 3-methylbutanoylamino) optionally substituted by 1 to 3 substituents selected from
    (i) a hydroxy group,
    (ii) a halogen atom (e.g., a fluorine atom),
    (iii) a cyano group,
    (iv) a $C_{3-10}$ cycloalkyl group (e.g., cyclopentyl) optionally substituted by 1 to 3 hydroxy groups, and
    (v) a 3- to 14-membered (preferably 4- to 10-membered) non-aromatic heterocyclic group (preferably a 3- to 8-membered monocyclic non-aromatic heterocyclic group (e.g., pyrazolidinyl, pyrrolidinyl)) optionally substituted by 1 to 3 oxo groups,
  (g) a $C_{1-6}$ alkoxy-carbonylamino group (e.g., tert-butoxycarbonylamino),
  (h) a $C_{3-10}$ cycloalkyl-carbonylamino group (e.g., cyclopropylcarbonylamino, cyclobutylcarbonylamino, bicyclo[1.1.1]pentylcarbonylamino) optionally substituted by 1 to 4 substituents selected from
    (i) a halogen atom (e.g., a fluorine atom),
    (ii) a cyano group,
    (iii) a hydroxy group,
    (iv) a $C_{1-6}$ alkyl group (e.g., methyl) optionally substituted by 1 to 3 hydroxy groups, and
    (v) a $C_{1-6}$ alkoxy group (e.g., methoxy),
  (i) a $C_{6-14}$ aryl-carbonylamino group (e.g., phenylcarbonylamino) optionally substituted by 1 to 3 cyano groups,
  (j) a 5- to 14-membered (preferably 5- to 10-membered) aromatic heterocyclylcarbonylamino group (preferably a 5- or 6-membered monocyclic aromatic heterocyclylcarbonylamino group (e.g., imidazolylcarbonylamino, pyrazolylcarbonylamino, oxazolylcarbonylamino, pyrimidinylcarbonylamino)) optionally substituted by 1 to 3 $C_{1-6}$ alkyl groups (e.g., methyl),
  (k) a 3- to 14-membered (preferably 4- to 10-membered) non-aromatic heterocyclylcarbonylamino group (e.g., oxetanylcarbonylamino, tetrahydrofurylcarbonylamino, tetrahydropyranylcarbonylamino, azetidinylcarbonylamino, pyrrolidinylcarbonylamino, piperidylcarbonylamino, imidazolidinylcarbonylamino, tetrahydropyridazinylcarbonylamino, oxepanylcarbonylamino, morpholinylcarbonylamino, 1,1-dioxidothiomorpholinylcarbonylamino, 3-oxa-6-azabicyclo[3.1.1]heptylcarbonylamino, 3-oxa-8-azabicyclo[3.2.1]octylcarbonylamino, 8-oxa-3-azabicyclo[3.2.1]octylcarbonylamino, 2-oxa-5-azabicyclo[2.2.1]heptylcarbonylamino, 6-oxa-3-azabicyclo[3.1.1]heptylcarbonylamino, 3-oxa-9-azabicyclo[3.3.1]nonylcarbonylamino, 2-oxa-6-azaspiro[3.3]heptylcarbonylamino) optionally substituted by 1 to 3 substituents selected from
    (i) an oxo group,
    (ii) a halogen atom (e.g., a fluorine atom),
    (iii) a $C_{1-6}$ alkyl group (e.g., methyl, ethyl, tert-butyl) optionally substituted by 1 to 3 hydroxy groups,
    (iv) a $C_{1-6}$ alkoxy group (e.g., methoxy), and
    (v) a $C_{6-14}$ aryl group (e.g., phenyl),
  (l) a mono- or di-$C_{1-6}$ alkyl-carbamoylamino group (e.g., diisopropylcarbamoylamino),
  (m) a $C_{3-10}$ cycloalkyl-carbamoylamino group (e.g., cyclopropylcarbamoylamino),
  (n) a ($C_{1-6}$ alkyl)($C_{3-10}$ cycloalkyl)carbamoylamino group (e.g., N-methyl-N-cyclopropylcarbamoylamino),
  (o) a 3- to 14-membered (preferably 4- to 10-membered) non-aromatic heterocyclylcarbamoylamino group (preferably a 3- to 8-membered monocyclic non-aromatic heterocyclylcarbamoylamino group (e.g., oxetanylcarbamoylamino)), and
  (p) a $C_{3-10}$ cycloalkylsulfonylamino group (e.g., cyclopropylsulfonylamino), or
(3) a 3- to 14-membered (preferably 4- to 10-membered) non-aromatic heterocyclic group (e.g., azetidinyl, pyrrolidinyl, piperidyl, tetrahydropyranyl, octahydrocyclopentapyrrolyl, 1-azaspiro[4.5]decyl) optionally substituted by 1 to 3 substituents selected from
  (a) an oxo group,
  (b) a $C_{6-14}$ aryl group (e.g., phenyl) optionally substituted by 1 to 3 substituents selected from
    (i) a halogen atom (e.g., a fluorine atom, a chlorine atom),
    (ii) a $C_{1-6}$ alkyl group (e.g., methyl), and
    (iii) a $C_{1-6}$ alkoxy group (e.g., methoxy),
  (c) a $C_{7-16}$ aralkyl group (e.g., benzyl, 1-phenylethyl),
  (d) a $C_{1-6}$ alkyl-carbonyl group (e.g., acetyl) optionally substituted by 3- to 14-membered non-aromatic heterocyclic group(s) (preferably a 9- to 14-membered fused polycyclic (preferably bicyclic or tricyclic) non-aromatic heterocyclic group (e.g., dihydrobenzoxazolyl)) optionally substituted by 1 to 3 oxo groups,
  (e) a $C_{1-6}$ alkoxy-carbonyl group (e.g., tert-butoxycarbonyl),
  (f) a $C_{3-10}$ cycloalkyl-carbonyl group (e.g., cyclopropylcarbonyl),
  (g) a $C_{6-14}$ aryl-carbonyl group (e.g., benzoyl),
  (h) a $C_{7-16}$ aralkyl-carbonyl group (e.g., benzylcarbonyl) optionally substituted by 1 to 3 halogen atoms (e.g., a fluorine atom),
  (i) a carbamoyl group,
  (j) a $C_{1-6}$ alkyl-carbamoyl group (e.g., ethylcarbamoyl),
  (k) a $C_{1-6}$ alkoxy-carbonylamino group (e.g., tert-butoxycarbonylamino),
  (l) a $C_{3-10}$ cycloalkyl-carbonylamino group (e.g., cyclopropylcarbonylamino) optionally substituted by 1 to 3 halogen atoms (e.g., a fluorine atom),
  (m) a 3- to 14-membered (preferably 4- to 10-membered) non-aromatic heterocyclylcarbonylamino group (preferably a 3- to 8-membered monocyclic non-aromatic heterocyclylcarbonylamino group (e.g., oxetanylcarbonylamino)) optionally substituted by 1 to 3 $C_{1-6}$ alkyl groups (e.g., methyl),
- (n) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups, and
- (o) a hydroxy group.

[Compound C-2]

Compound (I) wherein

X is CH or N;

one of Y and Z is C(O), and the other is $C(R^2)(R^3)$ (preferably Y is C(O), and Z is $C(R^2)(R^3)$);

$R^2$ and $R^3$ are both hydrogen atoms; and $R^1$ is (1) a $C_{3-10}$ cycloalkyl group (e.g., cyclohexyl) optionally substituted by 1 to 3 substituents selected from
- (a) a halogen atom (e.g., a fluorine atom),
- (b) a $C_{6-14}$ aryl group (e.g., phenyl),
- (c) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups,
- (d) a $C_{1-6}$ alkyl-carbonylamino group (e.g., acetylamino, 2-methylpropanoylamino, 3-methylbutanoylamino) optionally substituted by 1 to 3 hydroxy groups,
- (e) a $C_{1-6}$ alkoxy-carbonylamino group (e.g., tert-butoxycarbonylamino),
- (f) a $C_{3-10}$ cycloalkyl-carbonylamino group (e.g., cyclopropylcarbonylamino, cyclobutylcarbonylamino, bicyclo[1.1.1]pentylcarbonylamino) optionally substituted by 1 to 3 substituents selected from
  - (i) a halogen atom (e.g., a fluorine atom),
  - (ii) a cyano group,
  - (iii) a hydroxy group,
  - (iv) a $C_{1-6}$ alkyl group (e.g., methyl) optionally substituted by 1 to 3 hydroxy groups, and
  - (v) a $C_{1-6}$ alkoxy group (e.g., methoxy),
- (g) a $C_{6-14}$ aryl-carbonylamino group (e.g., phenylcarbonylamino),
- (h) a 3- to 14-membered (preferably 4- to 10-membered) non-aromatic heterocyclylcarbonylamino group (e.g., oxetanylcarbonylamino, tetrahydropyranylcarbonylamino, azetidinylcarbonylamino, pyrrolidinylcarbonylamino, morpholinylcarbonylamino, 1,1-dioxidothiomorpholinylcarbonylamino, 3-oxa-6-azabicyclo[3.1.1]heptylcarbonylamino, 3-oxa-8-azabicyclo[3.2.1]octylcarbonylamino, 8-oxa-3-azabicyclo[3.2.1]octylcarbonylamino, 2-oxa-5-azabicyclo[2.2.1]heptylcarbonylamino, 6-oxa-3-azabicyclo[3.1.1]heptylcarbonylamino, 3-oxa-9-azabicyclo[3.3.1]nonylcarbonylamino) optionally substituted by 1 to 3 substituents selected from
  - (i) a halogen atom (e.g., a fluorine atom),
  - (ii) a $C_{1-6}$ alkyl group (e.g., methyl, ethyl), and
  - (iii) a $C_{6-14}$ aryl group (e.g., phenyl),
- (i) a mono- or di-$C_{1-6}$ alkyl-carbamoylamino group (e.g., diisopropylcarbamoylamino),
- (j) a $C_{3-10}$ cycloalkyl-carbamoylamino group (e.g., cyclopropylcarbamoylamino),
- (k) a ($C_{1-6}$ alkyl)($C_{3-10}$ cycloalkyl)carbamoylamino group (e.g., N-methyl-N-cyclopropylcarbamoylamino),
- (l) a 3- to 14-membered (preferably 4- to 10-membered) non-aromatic heterocyclylcarbamoylamino group (preferably a 3- to 8-membered monocyclic non-aromatic heterocyclylcarbamoylamino group (e.g., oxetanylcarbamoylamino)), and
- (m) a $C_{3-10}$ cycloalkylsulfonylamino group (e.g., cyclopropylsulfonylamino), or (2) a 3- to 14-membered (preferably 4- to 10-membered) non-aromatic heterocyclic group (preferably a 3- to 8-membered monocyclic non-aromatic heterocyclic group (e.g., pyrrolidinyl, piperidyl, tetrahydropyranyl)) optionally substituted by 1 to 3 substituents selected from
- (a) a $C_{6-14}$ aryl group (e.g., phenyl),
- (b) a $C_{1-6}$ alkyl-carbonyl group (e.g., acetyl),
- (c) a $C_{1-6}$ alkoxy-carbonyl group (e.g., tert-butoxycarbonyl),
- (d) a $C_{3-10}$ cycloalkyl-carbonyl group (e.g., cyclopropylcarbonyl),
- (e) a $C_{6-14}$ aryl-carbonyl group (e.g., benzoyl),
- (f) a carbamoyl group,
- (g) a $C_{1-6}$ alkyl-carbamoyl group (e.g., ethylcarbamoyl),
- (h) a $C_{1-6}$ alkoxy-carbonylamino group (e.g., tert-butoxycarbonylamino),
- (i) a $C_{3-10}$ cycloalkyl-carbonylamino group (e.g., cyclopropylcarbonylamino) optionally substituted by 1 to 3 halogen atoms (e.g., a fluorine atom),
- (j) a 3- to 14-membered (preferably 4- to 10-membered) non-aromatic heterocyclylcarbonylamino group (preferably a 3- to 8-membered monocyclic non-aromatic heterocyclylcarbonylamino group (e.g., oxetanylcarbonylamino)) optionally substituted by 1 to 3 $C_{1-6}$ alkyl groups (e.g., methyl), and
- (k) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups.

[Compound D-2]

Compound (I) wherein

X is CH;

one of Y and Z is C(O), and the other is $C(R^2)(R^3)$ (preferably Y is C(O), and Z is $C(R^2)(R^3)$);

$R^2$ and $R^3$ are both hydrogen atoms; and $R^1$ is (1) a $C_{3-10}$ cycloalkyl group (e.g., cyclohexyl) optionally substituted by 1 to 3 of 3- to 14-membered (preferably 4- to 10-membered) non-aromatic heterocyclylcarbonylamino groups (preferably a 3- to 8-membered monocyclic non-aromatic heterocyclylcarbonylamino group (e.g., oxetanylcarbonylamino)) optionally substituted by 1 to 3 $C_{1-6}$ alkyl groups (e.g., methyl), or (2) a 3- to 14-membered (preferably 4- to 10-membered) non-aromatic heterocyclic group (preferably a 3- to 8-membered monocyclic non-aromatic heterocyclic group (e.g., pyrrolidinyl, piperidyl, tetrahydropyranyl)) optionally substituted by 1 to 3 substituents selected from
- (a) a $C_{3-10}$ cycloalkyl-carbonylamino group (e.g., cyclopropylcarbonylamino) optionally substituted by 1 to 3 halogen atoms (e.g., a fluorine atom), and
- (b) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups.

[Compound A-3]

Compound (I) wherein

X is CH or N;

one of Y and Z is C(O), and the other is $C(R^2)(R^3)$;

$R^2$ and $R^3$ are both hydrogen atoms;
the atom on $R^1$ bonded to N of the Y—N—Z is C; and
$R^1$ is an optionally substituted $C_{6-14}$ aryl group, an optionally substituted $C_{3-10}$ cycloalkyl group which is optionally fused with an optionally substituted benzene ring, or an optionally substituted non-aromatic heterocyclic group.

[Compound B-3]

Compound (I) wherein
X is CH or N;
one of Y and Z is C(O), and the other is $C(R^2)(R^3)$;
$R^2$ and $R^3$ are both hydrogen atoms;
the atom on $R^1$ bonded to N of the Y—N—Z is C; and
$R^1$ is
(1) a $C_{6-14}$ aryl group (e.g., phenyl) optionally substituted by 1 to 3 substituents selected from
  (a) a halogen atom (e.g., a chlorine atom),
  (b) a mono- or di-$C_{1-6}$ alkyl-carbamoyl group (e.g., dimethylcarbamoyl), and
  (c) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups,
(2) a $C_{3-10}$ cycloalkyl group optionally fused with a benzene ring (e.g., cyclopropyl, cyclobutyl, cyclopentyl, cyclohexyl, indanyl) and optionally substituted by 1 to 3 substituents selected from
  (a) a halogen atom (e.g., a fluorine atom),
  (b) an amino group,
  (c) a $C_{6-14}$ aryl group (e.g., phenyl),
  (d) a $C_{7-16}$ aralkyl group (e.g., benzyl),
  (e) a 3- to 14-membered (preferably 4- to 10-membered) non-aromatic heterocyclic group (preferably a 3- to 8-membered monocyclic non-aromatic heterocyclic group (e.g., pyrrolidinyl, morpholinyl)) optionally substituted by 1 to 3 oxo groups,
  (f) a $C_{1-6}$ alkyl-carbonylamino group (e.g., acetylamino, 2-methylpropanoylamino, butanoylamino, 3-methylbutanoylamino, 2,2-dimethylpropanoylamino) optionally substituted by 1 to 3 substituents selected from
    (i) a hydroxy group,
    (ii) a halogen atom (e.g., a fluorine atom, a chlorine atom),
    (iii) a cyano group,
    (iv) a $C_{3-10}$ cycloalkyl group (e.g., cyclopentyl) optionally substituted by 1 to 3 hydroxy groups, and
    (v) a 3- to 14-membered (preferably 4- to 10-membered) non-aromatic heterocyclic group (preferably a 3- to 8-membered monocyclic non-aromatic heterocyclic group (e.g., pyrazolidinyl, pyrrolidinyl)) optionally substituted by 1 to 3 oxo groups,
  (g) a $C_{1-6}$ alkoxy-carbonylamino group (e.g., tert-butoxycarbonylamino),
  (h) a $C_{3-10}$ cycloalkyl-carbonylamino group (e.g., cyclopropylcarbonylamino, cyclobutylcarbonylamino, bicyclo[1.1.1]pentylcarbonylamino) optionally substituted by 1 to 4 substituents selected from
    (i) a halogen atom (e.g., a fluorine atom),
    (ii) a cyano group,
    (iii) a hydroxy group,
    (iv) a $C_{1-6}$ alkyl group (e.g., methyl) optionally substituted by 1 to 3 hydroxy groups, and
    (v) a $C_{1-6}$ alkoxy group (e.g., methoxy),
  (i) a $C_{6-14}$ aryl-carbonylamino group (e.g., phenylcarbonylamino) optionally substituted by 1 to 3 cyano groups,
  (j) a 5- to 14-membered (preferably 5- to 10-membered) aromatic heterocyclylcarbonylamino group (preferably a 5- or 6-membered monocyclic aromatic heterocyclylcarbonylamino group (e.g., imidazolylcarbonylamino, pyrazolylcarbonylamino, oxazolylcarbonylamino, pyrimidinylcarbonylamino)) optionally substituted by 1 to 3 $C_{1-6}$ alkyl groups (e.g., methyl),
  (k) a 3- to 14-membered (preferably 4- to 10-membered) non-aromatic heterocyclylcarbonylamino group (e.g., oxetanylcarbonylamino, tetrahydrofurylcarbonylamino, tetrahydropyranylcarbonylamino, azetidinylcarbonylamino, pyrrolidinylcarbonylamino, piperidylcarbonylamino, imidazolidinylcarbonylamino, tetrahydropyridazinylcarbonylamino, oxepanylcarbonylamino, morpholinylcarbonylamino, 1,1-dioxidothiomorpholinylcarbonylamino, 3-oxa-6-azabicyclo[3.1.1]heptylcarbonylamino, 3-oxa-8-azabicyclo[3.2.1]octylcarbonylamino, 8-oxa-3-azabicyclo[3.2.1]octylcarbonylamino, 2-oxa-5-azabicyclo[2.2.1]heptylcarbonylamino, 6-oxa-3-azabicyclo[3.1.1]heptylcarbonylamino, 3-oxa-9-azabicyclo[3.3.1]nonylcarbonylamino, 2-oxa-6-azaspiro[3.3]heptylcarbonylamino) optionally substituted by 1 to 3 substituents selected from
    (i) an oxo group,
    (ii) a halogen atom (e.g., a fluorine atom),
    (iii) a $C_{1-6}$ alkyl group (e.g., methyl, ethyl, tert-butyl) optionally substituted by 1 to 3 hydroxy groups,
    (iv) a $C_{1-6}$ alkoxy group (e.g., methoxy),
    (v) a $C_{6-14}$ aryl group (e.g., phenyl),
    (vi) a $C_{1-6}$ alkyl-carbonyl group (e.g., acetyl), and
    (vii) a $C_{1-6}$ alkoxy-carbonyl group (e.g., tert-butoxycarbonyl),
  (l) a mono- or di-$C_{1-6}$ alkyl-carbamoylamino group (e.g., diisopropylcarbamoylamino),
  (m) a $C_{3-10}$ cycloalkyl-carbamoylamino group (e.g., cyclopropylcarbamoylamino),
  (n) a ($C_{1-6}$ alkyl)($C_{3-10}$ cycloalkyl)carbamoylamino group (e.g., N-methyl-N-cyclopropylcarbamoylamino),
  (o) a 3- to 14-membered (preferably 4- to 10-membered) non-aromatic heterocyclylcarbamoylamino group (preferably a 3- to 8-membered monocyclic non-aromatic heterocyclylcarbamoylamino group (e.g., oxetanylcarbamoylamino)), and
  (p) a $C_{3-10}$ cycloalkylsulfonylamino group (e.g., cyclopropylsulfonylamino), or
(3) a 3- to 14-membered (preferably 4- to 10-membered) non-aromatic heterocyclic group (e.g., azetidinyl, pyrrolidinyl, piperidyl, tetrahydropyranyl, octahydrocyclopentapyrrolyl, 1-azaspiro[4.5]decyl) optionally substituted by 1 to 3 substituents selected from
  (a) an oxo group,
  (b) a $C_{6-14}$ aryl group (e.g., phenyl) optionally substituted by 1 to 3 substituents selected from
    (i) a halogen atom (e.g., a fluorine atom, a chlorine atom),
    (ii) a $C_{1-6}$ alkyl group (e.g., methyl), and
    (iii) a $C_{1-6}$ alkoxy group (e.g., methoxy),
  (c) a $C_{7-16}$ aralkyl group (e.g., benzyl, 1-phenylethyl),
  (d) a $C_{1-6}$ alkyl-carbonyl group (e.g., acetyl) optionally substituted by 3- to 14-membered non-aromatic heterocyclic group(s) (preferably a 9- to 14-membered fused polycyclic (preferably bicyclic or tricyclic) non-aromatic heterocyclic group (e.g., dihydrobenzoxazolyl)) optionally substituted by 1 to 3 oxo groups,
  (e) a $C_{1-6}$ alkoxy-carbonyl group (e.g., tert-butoxycarbonyl), (f) a $C_{3-10}$ cycloalkyl-carbonyl group (e.g., cyclopropylcarbonyl),
(g) a $C_{6-14}$ aryl-carbonyl group (e.g., benzoyl),
(h) a $C_{7-16}$ aralkyl-carbonyl group (e.g., benzylcarbonyl) optionally substituted by 1 to 3 halogen atoms (e.g., a fluorine atom),
(i) a carbamoyl group,
(j) a $C_{1-6}$ alkyl-carbamoyl group (e.g., ethylcarbamoyl),
(k) a $C_{1-6}$ alkoxy-carbonylamino group (e.g., tert-butoxycarbonylamino),
(l) a $C_{3-10}$ cycloalkyl-carbonylamino group (e.g., cyclopropylcarbonylamino) optionally substituted by 1 to 3 halogen atoms (e.g., a fluorine atom),
(m) a 3- to 14-membered (preferably 4- to 10-membered) non-aromatic heterocyclylcarbonylamino group (preferably a 3- to 8-membered monocyclic non-aromatic heterocyclylcarbonylamino group (e.g., oxetanylcarbonylamino, tetrahydrofurylcarbonylamino)) optionally substituted by 1 to 3 $C_{1-6}$ alkyl groups (e.g., methyl),
(n) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups,
(o) a hydroxy group,
(p) an amino group, and
(q) a $C_{1-6}$ alkyl-carbonylamino group (e.g., acetylamino) optionally substituted by 1 to 3 halogen atoms (e.g., a chlorine atom).

[Compound C-3]
Compound (I) wherein
X is CH or N;
one of Y and Z is C(O), and the other is $C(R^2)(R^3)$ (preferably Y is C(O), and Z is $C(R^2)(R^3)$);
$R^2$ and $R^3$ are both hydrogen atoms;
the atom on $R^1$ bonded to N of the Y—N—Z is C; and
$R^1$ is
(1) a $C_{3-10}$ cycloalkyl group (e.g., cyclohexyl) optionally substituted by 1 to 3 substituents selected from
  (a) a halogen atom (e.g., a fluorine atom),
  (b) a $C_{6-14}$ aryl group (e.g., phenyl),
  (c) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups,
  (d) a $C_{1-6}$ alkyl-carbonylamino group (e.g., acetylamino, 2-methylpropanoylamino, 3-methylbutanoylamino) optionally substituted by 1 to 3 hydroxy groups,
  (e) a $C_{1-6}$ alkoxy-carbonylamino group (e.g., tert-butoxycarbonylamino),
  (f) a $C_{3-10}$ cycloalkyl-carbonylamino group (e.g., cyclopropylcarbonylamino, cyclobutylcarbonylamino, bicyclo[1.1.1]pentylcarbonylamino) optionally substituted by 1 to 3 substituents selected from
    (i) a halogen atom (e.g., a fluorine atom),
    (ii) a cyano group,
    (iii) a hydroxy group,
    (iv) a $C_{1-6}$ alkyl group (e.g., methyl) optionally substituted by 1 to 3 hydroxy groups, and
    (v) a $C_{1-6}$ alkoxy group (e.g., methoxy),
  (g) a $C_{6-14}$ aryl-carbonylamino group (e.g., phenylcarbonylamino),
  (h) a 3- to 14-membered (preferably 4- to 10-membered) non-aromatic heterocyclylcarbonylamino group (e.g., oxetanylcarbonylamino, tetrahydrofurylcarbonylamino, tetrahydropyranylcarbonylamino, azetidinylcarbonylamino, pyrrolidinylcarbonylamino, morpholinylcarbonylamino, 1,1-dioxidothiomorpholinylcarbonylamino, 3-oxa-6-azabicyclo[3.1.1]heptylcarbonylamino, 3-oxa-8-azabicyclo[3.2.1]octylcarbonylamino, 8-oxa-3-azabicyclo[3.2.1]octylcarbonylamino, 2-oxa-5-azabicyclo[2.2.1]heptylcarbonylamino, 6-oxa-3-azabicyclo[3.1.1]heptylcarbonylamino, 3-oxa-9-azabicyclo[3.3.1]nonylcarbonylamino) optionally substituted by 1 to 3 substituents selected from
    (i) a halogen atom (e.g., a fluorine atom),
    (ii) a $C_{1-6}$ alkyl group (e.g., methyl, ethyl), and
    (iii) a $C_{6-14}$ aryl group (e.g., phenyl),
  (i) a mono- or di-$C_{1-6}$ alkyl-carbamoylamino group (e.g., diisopropylcarbamoylamino),
  (j) a $C_{3-10}$ cycloalkyl-carbamoylamino group (e.g., cyclopropylcarbamoylamino),
  (k) a ($C_{1-6}$ alkyl)($C_{3-10}$ cycloalkyl)carbamoylamino group (e.g., N-methyl-N-cyclopropylcarbamoylamino),
  (l) a 3- to 14-membered (preferably 4- to 10-membered) non-aromatic heterocyclylcarbamoylamino group (preferably a 3- to 8-membered monocyclic non-aromatic heterocyclylcarbamoylamino group (e.g., oxetanylcarbamoylamino)), and
  (m) a $C_{3-10}$ cycloalkylsulfonylamino group (e.g., cyclopropylsulfonylamino), or
(2) a 3- to 14-membered (preferably 4- to 10-membered) non-aromatic heterocyclic group (preferably a 3- to 8-membered monocyclic non-aromatic heterocyclic group (e.g., pyrrolidinyl, piperidyl, tetrahydropyranyl)) optionally substituted by 1 to 3 substituents selected from
  (a) a $C_{6-14}$ aryl group (e.g., phenyl),
  (b) a $C_{1-6}$ alkyl-carbonyl group (e.g., acetyl),
  (c) a $C_{1-6}$ alkoxy-carbonyl group (e.g., tert-butoxycarbonyl),
  (d) a $C_{3-10}$ cycloalkyl-carbonyl group (e.g., cyclopropylcarbonyl),
  (e) a $C_{6-14}$ aryl-carbonyl group (e.g., benzoyl),
  (f) a carbamoyl group,
  (g) a $C_{1-6}$ alkyl-carbamoyl group (e.g., ethylcarbamoyl),
  (h) a $C_{1-6}$ alkoxy-carbonylamino group (e.g., tert-butoxycarbonylamino),
  (i) a $C_{3-10}$ cycloalkyl-carbonylamino group (e.g., cyclopropylcarbonylamino) optionally substituted by 1 to 3 halogen atoms (e.g., a fluorine atom),
  (j) a 3- to 14-membered (preferably 4- to 10-membered) non-aromatic heterocyclylcarbonylamino group (preferably a 3- to 8-membered monocyclic non-aromatic heterocyclylcarbonylamino group (e.g., oxetanylcarbonylamino)) optionally substituted by 1 to 3 $C_{1-6}$ alkyl groups (e.g., methyl), and
  (k) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups.

[Compound D-3]
Compound (I) wherein
X is CH or N;
one of Y and Z is C(O), and the other is $C(R^2)(R^3)$ (preferably Y is C(O), and Z is $C(R^2)(R^3)$);
$R^2$ and $R^3$ are both hydrogen atoms; and
$R^1$ is an optionally substituted cyclohexyl group or an optionally substituted tetrahydropyranyl group.

[Compound E-3]
Compound (I) wherein
X is CH or N;
Y is C(O);
Z is C($R^2$)($R^3$);
$R^2$ and $R^3$ are both hydrogen atoms;
the atom on $R^1$ bonded to N of the Y—N—Z is C; and
$R^1$ is an optionally substituted $C_{6-14}$ aryl group, an optionally substituted $C_{3-10}$ cycloalkyl group which is optionally fused with an optionally substituted benzene ring, or an optionally substituted non-aromatic heterocyclic group.

[Compound F-3]
Compound (I) wherein
X is CH;
Y is C(O);
Z is C($R^2$)($R^3$);
$R^2$ and $R^3$ are both hydrogen atoms; and
$R^1$ is
(1) a $C_{3-10}$ cycloalkyl group (e.g., cyclohexyl) optionally substituted by 1 to 3 substituents selected from
  (a) a 3- to 14-membered (preferably 4- to 10-membered) non-aromatic heterocyclylcarbonylamino group (preferably a 3- to 8-membered monocyclic non-aromatic heterocyclylcarbonylamino group (e.g., oxetanylcarbonylamino, tetrahydrofurylcarbonylamino)) optionally substituted by 1 to 3 $C_{1-6}$ alkyl groups (e.g., methyl), and
  (b) a $C_{1-6}$ alkyl-carbonylamino group (e.g., 2-methylpropanoylamino) optionally substituted by 1 to 3 hydroxy groups, or
(2) a 3- to 14-membered (preferably 4- to 10-membered) non-aromatic heterocyclic group (preferably a 3- to 8-membered monocyclic non-aromatic heterocyclic group (e.g., tetrahydropyranyl)) optionally substituted by 1 to 3 substituents selected from
  (a) a $C_{3-10}$ cycloalkyl-carbonylamino group (e.g., cyclopropylcarbonylamino) optionally substituted by 1 to 3 halogen atoms (e.g., a fluorine atom).

[Compound G-3]
Compound (I) wherein
X is CH;
Y is C(O);
Z is C($R^2$)($R^3$);
$R^2$ and $R^3$ are both hydrogen atoms; and
$R^1$ is an optionally substituted cyclohexyl group or an optionally substituted tetrahydropyranyl group.

[Compound H-3]
Compound (I) wherein
X is CH;
Y is C(O);
Z is C($R^2$)($R^3$);
$R^2$ and $R^3$ are both hydrogen atoms; and
$R^1$ is
(1) a cyclohexyl group optionally substituted by 1 to 3 substituents selected from
  (a) a 3- to 14-membered (preferably 4- to 10-membered) non-aromatic heterocyclylcarbonylamino group (preferably a 3- to 8-membered monocyclic non-aromatic heterocyclylcarbonylamino group (e.g., oxetanylcarbonylamino, tetrahydrofurylcarbonylamino)) optionally substituted by 1 to 3 $C_{1-6}$ alkyl groups (e.g., methyl), and
  (b) a $C_{1-6}$ alkyl-carbonylamino group (e.g., 2-methylpropanoylamino) optionally substituted by 1 to 3 hydroxy groups, or
(2) a tetrahydropyranyl group optionally substituted by 1 to 3 substituents selected from
  (a) a $C_{3-10}$ cycloalkyl-carbonylamino group (e.g., cyclopropylcarbonylamino) optionally substituted by 1 to 3 halogen atoms (e.g., a fluorine atom).

When compound (I) is in a form of a salt, examples thereof include metal salts, an ammonium salt, salts with organic base, salts with inorganic acid, salts with organic acid, salts with basic or acidic amino acid, and the like. Preferable examples of the metal salt include alkali metal salts such as sodium salt, potassium salt and the like; alkaline earth metal salts such as calcium salt, magnesium salt, barium salt and the like; an aluminum salt, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Among them, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

[Production Method]

The production method of the compound of the present invention is explained in the followings.

The raw material compound and reagent used and the compound obtained in each step in the following production method may be each in a form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature −300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents −20 equivalents, preferably 0.8 equivalents −5 equivalents, relative to the substrate, unless otherwise specified. When the reagent is used as a catalyst, the reagent is used in an amount of 0.001 equivalent −1 equivalent, preferably 0.01 equivalent −0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.

inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.

inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
Lewis acid: boron trifluoride diethyl ether complex, zinc iodide, anhydrous aluminium chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & SonsInc); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protected hydroxy group of an alcohol and a phenol include ether groups such as methoxymethyl ether, benzyl ether, t-butyldimethylsilyl ether, tetrahydropyranyl ether and the like; carboxylate groups such as acetate and the like; sulfonate groups such as methanesulfonate and the like; carbonate groups such as t-butyl carbonate and the like, and the like.

Examples of the protected carbonyl group of an aldehyde include acetal groups such as dimethyl acetal and the like; cyclic acetal groups such as cyclic 1,3-dioxane and the like, and the like.

Examples of the protected carbonyl group of a ketone include ketal groups such as dimethyl ketal and the like; cyclic ketal groups such as cyclic 1,3-dioxane and the like; oxime groups such as O-methyloxime and the like; hydrazone groups such as N,N-dimethylhydrazone and the like, and the like.

Examples of the protected carboxyl group include ester groups such as methyl ester and the like; amido groups such as N,N-dimethylamide and the like, and the like.

Examples of the protected thiol group include ether groups such as benzylthio ether and the like; ester groups such as thioacetate, thiocarbonate, thiocarbamate and the like, and the like.

Examples of the protected amino group and aromatic heterocycle (e.g., imidazole, pyrrole, indole etc.) include carbamate groups such as benzyl carbamate and the like; amido groups such as acetamide and the like; alkyl amine groups such as N-triphenylmethylamine and the like; sulfonamido groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminium hydride, sodium triacetoxyborohydride, sodium cyanoborohydride, diisobutylaluminium hydride (DIBAL-H), sodium borohydride, tetramethylammonium triacetoxyborohydride and the like; boranes such as borane tetrahydrofuran complex and the like; Raney nickel; Raney cobalt; hydrogen; formic acid and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (MCPBA), hydrogen peroxide, t-butylhydroperoxide and the like; perchlorates such as tetrabutylammonium perchlorate and the like; chlorates such as sodium chlorate and the like; chlorites such as sodium chlorite and the like; periodic acids such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, examples of the reagent to be used include a combination of a Lewis acid and an acid chloride or a combination of a Lewis acid and an alkylating agent (e.g., an alkyl halide, an alcohol, an olefin etc.). Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, examples of the reagent to be used include a nucleophile (e.g., an amine, imidazole etc.) and a base (e.g., an organic base etc.).

When nucleophilic addition reaction by a carbo anion, nucleophilic 1,4-addition reaction (Michael addition reaction) by a carbo anion or nucleophilic displacement reaction by a carbo anion is carried out in each step, examples of the base to be used for generation of the carbo anion include organic lithiums, metal alkoxides, inorganic bases, organic bases and the like.

When Grignard reagent is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or ureation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, so examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, palladium (II) acetate and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl-1,3,2,4-dithiadiphosphetane-2,4-disulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two step comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of t-butyl ester, formic acid, triethylsilane and the like may be added to reductively-trap t-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

When Curtius rearrangement reaction is carried out in each step, examples of the reagent to be used include diphenylphosphoryl azide, trimethylsilylazide, sodium azide and the like.

Compound (Ia) can be produced from compound (IIa) according to the below method.

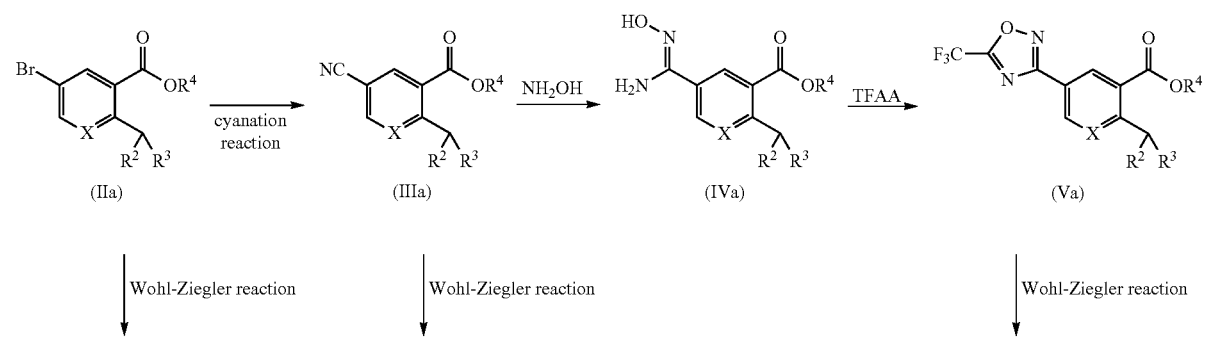

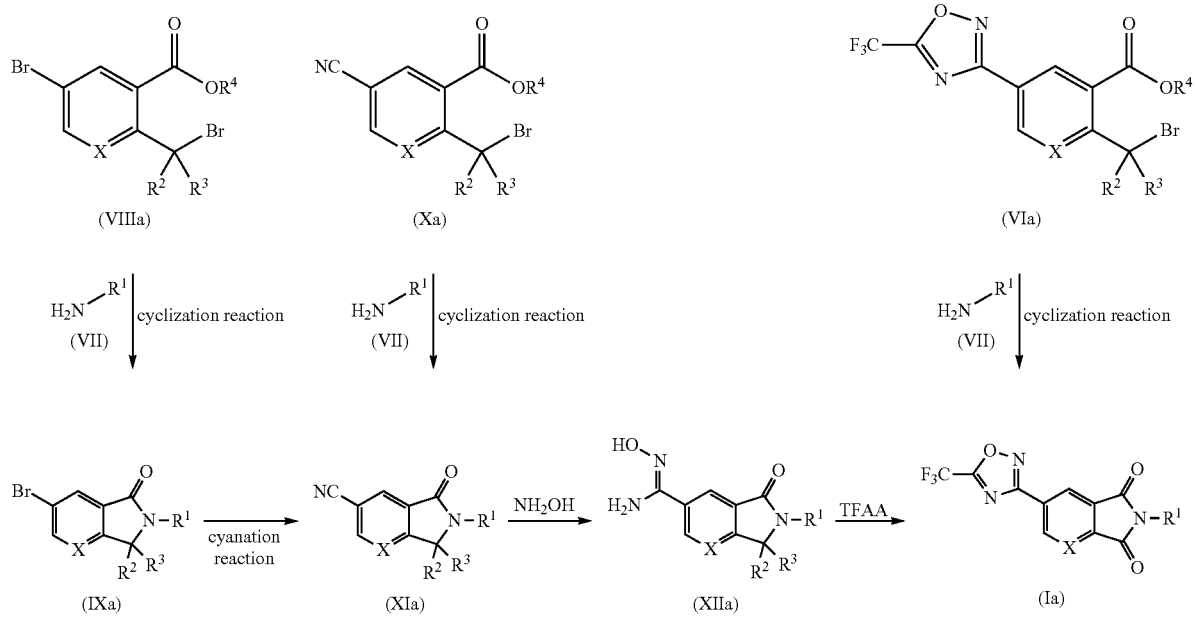

wherein $R^4$ is a methyl group or an ethyl group, and the other symbols are as defined above.

Compound (Ia) can be produced by subjecting compound (VIa) and compound (VII) to a cyclization reaction with a base. Examples of the base to be used include diisopropylethylamine and the like. The reaction for producing compound (IXa) from compound (VIIIa) and the reaction for producing compound (XIa) from compound (Xa) are also carried out by a method similar to this reaction.

Compound (VIa) can be produced by subjecting compound (Va) to a Wohl-Ziegler reaction. The reaction for producing compound (VIIIa) from compound (IIa) and the reaction for producing compound (Xa) from compound (IIIa) are also carried out by a method similar to this reaction.

Compound (Va) can be produced by reacting compound (IIIa) with a hydroxylamine reagent, and reacting the obtained compound (IVa) with trifluoroacetic anhydride (TFAA). Examples of the hydroxylamine reagent include 50% aqueous hydroxylamine solution, hydroxylamine hydrochloride and the like. The reaction for producing compound (Ia) from compound (XIa) via compound (XIIa) is also carried out by a method similar to this reaction.

Compound (IIIa) can be produced by subjecting compound (IIa) to a cyanation reaction with a cyanating reagent. Examples of the cyanating reagent to be used include a combination of zinc(II) cyanide and 1,1'-bis(diphenylphosphino)ferrocene palladium(II) chloride, and copper(I) cyanide.

The reaction for producing compound (XIa) from compound (IXa) is also carried out by a method similar to this reaction.

Compound (Ib) can be produced from compound (IIb) according to the below method.

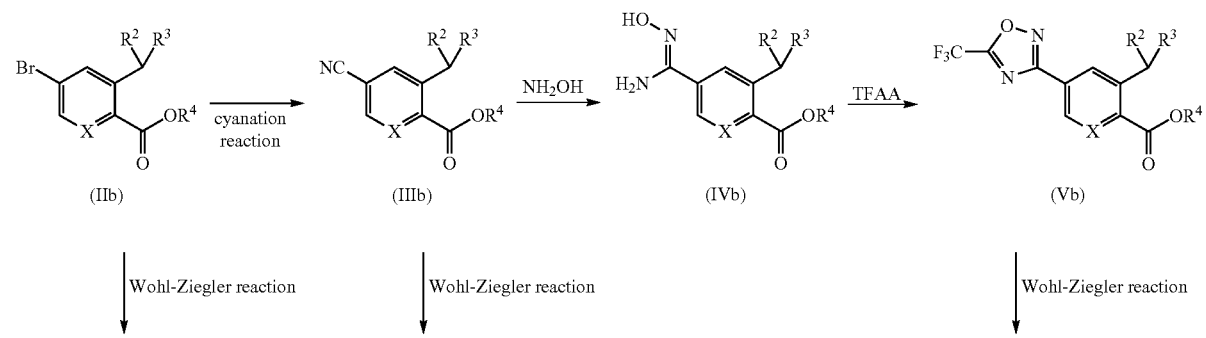

wherein each symbol is as defined above.

Compound (Ib) can be produced by subjecting compound (VIb) and compound (VII) to a cyclization reaction with a base. Examples of the base to be used include diisopropylethylamine and the like. The reaction for producing compound (IXb) from compound (VIIIb) and the reaction for producing compound (XIb) form compound (Xb) are also carried out by a method similar to this reaction.

Compound (VIb) can be produced by subjecting compound (Vb) to a Wohl-Ziegler reaction. The reaction for producing compound (VIIIb) from compound (IIb) and the reaction for producing compound (Xb) from compound (IIIb) are also carried out by a method similar to this reaction.

Compound (Vb) can be produced by reacting compound (IIIb) with a hydroxylamine reagent, and reacting the obtained compound (IVb) with trifluoroacetic anhydride (TFAA). Examples of the hydroxylamine reagent include 50% aqueous hydroxylamine solution, hydroxylamine hydrochloride and the like. The reaction for producing compound (Ib) from compound (XIb) via compound (XIIb) is also carried out by a method similar to this reaction.

Compound (IIIb) can be produced by subjecting compound (IIb) to a cyanation reaction with a cyanating reagent. Examples of the cyanating reagent to be used include a combination of zinc(II) cyanide and 1,1'-bis(diphenylphosphino)ferrocene palladium(II) chloride, and copper(I) cyanide.

The reaction for producing compound (XIb) from compound (IXb) is also carried out by a method similar to this reaction.

Compound (VII) may be a commercially available product, or can also be produced according to a method known per se or a method analogous thereto. Alternatively, compound (VII) can be also produced as compound (XVI) according to the below method.

Compound (XVI) can be produced from compound (XIII) according to the below method.

wherein Ring A is an optionally substituted cyclic group.

Compound (XVI) can be produced by subjecting compound (XV) to a deprotection reaction.

Compound (XV) can be produced by subjecting compound (XIV) to a Curtius rearrangement reaction.

Compound (XIV) can be produced by subjecting compound (XIII) to a hydrolysis reaction.

Compound (XIII) may be a commercially available product, or can also be produced according to a method known per se or a method analogous thereto. Alternatively, compound (XIII) can be also produced as compound (XX) according to the below method.

Compound (XX) can be produced from compound (XVII) according to the below method.

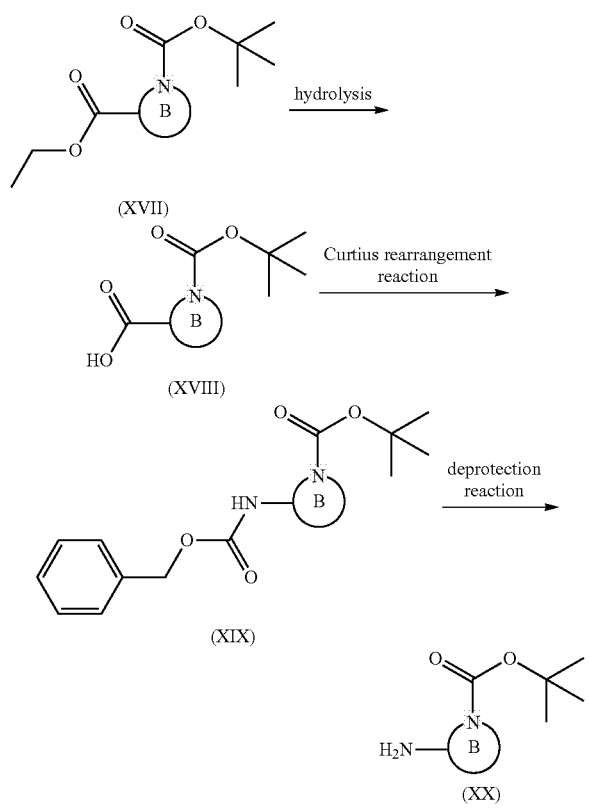

wherein Ring B is an optionally substituted cyclic group.

Compound (XX) can be produced by subjecting compound (XIX) to a deprotection reaction.

Compound (XIX) can be produced by subjecting compound (XVIII) to a Curtius rearrangement reaction.

Compound (XVIII) can be produced by subjecting compound (XVII) to a hydrolysis reaction.

Compounds (IIa), (IIb), (VII), (XIII), (XVII) and other raw material compounds may be a commercially available product, or can also be produced according to a method known per se or a method analogous thereto.

When compound (I) has an optical isomer, a stereoisomer, a regioisomer or a rotamer, these are also encompassed in compound (I), and can be obtained as a single product according to a synthesis method and separation method known per se (e.g., concentration, solvent extraction, column chromatography, recrystallization etc.). For example, when compound (I) has an optical isomer, the optical isomer resolved from the compound is also encompassed in compound (I).

The optical isomer can be produced according to a method known per se. Specifically, the optical isomer is obtained using an optically active synthetic intermediate or by subjecting the racemic final product to an optical resolution according to a known method.

The optical resolution may be a method known per se, such as a fractional recrystallization method, a chiral column method, a diastereomer method etc.

1) Fractional Recrystallized Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallized method, and if desired, a neutralization step to give a free optical isomer.

2) Chiral Column Method

A method wherein a racemate or a salt thereof is applied to a column (a chiral column) for separation of an optical isomer to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, 2-propanol, acetonitrile, trifluoroacetic acid, diethylamine, etc.) as an eluent, solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallized method, a chromatography method etc.) and the like, and is subjected to a chemical treatment such as hydrolysis and the like to separate an optically active reagent moiety, whereby an optical isomer is obtained. For example, when compound (I) contains hydroxy or primary or secondary amino in a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxy group, the compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis.

Compound (I) may be a crystal.

The crystal of compound (I) can be produced according to a crystallization method known per se.

Examples of the crystallization method include crystallization method from a solution, crystallization method from vapor, crystallization method from a melt, and the like.

The "crystallization method from a solution" is typically a method of shifting a non-saturated state to supersaturated state by varying factors involved in solubility of compounds (solvent composition, pH, temperature, ionic strength, redox state, etc.) or the amount of solvent. Specific examples thereof include a concentration method, a slow cooling method, a reaction method (a diffusion method, an electrolysis method), a hydrothermal growth method, a flux method and the like. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, 1,4-dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, etc.), alcohols (e.g., methanol, ethanol, 2-propanol, etc.), water and the like. These solvents are used alone or in a combination of two or more at a suitable ratio (e.g., 1:1 to 1:100 (a volume ratio)). Where necessary, a seed crystal can be used.

The "crystallization method from vapor" is, for example, a vaporization method (a sealed tube method, a gas stream method), a gas phase reaction method, a chemical transportation method and the like.

The "crystallization method from a melt" is, for example, a normal freezing method (a pulling method, a temperature gradient method, a Bridgman method), a zone melting method (a zone leveling method, a floating zone method), a special growth method (a VLS method, a liquid phase epitaxy method) and the like.

Preferable examples of the crystallization method include a method comprising dissolving compound (I) in a suitable solvent (e.g., alcohols such as methanol, ethanol etc.) at 20° C. to 120° C., and cooling the obtained solution to a temperature (e.g., 0 to 50° C., preferably 0 to 20° C.) not higher than the dissolution temperature, and the like.

The thus-obtained crystals of the present invention can be isolated, for example, by filtration and the like.

An analysis method of the obtained crystal is generally a method of crystal analysis by powder X-ray diffraction. As a method of determining crystal orientation, a mechanical method or an optical method and the like can also be used.

The crystal of compound (I) obtained by the above-mentioned production method may have high purity, high quality, and low hygroscopicity, may not be denatured even after a long-term preservation under general conditions, and may be expected to be extremely superior in the stability. In addition, it may be also superior in the biological properties (e.g., pharmacokinetics (absorption, distribution, metabolism, excretion), efficacy expression etc.) and may be extremely useful as a medicament.

The prodrug of compound (I) means a compound which is converted to compound (I) with a reaction due to an enzyme, gastric acid and the like under the physiological condition in the living body, that is, a compound which is converted to compound (I) by enzymatic oxidation, reduction, hydrolysis and the like; a compound which is converted to compound (I) by hydrolysis and the like due to gastric acid, and the like. Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, tert-butylation, and the like); a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation, and the like); a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, and the like) and the like. These compounds can be produced from compound (I) according to a method known per se. The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I) and the prodrug of compound (I) are sometimes collectively abbreviated as "the compound of the present invention".

Compound (I) may be a hydrate, a non-hydrate, a solvate or a non-solvate.

In addition, compound (I) may be a compound labeled or substituted with an isotope (e.g., $^2$H, $^3$H, $^{11}$C, $^{14}$C, $^{18}$F, $^{35}$S, $^{125}$I and the like) and the like. The compound labeled or substituted with an isotope may be used, for example, as a tracer (PET tracer) used in positron emission tomography (PET), and useful in the field of medical diagnosis and the like.

Compound (I) also encompasses a deuterium conversion form wherein $^1$H is converted to $^2$H(D)

Compound (I) also encompasses a tautomer thereof.

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability etc.). The cocrystal or a salt thereof can be produced according to a cocrystallization a method known per se.

Compound (I) may also be used as a PET tracer.

Since the compound of the present invention has a superior HDAC inhibitory action, preferably class II HDAC inhibitory action, more preferably HDAC6 inhibitory action, it may be also useful as safe medicaments based on such action.

For example, the medicament of the present invention containing the compound of the present invention may be expected to show low toxicity (e.g., acute toxicity, chronic toxicity, genetic toxicity, reproductive toxicity, cardiotoxicity, carcinogenicity), and used for a mammal (e.g., mouse, rat, hamster, rabbit, cat, dog, bovine, sheep, monkey, human etc.) as a prophylactic or therapeutic agent for HDAC-associated diseases, preferably class II HDAC-associated diseases, more preferably HDAC6-associated diseases, more specifically, the diseases described in (1)-(7) below.

(1) inflammatory diseases (e.g., acute pancreatitis, chronic pancreatitis, asthma, adult respiratory distress syndrome, chronic obstructive pulmonary disease (COPD), idiopathic pulmonary fibrosis, inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, meningitis, spondylitis, arthritis, dermatitis, chronic pneumonia, bronchitis, pulmonary infarction, silicosis, pulmonary sarcoidosis, diabetic nephropathy, uveitis, suppurative hidradenitis etc.), (2) autoimmune diseases (e.g., rheumatoid arthritis, psoriasis, inflammatory bowel disease (e.g., Crohn's disease, ulcerative colitis etc.), Sjogren's syndrome, Behcet's disease, multiple sclerosis, systemic lupus erythematosus, lupus nephritis, discoid lupus erythematosus, Castleman's disease, ankylopoietic spondylarthritis, polymyositis, dermatomyositis (DM), polyarteritis *nodosa* (PN), mixed connective tissue disease (MCTD), scleroderma, *profundus* lupus erythematosus, chronic thyroiditis, Graves' disease, autoimmune gastritis, type I diabetes, autoimmune hemolytic anemia, autoimmune neutropenia, thrombocytopenia, atopic dermatitis, pemphigus, chronic active hepatitis, myasthenia gravis, graft versus host disease, Addison's disease, abnormal immunoresponse, arthritis, dermatitis, radiodermatitis, primary biliary cirrhosis etc.), (3) osteoarticular degenerative disease (e.g., rheumatoid arthritis, osteoporosis, osteoarthritis etc.), (4) neoplastic diseases [e.g., malignant tumor, angiogenesis glaucoma, infantile hemangioma, multiple myeloma, chronic sarcoma, metastasis melanoma, Kaposi's sacroma, vascular proliferation, cachexia, metastasis of the breast cancer, cancer (e.g., colorectal cancer (e.g., familial colorectal cancer, hereditary nonpolyposis colorectal cancer, gastrointestinal stromal tumor etc.), lung cancer (e.g., non-small cell lung cancer, small cell lung cancer, malignant mesothelioma etc.), mesothelioma, pancreatic cancer (e.g., pancreatic duct cancer etc.), gastric cancer (e.g., papillary adenocarcinoma, mucinous adenocarcinoma, adenosquamous carcinoma, etc.), breast cancer (e.g., invasive ductal carcinoma, ductal carcinoma in situ, inflammatory breast cancer etc.), ovarian cancer (e.g., ovarian epithelial carcinoma, extragonadal germ cell tumor, ovarian germ cell tumor, ovarian low malignant potential tumor etc.), prostate cancer (e.g., hormone-dependent prostate cancer, non-hormone dependent prostate cancer etc.), liver cancer (e.g., primary liver cancer, extrahepatic bile duct cancer etc.), thyroid cancer (e.g., medullary thyroid carcinoma etc.), kidney cancer (e.g., renal cell carcinoma, transitional cell carcinoma in kidney and urinary duct etc.), uterine cancer, brain tumor (e.g., pineal astrocytoma, pilocytic astrocytoma, diffuse astrocytoma, anaplastic astrocytoma etc.), melanoma, sarcoma, urinary bladder cancer, hematologic cancer and the like including multiple myeloma, hypophyseal adenoma, glioma, acoustic neurinoma, retinoblastoma, pharyngeal cancer, laryngeal cancer, cancer of the tongue, thymoma, esophagus cancer, duodenal cancer, colorectal cancer, rectal cancer, hepatoma, pancreatic endocrine tumor, bile duct cancer, gallbladder cancer, penile cancer, urinary duct cancer, testis tumor, vulvar cancer, cervix cancer, endometrial cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, adult T cell leukemia, chronic bone marrow proliferative disease, pancreatic endocrine tumor fibrous histiocytoma, leiomyosarcoma, rhabdomyosarcoma, cancer of unknown primary), leukemia (e.g., acute leukemia (e.g., acute lymphatic leukemia, acute myelocytic leukemia etc.), chronic leukemia (e.g., chronic lymphatic leukemia, chronic myelocytic leukemia etc.), myelodysplastic syndrome), uterine sarcoma (e.g., mixed mesodermal tumor, uterine leiomyosarcoma, endometrial stromal tumor etc.), myelofibrosis etc.], (5) neurodegenerative diseases and/or central diseases (i) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, autistic spectrum syndrome, fragile X syndrome, Rett syndrome, adjustment disorder, bipolar disorder, neurosis, schizophrenia (e.g., positive symptom, negative symptom, cognitive symptom), cognitive dysfunction associated with schizophrenia, hronic fatigue syndrome, anxiety neurosis, compulsive neurosis, epilepsy, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression, hreditary sastic praplegia], (ii) neurodegenerative diseases [e.g., Alzheimer's disease, dementia of Alzheimer type, Alzheimer-type senile dementia, Parkinson's disease, muscular dystrophy, Parkinson's disease associated with dementia, Huntington's disease, multi-infarct dementia, frontotemporal lobar degeneration, frontotemporal dementia, Parkinson's type dementia, progressive supranuclear palsy, Pick's syndrome, Niemann-Pick syndrome, corticobasal degeneration, Down's disease, vascular dementia, postencephalitic parkinsonism, Lewy body dementia, Rubinstein-Taybi syndrome, Charcot-Marie-Tooth disease, HIV dementia, amyotrophic lateral sclerosis (ALS), motor neurogenesis disease (MND), Creutzfeldt-Jakob disease or prion disease, cerebral palsy, multiple sclerosis, Riley-Day syndrome], (iii) age-related cognition memory disorders [e.g., age-related memory disorders, senile dementia], (iv) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (v) respiratory depression caused by anesthetics, traumatic disease, or neurodegenerative disease and the like, (vi) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, peptic ulcer, diarrhea, constipation, postoperative ileus, (vii) pain, (6) chronic heart failure or acute heart failure, acute decompensated heart failure, ischemic heart disease, cardiomyopathy, myocarditis, valvular disease, (7) peripheral neuropathy and the like.

The medicament of the present invention may be preferably used as an agent for the prophylaxis or treatment of autoimmune disease, inflammatory disease, osteoarticular degenerative disease, neurodegenerative disease, central disease, neoplastic disease, or peripheral neuropathy, more preferably inflammatory bowel disease (inflammatory bowel disease) (preferably Crohn's disease or ulcerative colitis, systemic lupus erythematosus, rheumatoid arthritis, psoriasis, Sjogren's syndrome, Behcet's syndrome, multiple sclerosis, graft versus host disease, Alzheimer's disease (preferably dementia of Alzheimer type), schizophrenia, dementia with Lewy Bodies, frontotemporal lobar degeneration (preferably frontotemporal dementia, progressive supranuclea palsy, corticobasal degeneration), Parkinson's disease, Huntington's disease, Rubinstein-Taybi Syndrome, muscular dystrophy, Rett Syndrome, amyotrophic lateral sclerosis, Charcot-Marie-Tooth disease, depression, hreditary sastic praplegia, Riley-Day syndrome, Castleman's disease, leukemia, uterine leiomyosarcoma, prostate cancer, colon cancer, multiple myeloma, cachexia or myelofibrosis, chronic heart failure or acute heart failure, acute decompensated heart failure, ischemic heart disease, cardiomyopathy, myocarditis, valvular disease, peripheral neuropathy and the like.

The medicament of the present invention may be more preferably used as an agent for the prophylaxis or treatment of neurodegenerative diseases such as Alzheimer's disease, frontotemporal lobar degeneration, progressive supranuclea palsy and the like, Charcot-Marie-Tooth disease and the like.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

A medicament containing the compound of the present invention may be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal etc.), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, cream, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor and direct administration to the lesion).

The content of the compound of the present invention in the medicament of the present invention is about 0.01 to 100% by weight of the entire medicament. The dose may vary depending on administration subject, administration route, disease and the like. For example, for oral administration to patients (body weight about 60 kg) with psoriasis, rheumatoid arthritis, inflammatory bowel disease, Sjogren's syndrome, Behcet's disease, multiple sclerosis or systemic lupus erythematosus, about 0.01 mg/kg body weight-about 500 mg/kg body weight, preferably about 0.1 mg/kg body weight-about 50 mg/kg body weight, more preferably about 1 mg/kg body weight-about 30 mg/kg body weight of an active ingredient (compound (I)) may be administered once to several portions per day.

The pharmaceutically acceptable carrier, which may be used for the production of the medicament of the present invention, may be exemplified by various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbing agent, wetting agent and the like can be also used as appropriate in an appropriate amount.

The dose of the pharmaceutical composition of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human etc.), and administration object. For example, for application by parenteral administration, about 0.1 to about 100 mg of compound (I) needs to be released from the administered preparation per 1 week.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

For the prophylaxis or treatment of various diseases, the compound of the present invention may also be used together with other medicaments. In the following, a medicament to be used when the compound of the present invention is used together with other drug is referred to as "the combination agent of the present invention".

For example, when the compound of the present invention is used as a HDAC inhibitor, preferably a class II HDAC inhibitor, more preferably a HDAC6 inhibitor, it may be used together with the following drugs.

(1) Non-Steroidal Anti-Inflammatory Drug (NSAIDs)
(i) Classical NSAIDs
alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, ketophenylbutazone, loxoprofen sodium, phenylbutazone, indomethacin, ibuprofen, ketoprofen, naproxen, oxaprozin, flurbiprofen, fenbufen, pranoprofen, floctafenine, piroxicam, tenoxicam, epirizole, tiaramide hydrochloride, zaltoprofen, gabexate mesylate, camostat mesylate, ulinastatin, colchicine, probenecid, sulfinpyrazone, bucolome, benzbromarone, allopurinol, sodium aurothiomalate, hyaluronate sodium, sodium salicylate, salicylic acid, atropine, scopolamine, levorphanol, oxymorphone or a salt thereof and the like.
(ii) cyclooxygenase inhibitor (COX-1 selective inhibitor, COX-2 selective inhibitor etc.)
salicylic acid derivatives (e.g., celecoxib, aspirin), etoricoxib, valdecoxib, diclofenac sodium, indomethacin, loxoprofen and the like.
(iii) nitric oxide-releasing NSAIDs.
(iv) JAK inhibitor
tofacitinib, ruxolitinib and the like.
(2) Disease-Modifying Anti-Rheumatic Drugs (DMARDs)
(i) Gold preparation
auranofin, sodium aurothiomalate and the like.
(ii) penicillamine
D-penicillamine and the like.
(iii) aminosalicylic acid preparation
sulfasalazine, mesalazine, olsalazine, balsalazide and the like.

(iv) antimalarial drug
chloroquine and the like.
(v) pyrimidine synthesis inhibitor
leflunomide and the like.
(vi) prograf
(3) Anti-Cytokine Drug
(I) Protein Drug
(i) TNF inhibitor
etanercept, infliximab, adalimumab, certolizumab pegol, golimumab, PASSTNF-α, soluble TNF-α receptor, TNF-α binding protein, anti-TNF-α antibody and the like.
(ii) interleukin-1 inhibitor
anakinra (interleukin-1 receptor antagonist), soluble interleukin-1 receptor and the like.
(iii) interleukin-6 inhibitor
tocilizumab (anti-interleukin-6 receptor antibody), anti-interleukin-6 antibody and the like.
(iv) interleukin-10 drug
interleukin-10 and the like.
(v) interleukin-12/23 inhibitor
ustekinumab, briakinumab (anti-interleukin-12/23 antibody) and the like.
(II) Non-Protein Drug
(i) MAPK inhibitor
BMS-582949 and the like.
(ii) gene modulator
inhibitor of molecule involved in signal transduction, such as NF-κ, NF-κB, IKK-1, IKK-2, AP-1 and the like, and the like.
(iii) cytokine production inhibitor
iguratimod, tetomilast and the like.
(iv) TNF-α converting enzyme inhibitor
(v) interleukin-1β converting enzyme inhibitor
VX-765 and the like.
(vi) interleukin-6 antagonist
HMPL-004 and the like.
(vii) interleukin-8 inhibitor
IL-8 antagonist, CXCR1 & CXCR2 antagonist, reparixin and the like.
(viii) chemokine antagonist
CCR9 antagonist (CCX-282, CCX-025), MCP-1 antagonist and the like.
(ix) interleukin-2 receptor antagonist
Denileukin diftitox and the like.
(x) therapeutic vaccines
TNF-α vaccine and the like.
(xi) gene therapy drug
gene therapy drugs aiming at promoting the expression of gene having an anti-inflammatory action such as interleukin-4, interleukin-10, soluble interleukin-1 receptor, soluble TNF-α receptor and the like.
(xii) antisense compound
ISIS 104838 and the like.
(4) Integrin Inhibitor
natalizumab, vedolizumab, AJM300, TRK-170, E-6007 and the like.
(5) Immunomodulator (Immunosuppressant)
methotrexate, cyclophosphamide, MX-68, atiprimod dihydrochloride, BMS-188667, CKD-461, rimexolone, cyclosporine, tacrolimus, gusperimus, azathioprine, anti-lymphocyte serum, freeze-dried sulfonated normal immunoglobulin, erythropoietin, colony stimulating factor, interleukin, interferon and the like.
(6) Steroid
dexamethasone, hexestrol, methimazole, betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol, paramethasone acetate, fludrocortisone acetate, clobetasol propionate, diflorasone acetate, dexamethasone propionate, difluprednate, betamethasone dipropionate, budesonide, diflucortolone valerate, amcinonide, halcinonide, mometasone furoate, hydrocortisone butyrate propionate, flumetasone pivalate, clobetasone butyrate, dexametasone acetate and the like.

(7) Angiotensin Converting Enzyme Inhibitor
  enalapril, captopril, ramipril, lisinopril, cilazapril, perindopril and the like.

(8) Angiotensin II Receptor Antagonist
  candesartan, candesartan cilexetil, azilsartan, azilsartan medoxomil, valsartan, irbesartan, olmesartan, eprosartan and the like.

(9) Diuretic Drug
  hydrochlorothiazide, spironolactone, furosemide, indapamide, bendrofluazide, cyclopenthiazide and the like.

(10) Cardiotonic Drug
  digoxin, dobutamine and the like.

(11) β Receptor Antagonist
  carvedilol, metoprolol, atenolol and the like.

(12) Ca Sensitizer
  MCC-135 and the like.

(13) Ca Channel Antagonist
  nifedipine, diltiazem, verapamil, lomerizine hydrochloride, amlodipine besylate and the like.

(14) Anti-Platelet Drug, Anticoagulator
  heparin, aspirin, warfarin, dabigatran, rivaroxaban, apixaban, edoxaban and the like.

(15) HMG-CoA Reductase Inhibitor
  atorvastatin, simvastatin and the like.

(16) Vasodilator
  relaxin and the like.

(17) Angiotensin Receptor Neprilysin Inhibitor
  LCZ696 and the like.

(18) Heart Rate-Lowering Drug
  ivabradine and the like.

(19) Hypouricemic Drug
  probenecid, allopurinol, febuxostat and the like.

(20) Anti-Aldosterone Drug
  spironolactone, eplerenone and the like.

(21) Renin Inhibitor
  aliskiren and the like.

(22) α-Blocker
  doxazosin and the like.

(23) Oraladsorptive Agent
  kremezin and the like.

(24) Therapeutic Drug For Hyperkalemia
  *calcicol* and the like.

(25) Therapeutic Drug For Hyperphosphatemia
  sevelamer, lanthanum carbonate and the like.

(26) Metabolic Acidosis Improving Drug
  sodium bicarbonate and the like.

(27) Activity Type Vitamin

(28) calcium receptor agonists
  cinacalcet and the like.

(29) Intravenous Cardiotonic Drug
  h-ANP and the like.

(30) Contraceptive
(i) sex hormone or derivatives thereof
  gestagen or a derivative thereof (progesterone, 17α-hydroxy progesterone, medroxyprogesterone, medroxyprogesterone acetate, norethisterone, norethisterone enanthate, norethindrone, norethindrone acetate, norethynodrel, levonorgestrel, norgestrel, ethynodiol diacetate, desogestrel, norgestimate, gestodene, progestin, etonogestrel, drospirenone, dienogest, trimegestone, nestorone, chlormadinone acetate, mifepristone, nomegestrol acetate, Org-30659, TX-525, EMM-310525) or a combination agent of a gestagen or a derivative thereof and an estrogen or a derivative thereof (estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethinylestradiol, mestranol) and the like.

(ii) antiestrogen
  ormeloxifene, mifepristone, Org-33628 and the like.

(iii) spermatocide
  ushercell and the like.

(31) others
(i) T cell inhibitors
(ii) inosine monophosphate dehydrogenase (IMPDH) inhibitor
  mycophenolate mofetil and the like.
(iii) adhesion molecule inhibitor
  ISIS-2302, selectin inhibitor, ELAM-1, VCAM-1, ICAM-1 and the like.
(iv) thalidomide
(v) cathepsin inhibitor
(vi) matrix metalloprotease (MMPs) inhibitor
  V-85546 and the like.
(vii) glucose-6-phosphate dehydrogenase inhibitor
(viii) Dihydroorotate dehydrogenase (DHODH) inhibitor
(ix) phosphodiesterase IV (PDE IV) inhibitor
  roflumilast, CG-1088 and the like.
(x) phospholipase A$_2$ inhibitor
(xi) iNOS inhibitor
  VAS-203 and the like.
(xii) microtubule stimulating drug
  paclitaxel, docetaxel hydrate and the like.
(xiii) microtuble inhibitor
  reumacon and the like.
(xiv) MHC class II antagonist
(xv) prostacyclin agonist
  iloprost and the like.
(xvi) CD4 antagonist
  zanolimumab and the like.
(xvii) CD23 antagonist
(xviii) LTB4 receptor antagonist
  DW-1305 and the like.
(xix) 5-lipoxygenase inhibitor
  zileuton and the like.
(xx) acetylcholinesterase inhibitor
  donepezil hydrochloride, galanthamine, rivastigmine, neostigmine bromide, pyridostigmine bromide, ambenonium chloride, edrophonium chloride and the like.
(xxi) tyrosine kinase inhibitor
  Tyk2 inhibitor (WO2010142752) and the like.
(xxii) cathepsin B inhibitor
(xxiii) adenosine deaminase inhibitor
  pentostatin and the like.
(xxiv) osteogenesis stimulator
(xxv) dipeptidylpeptidase inhibitor
(xxvi) collagen agonist
(xxvii) capsaicin cream
(xxviii) hyaluronic acid derivative
  synvisc (hylan G-F 20), orthovisc and the like.
(xxix) glucosamine sulfate
(xxx) amiprilose
(xxxi) CD-20 inhibitor
  rituximab, ibritumomab, tositumomab, ofatumumab and the like.

(xxxii) BAFF inhibitor
belimumab, tabalumab, atacicept, A-623 and the like.
(xxxiii) CD52 inhibitor
alemtuzumab and the like.
(xxxiv) IL-17 inhibitor
secukinumab (AIN-457), LY-2439821, AMG827 and the like.
(xxxv) PDE4 inhibitor
Roflumilast, Apremilast and the like.
(xxxvi) therapeutic drug for Alzheimer's disease
memantine and the like.
(xxxvii) therapeutic drug for Parkinson's disease
levodopa, droxidopa, amantadine hydrochloride, bromocriptine mesylate, trihexyphenidyl hydrochloride, selegiline hydrochloride and the like.
(xxxviii) ALS therapeutic drug
riluzole, neurotrophic factor and the like.
(xxxix) therapeutic drug for insomnia
etizolam, zopiclone, triazolam, zolpidem, ramelteon, indiplon and the like.
(xxxx) anti-ADHD drug
methylphenidate hydrochloride, methamphetamine hydrochloride and the like.
(xxxxi) immune checkpoint inhibitor
anti-CTLA-4 antibody (ipilimumab, tremelimumab etc.), anti-PD-1 antibody (nivolumab, pembrolizumab, AMP-224, pidilizumab etc.), anti-PD-L1 antibody (BMS-936559, atezolizumab, MEDI4736, avelumab etc.)
(xxxxii) proteasome inhibitor
bortezomib, ixazomib and the like.

Other concomitant drugs besides the above-mentioned include, for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug and therapeutic drug for arteriosclerosis, muscle relaxant, antiepileptic drug, antidepressant and therapeutic drug for manic psychosis, antiallergic drug, cardiac stimulants, therapeutic drug for arrhythmia, vasodilator, vasoconstrictor, hypotensive diuretic, therapeutic drug for diabetes, antiobesity drug, antinarcotic, vitamin, vitamin derivative, antiasthmatic, therapeutic agent for pollakisuria/anischuria, antipruritic drug, therapeutic agent for atopic dermatitis, therapeutic agent for allergic rhinitis, hypertensor, narcotic analgesic, non-narcotic analgesic, therapeutic drug for ocular disease, therapeutic drug for nausea and vomiting, therapeutic drug for coprostasis and diarrhea, therapeutic drug for osteoporosis, therapeutic drug for thyroid dysfunction, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.
(1) Antibacterial Agent
(i) sulfa drug
sulfamethizole, sulfisoxazole, sulfamonomethoxine, salazosulfapyridine, silver sulfadiazine and the like.
(ii) quinolone antibacterial agent
nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin and the like.
(iii) antiphthisic
isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.
(iv) antiacidfast bacterium drug
diaphenylsulfone, rifampicin and the like.
(v) antiviral drug
idoxuridine, acyclovir, vidarabine, gancyclovir, foscarnet sodium, influenza HA vaccine, zanamivir, oseltamivir phosphate, amantadine hydrochloride and the like.
(vi) anti-HIV agent
zidovudine, didanosine, zalcitabine, indinavir sulfate ethanolate, ritonavir, lamivudine, abacavir sulfate, nevirapine, efavirenz, saquinavir mesylate, nelfinavir mesylate, amprenavir and the like.
(vii) antispirochetele
(viii) antibiotic
tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt thereof, griseofulvin, lankacidin-group [Journal of Antibiotics (J. Antibiotics), 38, 877-885 (1985)], azole compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone, fluconazole, itraconazole and the like], ceftriaxone sodium, vancomycin hydrochloride, benzylpenicillin potassium, chloramphenicol, amoxicillin, amoxicillin-clavulanate potassium, sulfamethoxazole-trimethoprim, erythromycin, norfloxacin, ciprofloxacin hydrochloride, imipenem-cilastatin sodium, ampicillin-cloxacillin, cefoxitin sodium, cefotetan sodium, clindamycin hydrochlorid, clarithromycin, netilmicin sulfate, sulbenicillin sodium, ampicillin sodium-sulbactam sodium, cefuroxime sodium, aztreonam and the like.
(2) antifungal agent
(i) polyethylene antibiotic (e.g., amphotericin B, nystatin, trichomycin)
(ii) griseofulvin, pyrrolnitrin and the like
(iii) cytosine metabolism antagonist (e.g., flucytosine)
(iv) imidazole derivative (e.g., econazole, clotrimazole, miconazole nitrate, bifonazole, croconazole)
(v) triazole derivative (e.g., fluconazole, itraconazole)
(vi) thiocarbamic acid derivative (e.g., trinaphthol) and the like.
(3) antiprotozoal agent
metronidazole, tinidazole, diethylcarbamazine citrate, quinine hydrochloride, quinine sulfate and the like.
(4) antitussive and expectorant drug
ephedrine hydrochloride, noscapine hydrochloride, codeine phosphate, dihydrocodeine phosphate, isoproterenol hydrochloride, methylephedrine hydrochloride, alloclamide, chlophedianol, picoperidamine, cloperastine, protokylol, isoproterenol, salbutamol, terbutaline, oxymetebanol, morphine hydrochloride, dextromethorphan hydrobromide, oxycodone hydrochloride, dimemorfan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(5) sedative chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(6) Anesthetic (6-1) Local Anesthetic cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like.

(6-2) General Anesthetic (i) inhalation anesthetic (e.g., ether, halothane, nitrous oxide, isoflurane, enflurane), (ii) intravenous anesthetic (e.g., ketamine hydrochloride, droperidol, thiopental sodium, thiamylal sodium, pentobarbital) and the like.

(7) Antiulcer Drug histidine hydrochloride, lansoprazole, metoclopramide, pirenzepine, cimetidine, ranitidine, famotidine, urogastrone, oxethazaine, proglumide, omeprazole, sucralfate, sulpiride, cetraxate, gefarnate, aldioxa, teprenone, prostaglandin, propantheline bromide, misoprostol, ornoprostil and the like.

(8) Antiarrhythmic Agent (i) sodium channel blocker (e.g., quinidine, procainamide, disopyramide, ajmaline, lidocaine, mexiletine, phenytoin, flecainide acetate, propafenone hydrochloride), (ii) β-blocker (e.g., propranolol, alprenolol, bufetolol hydrochloride, oxprenolol, atenolol, acebutolol, metoprolol, bisoprolol, pindolol, carteolol, arotinolol hydrochloride), (iii) potassium channel blocker (e.g., amiodarone, sotalol hydrochloride), (iv) calcium channel blocker (e.g., verapamil, diltiazem), (v) nitrate (e.g., nitroglycerin, isosorbide dinitrate) and the like.

(9) Hypotensive Diuretic Drug hexamethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline, carperitide, torasemide and the like.

(10) Anticoagulant heparin sodium, sodium citrate, activated protein C, tissue factor pathway inhibitor, antithrombin III, dalteparin sodium, warfarin potassium, argatroban, gabexate, ozagrel sodium, ethyl icosapentate, beraprost sodium, alprostadil, ticlopidine hydrochloride, pentoxifylline, dipyridamole, tisokinase, urokinase, streptokinase, alteplase and the like.

(11) Tranquilizer diazepam, lorazepam, clorazepate dipotassium, oxazepam, chlordiazepoxide, medazepam, oxazolam, cloxazolam, clotiazepam, bromazepam, etizolam, fludiazepam, hydroxyzine, nitrazepam, triazolam, alprazolam and the like.

(12) Antipsychotic chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, clozapine, trifluoperazine dihydrochloride, fluphenazine hydrochloride, olanzapine, quetiapine fumarate, risperidone, aripiprazole, bromperidol, spiperone, reserpine, clocapramine hydrochloride, sulpiride, zotepine, tiotixene and the like.

(13) Antitumor Drug (i) cytotoxic cancer drug

6-O—(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, peplomycin sulfate, vincristine sulfate, vinblastine sulfate, irinotecan hydrochloride, cyclophosphamide, melphalan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate, ifosfamide, busulfan, ranimustine, dacarbazine, nedaplatin, carboplatin, gemcitabine hydrochloride, fludarabine hydrochloride, vinorelbine ditartarate, etoposide, L-asparaginase and the like.

(ii) therapeutic drug for hormone tamoxifen citrate, toremifene citrate, fadrozole hydrochloride hydrate, flutamide, bicalutamide and the like.

(14) Hypolipidemic Drug And Therapeutic Drug For Arteriosclerosis clofibrate, ethyl 2-chloro-3-[4-(2-methyl-2-phenylpropoxy)phenyl]propionate [Chemical and Pharmaceutical Bulletin], 1990, 38, 2792-2796], pravastatin, simvastatin, probucol, bezafibrate, clinofibrate, nicomol, cholestyramine, dextran sulfate sodium, fluvastatin sodium, cerivastatin sodium, colestimide, nicotinic acid, niceritrol, clofibrate, fenofibrate and the like.

(15) Muscle Relaxant pridinol, tubocurarine, pancuronium, tolperisone hydrochloride, chlorphenesin carbamate, baclofen, chlormezanone, mephenesin, chlorzoxazone, eperisone, tizanidine and the like.

(16) Antiepileptic Drug phenytoin, ethosuximide, acetazolamide, chlordiazepoxide, trimethadione, carbamazepine, phenobarbital, primidone, sulthiame, sodium valproate, clonazepam, diazepam, nitrazepam and the like.

(17) Antidepressant And Therapeutic Drug For Manic Psychosis imipramine, clomipramine, desipramine hydrochloride, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride, paroxetine hydrochloride hydrate, lithium carbonate, selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenalin reuptake inhibitor (venlafaxine hydrochloride, duloxetine hydrochloride, venlafaxine hydrochloride etc.), noradrenalin reuptake inhibitor (reboxetine mesylate etc.), noradrenalin-dopamine reuptake inhibitor (bupropion hydrochloride etc.), mirtazapine, trazodone hydrochloride, nefazodone hydrochloride, bupropion hydrochloride, setiptiline maleate, 5-HT1A agonist (buspirone hydrochloride, tandospirone citrate, osemozotan hydrochloride) and the like.

(18) Antiallergic Drug diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like.

(19) Cardiac Stimulants trans-π-oxocamphor, terephyllol, aminophylline, etilefrine, dopamine, dobutamine, denopamine, amrinone, pimobendan, ubidecarenone, digitoxin, digoxin, methyldigoxin, lanatoside C, G-strophanthin, milrinone, vesnarinone, docarpamine and the like.

(20) Vasodilator oxyfedrine, diltiazem, tolazoline, hexobendine, bamethan, clonidine, methyldopa, guanabenz, hydralazine hydrochloride and the like.

(21) Vasoconstrictor dopamine, dobutamine, denopamine and the like.

(22) Hypotensive Diuretic hexamethonium bromide, pentolinium, mecamylamine, ecarazine, clonidine, diltiazem, nifedipine and the like.

(23) Therapeutic Drug For Diabetes tolbutamide, chlorpropamide, acetohexamide, glibenclamide, tolazamide, acarbose, epalrestat, troglitazone, glucagon, glymidine, glipizide, phenformin, buformin, metformin, gliclazide, nateglinide, voglibose, insulin and the like.

(24) Antiobesity Drugs glucagon-like peptide-1 (GLP-1) preparation and the like.

(25) Antinarcotic levallorphan, nalorphine, naloxone or a salt thereof and the like.

(26) Liposoluble Vitamins (i) vitamin A: vitamin $A_1$, vitamin $A_2$ and retinol palmitate
(ii) vitamin D: alfalcalcidol, calcitriol, vitamin $D_1$, $D_2$, $D3$, $D_4$ and $D_5$
(iii) vitamin E: α-tocopherol, β-tocopherol, γ-tocopherol, δ-tocopherol, dl-α-tocopherol nicotinate
(iv) vitamin K: menatetrenone, vitamin $K_1$, $K_2$, $K_3$ and $K_4$
(v) folic acid (vitamin M) and the like.

(27) Vitamin Derivative various derivatives of vitamins, for example, vitamin $D_3$ derivatives such as 5,6-trans-cholecalciferol, 2,5-hydroxycholecalciferol, 1-α-hydroxycholecalciferol and the like, vitamin $D_2$ derivatives such as 5,6-trans-ergocalciferol and the like, and the like.

(28) Antiasthmatic isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlkast hydrate, seratrodast, dexamethasone, prednisolone, hydrocortisone, hydrocortisone sodium succinate, beclometasone dipropionate, epinephrine, fluticasone propionate, zafirlukast and the like.

(29) Therapeutic Agent For Pollakisuria/Anischuria flavoxate hydrochloride and the like.

(30) Therapeutic Agent For Atopic Dermatitis sodium cromoglicate and the like.

(31) Therapeutic Agent For Allergic Rhinitis sodium cromoglicate, chlorpheniramine maleate, alimemazine tartrate, clemastine fumarate, homochlorcyclizine hydrochloride, fexofenadine, mequitazine and the like.

(32) Hypertensor dopamine, dobutamine, denopamine, digitoxin, digoxin, methyldigoxin, lanatoside C, G-strophanthin and the like.

(33) Narcotic Analgesic morphine hydrochloride, morphine sulfate sustained tablet, morphine-atropine, pethidine hydrochloride, fentanyl citrate and the like.

(34) Non-Narcotic Analgesic pentazocine, buprenorphine hydrochloride and the like.

(35) Therapeutic Drug For Ocular Disease pilocarpine hydrochloride, distigmine bromide, ecothiopate iodide, timolol maleate, carteolol hydrochloride, phenylephrine hydrochloride, epinephrine, dorzolamide, isopropyl unoprostone, latanoprost and the like.

(36) Therapeutic Drug For Nausea And Vomiting domperidone, prochlorperazine, chlorpromazine, promethazine hydrochloride, diphenhydramine hydrochloride-diprophylline combination drug, scopolamine butylbromide, granisetron hydrochloride, ondansetron hydrochloride, azasetron hydrochloride, ramosetron hydrochloride and the like.

(37) Therapeutic Drug For Coprostasis And Diarrhea carmellose sodium, lactulose, D-sorbitol, magnesium citriate, magnesium oxide, *senna* extract, sennoside, picosulfate sodium, bisacodyl, cisapride, itopride hydrochloride, loperamide hydrochloride and the like.

(38) Therapeutic Drug For Osteoporosis alfacalcidol, calcitriol, estriol, elcatonin, salmon calcitonin, etidronate disodium, pamidronate disodium, alendronate sodium hydrate and the like.

(39) Therapeutic Drug For Thyroid Dysfunction liothyronine sodium, propylthiouracil, thiamazole, potassium iodide, sodium iodide, levothyroxine sodium and the like.

(40) Others diacerein, megestrol acetate, nicergoline, prostaglandins.

(41) Therapeutic Drug For Central Disease And The Like benzodiazepine (chlordiazepoxide, diazepam, clorazepate dipotassium, lorazepam, clonazepam, alprazolam etc.), L-type calcium channel inhibitor (pregabalin etc.), tricyclic or tetracyclic antidepressant drug (imipramine hydrochloride, amitriptyline hydrochloride, desipramine hydrochloride, clomipramine hydrochloride, etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenalin reuptake inhibitor (venlafaxine hydrochloride, duloxetine hydrochloride, venlafaxine hydrochloride etc.), noradrenalin reuptake inhibitor (reboxetine mesylate etc.), noradrenalin-dopamine reuptake inhibitor (bupropion hydrochloride etc.), mirtazapine, trazodone hydrochloride, nefazodone hydrochloride, bupropion hydrochloride, setiptiline maleate, 5-HT1A agonist (buspirone hydrochloride, tandospirone citrate, osemozotan hydrochloride), 5-$HT_3$ antagonist (cyamemazine etc.), heart non-selective β inhibitor (propranolol hydrochloride, oxiprenolol hydrochloride etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), drug that acts on metabotropic glutamate receptor, CCK antagonist, 33 adrenaline antagonist (amibegron hydrochloride etc.), GAT-1 inhibitor (tiagabine hydrochloride etc.), N-type calcium channel inhibitor, type II carbonic anhydrase inhibitor, NMDA glycine site agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioids antagonist, opioids agonist, uridine, nicotinic acid receptor agonists, thyroid hormone (T3, T4), TSH, TRH, MAO inhibitor (acidphenelzine sulfate, tranylcypromine sulfate, e moclobemid etc.), 5-HT$_{2A}$ antagonist, 5-HT$_{2A}$ inverse agonist, COMT inhibitor (entacapone, etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for convulsion, therapeutic drug forfibromyalgia, therapeutic drug for headache, therapeutic drug for insomnia (etizolam, zopiclone, triazolam, xolpidem, rameleon, indiplon etc.), therapeutic drug for quitting smoking, therapeutic drug for myasthenia gravis, therapeutic drug for cerebral infarction, therapeutic drug for manic psychosis, therapeutic drug for hypersomnia, therapeutic drug for pain, therapeutic drug for dysthymia, therapeutic drug for dysautonomia, therapeutic drug for male and female sexual dysfunction, therapeutic drug for migraine, therapeutic drug for pathological gambling, therapeutic drug for restless legs syndrome, therapeutic drug for substance dependence, therapeutic drug for alcohol-related disease, therapeutic drug for irritable bowel syndrome, therapeutic drug for Alzheimer's disease (donepezil, galanthamine, memantine, rivastigmine, etc.), therapeutic drug for Parkinson's disease (levodopa, carbidopa, benserazide, selegiline, rasagiline, zonisamide, entacapone, amantadine, talipexole, pramipexole, ropinirole, rotigotine, apomorphine, cabergoline, pergolide, bromocriptine, istradefylline, trihexyphenidyl, biperiden, piroheptine, profenamine, promethazine, droxidopa, combination thereof etc.), therapeutic drug for Parkinson's disease associated with dementia (rivastigmine), therapeutic drug for Lewy body dementia (donepezil), therapeutic drug for ALS (riluzole, neurotrophic factor, etc.), therapeutic drug for hyperlipidemia such as cholesterol-lowering drug (statin series (pravastatin sodium, atorvastatin, simvastatin, rosuvastatin, etc.), fibrate (clofibrate etc.), squalene synthase inhibitor), therapeutic drug for abnormal behavior or dementia-related wandering (sedative drug, antianxiety drug, etc.), apoptosis inhibitor, antiobesity drug, antidiabetic drug, therapeutic drug for hypertension, therapeutic drug for hypotension, therapeutic drug for rheumatism (DMARD), anticancer drug, therapeutic drug for hypoparathyroidism (PTH), calcium receptor antagonist, sex hormone or derivative thereof (progesterone, estradiol, estradiol benzoate etc.), neuron differentiation accelerator, neurogeneration promotor, non-steroidal anti-inflammatory drug (meloxicam, tenoxicam, indomethacin, ibuprofen, celecoxib, rofecoxib, aspirin etc.), steroid (dexamethasone, cortisone acetate, etc.), anti-cytokine drug (TNF inhibitor, MAP kinase inhibitor, etc.), antibody medicament, nucleic acid or nucleic acid derivative, aptamer and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times, divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, "basic" means use of aminopropylsilane-bound silica gel. The ratios of elution solvents are volume mixing ratios, unless otherwise specified.

In Examples, the following abbreviations are used.
DMF: N,N-dimethylformamide
THF: tetrahydrofuran
EDCI: 1-ethyl-3-(3-dimethylaminopropyl)carbodiimide
DMSO: dimethyl sulfoxide
HOBt: 1-hydroxybenzotriazole
HATU: O-(7-azabenzotriazol-1-yl)-N,N,N',N',-tetramethyluroniumhexafluorophosphoric acid
TEA: triethylamine
DIEA: N,N-diisopropylethylamine
CPME: cyclopentyl methyl ether
N: normal
M: mol concentration
$^1$H NMR (protone nuclear magnetic resonance spectrum) was measured by Fourier-transform type NMR. For the analysis, ACD/SpecManager (trade name) and the like were used. Peaks with very mild protons such as a hydroxy group, an amino group and the like are not described.

The following abbreviations are used for $^1$H NMR measurement.
s: singlet, d: doublet, dd: double doublet, dt: double triplet, t: triplet, q: quartet, m: multiplet, brs: broad singlet, quin: quintet, J: coupling constant, Hz: hertz.

MS (mass spectrum) was measured by LC/MS (liquid chromatography mass spectrometer). As ionization method, ESI (Electro Spray Ionization) method or APCI (Atomospheric Pressure Chemical Ionization) method was used. The data indicates those found.

Example 1

2-phenyl-5-(5-(trifluoromethyl)-1,2,4-oxadiazol-3-yl)isoindolin-1-one

A) methyl 4-bromo-2-methylbenzoate

To a mixture of 4-bromo-2-methylbenzoic acid (25.0 g) and MeOH (200 mL) was added sulfuric acid (12.4 mL) at room temperature, and the mixture was stirred overnight at 60° C. The reaction mixture was neutralized with 1N aqueous sodium hydroxide solution at 0° C., and extracted with ethyl acetate. The extract was washed with water and saturated brine, and dried over anhydrous sodium sulfate, and the solvent was evaporated under reduced pressure to give the title compound (26.6 g).
$^1$H NMR (300 MHz, CDCl$_3$) δ 2.51 (3H, s), 3.82 (3H, s), 7.31 (1H, dd, J=8.3, 1.5 Hz), 7.35 (1H, s), 7.71 (1H, d, J=8.3 Hz).

B) methyl 4-bromo-2-(bromomethyl)benzoate

To a mixture of methyl 4-bromo-2-methylbenzoate (25.0 g) and (trifluoromethyl)benzene (400 mL) were slowly added N-bromosuccinimide (19.4 g) and 2,2'-azobis(isobutyronitrile) (1.79 g) at room temperature. The mixture was heated under reflux under nitrogen atmosphere at 80° C. for 18 hr, and cooled to room temperature. The insoluble substance was filtered off, the obtained filtrate was concentrated under reduced pressure, and the residue was purified by silica gel column chromatography (hexane/ethyl acetate) to give the title compound (33.1 g).
$^1$H NMR (300 MHz, DMSO-d$_6$) δ 3.87 (3H, s), 4.99 (2H, s), 7.65-7.73 (1H, m), 7.78-7.84 (1H, m), 7.89 (1H, d, J=2.3 Hz).

C) methyl 4-bromo-2-((phenylamino)methyl)benzoate

To a mixture of methyl 4-bromo-2-(bromomethyl)benzoate (500 mg) and THF (30 mL) were added DIEA (0.340 mL) and aniline (0.178 mL), and the mixture was stirred overnight at room temperature. To the reaction mixture were added water and ethyl acetate, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (303 mg).
$^1$H NMR (300 MHz, DMSO-d$_6$) δ 3.85 (3H, s), 4.58 (2H, d, J=6.4 Hz), 6.26 (1H, t, J=6.0 Hz), 6.47-6.56 (3H, m), 7.05 (2H, dd, J=8.3, 7.6 Hz), 7.58 (1H, dd, J=8.3, 2.3 Hz), 7.67 (1H, d, J=1.9 Hz), 7.80 (1H, d, J=8.3 Hz).

D) 5-bromo-2-phenylisoindolin-1-one

To a mixture of methyl 4-bromo-2-((phenylamino)methyl)benzoate (300 mg) and MeCN (5 mL) was added trifluoroacetic acid (0.072 mL), and the mixture was stirred at 80° C. for 30 min, and cooled to room temperature. The precipitated solid was collected by filtration, washed with ethyl acetate, and dried under reduced pressure to give the title compound (195 mg).
$^1$H NMR (300 MHz, CDCl$_3$) δ 4.85 (2H, s), 7.16-7.24 (1H, m), 7.40-7.48 (2H, m), 7.62-7.70 (2H, m), 7.79 (1H, d, J=8.3 Hz), 7.82-7.87 (2H, m).

E) 1-oxo-2-phenylisoindoline-5-carbonitrile

A mixture of 5-bromo-2-phenylisoindolin-1-one (100 mg), zinc(II) cyanide (48.9 mg), zinc powder (11.4 mg), tetrakis(triphenylphosphine)palladium(0) (201 mg) and anhydrous DMF (10 mL) was stirred under microwave irradiation at 140° C. for 30 min under nitrogen atmosphere. The reaction mixture was diluted with ethyl acetate, and filtered through Celite. The filtrate was washed with water and saturated brine, dried over anhydrous sodium sulfate, filtered, and concentrated under reduced pressure. The residue was purified by silica gel column chromatography (hexane/ethyl acetate) to give the title compound (61.1 mg).
$^1$H NMR (300 MHz, DMSO-$d_6$) δ 5.11 (2H, s), 7.18-7.27 (1H, m), 7.42-7.51 (2H, m), 7.88-8.04 (4H, m), 8.21 (1H, s).

F) (Z)—N'-hydroxy-1-oxo-2-phenylisoindoline-5-carboxyimidamide

To a mixture of 1-oxo-2-phenylisoindoline-5-carbonitrile (59.0 mg) and ethanol (8 mL) were added a mixture of hydroxylamine hydrochloride (35.0 mg) and water (1 mL) and a mixture of sodium carbonate (42.7 mg) and water (2 mL), and the mixture was refluxed for 5 hr. The obtained reaction mixture was concentrated, ethyl acetate and water were added thereto, and the mixture was extracted with ethyl acetate. The extract was washed successively with water and saturated brine, and dried over anhydrous sodium sulfate, and the solvent was evaporated under reduced pressure to give the title compound (49.5 mg).
$^1$H NMR (300 MHz, DMSO-$d_6$) δ 5.09 (2H, s), 7.16-7.25 (1H, m), 7.40-7.51 (3H, m), 7.82-7.89 (1H, m), 7.93 (3H, d, J=7.6 Hz), 8.03 (1H, d, J=7.9 Hz), 8.13 (1H, s), 8.19 (1H, brs).

G) 2-phenyl-5-(5-(trifluoromethyl)-1,2,4-oxadiazol-3-yl)isoindolin-1-one

To a mixture of (Z)—N'-hydroxy-1-oxo-2-phenylisoindoline-5-carboxyimidamide (46.0 mg) and THF (6 mL) was added trifluoroacetic anhydride (0.073 mL) at 0° C., and the mixture was stirred at 50° C. for 5 hr. The obtained reaction mixture was concentrated, ethyl acetate and water were added thereto, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (18.9 mg).
$^1$H NMR (300 MHz, DMSO-$d_6$) δ 5.16 (2H, s), 7.18-7.28 (1H, m), 7.48 (2H, t, J=7.9 Hz), 7.93 (2H, d, J=7.9 Hz), 8.02 (1H, d, J=7.9 Hz), 8.24 (1H, d, J=7.9 Hz), 8.37 (1H, s).

Example 2 tert-butyl trans-3-(1-oxo-6-(5-(trifluoromethyl)-1,2,4-oxadiazol-3-yl)-1,3-dihydro-2H-isoindol-2-yl)-4-phenylpyrrolidine-1-carboxylate A) methyl 5-bromo-2-(bromomethyl)benzoate A mixture of methyl 5-bromo-2-methylbenzoate (3.5 g), N-bromosuccinimide (3.0 g), 2,2'-azobis(isobutyronitrile) (0.251 g) and (trifluoromethyl)benzene (40 mL) was stirred under nitrogen atmosphere at 80° C. for 5 hr. The reaction mixture was diluted with a mixture of ethyl acetate-hexane, purified by silica gel column chromatography (hexane/ethyl acetate), and concentrated under reduced pressure. The residue was purified by silica gel column chromatography (hexane/ethyl acetate) to give the title compound (3.88 g).
$^1$H NMR (300 MHz, CDCl$_3$) δ 3.95 (3H, s), 4.90 (2H, s), 7.34 (1H, d, J=8.3 Hz), 7.62 (1H, dd, J=8.3, 2.3 Hz), 8.11 (1H, d, J =2.3 Hz).

B) tert-butyl trans-3-(6-bromo-1-oxo-1,3-dihydro-2H-isoindol-2-yl)-4-phenylpyrrolidine-1-carboxylate A mixture of methyl 5-bromo-2-(bromomethyl)benzoate (485 mg), tert-butyl trans-3-amino-4-phenylpyrrolidine-1-carboxylate (485 mg), DIEA (0.330 ml) and THF (30 ml) was stirred overnight at 50° C. under nitrogen atmosphere, and the reaction mixture was concentrated under reduced pressure. To the residue was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (515 mg).
$^1$H NMR (300 MHz, CDCl$_3$) δ 1.48 (9H, s), 3.34-3.57 (2H, m), 3.60-3.76 (1H, m), 3.87-4.06 (2H, m), 4.23-4.39 (2H, m), 5.14 (1H, quin, J=9.4 Hz), 7.19-7.25 (1H, m), 7.27-7.35 (5H, m), 7.63 (1H, dd, J=7.9, 1.9 Hz), 7.93 (1H, d, J=1.1 Hz).

C) tert-butyl trans-3-(6-cyano-1-oxo-1,3-dihydro-2H-isoindol-2-yl)-4-phenylpyrrolidine-1-carboxylate A mixture of tert-butyl trans-3-(6-bromo-1-oxo-1,3-dihydro-2H-isoindol-2-yl)-4-phenylpyrrolidine-1-carboxylate (515 mg), zinc(II) cyanide (264 mg), zinc powder (37 mg), dichloro[1,1'-bis(diphenylphosphino)ferrocene]palladium (II) (58 mg) and DMF (10 ml) was heated under microwave irradiation at 140° C. for 60 min. The reaction mixture was diluted with ethyl acetate, the insoluble substance was removed by filtration through Celite, and the filtrate was concentrated under reduced pressure. To the residue was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (417 mg).
MS (API–), found: 402.0.

D) tert-butyl trans-3-(1-oxo-6-(5-(trifluoromethyl)-1,2,4-oxadiazol-3-yl)-1,3-dihydro-2H-isoindol-2-yl)-4-phenylpyrrolidine-1-carboxylate To a mixture of tert-butyl trans-3-(6-cyano-1-oxo-1,3-dihydro-2H-isoindol-2-yl)-4-phenylpyrrolidine-1-carboxylate (417 mg), methanol (5 ml) and ethanol (5 ml) was added 50% aqueous hydroxylamine solution (0.317 ml), and the mixture was stirred under nitrogen atmosphere at 50° C. for 3 hr. The reaction mixture was concentrated under reduced pressure, to the residue was added water, and the mixture was extracted with ethyl acetate. The organic layer was washed with saturated brine, dried over anhydrous sodium sulfate, and concentrated under reduced pressure to give a residue. To a mixture of the obtained residue and THF (10 ml) was added trifluoroacetic anhydride (0.365 ml), and the mixture was stirred under nitrogen atmosphere at 50° C. for 2 hr. The reaction mixture was concentrated under reduced pressure, water was added thereto, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (479 mg).
$^1$H NMR (300 MHz, CDCl$_3$) δ 1.49 (9H, s), 3.36-3.60 (2H, m), 3.64-3.80 (1H, m), 3.88-4.09 (2H, m), 4.37-4.54 (2H, m), 5.11-5.29 (1H, m), 7.27-7.36 (5H, m), 7.58 (1H, d, J=7.9 Hz), 8.28 (1H, dd, J=7.9, 1.5 Hz), 8.57 (1H, s).

Example 3 trans-2-(4-phenylpyrrolidin-3-yl)-6-(5-(trifluoromethyl)-1,2,4-oxadiazol-3-yl)isoindolin-1-one hydrochloride To a mixture of tert-butyl trans-3-(1-oxo-6-(5-(trifluoromethyl)-1,2,4-oxadiazol-3-yl)-1,3-dihydro-2H-isoindol- 2-yl)-4-phenylpyrrolidine-1-carboxylate (469 mg) and methanol (15 ml) was added 4 M hydrogen chloride-CPME solution (4 ml), and the mixture was stirred at room temperature for 3 days. The reaction mixture was concentrated under reduced pressure to give the title compound (404 mg).

$^1$H NMR (300 MHz, DMSO-d$_6$) δ 1.36-1.68 (1H, m), 3.41-3.51 (1H, m), 3.55-3.66 (1H, m), 3.69-3.87 (2H, m), 4.61-4.82 (2H, m), 5.03-5.24 (1H, m), 7.21-7.37 (3H, m), 7.38-7.47 (2H, m), 7.89 (1H, d, J=7.9 Hz), 8.19 (1H, d, J=0.8 Hz), 8.31 (1H, dd, J=7.9, 1.5 Hz), 9.10 (2H, brs).

Example 4 trans-2-(1-acetyl-4-phenylpyrrolidin-3-yl)-6-(5-(trifluoromethyl)-1,2,4-oxadiazol-3-yl)isoindolin-1-one To a mixture of trans-2-(4-phenylpyrrolidin-3-yl)-6-(5-(trifluoromethyl)-1,2,4-oxadiazol-3-yl)isoindolin-1-one hydrochloride (75 mg), TEA (0.070 ml), 4,4-dimethylaminopyridine (6.1 mg) and THF (5 ml) was added acetic anhydride (0.022 ml) at 0° C., and the mixture was stirred at room temperature for 2 hr. To the reaction mixture was added water at 0° C., and the mixture was extracted with ethyl acetate. The organic layer was washed with saturated brine, dried over anhydrous sodium sulfate, and concentrated under reduced pressure. The residue was purified by Diol (3-(2,3-dihydroxypropoxy)propylsilane-bonded silica gel) silica gel column chromatography (hexane/ethyl acetate), and the fraction was concentrated under reduced pressure. The obtained residue was crystallized from diethyl ether/hexane to give the title compound (50.1 mg).

$^1$H NMR (300 MHz, CDCl$_3$) δ 2.11 (3H, s), 3.41-3.92 (3H, m), 3.98-4.30 (2H, m), 4.37-4.54 (2H, m), 5.09-5.29 (1H, m), 7.27-7.38 (5H, m), 7.55-7.62 (1H, m), 8.29 (1H, ddd, J=7.9, 3.4, 1.5 Hz), 8.58 (1H, d, J=5.7 Hz).

Example 5 trans-2-(3-phenyltetrahydro-2H-pyran-4-yl)-6-(5-(trifluoromethyl)-1,2,4-oxadiazol-3-yl)isoindolin-1-one A) ethyl 5-(((trifluoromethyl)sulfonyl)oxy)-3,6-dihydro-2H-pyran-4-carboxylate To a mixture of ethyl 5-hydroxy-3,6-dihydro-2H-pyran-4-carboxylate (50 g), diethyl ether (400 ml) and THF (100 ml) was added sodium hydride (60%, oil, 17.4 g) at room temperature, and the mixture was stirred for 1 hr. Trifluoromethanesulfonic anhydride (99 g) was added thereto at room temperature, and the mixture was stirred for 2 hr. The reaction mixture was poured into saturated aqueous ammonium chloride solution (500 ml), and the mixture was extracted with ethyl acetate. The organic layer was washed with saturated brine, dried over anhydrous sodium sulfate, and concentrated under reduced pressure. The obtained residue was purified by silica gel column chromatography (petroleum ether/ethyl acetate) to give the title compound (68 g).

$^1$H NMR (400 MHz, CDCl$_3$) δ 1.34 (3H, t, J=6.8 Hz), 2.60-2.70 (2H, m), 3.82 (2H, t, J=5.2 Hz), 4.18 (2H, t, J=2.4 Hz), 4.31 (2H, q, J=6.8 Hz).

B) ethyl 5-phenyl-3,6-dihydro-2H-pyran-4-carboxylate

A mixture of ethyl 5-(((trifluoromethyl)sulfonyl)oxy)-3,6-dihydro-2H-pyran-4-carboxylate (65 g), phenylboronic acid (28.7 g), tetrakis(triphenylphosphine)palladium(0) (7.43 g), potassium carbonate (71 g) and THF (500 ml) was stirred under nitrogen atmosphere at 60-70° C. for 20 hr. The reaction mixture was poured into water (500 ml), and the mixture was extracted with ethyl acetate. The organic layer was washed with saturated brine, dried over anhydrous sodium sulfate, and concentrated under reduced pressure. The obtained residue was purified by silica gel column chromatography (petroleum ether/ethyl acetate) to give the title compound (45 g).

$^1$H NMR (400 MHz, CDCl$_3$) δ 0.87 (3H, t, J=7.2 Hz), 2.50-2.60 (2H, m), 3.80-3.95 (4H, m), 4.30 (2H, t, J=2.8 Hz), 7.10-7.20 (2H, m), 7.30-7.40 (3H, m).

C) ethyl cis-3-phenyltetrahydro-2H-pyran-4-carboxylate

A mixture of ethyl 5-phenyl-3,6-dihydro-2H-pyran-4-carboxylate (25 g), ethanol (600 ml) and 10% palladium-carbon (50% wet, 3.75 g) was stirred under hydrogen pressure (3.4 atm) at 35-60° C. for 16 hr. The insoluble substance was filtered off, and the filtrate was concentrated under reduced pressure to give the title compound (22 g).

$^1$H NMR (400 MHz, CDCl$_3$) δ 1.05 (3H, t, J=7.2 Hz), 1.70-1.80 (1H, m), 2.00-2.15 (1H, m), 2.95-3.05 (1H, m), 3.20-3.30 (1H, m), 3.60-3.70 (1H, m), 3.80-4.00 (3H, m), 4.10-4.20 (1H, m), 4.29 (1H, dd, J=11.2, 4.8 Hz), 7.15-7.30 (3H, m), 7.30-7.50 (2H, m).

D) ethyl trans-3-phenyltetrahydro-2H-pyran-4-carboxylate

A mixture of ethyl cis-3-phenyltetrahydro-2H-pyran-4-carboxylate (22 g), anhydrous ethanol (250 ml) and sodium ethoxide (7.68 g) was heated under reflux for 18 hr, and concentrated under reduced pressure. Saturated aqueous ammonium chloride solution (300 ml) was added thereto, and the mixture was extracted with dichloromethane. The organic layer was washed with saturated brine, dried over anhydrous sodium sulfate, and concentrated under reduced pressure to give the title compound (10.4 g).

$^1$H NMR (400 MHz, CDCl$_3$) δ 0.99 (3H, t, J=7.2 Hz), 1.90-2.00 (2H, m), 2.85 (1H, td, J=11.2, 4.8 Hz), 3.11 (1H, td, J=11.2, 4.4 Hz), 3.39 (1H, t, J=11.2 Hz), 3.50-3.60 (1H, m), 3.85-4.00 (3H, m), 4.05-4.15 (1H, m), 7.15-7.25 (3H, m), 7.25-7.35 (2H, m).

E) trans-3-phenyltetrahydro-2H-pyran-4-carboxylic acid

To a mixture of ethyl trans-3-phenyltetrahydro-2H-pyran-4-carboxylate (10.4 g) and methanol (160 ml) was added 2 M aqueous sodium hydroxide solution (80 ml), and the mixture was stirred at 70° C. for 16 hr. The reaction mixture was concentrated under reduced pressure, the residue was diluted so with water (50 ml), and the mixture was washed with methyl tert-butyl ether. The aqueous layer was acidified with 2 M hydrochloric acid (pH=2), and the mixture was extracted with ethyl acetate. The organic layer was washed with saturated brine, dried over anhydrous sodium sulfate, and concentrated under reduced pressure. The obtained residue was washed with a mixture of petroleum ether-ethyl acetate to give the title compound (8.0 g).

$^1$H NMR (400 MHz, CDCl$_3$) δ 1.85-2.00 (2H, m), 2.87 (1H, td, J=11.2, 4.8 Hz), 3.08 (1H, td, J=11.2, 4.4 Hz), 3.34

(1H, t, J=11.2 Hz), 3.50 (1H, td, J=11.2, 3.2 Hz), 3.93 (1H, dd, J=11.6, 4.4 Hz), 4.05-4.15 (1H, m), 7.15-7.35 (5H, m).

F) benzyl trans-(3-phenyltetrahydro-2H-pyran-4-yl)carbamate

A mixture of trans-3-phenyltetrahydro-2H-pyran-4-carboxylic acid (8.0 g), TEA (5.89 g), anhydrous toluene (200 ml) and diphenylphosphoryl azide (16 g) was stirred at room temperature for 1 hr. To the reaction mixture was added benzyl alcohol (8.39 g), and the mixture was stirred at 70-75° C. for 16 hr. The reaction mixture was diluted with ethyl acetate, washed successively with 1 M aqueous sodium hydroxide solution, water and saturated brine, dried over anhydrous sodium sulfate, and concentrated under reduced pressure. The obtained residue was purified by silica gel column chromatography (petroleum ether/ethyl acetate), and the fraction was concentrated under reduced pressure. The obtained residue was washed with a mixture of petroleum ether-ethyl acetate to give the title compound (9.0 g).
$^1$H NMR (400 MHz, CDCl$_3$) δ 1.55-1.70 (1H, m), 2.10-2.30 (1H, m), 2.60-2.80 (1H, m), 3.40 (1H, t, J=11.6 Hz), 3.59 (1H, t, J=11.6 Hz), 3.95 (1H, dd, J=11.6, 4.4 Hz), 4.00-4.10 (2H, m), 4.50-4.65 (1H, m), 4.90-5.05 (2H, m), 7.10-7.40 (10H, m).

G) trans-3-phenyltetrahydro-2H-pyran-4-amine

A mixture of benzyl trans-(3-phenyltetrahydro-2H-pyran-4-yl)carbamate (9.0 g), methanol (200 ml) and 10% palladium-carbon (50% wet, 1.8 g) was stirred under hydrogen atmosphere at room temperature for 3 hr. The insoluble substance was filtered off, the filtrate was concentrated under reduced pressure, and the obtained residue was diluted with dichloromethane. The insoluble substance was filtered off, and the filtrate was concentrated under reduced pressure to give the title compound (4.6 g).
$^1$H NMR (400 MHz, CDCl$_3$) δ 1.37 (2H, brs), 1.50-1.70 (1H, m), 1.90-2.00 (1H, m), 2.54 (1H, td, J=10.8, 4.4 Hz), 3.10 (1H, td, J=10.8, 4.4 Hz), 3.38 (1H, t, J=11.2 Hz), 3.58 (1H, td, J=12.0, 2.0 Hz), 3.90 (1H, dd, J=11.6, 4.4 Hz), 4.08 (1H, dd, J=11.6, 4.8 Hz), 7.20-7.40 (5H, m).

H) trans-3-oxo-2-(3-phenyltetrahydro-2H-pyran-4-yl)isoindoline-5-carbonitrile

A mixture of methyl 5-bromo-2-(bromomethyl)benzoate (300 mg), trans-3-phenyltetrahydro-2H-pyran-4-amine (207 mg), DIEA (0.204 ml) and THF (20 ml) was stirred overnight at 50° C. under nitrogen atmosphere, and the reaction mixture was concentrated under reduced pressure. To the residue was added water, and the mixture was extracted with ethyl acetate. The organic layer was washed with saturated brine, dried over anhydrous sodium sulfate, and concentrated under reduced pressure. The obtained residue was purified by silica gel column chromatography (hexane/ethyl acetate), and the fraction was concentrated under reduced pressure to give a residue. A mixture of the obtained residue (271 mg), zinc(II) cyanide (171 mg), zinc powder (24 mg), dichloro[1,1'-bis(diphenylphosphino) ferrocene]palladium (II) (37 mg) and DMF (5 ml) was heated under microwave irradiation at 140° C. for 60 min. The reaction mixture was diluted with ethyl acetate, the insoluble substance was removed by filtration through Celite, and the filtrate was concentrated under reduced pressure. To the residue was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (223 mg).
MS (API+), found: 319.1.

I) trans-2-(3-phenyltetrahydro-2H-pyran-4-yl)-6-(5-(trifluoromethyl)-1,2,4-oxadiazol-3-yl)isoindolin-1-one To a mixture of trans-3-oxo-2-(3-phenyltetrahydro-2H-pyran-4-yl)isoindoline-5-carbonitrile (223 mg), methanol (2.5 ml) and ethanol (2.5 ml) was added 50% aqueous hydroxylamine solution (0.215 ml), and the mixture was stirred at 50° C. for 3 hr, and then overnight at room temperature, under nitrogen atmosphere. The reaction mixture was concentrated under reduced pressure, to the residue was added water, and the mixture was extracted with ethyl acetate. The organic layer was washed with saturated brine, dried over anhydrous sodium sulfate, and concentrated under reduced pressure to give a residue. To a mixture of the obtained residue and THF (6 ml) was added trifluoroacetic anhydride (0.223 ml), and the mixture was stirred under nitrogen atmosphere at 50° C. for 4 hr. The reaction mixture was concentrated under reduced pressure, water was added thereto, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate), and the fraction was concentrated under reduced pressure to give the title compound (200 mg).
$^1$H NMR (300 MHz, CDCl$_3$) δ 1.91-2.14 (2H, m), 3.21 (1H, td, J=11.2, 4.3 Hz), 3.45 (1H, t, J=11.1 Hz), 3.73 (1H, td, J=11.7, 3.0 Hz), 4.07 (1H, dd, J=11.5, 4.0 Hz), 4.12-4.24 (2H, m), 4.36-4.49 (1H, m), 4.94 (1H, td, J=11.3, 4.9 Hz), 7.12-7.24 (1H, m), 7.26-7.30 (4H, m), 7.51 (1H, d, J=7.9 Hz), 8.22 (1H, dd, J=7.9, 1.9 Hz), 8.51 (0.1H, d, J=1.9 Hz)

Example 6 tert-butyl trans-(2-(1-oxo-6-(5-(trifluoromethyl)-1,2,4-oxadiazol-3-yl)-1,3-dihydro-2H-isoindol-2-yl)cyclohexyl)carbamate A) methyl 5-cyano-2-methylbenzoate To a solution of methyl 5-bromo-2-methylbenzoate (14.4 g) in DMF (60 ml) was added copper(I) cyanide (8.45 g), and the mixture was stirred overnight at 150° C. under nitrogen atmosphere. The reaction mixture was allowed to cool to room temperature, and diluted with ethyl acetate, and purified by silica gel column chromatography (ethyl acetate). To the obtained fraction was added saturated aqueous ammonium chloride solution, and the mixture was stirred at room temperature for 30 min. The insoluble substance was filtered off, and the organic layer was washed with water and saturated brine, dried over anhydrous sodium sulfate, purified by silica gel column chromatography (hexane/ethyl acetate), and concentrated under reduced pressure. The residue was purified by silica gel column chromatography (hexane/ethyl acetate) to give the title compound (9.0 g).
$^1$H NMR (300 MHz, CDCl$_3$) δ 2.68 (3H, s), 3.93 (3H, s), 7.37 (1H, d, J=7.9 Hz), 7.66 (1H, dd, J=7.9, 1.9 Hz), 8.22 (1H, d, J=1.9 Hz).

B) methyl 2-(bromomethyl)-5-cyanobenzoate

A suspension of methyl 5-cyano-2-methylbenzoate (8.9 g), N-bromosuccinimide (9.5 g) in (trifluoromethyl)benzene (200 mL) was added 2,2'-azobis(isobutyronitrile) (0.834 g) at room temperature, and the mixture was stirred at 80° C. for 6 hr under nitrogen atmosphere. The reaction mixture was poured into water at room temperature, and the organic layer was separated, dried over anhydrous sodium sulfate, and concentrated under reduced pressure. The residue was purified by silica gel column chromatography (hexane/ethyl acetate), and the fraction was concentrated under reduced pressure to give the title compound (8.05 g).

$^1$H NMR (300 MHz, CDCl$_3$) δ 3.98 (3H, s), 4.96 (2H, s), 7.61 (1H, d, J=7.9 Hz), 7.77 (1H, dd, J=7.9, 1.9 Hz), 8.27 (1H, d, J=1.9 Hz).

C) tert-butyl trans-(2-(6-cyano-1-oxo-1,3-dihydro-2H-isoindol-2-yl)cyclohexyl)carbamate A mixture of methyl 2-(bromomethyl)-5-cyanobenzoate (250 mg), tert-butyl trans-(2-aminocyclohexyl)carbamate (253 mg), DIEA (0.206 ml) and THF (15 ml) was stirred overnight at 50° C. under nitrogen atmosphere, and the reaction mixture was concentrated under reduced pressure. To the residue was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (308 mg).

MS (API+), found: 256.1 (M+1-Boc).

D) tert-butyl trans-(2-(1-oxo-6-(5-(trifluoromethyl)-1,2,4-oxadiazol-3-yl)-1,3-dihydro-2H-isoindol-2-yl)cyclohexyl)carbamate To a mixture of tert-butyl trans-(2-(6-cyano-1-oxo-1,3-dihydro-2H-isoindol-2-yl)cyclohexyl)carbamate (308 mg), methanol (4 ml) and ethanol (4 ml) was added 50% aqueous hydroxylamine solution (0.266 ml), and the mixture was stirred at 50° C. for 3 hr, and then overnight at room temperature, under nitrogen atmosphere. The reaction mixture was concentrated under reduced pressure, to the residue was added water, and the mixture was extracted with ethyl acetate. The organic layer was washed with saturated brine, dried over anhydrous sodium so sulfate, and concentrated under reduced pressure to give a residue. To a mixture of the obtained residue and THF (6 ml) was added trifluoroacetic anhydride (0.202 ml), and the mixture was stirred under nitrogen atmosphere at 50° C. for 2 hr. The reaction mixture was concentrated under reduced pressure, water was added thereto, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate), and the fraction was concentrated under reduced pressure to give the title compound (377 mg).

$^1$H NMR (300 MHz, CDCl$_3$) δ 1.07 (9H, s), 1.33-1.44 (2H, m), 1.59-1.73 (1H, m), 1.85-1.97 (4H, m), 2.07-2.14 (1H, m), 3.58-3.74 (1H, m), 4.12-4.20 (1H, m), 4.39 (1H, d, J=17.4 Hz), 4.64 (1H, d, J=9.8 Hz), 4.78 (1H, d, J=17.4 Hz), 7.62 (1H, d, J=7.9 Hz), 8.28 (1H, dd, J=7.9, 1.5 Hz), 8.59 (1H, s).

Example 7 trans-2-(2-aminocyclohexyl)-6-(5-(trifluoromethyl)-1,2,4-oxadiazol-3-yl)isoindolin-1-one hydrochloride To a mixture of tert-butyl trans-(2-(1-oxo-6-(5-(trifluoromethyl)-1,2,4-oxadiazol-3-yl)-1,3-dihydro-2H-isoindol-2-yl)cyclohexyl)carbamate (373 mg) and methanol (10 ml) was added 4 M hydrogen chloride-CPME solution (4 ml), and the mixture was stirred at room temperature for 3 days. The reaction mixture was concentrated under reduced pressure to give the title compound (295 mg).

Example 8 trans-N-(2-(1-oxo-6-(5-(trifluoromethyl)-1,2,4-oxadiazol-3-yl)-1,3-dihydro-2H-isoindol-2-yl)cyclohexyl)acetamide To a mixture of trans-2-(2-aminocyclohexyl)-6-(5-(trifluoromethyl)-1,2,4-oxadiazol-3-yl)isoindolin-1-one hydrochloride (75 mg), TEA (0.078 ml), 4,4-dimethylaminopyridine (6.8 mg) and THF (5 ml) was added acetic anhydride (0.025 ml) at 0° C., and the mixture was stirred at room temperature for 2 hr. To the reaction mixture was added water, and the mixture was extracted with ethyl acetate. The organic layer was washed with saturated brine, dried over anhydrous sodium sulfate, purified by silica gel column chromatography (ethyl acetate), and concentrated under reduced pressure. The obtained residue was crystallized from a mixture of diethyl ether-ethyl acetate/hexane to give the title compound (23.3 mg).

$^1$H NMR (300 MHz, CDCl$_3$) δ 1.29-1.52 (3H, m), 1.68 (1H, dd, J=11.9, 3.2 Hz), 1.74 (3H, s), 1.79-2.02 (3H, m), 2.05-2.17 (1H, m), 3.94-4.10 (1H, m), 4.13-4.26 (1H, m), 4.34-4.71 (2H, m), 5.75 (1H, d, J=9.4 Hz), 7.62 (1H, d, J=8.7 Hz), 8.30 (1H, dd, J=8.7, 1.5 Hz), 8.58 (1H, s).

Example 9 trans-N-(2-(1-oxo-6-(5-(trifluoromethyl)-1,2,4-oxadiazol-3-yl)-1,3-dihydro-2H-isoindol-2-yl)cyclohexyl)benzamide To a mixture of trans-2-(2-aminocyclohexyl)-6-(5-(trifluoromethyl)-1,2,4-oxadiazol-3-yl) isoindolin-1-one hydrochloride (75 mg), TEA (0.078 ml), 4,4-dimethylaminopyridine (6.8 mg) and THF (5 ml) was added benzoyl chloride (0.030 ml) at 0° C., and the mixture was stirred at room temperature for 2 hr. To the reaction mixture was added water, and the mixture was extracted with ethyl acetate. The organic layer was washed with saturated brine, dried over anhydrous sodium sulfate, purified by silica gel column chromatography (ethyl acetate), and concentrated under reduced pressure. The obtained residue was crystallized from diethyl ether/hexane to give the title compound (25.9 mg).

$^1$H NMR (300 MHz, CDCl$_3$) δ 1.40-1.54 (3H, m), 1.67-2.11 (4H, m), 2.20-2.36 (1H, m), 4.14-4.30 (1H, m), 4.31-4.41 (1H, m), 4.42-4.74 (2H, m), 6.57 (1H, d, J=9.1 Hz), 7.28-7.44 (3H, m), 7.60 (3H, d, J=8.3 Hz), 8.25 (1H, dd, J=7.9, 1.5 Hz), 8.52 (1H, s).

Example 10 trans-2-(1-benzoyl-4-phenylpyrrolidin-3-yl)-6-(5-(trifluoromethyl)-1,2,4-oxadiazol-3-yl)isoindolin-1-one To a mixture of trans-2-(4-phenylpyrrolidin-3-yl)-6-(5-(trifluoromethyl)-1,2,4-oxadiazol-3-yl)isoindolin-1-one hydrochloride (75 mg), TEA (0.070 ml), 4,4-dimethylaminopyridine (6.1 mg) and THF (5 ml) was added benzoyl chloride (0.027 ml) at 0° C., and the mixture was stirred at room temperature for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate), and the fraction was concentrated under reduced pressure. The residue was purified by silica gel column chromatography (hexane/ethyl acetate), and the fraction was concentrated under reduced pressure. The obtained residue was crystallized from diethyl ether/hexane to give the title compound (46.2 mg).

$^1$H NMR (300 MHz, CDCl$_3$) δ 3.59-3.81 (2H, m), 3.83-4.05 (2H, m), 4.11-4.38 (1H, m), 4.38-4.61 (2H, m), 5.01-5.52 (1H, m), 7.27-7.48 (8H, m), 7.50-7.65 (3H, m), 8.28 (1H, t, J=6.6 Hz), 8.56 (1H, d, J=12.8 Hz).

Example 11 trans-2-(1-(cyclopropylcarbonyl)-4-phenylpyrrolidin-3-yl)-6-(5-(trifluoromethyl)-1,2,4-oxadiazol-3-yl)isoindolin-1-one To a mixture of trans-2-(4-phenylpyrrolidin-3-yl)-6-(5-(trifluoromethyl)-1,2,4-oxadiazol-3-yl)isoindolin-1-one hydrochloride (75 mg), TEA (0.070 ml), 4,4-dimethylaminopyridine (6.1 mg) and THF (5 ml) was added cyclopropanecarbonyl chloride (0.021 ml) at 0° C., and the mixture was stirred at room temperature for 1 hr. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (ethyl acetate), and the fraction was concentrated under reduced pressure. The obtained residue was crystallized from a mixture of diethyl ether/hexane-diisopropyl ether to give the title compound (17.6 mg).

$^1$H NMR (300 MHz, CDCl$_3$) δ 0.76-0.89 (2H, m), 0.97-1.10 (2H, m), 1.57-1.69 (1H, m), 3.44-4.34 (5H, m), 4.38-4.56 (2H, m), 5.16-5.30 (1H, m), 7.27-7.39 (5H, m), 7.58 (1H, d, J=7.9 Hz), 8.29 (1H, ddd, J=7.9, 4.3, 1.7 Hz), 8.58 (1H, d, J=5.3 Hz).

Example 12 trans-N-(2-(1-oxo-6-(5-(trifluoromethyl)-1,2,4-oxadiazol-3-yl)-1,3-dihydro-2H-isoindol-2-yl)cyclohexyl)cyclopropanecarboxamide To a mixture of trans-2-(2-aminocyclohexyl)-6-(5-(trifluoromethyl)-1,2,4-oxadiazol-3-yl)isoindolin-1-one hydrochloride (50 mg), TEA (0.052 ml), 4,4-dimethylaminopyridine (4.6 mg) and THF (5 ml) was added cyclopropanecarbonyl chloride (0.016 ml) at 0° C., and the mixture was stirred at room temperature for 1 hr. To the reaction mixture was added water, and the mixture was extracted with ethyl acetate. The organic layer was washed with saturated brine, dried over anhydrous sodium sulfate, purified by silica gel column chromatography (ethyl acetate), and concentrated under reduced pressure. The obtained residue was crystallized from ethyl acetate/hexane to give the title compound (30.4 mg).

$^1$H NMR (300 MHz, CDCl$_3$) δ 0.07-0.21 (1H, m), 0.32-0.46 (1H, m), 0.49-0.62 (1H, m), 0.67-0.80 (1H, m), 1.08-1.23 (1H, m), 1.22-1.33 (1H, m), 1.34-1.51 (3H, m), 1.59-1.77 (1H, m), 1.83-2.00 (2H, m), 2.05-2.18 (1H, m), 3.94-4.14 (1H, m), 4.14-4.28 (1H, m), 4.31-4.72 (2H, m), 5.78 (1H, d, J=9.4 Hz), 7.55-7.67 (1H, m), 8.29 (1H, dd, J=7.9, 1.5 Hz), 8.59 (1H, s).

Example 13 tert-butyl (3R,4R)-4-(1-oxo-6-(5-(trifluoromethyl)-1,2,4-oxadiazol-3-yl)-1,3-dihydro-2H-isoindol-2-yl)-3-phenylpiperidine-1-carboxylate A) tert-butyl (3R,4R)-4-(6-cyano-1-oxo-1,3-dihydro-2H-isoindol-2-yl)-3-phenylpiperidine-1-carboxylate A mixture of methyl 2-(bromomethyl)-5-cyanobenzoate (200 mg), DIEA (0.302 ml), tert-butyl (3R,4R)-4-amino-3-phenylpiperidine-1-carboxylate 4-methylbenzenesulfonate (353 mg) and THF (15 ml) was stirred overnight at 50° C. under nitrogen atmosphere, and concentrated under reduced pressure. To the residue was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (240 mg).

MS (API–), found: 416.0.

B) tert-butyl (3R,4R)-4-(1-oxo-6-(5-(trifluoromethyl)-1,2,4-oxadiazol-3-yl)-1,3-dihydro-2H-isoindol-2-yl)-3-phenylpiperidine-1-carboxylate To a mixture of tert-butyl (3R,4R)-4-(6-cyano-1-oxo-1,3-dihydro-2H-isoindol-2-yl)-3-phenylpiperidine-1-carboxylate (240 mg), methanol (3 ml) and ethanol (3 ml) was added 50% aqueous hydroxylamine solution (0.176 ml), and the mixture was stirred at 50° C. for 2 hr and 30 min, and then overnight at room temperature, under nitrogen atmosphere. The reaction mixture was concentrated under reduced pressure, to the residue was added water, and the mixture was extracted with ethyl acetate. The organic layer was washed with saturated brine, dried over anhydrous sodium sulfate, and concentrated under reduced pressure to give a residue. To a mixture of the obtained residue and THF (10 ml) was added trifluoroacetic anhydride (0.203 ml), and the mixture was stirred under nitrogen atmosphere at 50° C. for 9 hr. The reaction mixture was concentrated under reduced pressure, water was added thereto, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate), and the fraction was concentrated under reduced pressure to give the title compound (230 mg).

$^1$H NMR (300 MHz, CDCl$_3$) δ 1.50 (9H, s), 1.83-2.01 (2H, m), 2.75-2.91 (1H, m), 3.03 (2H, td, J=11.4, 3.6 Hz), 4.13-4.43 (4H, m), 4.83 (1H, td, J=11.5, 4.2 Hz), 7.11-7.19 (1H, m), 7.22-7.26 (1H, m), 7.27-7.32 (3H, m), 7.49 (1H, d, J=7.9 Hz), 8.21 (1H, dd, J=7.9, 1.5 Hz), 8.50 (1H, s).

Example 14 tert-butyl (3R,4S)-4-(1-oxo-6-(5-(trifluoromethyl)-1,2,4-oxadiazol-3-yl)-1,3-dihydro-2H-isoindol-2-yl)-3-phenylpiperidine-1-carboxylate A) tert-butyl (3R,4S)-4-(6-cyano-1-oxo-1,3-dihydro-2H-isoindol-2-yl)-3-phenylpiperidine-1-carboxylate A mixture of methyl 2-(bromomethyl)-5-cyanobenzoate (200 mg), DIEA (0.165 ml), tert-butyl (3R,4S)-4-amino-3- phenylpiperidine-1-carboxylate (261 mg) and THF (15 ml) was stirred overnight at 50° C., and then at 75° C. for 20 hr. under nitrogen atmosphere. The reaction mixture was concentrated under reduced pressure, to the residue was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (221 mg).

MS (API–), found: 416.0.

B) tert-butyl (3R,4S)-4-(1-oxo-6-(5-(trifluoromethyl)-1,2,4-oxadiazol-3-yl)-1,3-dihydro-2H-isoindol-2-yl)-3-phenylpiperidine-1-carboxylate To a mixture of tert-butyl (3R,4S)-4-(6-cyano-1-oxo-1,3-dihydro-2H-isoindol-2-yl)-3-phenylpiperidine-1-carboxylate (221 mg), methanol (6 ml) and ethanol (3 ml) was added 50% aqueous hydroxylamine solution (0.176 ml), and the mixture was stirred under nitrogen atmosphere at 50° C. for 2 hr. The reaction mixture was concentrated under reduced pressure, to the residue was added water, and the mixture was extracted with ethyl acetate. The organic layer was washed with saturated brine, dried over anhydrous sodium sulfate, and concentrated under reduced pressure to give a residue. To a mixture of the obtained residue and THF (10 ml) was added trifluoroacetic anhydride (0.187 ml), and the mixture was stirred under nitrogen atmosphere at 50° C. for 9 hr. The reaction mixture was concentrated under reduced pressure, water was added thereto, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate), and the fraction was concentrated under reduced pressure to give the title compound (240 mg).

Example 15

2-((3R,4R)-3-phenylpiperidin-4-yl)-6-(5-(trifluoromethyl)-1,2,4-oxadiazol-3-yl)isoindolin-1-one hydrochloride To a mixture of tert-butyl (3R,4R)-4-(1-oxo-6-(5-(trifluoromethyl)-1,2,4-oxadiazol-3-yl)-1,3-dihydro-2H-isoindol-2-yl)-3-phenylpiperidine-1-carboxylate (225 mg) and methanol (7 ml) was added 4 M hydrogen chloride-CPME solution (2 ml), and the mixture was stirred at room temperature for 3 days. The reaction mixture was concentrated under reduced pressure to give the title compound (186 mg).

$^1$H NMR (300 MHz, DMSO-$d_6$) δ 1.90-2.12 (1H, m), 2.16-2.37 (1H, m), 3.19-3.30 (2H, m), 3.35-3.54 (3H, m), 4.32-4.53 (2H, m), 4.67-4.83 (1H, m), 7.11-7.20 (1H, m), 7.25 (2H, t, J=7.4 Hz), 7.32-7.39 (2H, m), 7.78 (1H, d, J=7.9 Hz), 8.11 (1H, d, J=1.1 Hz), 8.17-8.27 (1H, m), 8.80 (2H, brs).

Example 16

2-((3R,4S)-3-phenylpiperidin-4-yl)-6-(5-(trifluoromethyl)-1,2,4-oxadiazol-3-yl)isoindolin-1-one hydrochloride To a mixture of tert-butyl (3R,4S)-4-(1-oxo-6-(5-(trifluoromethyl)-1,2,4-oxadiazol-3-yl)-1,3-dihydro-2H-isoindol-2-yl)-3-phenylpiperidine-1-carboxylate (225 mg) and methanol (7 ml) was added 4 M hydrogen chloride-CPME solution (2 ml), and the mixture was stirred overnight at room temperature. The reaction mixture was concentrated under reduced pressure to give the title compound (190 mg).

$^1$H NMR (300 MHz, DMSO-$d_5$) δ 2.13-2.42 (2H, m), 3.34-3.41 (1H, m), 3.43-3.66 (3H, m), 3.71-3.87 (1H, m), 4.24-4.55 (2H, m), 4.79 (1H, q, J=4.5 Hz), 7.07-7.31 (5H, m), 7.72 (1H, d, J=7.9 Hz), 8.13 (1H, d, J=0.8 Hz), 8.23 (1H, dd, J=7.9, 1.5 Hz), 9.05 (2H, brs)

Example 17 trans-2-(2-phenylcyclohexyl)-6-(5-(trifluoromethyl)-1,2,4-oxadiazol-3-yl) isoindolin-1-one

A) trans-3-oxo-2-(2-phenylcyclohexyl)isoindoline-5-carbonitrile

A mixture of methyl 2-(bromomethyl)-5-cyanobenzoate (100 mg), trans-2-phenylcyclohexanamine (76 mg), DIEA (0.082 ml) and THF (7 ml) was stirred overnight at 50° C. under nitrogen atmosphere, and the reaction mixture was concentrated under reduced pressure. To the residue was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (73 mg).

MS (API+), found: 317.2.

B) trans-2-(2-phenylcyclohexyl)-6-(5-(trifluoromethyl)-1,2,4-oxadiazol-3-yl)isoindolin-1-one To a mixture of trans-3-oxo-2-(2-phenylcyclohexyl)isoindoline-5-carbonitrile (70 mg), methanol (2 ml) and ethanol (2 ml) was added 50% aqueous hydroxylamine solution (0.071 ml), and the mixture was stirred under nitrogen atmosphere at 50° C. for 2 hr. The reaction mixture was concentrated under reduced pressure, to the residue was added water, and the mixture was extracted with ethyl acetate. The organic layer was washed with saturated brine, dried over anhydrous sodium sulfate, and concentrated under reduced pressure to give a residue. To a mixture of the obtained residue and THF (4 ml) was added trifluoroacetic anhydride (0.082 ml), and the mixture was stirred overnight at 50° C. under nitrogen atmosphere. The reaction mixture was concentrated under reduced pressure, the residue was purified by silica gel column chromatography (hexane/ethyl acetate), and the fraction was concentrated under reduced pressure to give the title compound (99 mg).

$^1$H NMR (300 MHz, CDCl$_3$) δ 1.35-2.10 (8H, m), 2.88 (1H, td, J=11.6, 3.6 Hz), 4.13-4.43 (2H, m), 4.62 (1H, td, J=11.6, 3.6 Hz), 7.05-7.12 (1H, m), 7.17-7.25 (4H, m), 7.48 (1H, d, J=8.3 Hz), 8.20 (1H, dd, J=7.9, 1.5 Hz), 8.48 (1H, s).

Example 18 trans-2-(2-(2-oxopyrrolidin-1-yl)cyclohexyl)-6-(5-(trifluoromethyl)-1,2,4-oxadiazol-3-yl)isoindolin-1-one

A) trans-4-chloro-N-(2-(1-oxo-6-(5-(trifluoromethyl)-1,2,4-oxadiazol-3-yl)-1,3-dihydro-2H-isoindol-2-yl)cyclohexyl)butanamide To a mixture of trans-2-(2-aminocyclohexyl)-6-(5-(trifluoromethyl)-1,2,4-oxadiazol-3-yl)isoindolin-1-one hydrochloride (36 mg), TEA (0.037 ml), 4,4-dimethylaminopyridine (3.3 mg) and THF (5 ml) was added 4-chlorobutanoyl chloride (0.014 ml) at 0° C., and the mixture was stirred at room temperature for 1 hr. To the reaction mixture was added water, and the mixture was extracted with ethyl acetate. The organic layer was washed with saturated brine, dried over anhydrous sodium sulfate, purified by silica gel column chromatography (ethyl acetate), and concentrated under reduced pressure to give the title compound (42 mg).
MS (API+), found: 471.2.

B) trans-2-(2-(2-oxopyrrolidin-1-yl)cyclohexyl)-6-(5-(trifluoromethyl)-1,2,4-oxadiazol-3-yl)isoindolin-1-one To a mixture of trans-4-chloro-N-(2-(1-oxo-6-(5-(trifluoromethyl)-1,2,4-oxadiazol-3-yl)-1,3-dihydro-2H-isoindol-2-yl)cyclohexyl)butanamide (42 mg) and THF (5 ml) was added sodium hydride (60%, oil, 10.7 mg) at 0° C., and the mixture was stirred at room temperature for 3 hr and 30 min. To the reaction mixture was added saturated aqueous ammonium chloride solution at 0° C., and the mixture was extracted with ethyl acetate. The organic layer was washed with saturated brine, dried over anhydrous sodium sulfate, and concentrated under reduced pressure to give a residue. The obtained residue was purified by preparative HPLC (column: L-Column 2 ODS, mobile phase: acetonitrile/0.1% aqueous trifluoroacetic acid solution), the fraction was neutralized with saturated aqueous sodium hydrogencarbonate solution, and the mixture was extracted with ethyl acetate. The organic layer was washed with saturated brine, dried over anhydrous sodium sulfate, and concentrated under reduced pressure to give the title compound (4.5 mg).
$^1$H NMR (300 MHz, CDCl$_3$) δ 1.55-2.08 (11H, m), 2.13-2.24 (1H, m), 3.25-3.39 (1H, m), 3.64 (1H, dt, J=9.3, 6.7 Hz), 4.18 (1H, td, J=11.4, 3.6 Hz), 4.29-4.46 (2H, m), 4.75 (1H, d, J=17.8 Hz), 7.60 (1H, d, J=7.9 Hz), 8.28 (1H, dd, J=7.9, 1.9 Hz), 8.55 (1H, s).

Example 19 tert-butyl (3S,4R)-4-(1-oxo-6-(5-(trifluoromethyl)-1,2,4-oxadiazol-3-yl)-1,3-dihydro-2H-isoindol-2-yl)-3-phenylpiperidine-1-carboxylate A) tert-butyl (3S,4R)-4-(6-cyano-1-oxo-1,3-dihydro-2H-isoindol-2-yl)-3-phenylpiperidine-1-carboxylate A mixture of methyl 2-(bromomethyl)-5-cyanobenzoate (200 mg), DIEA (0.072 ml), tert-butyl (3S,4R)-4-amino-3-phenylpiperidine-1-carboxylate (100 mg) and THF (7 ml) was stirred at 75° C. for 20 hr under nitrogen atmosphere. The reaction mixture was concentrated under reduced pressure, to the residue was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (102 mg).
MS (API−), found: 416.0.

B) tert-butyl (3S,4R)-4-(1-oxo-6-(5-(trifluoromethyl)-1,2,4-oxadiazol-3-yl)-1,3-dihydro-2H-isoindol-2-yl)-3-phenylpiperidine-1-carboxylate To a mixture of tert-butyl (3S,4R)-4-(6-cyano-1-oxo-1,3-dihydro-2H-isoindol-2-yl)-3-phenylpiperidine-1-carboxylate (102 mg), methanol (3 ml) and ethanol (1.5 ml) was added 50% aqueous hydroxylamine solution (0.176 ml), and the mixture was stirred under nitrogen atmosphere at 50° C. for 2 hr. The reaction mixture was concentrated under reduced pressure, to the residue was added water, and the mixture was extracted with ethyl acetate. The organic layer was washed with saturated brine, dried over anhydrous sodium sulfate, and concentrated under reduced pressure to give a residue. To a mixture of the obtained residue and THF (5 ml) was added trifluoroacetic anhydride (0.086 ml), and the mixture was stirred overnight at 50° C. under nitrogen atmosphere. The reaction mixture was concentrated under reduced pressure, water was added thereto, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate), and the fraction was concentrated under reduced pressure to give the title compound (115 mg).
$^1$H NMR (300 MHz, CDCl$_3$) δ 1.48 (9H, brs), 1.68-1.79 (1H, m), 2.08-2.26 (1H, m), 2.91 (1H, d, J=18.1 Hz), 2.97-3.12 (1H, m), 3.34-3.52 (2H, m), 4.00 (1H, d, J=17.8 Hz), 4.37-4.64 (2H, m), 4.74 (1H, dt, J=13.1, 4.6 Hz), 7.06-7.23 (5H, m), 7.33 (1H, d, J=8.3 Hz), 8.21 (1H, dd, J=8.1, 1.7 Hz), 8.64 (1H, s).

Example 20

2-((3R,4R)-1-acetyl-3-phenylpiperidin-4-yl)-6-(5-(trifluoromethyl)-1,2,4-oxadiazol-3-yl)isoindolin-1-one To a mixture of 2-((3R,4R)-3-phenylpiperidin-4-yl)-6-(5-(trifluoromethyl)-1,2,4-oxadiazol-3-yl)isoindolin-1-one hydrochloride (50 mg), TEA (0.045 ml), 4,4-dimethylaminopyridine (3.9 mg) and THF (5 ml) was added acetic anhydride (0.020 ml) at 0° C., and the mixture was stirred at room temperature for 1 hr. To the reaction mixture was added water, and the mixture was extracted with ethyl acetate. The organic layer was washed with saturated brine, dried over anhydrous sodium sulfate, and concentrated under reduced pressure. The residue was purified by Diol (3-(2,3-dihydroxypropoxy)propylsilane-bonded silica gel) silica gel column chromatography (hexane/ethyl acetate), and the fraction was concentrated under reduced pressure. The obtained residue was crystallized from diethyl ether/hexane to give the title compound (35.1 mg).
$^1$H NMR (300 MHz, CDCl$_3$) δ 1.80-1.96 (1H, m), 1.98-2.12 (1H, m), 2.14-2.22 (3H, m), 2.55-2.90 (1H, m), 2.97-3.11 (1H, m), 3.17-3.48 (1H, m), 3.91-4.08 (1H, m), 4.10-4.21 (1H, m), 4.27-4.39 (1H, m), 4.78-5.01 (2H, m), 7.10-7.24 (2H, m), 7.27-7.32 (3H, m), 7.50 (1H, d, J=7.9 Hz), 8.22 (1H, dd, J=7.9, 1.5 Hz), 8.46-8.54 (1H, m).

Example 21

2-(((3R,4S))-1-acetyl-3-phenylpiperidin-4-yl)-6-(5-(trifluoromethyl)-1,2,4-oxadiazol-3-yl)isoindolin-1-one The title compound was obtained using the corresponding amine by a method similar to Example 20.

Example 22

2-((3S,4R)-3-phenylpiperidin-4-yl)-6-(5-(trifluoromethyl)-1,2,4-oxadiazol-3-yl)isoindolin-1-one hydrochloride To a mixture of tert-butyl (3S,4R)-4-(1-oxo-6-(5-(trifluoromethyl)-1,2,4-oxadiazol-3-yl)-1,3-dihydro-2H-isoindol- 2-yl)-3-phenylpiperidine-1-carboxylate (110 mg) and methanol (5 ml) was added 4 M hydrogen chloride-CPME solution (1 ml), and the mixture was stirred overnight at room temperature. The reaction mixture was concentrated under reduced pressure to give the title compound (95 mg).

$^1$H NMR (300 MHz, DMSO-d$_6$) δ 2.11-2.33 (2H, m), 3.33-3.41 (1H, m), 3.38-3.68 (3H, m), 3.71-3.87 (1H, m), 4.25-4.54 (2H, m), 4.73-4.84 (1H, m), 7.10-7.27 (5H, m), 7.71 (1H, d, J=7.9 Hz), 8.13 (1H, d, J=1.1 Hz), 8.23 (1H, dd, J=7.9, 1.9 Hz), 8.98 (2H, brs).

Example 23

2-((3S,4R)-1-acetyl-3-phenylpiperidin-4-yl)-6-(5-(trifluoromethyl)-1,2,4-oxadiazol-3-yl)isoindolin-1-one To a mixture of 2-((3S,4R)-3-phenylpiperidin-4-yl)-6-(5-(trifluoromethyl)-1,2,4-oxadiazol-3-yl)isoindolin-1-one hydrochloride (45 mg), TEA (0.040 ml), 4,4-dimethylaminopyridine (3.6 mg) and THF (4 ml) was added acetic anhydride (0.018 ml) at 0° C., and the mixture was stirred at room temperature for 1 hr. To the reaction mixture was added water, and the mixture was extracted with ethyl acetate. The organic layer was washed with saturated brine, dried over anhydrous sodium sulfate, and concentrated under reduced pressure. The residue was purified by Diol (3-(2,3-dihydroxypropoxy)propylsilane-bonded silica gel) silica gel column chromatography (hexane/ethyl acetate), and the fraction was concentrated under reduced pressure to give the title compound (40 mg)

$^1$H NMR (300 MHz, CDCl$_3$) δ 1.76-1.91 (1H, m), 2.06-2.11 (3H, m), 2.18-2.27 (1H, m), 2.81-3.02 (2H, m), 3.49-3.61 (1H, m), 3.73 (1H, dd, J=13.8, 4.0 Hz), 3.94-4.06 (1H, m), 4.08-4.14 (1H, m), 4.74-4.85 (1H, m), 4.94-5.17 (1H, m), 7.04-7.25 (5H, m), 7.33 (1H, d, J=8.0 Hz), 8.17-8.28 (1H, m), 8.59-8.69 (1H, m).

Example 24

2-((1S)-2,3-dihydro-1H-inden-1-yl)-6-(5-(trifluoromethyl)-1,2,4-oxadiazol-3-yl)isoindolin-1-one A) methyl 2-methyl-5-(5-(trifluoromethyl)-1,2,4-oxadiazol-3-yl)benzoate The title compound was obtained using methyl 5-cyano-2-methylbenzoate by a method similar to Step D of Example 6.

$^1$H NMR (300 MHz, CDCl$_3$) δ 2.69 (3H, s), 3.95 (3H, s), 7.42 (1H, d, J=7.9 Hz), 8.13 (1H, dd, J=7.9, 1.9 Hz), 8.65 (1H, d, J=1.9 Hz).
Alternative Step
To a mixture of methyl 5-cyano-2-methylbenzoate (1.08 g) and methanol (20 ml) was added 50% aqueous hydroxylamine solution (1.89 ml), and the mixture was stirred overnight at room temperature. The reaction mixture was concentrated under reduced pressure, to the residue was added water, and the mixture was extracted with a mixture of ethyl acetate-THF. The organic layer was washed with saturated brine, dried over anhydrous sodium sulfate, and concentrated under reduced pressure. To a mixture of the obtained residue (250 mg) and THF (15 ml) was added trifluoroacetic anhydride (0.424 ml), and the mixture was stirred overnight at 50° C. under nitrogen atmosphere. The reaction mixture was concentrated under reduced pressure, water was added thereto, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate), and the fraction was concentrated under reduced pressure to give the title compound (228 mg)

B) methyl 2-(bromomethyl)-5-(5-(trifluoromethyl)-1,2,4-oxadiazol-3-yl)benzoate

The title compound was obtained using methyl 2-methyl-5-(5-(trifluoromethyl)-1,2,4-oxadiazol-3-yl)benzoate by a method similar to Step B of Example 6.

$^1$H NMR (300 MHz, CDCl$_3$) δ 4.00 (3H, s), 5.01 (2H, s), 7.66 (1H, d, J=7.9 Hz), 8.24 (1H, dd, J=7.9, 1.9 Hz), 8.71 (1H, d, J=1.9 Hz).
Alternative Step
A suspension of methyl 2-methyl-5-(5-(trifluoromethyl)-1,2,4-oxadiazol-3-yl)benzoate (2.91 g) in (trifluoromethyl)benzene (60 ml) were added N-bromosuccinimide (1.90 g) and 2,2'-azobis(isobutyronitrile) (0.167 g), and the mixture was stirred under nitrogen atmosphere at 80° C. for 2 hr. To the reaction mixture was added water at room temperature, and the organic layer was separated, washed with water and saturated brine, dried over anhydrous sodium sulfate, and concentrated under reduced pressure. The residue was purified by silica gel column chromatography (hexane/ethyl acetate) to give the title compound (3.62 g).

C) 2-((1S)-2,3-dihydro-1H-inden-1-yl)-6-(5-(trifluoromethyl)-1,2,4-oxadiazol-3-yl)isoindolin-1-one A mixture of methyl 2-(bromomethyl)-5-(5-(trifluoromethyl)-1,2,4-oxadiazol-3-yl)benzoate (50 mg), (S)-2,3-dihydro-1H-inden-1-amine (0.022 ml), DIEA (0.021 ml) and THF (3 ml) was stirred overnight at 50° C. under nitrogen atmosphere. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate), and the fraction was concentrated under reduced pressure. The obtained residue was crystallized from diethyl ether/hexane to give the title compound (24 mg).

Example 25

2-((1R)-2,3-dihydro-1H-inden-1-yl)-6-(5-(trifluoromethyl)-1,2,4-oxadiazol-3-yl)isoindolin-1-one The title compound was obtained by a method similar to Example 24.

Example 26 tert-butyl ((1R,2R)-2-(1-oxo-6-(5-(trifluoromethyl)-1,2,4-oxadiazol-3-yl)-1,3-dihydro-2H-isoindol-2-yl)cyclohexyl)carbamate A) tert-butyl ((1R,2R)-2-(6-cyano-1-oxo-1,3-dihydro-2H-isoindol-2-yl)cyclohexyl)carbamate To a mixture of methyl 2-(bromomethyl)-5-cyanobenzoate (200 mg), tert-butyl ((1R,2R)-2-aminocyclohexyl)carbamate (202 mg) and THF (15 ml) was added DIEA (0.165 ml) at room temperature, and the mixture was stirred overnight at 50° C. under nitrogen atmosphere. The reaction mixture was concentrated under reduced pressure. To the residue was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (230 mg).

MS (API+), found: 256.2 (M+1-Boc).

B) tert-butyl ((1R,2R)-2-(1-oxo-6-(5-(trifluoromethyl)-1,2,4-oxadiazol-3-yl)-1,3-dihydro-2H-isoindol-2-yl)cyclohexyl)carbamate To a mixture of tert-butyl ((1R,2R)-2-(6-cyano-1-oxo-1,3-dihydro-2H-isoindol-2-yl)cyclohexyl)carbamate (230 mg), methanol (3 ml) and ethanol (3 ml) was added 50% aqueous hydroxylamine solution (0.198 ml), and the mixture was stirred at 50° C. for 3 hr, and then overnight at room temperature, under nitrogen atmosphere e. The reaction mixture was concentrated under reduced pressure, to the residue was added water, and the mixture was extracted with ethyl acetate. The organic layer was washed with saturated brine, dried over anhydrous sodium sulfate, and concentrated under reduced pressure to give a residue. To a mixture of the obtained residue and THF (6 ml) was added trifluoroacetic anhydride (0.183 ml), and the mixture was stirred overnight at room temperature, and then at 50° C. for 2 hr, under nitrogen atmosphere. The reaction mixture was concentrated under reduced pressure, water was added thereto, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate), and the fraction was concentrated under reduced pressure to give the title compound (277 mg).

$^1$H NMR (300 MHz, CDCl$_3$) δ 1.07 (9H, s), 1.32-1.45 (2H, m), 1.58-1.71 (1H, m), 1.79-2.01 (4H, m), 2.03-2.17 (1H, m), 3.58-3.76 (1H, m), 4.08-4.21 (1H, m), 4.38 (1H, d, J=17.4 Hz), 4.55-4.68 (1H, m), 4.78 (1H, d, J=17.4 Hz), 7.62 (1H, d, J=8.7 Hz), 8.24-8.34 (1H, m), 8.59 (1H, s).

Example 27 tert-butyl ((1S,2S)-2-(1-oxo-6-(5-(trifluoromethyl)-1,2,4-oxadiazol-3-yl)-1,3-dihydro-2H-isoindol-2-yl)cyclohexyl)carbamate The title compound was obtained using the corresponding amine by a method similar to Example 26.

Example 28

2-((1R,2R)-2-aminocyclohexyl)-6-(5-(trifluoromethyl)-1,2,4-oxadiazol-3-yl)isoindolin-1-one hydrochloride To a mixture of tert-butyl ((1R,2R)-2-(1-oxo-6-(5-(trifluoromethyl)-1,2,4-oxadiazol-3-yl)-1,3-dihydro-2H-isoindol-2-yl)cyclohexyl)carbamate (272 mg) and methanol (6 ml) was added 4 M hydrogen chloride-CPME solution (3 ml), and the mixture was stirred at room temperature for 3 days. The reaction mixture was concentrated under reduced pressure to give the title compound (220 mg).

Example 29

2-((1S,2S)-2-aminocyclohexyl)-6-(5-(trifluoromethyl)-1,2,4-oxadiazol-3-yl)isoindolin-1-one hydrochloride The title compound was obtained using the corresponding amine by a method similar to Example 28.

Example 30 tert-butyl (3S,4S)-4-(1-oxo-6-(5-(trifluoromethyl)-1,2,4-oxadiazol-3-yl)-1,3-dihydro-2H-isoindol-2-yl)-3-phenylpiperidine-1-carboxylate A) (3S,4S)-1-(tert-butoxycarbonyl)-3-phenylpiperidine-4-carboxylic acid To (3S,4S)-1-(tert-butoxycarbonyl)-3-phenylpiperidine-4-carboxylic acid (1S)-1-phenylethanamine salt (3.05 g) were added ethyl acetate (100 ml) and 10% aqueous citric acid solution (100 ml), and the mixture was stirred. The organic layer was separated, washed with water and saturated brine, dried over anhydrous sodium sulfate, and concentrated under reduced pressure to give the title compound (2.18 g).

$^1$H NMR (300 MHz, CDCl$_3$) δ 1.45 (9H, s), 1.65-1.88 (1H, m), 1.94-2.08 (1H, m), 2.64-2.98 (4H, m), 4.06-4.37 (2H, m), 7.18-7.25 (3H, m), 7.27-7.33 (2H, m).

The 1H peak of COOH group was not observed.

B) tert-butyl (3S,4S)-4-(((benzyloxy)carbonyl)amino)-3-phenylpiperidine-1-carboxylate A mixture of (3S,4S)-1-(tert-butoxycarbonyl)-3-phenylpiperidine-4-carboxylic acid (1.0 g), TEA (0.502 ml), diphenylphosphoryl azide (0.774 ml) and toluene (25 ml) was refluxed under nitrogen atmosphere for 50 min, benzyl alcohol (0.409 ml) was added thereto, and the mixture was refluxed under nitrogen atmosphere for 5 hr. To the reaction mixture was added water, and the mixture was extracted with ethyl acetate. The organic layer was washed with saturated brine, dried over anhydrous sodium sulfate, and concentrated under reduced pressure. The obtained residue was diluted with toluene, and the mixture was purified by silica gel column chromatography (hexane/ethyl acetate), and concentrated under reduced pressure to give the title compound (1.02 g).

$^1$H NMR (300 MHz, CDCl$_3$) δ 1.46 (9H, s), 2.13-2.28 (1H, m), 2.47-2.62 (1H, m), 2.68-2.95 (2H, m), 3.86-4.00 (1H, m), 4.10-4.30 (2H, m), 4.40-4.54 (1H, m), 4.70 (1H, d, J=6.0 Hz), 4.95 (2H, s), 7.13-7.23 (5H, m), 7.28-7.38 (5H, m).

C) tert-butyl (3S,4S)-4-amino-3-phenylpiperidine-1-carboxylate

A mixture of tert-butyl (3S,4S)-4-(((benzyloxy)carbonyl)amino)-3-phenylpiperidine-1-carboxylate (1.02 g), methanol (25 ml) and 10% palladium-carbon (50% wet, 0.20 g) was stirred overnight at room temperature under hydrogen atmosphere. The insoluble substance was filtered off, and the filtrate was concentrated under reduced pressure to give the title compound (0.658 mg).

¹H NMR (300 MHz, CDCl₃) δ 1.46 (9H, s), 1.70-2.15 (4H, m), 2.33-2.47 (1H, m), 2.67-2.92 (2H, m), 3.00 (1H, td, J=10.8, 4.2 Hz), 4.02-4.31 (2H, m), 7.16-7.23 (2H, m), 7.28-7.37 (3H, m).

D) tert-butyl (3S,4S)-4-(6-cyano-1-oxo-1,3-dihydro-2H-isoindol-2-yl)-3-phenylpiperidine-1-carboxylate A mixture of methyl 2-(bromomethyl)-5-cyanobenzoate (147 mg), DIEA (0.121 ml), tert-butyl (3S,4S)-4-amino-3-phenylpiperidine-1-carboxylate (192 mg) and THF (10 ml) was stirred overnight at 50° C. under nitrogen atmosphere. The reaction mixture was concentrated under reduced pressure, to the residue was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (150 mg).
MS (API-), found: 416.2.

E) tert-butyl (3S,4S)-4-(1-oxo-6-(5-(trifluoromethyl)-1,2,4-oxadiazol-3-yl)-1,3-dihydro-2H-isoindol-2-yl)-3-phenylpiperidine-1-carboxylate To a mixture of tert-butyl ((3S,4S))-4-(6-cyano-1-oxo-1,3-dihydro-2H-isoindol-2-yl)-3-phenylpiperidine-1-carboxylate (150 mg), methanol (2 ml) and ethanol (2 ml) was added 50% aqueous hydroxylamine solution (0.110 ml), and the mixture was stirred under nitrogen atmosphere at 50° C. for 2 hr and 30 min. The reaction mixture was concentrated under reduced pressure, to the residue was added water, and the mixture was extracted with ethyl acetate. The organic layer was washed with saturated brine, dried over anhydrous sodium sulfate, and concentrated under reduced pressure to give a residue. To a mixture of the obtained residue and THF (5 ml) was added trifluoroacetic anhydride (0.125 ml), and the mixture was stirred overnight at 50° C. under nitrogen atmosphere. The reaction mixture was concentrated under reduced pressure, water was added thereto, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate), and the fraction was concentrated under reduced pressure to give the title compound (180 mg).
¹H NMR (300 MHz, CDCl₃) δ 1.50 (9H, s), 1.82-2.02 (2H, m), 2.75-2.92 (1H, m), 2.95-3.12 (2H, m), 4.12-4.42 (4H, m), 4.83 (1H, td, J=11.5, 4.2 Hz), 7.11-7.19 (1H, m), 7.21-7.26 (1H, m), 7.27-7.32 (3H, m), 7.49 (1H, d, J=7.9 Hz), 8.21 (1H, dd, J=7.9, 1.9 Hz), 8.50 (1H, d, J=0.8 Hz).

Example 31

2-(((3S,4S))-3-phenylpiperidin-4-yl)-6-(5-(trifluoromethyl)-1,2,4-oxadiazol-3-yl)isoindolin-1-one hydrochloride To a mixture of tert-butyl (3S,4S)-4-(1-oxo-6-(5-(trifluoromethyl)-1,2,4-oxadiazol-3-yl)-1,3-dihydro-2H-isoindol-2-yl)-3-phenylpiperidine-1-carboxylate (175 mg) and methanol (5 ml) was added 4 M hydrogen chloride-CPME solution (1.5 ml), and the mixture was stirred overnight at room temperature. The reaction mixture was concentrated under reduced pressure to give the title compound (143 mg).
¹H NMR (300 MHz, DMSO-d₆) δ 1.90-2.09 (1H, m), 2.16-2.39 (1H, m), 3.20-3.30 (2H, m), 3.36-3.59 (3H, m), 4.43 (2H, s), 4.66-4.83 (1H, m), 7.12-7.20 (1H, m), 7.20-7.29 (2H, m), 7.30-7.41 (2H, m), 7.78 (1H, d, J=7.9 Hz), 8.07-8.13 (1H, m), 8.22 (1H, dd, J=7.9, 1.5 Hz), 8.92 (1H, brs).
The 1H peak of HCl was not observed.

Example 32

N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide To a mixture of 2-((1R,2R)-2-aminocyclohexyl)-6-(5-(trifluoromethyl)-1,2,4-oxadiazol-3-yl)isoindolin-1-one hydrochloride (75 mg), TEA (0.078 ml), 4,4-dimethylaminopyridine (6.8 mg) and THF (5 ml) was added cyclopropanecarbonyl chloride (0.024 ml) at 0° C., and the mixture was stirred at room temperature for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate), and the fraction was concentrated under reduced pressure to give the title compound (76 mg).
¹H NMR (300 MHz, CDCl₃) δ 0.07-0.22 (1H, m), 0.32-0.45 (1H, m), 0.49-0.62 (1H, m), 0.68-0.81 (1H, m), 1.09-1.22 (1H, m), 1.34-1.52 (3H, m), 1.60-1.76 (1H, m), 1.79-2.01 (3H, m), 2.06-2.18 (1H, m), 3.98-4.11 (1H, m), 4.14-4.28 (1H, m), 4.37 (1H, d, J=17.4 Hz), 4.64 (1H, d, J=17.4 Hz), 5.80 (1H, d, J=9.5 Hz), 7.55-7.65 (1H, m), 8.29 (1H, dd, J=8.0, 1.5 Hz), 8.59 (1H, d, J=0.8 Hz).

Example 33

N-((1S,2S)-2-(1-oxo-6-(5-(trifluoromethyl)-1,2,4-oxadiazol-3-yl)-1,3-dihydro-2H-isoindol-2-yl)cyclohexyl)cyclopropanecarboxamide The title compound was obtained using the corresponding amine by a method similar to Example 32.

Example 34 trans-2-(3-phenyltetrahydro-2H-pyran-4-yl)-6-(5-(trifluoromethyl)-1,2,4-oxadiazol-3-yl)isoindolin-1-one A diastereomer mixture (140 mg) of trans-2-(3-phenyltetrahydro-2H-pyran-4-yl)-6-(5-(trifluoromethyl)-1,2,4-oxadiazol-3-yl)isoindolin-1-one was resolved by HPLC under the following condition to give the title compound (65.4 mg) having a shorter retention time.
column: CHIRALPAK IA (RC068), 4.6 mmID×250 mmL, manufactured by Daicel Chemical Industries,
mobile phase: hexane/ethanol=40/60 (v/v)
flow rate: 0.5 ml/min
temperature: 30° C.
detection: UV 220 nm
concentration: 0.5 mg/ml
injected amount: 0.010 ml
¹H NMR (300 MHz, CDCl₃) δ 1.90-2.16 (2H, m), 3.21 (1H, td, J=11.1, 4.2 Hz), 3.45 (1H, t, J=11.1 Hz), 3.73 (1H, td, J=11.6, 2.8 Hz), 4.07 (1H, dd, J=11.5, 4.3 Hz), 4.12-4.25 (2H, m), 4.36-4.48 (1H, m), 7.12-7.21 (1H, m), 7.12-7.22

(1H, m), 7.26-7.31 (4H, m), 7.51 (1H, d, J=7.9 Hz), 8.22 (1H, dd, J=7.9, 1.5 Hz), 8.51 (1H, d, J=0.8 Hz).

Example 35 trans-2-(3-phenyltetrahydro-2H-pyran-4-yl)-6-(5-(trifluoromethyl)-1,2,4-oxadiazol-3-yl)isoindolin-1-one A diastereomer mixture (140 mg) of trans-2-(3-phenyltetrahydro-2H-pyran-4-yl)-6-(5-(trifluoromethyl)-1,2,4-oxadiazol-3-yl)isoindolin-1-one was resolved by HPLC (column: CHIRALPAK IA (RC068), 4.6 mmID×250 mmL, manufactured by Daicel Chemical Industries, mobile phase: hexane/ethanol=40/60 (v/v)) to give the title compound (66.0 mg) having a longer retention time.

$^1$H NMR (300 MHz, CDCl$_3$) δ 1.91-2.16 (2H, m), 3.21 (1H, td, J=11.1, 4.5 Hz), 3.45 (1H, t, J=11.1 Hz), 3.73 (1H, td, J=11.6, 2.8 Hz), 4.06 (1H, dd, J=11.7, 3.8 Hz), 4.13-4.26 (1H, m), 4.13-4.26 (2H, m), 4.37-4.47 (1H, m), 7.12-7.21 (1H, m), 7.26-7.34 (4H, m), 7.51 (1H, d, J=8.3 Hz), 8.22 (1H, dd, J=7.9, 1.5 Hz), 8.51 (1H, d, J=0.8 Hz).

Example 36

1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide To a mixture of 2-((1R,2R)-2-aminocyclohexyl)-6-(5-(trifluoromethyl)-1,2,4-oxadiazol-3-yl)isoindolin-1-one hydrochloride (50 mg), TEA (0.052 ml), 4,4-dimethylaminopyridine (4.6 mg) and THF (3 ml) was added 1-methylcyclopropanecarbonyl chloride (30 mg) at 0° C., and the mixture was stirred overnight at room temperature. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate), and the fraction was concentrated under reduced pressure to give the title compound (55 mg).

$^1$H NMR (300 MHz, CDCl$_3$) δ 0.14-0.23 (1H, m), 0.31-0.43 (1H, m), 0.85-0.97 (1H, m), 1.17 (3H, s), 1.23-1.33 (1H, m), 1.37-1.50 (3H, m), 1.63-1.77 (1H, m), 1.78-2.04 (3H, m), 2.07-2.16 (1H, m), 3.95-4.09 (1H, m), 4.15-4.28 (1H, m), 4.32-4.42 (1H, m), 4.56-4.67 (1H, m), 5.95 (1H, d, J=9.1 Hz), 7.58-7.64 (1H, m), 8.29 (1H, dd, J=7.9, 1.5 Hz), 8.59 (1H, d, J=1.1 Hz).

Example 37

N-((1R,2R)-2-(1-oxo-6-(5-(trifluoromethyl)-1,2,4-oxadiazol-3-yl)-1,3-dihydro-2H-isoindol-2-yl)cyclohexyl)tetrahydro-2H-pyran-4-carboxamide To a mixture of 2-((1R,2R)-2-aminocyclohexyl)-6-(5-(trifluoromethyl)-1,2,4-oxadiazol-3-yl)isoindolin-1-one hydrochloride (50 mg), TEA (0.052 ml), 4,4-dimethylaminopyridine (4.6 mg) and THF (3 ml) was added tetrahydro-2H-pyran-4-carbonyl chloride (0.022 ml) at 0° C., and the mixture was stirred overnight at room temperature. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate), and the fraction was concentrated under reduced pressure to give the title compound (58 mg).

$^1$H NMR (300 MHz, CDCl$_3$) δ 1.28-1.56 (7H, m), 1.62-1.78 (1H, m), 1.82-2.01 (3H, m), 2.05-2.16 (2H, m), 3.15-3.33 (2H, m), 3.70-3.79 (1H, m), 3.82-3.90 (1H, m), 3.95-4.09 (1H, m), 4.14-4.27 (1H, m), 4.40 (1H, d, J=17.4 Hz), 4.67 (1H, d, J=17.4 Hz), 5.73 (1H, d, J=9.1 Hz), 7.62 (1H, d, J=8.7 Hz), 8.30 (1H, dd, J=8.1, 1.7 Hz), 8.55 (1H, s).

Example 38

6-(1-acetylpiperidin-4-yl)-3-(5-(trifluoromethyl)-1,2,4-oxadiazol-3-yl)-6,7-dihydro-5H-pyrrolo[3,4-b]pyridin-5-one A) 2-Bromoacrylic Aldehyde To a mixture of acrolein (100 g) and dichloromethane (1500 ml) was added dropwise bromine (96.3 ml) at −63° C., and TEA (658 ml) was added dropwise thereto. The reaction mixture was stirred at 0° C. for 1 hr, and acidified with 1 M aqueous citric acid solution (pH=4). The organic layer was separated, and the aqueous layer was extracted with dichloromethane. The organic layer were combined, washed with saturated brine, dried over anhydrous sodium sulfate, and concentrated under reduced pressure to give the title compound (112.6 g).

$^1$H NMR (400 MHz, CDCl$_3$) δ 7.18 (1H, d, J=2.5 Hz), 7.27 (1H, d, J=2.5 Hz), 9.32 (1H, s).

B) ethyl 5-bromo-2-methylnicotinate

To a mixture of 2-bromoacrylic aldehyde (220 g) and acetic acid (1500 ml) were added ammonium acetate (502.5 g) and ethyl 2-chloro-3-oxobutanoate (180 g) at room temperature, and the mixture was stirred for 48 hr. To the reaction mixture was added ice water (3000 ml), and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate), and the fraction was concentrated under reduced pressure to give the title compound (28.2 g).

$^1$H NMR (400 MHz, CDCl$_3$) δ 1.33 (3H, t, J=7.2 Hz), 2.66 (3H, s), 4.32 (2H, q, J=7.2 Hz), 8.29 (1H, d, J=2.0 Hz), 8.64 (1H, d, J=2.4 Hz).

C) ethyl 5-bromo-2-(bromomethyl)nicotinate

A mixture of ethyl 5-bromo-2-methylnicotinate (8.6 g), N-bromosuccinimide (6.27 g), 2,2'-azobis(isobutyronitrile) (0.579 g) and (trifluoromethyl)benzene (80 ml) was stirred under nitrogen atmosphere at 80° C. for 18 hr. The insoluble substance of the reaction mixture was filtered off, and the filtrate was concentrated under reduced pressure. The residue was purified by silica gel column chromatography (hexane/ethyl acetate) to give the title compound (4.2 g).

$^1$H NMR (400 MHz, DMSO-d$_6$) δ 1.33-1.37 (3H, m), 4.36 (2H, q, J =7.2 Hz), 4.94 (2H, s), 8.44 (1H, d, J=2.0 Hz), 8.90 (1H, d, J=2.4 Hz).

D) 6-(1-acetylpiperidin-4-yl)-3-(5-(trifluoromethyl)-1,2,4-oxadiazol-3-yl)-6,7-dihydro-5H-pyrrolo[3,4-b]pyridin-5-one The title compound was obtained using ethyl 5-bromo-2-(bromomethyl)nicotinate and the corresponding amine by a method similar to Examples 2, 3 and 4.

Examples 39-41

The compounds of Examples 39 to 41 were obtained using the corresponding amine by a method similar to Example 38.

Example 42

3-methyl-N-((1R,2R)-2-(1-oxo-6-(5-(trifluoromethyl)-1,2,4-oxadiazol-3-yl)-1,3-dihydro-2H-isoindol-2-yl)cyclohexyl)oxetane-3-carboxamide To a mixture of 2-((1R,2R)-2-aminocyclohexyl)-6-(5-(trifluoromethyl)-1,2,4-oxadiazol-3-yl)isoindolin-1-one hydrochloride (41 mg), TEA (0.043 ml), 3-methyloxetane-3-carboxylic acid (16.6 mg) and DMF (3 ml) was added HATU (61.9 mg) at 0° C., and the mixture was stirred at room temperature for 3 hr. To the reaction mixture was added water, and the mixture was extracted with ethyl acetate. The organic layer was washed with saturated aqueous sodium hydrogencarbonate solution and saturated brine, dried over anhydrous sodium sulfate, and concentrated under reduced pressure. The residue was purified by silica gel column chromatography (hexane/ethyl acetate) and Diol (3-(2,3-dihydroxypropoxy)propylsilane-bonded silica gel) silica gel column chromatography (hexane/ethyl acetate), and the fraction was concentrated under reduced pressure to give the title compound (33 mg).

$^1$H NMR (300 MHz, CDCl$_3$) δ 1.34 (3H, s), 1.38-1.57 (3H, m), 1.68-1.81 (1H, m), 1.81-2.05 (3H, m), 2.06-2.20 (1H, m), 3.99-4.16 (2H, m), 4.18-4.30 (2H, m), 4.36-4.51 (2H, m), 4.61-4.74 (2H, m), 5.95 (1H, d, J=9.1 Hz), 7.63 (1H, d, J=7.9 Hz), 8.31 (1H, dd, J=7.9, 1.5 Hz), 8.52-8.58 (1H, m).

Alternative Step

To a mixture of 2-((1R,2R)-2-aminocyclohexyl)-6-(5-(trifluoromethyl)-1,2,4-oxadiazol-3-yl)isoindolin-1-one hydrochloride (90 g), 3-methyloxetane-3-carboxylic acid (31.1 g), 4-(4,6-dimethoxy-1,3,5-triazin-2-yl)-4-methylmorpholin-4-ium (87 g), 2-propanol (360 ml) and water (180 ml) was added TEA (37.4 ml) at room temperature, and the mixture was stirred at room temperature for 4 hr. To the reaction mixture was added 4-(4,6-dimethoxy-1,3,5-triazin-2-yl)-4-methylmorpholin-4-ium (12.37 g), and the mixture was stirred at room temperature for 2 hr. To the reaction mixture was added water (360 ml), and the mixture was stirred overnight at room temperature. To the reaction mixture was added ethyl acetate, and the organic layer was washed with water and saturated brine, dried over anhydrous sodium sulfate, and concentrated under reduced pressure. The same procedure was repeated in another batch. The residues obtained from the two batches were combined, and purified by silica gel column chromatography (ethyl acetate), and the fraction was concentrated under reduced pressure. The residue was crystallized from ethyl acetate/heptane to give the title compound (179 g).

$^1$H NMR (300 MHz, DMSO-d$_6$) δ 1.14 (3H, s), 1.27-1.89 (8H, m), 3.78-4.15 (4H, m), 4.30 (1H, d, J=6.04 Hz), 4.43 (1H, d, J=5.67 Hz), 4.48-4.74 (2H, m), 7.83-7.89 (2H, m), 8.20 (1H, d, J=0.76 Hz), 8.26 (1H, dd, J=7.93, 1.51 Hz).

elemental analysis: Anal. for C$_{22}$H$_{23}$F$_3$N$_4$O$_4$ calculated value C, 56.89; H, 4.99; N, 12.06.

actual measured value C, 56.64; H, 4.88; N, 12.07.

Example 43

(3R,4R)-4-(1-oxo-6-(5-(trifluoromethyl)-1,2,4-oxadiazol-3-yl)-1,3-dihydro-2H-isoindol-2-yl)-3-phenylpiperidine-1-carboxamide To a mixture of 2-((3R,4R)-3-phenylpiperidin-4-yl)-6-(5-(trifluoromethyl)-1,2,4-oxadiazol-3-yl)isoindolin-1-one hydrochloride (45 mg), TEA (0.040 ml) and THF (1.5 ml) was added isocyanato(trimethyl)silane (0.026 ml) at 0° C., and the mixture was stirred at room temperature for 2 hr. To the reaction mixture was added methanol, and the mixture was concentrated under reduced pressure. To the residue was added water, and the mixture was extracted with ethyl acetate. The organic layer was washed with saturated brine, dried over anhydrous sodium sulfate, and concentrated under reduced pressure. The obtained residue was crystallized from ethyl acetate/diisopropyl ether to give the title compound (34.7 mg).

$^1$H NMR (300 MHz, CDCl$_3$) δ 1.84-2.09 (2H, m), 2.88-3.00 (1H, m), 3.05-3.24 (2H, m), 4.08-4.23 (3H, m), 4.30-4.40 (1H, m), 4.45-4.57 (2H, m), 4.88 (1H, td, J=11.3, 4.5 Hz), 7.13-7.20 (1H, m), 7.26-7.32 (4H, m), 7.50 (1H, d, J=7.9 Hz), 8.21 (1H, dd, J=7.9, 1.5 Hz), 8.50 (1H, d, J=1.5 Hz).

Example 44

(3R,4R)—N-ethyl-4-(1-oxo-6-(5-(trifluoromethyl)-1,2,4-oxadiazol-3-yl)-1,3-dihydro-2H-isoindol-2-yl)-3-phenylpiperidine-1-carboxamide To a mixture of 2-((3R,4R)-3-phenylpiperidin-4-yl)-6-(5-(trifluoromethyl)-1,2,4-oxadiazol-3-yl)isoindolin-1-one hydrochloride (45 mg), TEA (0.040 ml) and THF (1.5 ml) was added isocyanatoethane (0.015 ml) at 0° C., and the mixture was stirred at room temperature for 1 hr. To the reaction mixture was added water, and the mixture was extracted with ethyl acetate. The organic layer was washed with saturated brine, dried over anhydrous sodium sulfate, and concentrated under reduced pressure. The obtained residue was crystallized from ethyl acetate/hexane to give the title compound (40.4 mg).

$^1$H NMR (300 MHz, CDCl$_3$) δ 1.17 (3H, t, J=7.4 Hz), 1.82-2.07 (2H, m), 2.88 (1H, dd, J=13.2, 11.3 Hz), 3.02-3.17 (2H, m), 3.27-3.38 (2H, m), 4.08-4.21 (3H, m), 4.30-4.40 (1H, m), 4.46 (1H, t, J=5.1 Hz), 4.86 (1H, td, J=11.5, 4.2 Hz), 7.12-7.20 (1H, m), 7.26-7.34 (4H, m), 7.49 (1H, d, J=7.9 Hz), 8.21 (1H, dd, J=7.9, 1.5 Hz), 8.50 (1H, s).

Examples 45-58

The compound obtained using the corresponding amine by a method similar to Step C of Example 24 was diluted with ethyl acetate, 4 M hydrogen chloride-CPME solution was added thereto, and the mixture was stirred overnight. To the reaction mixture was added hexane, and the resulting solid was collected by filtration, and washed with hexane to give the compounds of Examples 45 to 58.

Examples 59-66

The compounds of Examples 59 to 66 were obtained using the corresponding amine by a method similar to Step C of Example 24.

Examples 67-70

The compounds of Examples 67 to 70 were obtained using the corresponding amine and acid chloride by a method similar to Example 38.

Example 71

The compound of Example 71 was obtained using methyl 2-(bromomethyl)-5-cyanobenzoate and tert-butyl 3-amino-4-phenylpiperidine-1-carboxylate by a method similar to Example 13.

Example 72

The compound of Example 72 was obtained using the compound obtained in Example 71 by a method similar to Example 15.

Example 73

The compound of Example 73 was obtained using the compound obtained in Example 72 by a method similar to Example 20.

Examples 74-77

The compounds of Examples 74 to 77 were obtained using the corresponding amine by a method similar to Example 38.

Example 78

The compound of Example 78 was obtained using methyl 2-(bromomethyl)-5-cyanobenzoate and tert-butyl 4-amino-3-phenylpiperidine-1-carboxylate by a method similar to Example 13.

$^1$H NMR (300 MHz, CDCl$_3$) δ 1.50 (9H, s), 1.76-2.03 (2H, m), 2.72-2.91 (1H, m), 3.05 (2H, td, J=11.3, 4.2 Hz), 4.12-4.22 (1H, m), 4.24-4.46 (3H, m), 4.81 (1H, td, J=11.6, 4.3 Hz), 7.11-7.19 (1H, m), 7.20-7.32 (4H, m), 7.88 (1H, d, J=7.9 Hz), 8.09 (1H, s), 8.16 (1H, dd, J=7.9, 1.1 Hz).

Example 79

The compound of Example 79 was obtained using the compound obtained in Example 78 by a method similar to Example 15.

Example 80

The compound of Example 80 was obtained using the compound obtained in Example 79 by a method similar to Example 20.

Example 81 tert-butyl ((3S,4R)-4-(1-oxo-6-(5-(trifluoromethyl)-1,2,4-oxadiazol-3-yl)-1,3-dihydro-2H-isoindol-2-yl)tetrahydro-2H-pyran-3-yl)carbamate

A) ethyl 5-(((1R)-1-phenylethyl)amino)-3,6-dihydro-2H-pyran-4-carboxylate

A mixture of ethyl 5-hydroxy-3,6-dihydro-2H-pyran-4-carboxylate (10 g), (1R)-1-phenylethanamine (8.13 ml), tris(trifluoromethanesulfonato)ytterbium (III) (1.80 g) and toluene (100 ml) was heated under reflux using Dean-Stark apparatus for 1 hr. The insoluble substance was filtered off, and the filtrate was concentrated under reduced pressure. The residue was purified by silica gel column chromatography (hexane/ethyl acetate) to give the title compound (13.7 g).

$^1$H NMR (300 MHz, CDCl$_3$) δ 1.27-1.33 (3H, m), 1.48 (3H, d, J=6.8 Hz), 2.34 (2H, t, J=5.7 Hz), 3.54-3.75 (2H, m), 3.91 (1H, d, J=15.9 Hz), 4.14-4.22 (2H, m), 4.31 (1H, d, J=15.9 Hz), 4.35-4.47 (1H, m), 7.19-7.26 (3H, m), 7.28-7.37 (2H, m), 8.97 (1H, d, J=7.2 Hz).

B) ethyl (3S,4S)-3-(((1R)-1-phenylethyl)amino)tetrahydro-2H-pyran-4-carboxylate A mixture of ethyl 5-(((1R)-1-phenylethyl)amino)-3,6-dihydro-2H-pyran-4-carboxylate (10.24 g), acetic acid (3.08 ml), platinum(IV) oxide (1.098 g), ethanol (280 ml) and THF (20 ml) was stirred for 10 min at room temperature, and then overnight at 35° C., under hydrogen atmosphere. The insoluble substance was filtered off, to the filtrate was added platinum(IV) oxide (1.098 g), and the mixture was stirred for 10 min at room temperature, and then overnight at 35° C., under hydrogen atmosphere. The insoluble substance was filtered off, the filtrate was concentrated under reduced pressure, and the obtained residue was purified by silica gel column chromatography (hexane/ethyl acetate) to give the title compound (5.42 g).

$^1$H NMR (300 MHz, CDCl$_3$) δ 1.25-1.35 (6H, m), 1.60-1.72 (1H, m), 1.94-2.04 (1H, m), 2.69 (1H, dt, J=10.6, 4.3 Hz), 3.00-3.09 (1H, m), 3.30-3.44 (2H, m), 3.62 (1H, dd, J=11.5, 4.0 Hz), 3.75-3.81 (1H, m), 3.82-3.92 (1H, m), 4.16-4.27 (2H, m), 7.18-7.25 (1H, m), 7.27-7.33 (4H, m).

C) ethyl (3S,4R)-3-(((1R)-1-phenylethyl)amino)tetrahydro-2H-pyran-4-carboxylate To a mixture of ethyl (3S,4S)-3-(((1R)-1-phenylethyl)amino)tetrahydro-2H-pyran-4-carboxylate (2.2 g) and ethanol (54 ml) was added 20% sodium ethoxide-ethanol solution (6.22 ml), and the mixture was stirred under nitrogen atmosphere at 65° C. for 3.5 hr. The reaction mixture was acidified with 2 M hydrogen chloride-ethanol solution (9.91 ml) so at 0° C. (pH=3 to 4), and concentrated under reduced pressure. To the residue was added saturated aqueous sodium hydrogencarbonate solution, and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (1.334 g).

$^1$H NMR (300 MHz, CDCl$_3$) δ 1.26-1.35 (6H, m), 1.78-1.89 (2H, m), 2.29-2.44 (1H, m), 2.83-2.95 (2H, m), 3.23-3.35 (1H, m), 3.62-3.74 (1H, m), 3.76-3.89 (2H, m), 4.08-4.26 (2H, m), 7.18-7.25 (1H, m), 7.27-7.33 (4H, m).

D) ethyl (3S,4R)-3-((tert-butoxycarbonyl)amino)tetrahydro-2H-pyran-4-carboxylate A mixture of ethyl (3S,4R)-3-(((1R)-1-phenylethyl)amino)tetrahydro-2H-pyran-4-carboxylate (1.334 g), 20% palladium hydroxide-carbon (50% wet, 0.204 g) and ethanol (35 ml) was stirred overnight at room temperature under hydrogen atmosphere. The insoluble substance was filtered off, and the filtrate was concentrated under reduced pressure. To a mixture of the obtained residue and THF (25 ml) were added TEA (2.021 ml) and di-tert-butyl dicarbonate (1.346 ml) at 0° C., and the mixture was stirred at room temperature for 3 hr. The reaction mixture was concentrated under reduced pressure, water was added thereto, and the mixture was extracted with ethyl acetate. The organic layer was washed with saturated aqueous ammonium chloride solution and saturated brine, dried over anhydrous sodium sulfate, purified by silica gel column chromatography (ethyl acetate), and concentrated under reduced pressure to give the title compound (1.32 g).

$^1$H NMR (300 MHz, CDCl$_3$) δ 1.23-1.30 (3H, m), 1.43 (9H, s), 1.84-2.00 (2H, m), 2.51-2.69 (1H, m), 3.21-3.34 (1H, m), 3.37-3.56 (1H, m), 3.77-3.99 (3H, m), 4.09-4.23 (2H, m), 4.76 (1H, brs).

E) (3S,4R)-3-((tert-butoxycarbonyl)amino)tetrahydro-2H-pyran-4-carboxylic acid

To a mixture of ethyl (3S,4R)-3-((tert-butoxycarbonyl) amino)tetrahydro-2H-pyran-4-carboxylate (1.32 g), THF (15 ml) and ethanol (15 ml) was added 2 M aqueous sodium hydroxide solution (15 ml), and the mixture was stirred at room temperature for 1 hr. The reaction mixture was concentrated under reduced pressure, the residue was diluted with water. The aqueous layer was washed with diethyl ether, and acidified with 2 M hydrochloric acid, and the mixture was extracted with ethyl acetate. The organic layer was washed with saturated brine, dried over anhydrous sodium sulfate, and concentrated under reduced pressure to give the title compound (0.876 g).

$^1$H NMR (300 MHz, CDCl$_3$) δ 1.45 (9H, s), 2.60-4.11 (8H, m), 4.73-5.87 (1H, m).

F) benzyl tert-butyl (3S,4R)-tetrahydro-2H-pyran-3,4-diylbiscarbamate

A mixture of (3S,4R)-3-((tert-butoxycarbonyl)amino)tetrahydro-2H-pyran-4-carboxylic acid (876 mg), diphenylphosphoryl azide (0.921 ml), TEA (0.597 ml) and toluene (12 ml) was stirred at room temperature for 2 hr under nitrogen atmosphere. To the reaction mixture was added benzyl alcohol (1.857 ml), and the mixture was stirred under nitrogen atmosphere at 80° C. for 3 hr. To the reaction mixture was added water at room temperature, and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (727 mg).

$^1$H NMR (300 MHz, CDCl$_3$) δ 1.31-1.49 (9H, m), 1.97-2.13 (1H, m), 2.98-3.14 (1H, m), 3.31-3.66 (3H, m), 3.85-4.12 (2H, m), 4.45-4.77 (1H, m), 4.99-5.21 (2H, m), 7.27-7.42 (5H, m).

G) tert-butyl ((3S,4R)-4-(1-oxo-6-(5-(trifluoromethyl)-1,2,4-oxadiazol-3-yl)-1,3-dihydro-2H-isoindol-2-yl)tetrahydro-2H-pyran-3-yl)carbamate A mixture of benzyl tert-butyl (3S,4R)-tetrahydro-2H-pyran-3,4-diylbiscarbamate (197 mg), ethanol (10 ml) and 10% palladium-carbon (50% wet, 29.9 mg) was stirred overnight at room temperature under hydrogen atmosphere. The insoluble substance was filtered off, and the filtrate was concentrated under reduced pressure. To a mixture of the obtained residue and THF (10 ml) were added methyl 2-(bromomethyl)-5-(5-(trifluoromethyl)-1,2,4-oxadiazol-3-yl)benzoate (203 mg) and DIEA (0.116 ml), and the mixture was stirred overnight at 60° C. under nitrogen atmosphere. The reaction mixture was concentrated under reduced pressure, water was added thereto, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (175 mg).

$^1$H NMR (300 MHz, CDCl$_3$) δ 1.14 (9H, s), 1.82-2.13 (2H, m), 3.20 (1H, t, J=10.8 Hz), 3.54 (1H, td, J=11.7, 2.3 Hz), 3.82-3.99 (1H, m), 4.12 (2H, td, J=12.2, 4.3 Hz), 4.28-4.61 (3H, m), 4.74 (1H, d, J=17.4 Hz), 7.65 (1H, d, J=7.9 Hz), 8.31 (1H, dd, J=7.9, 1.5 Hz), 8.61 (1H, s).

Example 82

N-((3S,4R)-4-(1-oxo-6-(5-(trifluoromethyl)-1,2,4-oxadiazol-3-yl)-1,3-dihydro-2H-isoindol-2-yl)tetrahydro-2H-pyran-3-yl)cyclopropanecarboxamide A) 2-((3S,4R)-3-aminotetrahydro-2H-pyran-4-yl)-6-(5-(trifluoromethyl)-1,2,4-oxadiazol-3-yl)isoindolin-1-one hydrochloride To a mixture of tert-butyl ((3S,4R)-4-(1-oxo-6-(5-(trifluoromethyl)-1,2,4-oxadiazol-3-yl)-1,3-dihydro-2H-isoindol-2-yl)tetrahydro-2H-pyran-3-yl)carbamate (170 mg) and methanol (6 ml) was added 4 M hydrogen chloride-CPME solution (2 ml), and the mixture was stirred overnight at room temperature. The reaction mixture was concentrated under reduced pressure to give the title compound (146 mg).

MS (API+), found: 369.0.

B) N-((3S,4R)-4-(1-oxo-6-(5-(trifluoromethyl)-1,2,4-oxadiazol-3-yl)-1,3-dihydro-2H-isoindol-2-yl) tetrahydro-2H-pyran-3-yl)cyclopropanecarboxamide To a mixture of 2-((3S,4R)-3-aminotetrahydro-2H-pyran-4-yl)-6-(5-(trifluoromethyl)-1,2,4-oxadiazol-3-yl)isoindolin-1-one hydrochloride (35 mg), TEA (0.036 ml), 4,4-dimethylaminopyridine (3.2 mg) and THF (2 ml) was added cyclopropanecarbonyl chloride (0.011 ml) at 0° C., and the mixture was stirred at room temperature for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate), and the fraction was concentrated under reduced pressure to give the title compound (35 mg).

$^1$H NMR (300 MHz, CDCl$_3$) δ 0.34-0.56 (2H, m), 0.58-0.70 (1H, m), 0.74-0.86 (1H, m), 1.17-1.26 (1H, m), 1.86-1.97 (1H, m), 1.99-2.16 (1H, m), 3.23 (1H, t, J=10.4 Hz), 3.56 (1H, td, J=11.7, 2.3 Hz), 4.07-4.33 (3H, m), 4.38-4.53 (2H, m), 4.57-4.69 (1H, m), 5.91 (1H, d, J=8.3 Hz), 7.64 (1H, d, J=7.6 Hz), 8.33 (1H, dd, J=7.9, 1.5 Hz), 8.58-8.63 (1H, m).

Example 83

3-methyl-N-((3S,4R)-4-(1-oxo-6-(5-(trifluoromethyl)-1,2,4-oxadiazol-3-yl)-1,3-dihydro-2H-isoindol-2-yl)tetrahydro-2H-pyran-3-yl)oxetane-3-carboxamide To a mixture of 2-((3S,4R)-3-aminotetrahydro-2H-pyran-4-yl)-6-(5-(trifluoromethyl)-1,2,4-oxadiazol-3-yl)isoindolin-1-one hydrochloride (35 mg), TEA (0.036 ml), 3-methyloxetane-3-carboxylic acid (14 mg) and DMF (2 ml) was added HATU (52.6 mg) at 0° C., and the mixture was stirred at room temperature for 1 hr. To the reaction mixture was added water, and the mixture was extracted with ethyl acetate. The organic layer was washed with saturated aqueous sodium hydrogencarbonate solution and saturated brine, dried over anhydrous sodium sulfate, and concentrated under reduced pressure. The residue was purified by Diol (3-(2,3-dihydroxypropoxy)propylsilane-bonded silica gel) silica gel column chromatography (hexane/ethyl acetate) to give the title compound (35 mg).

$^1$H NMR (300 MHz, CDCl$_3$) δ 1.39 (3H, s), 1.89-2.01 (1H, m), 2.04-2.20 (1H, m), 3.17-3.31 (1H, m), 3.50-3.64 (1H, m), 4.09-4.31 (5H, m), 4.40-4.72 (5H, m), 6.11 (1H, d, J=7.9 Hz), 7.66 (1H, d, J=7.9 Hz), 8.34 (1H, dd, J=7.9, 1.5 Hz), 8.54-8.61 (1H, m).

Example 84

N-((1R,2R)-2-(5-oxo-3-(5-(trifluoromethyl)-1,2,4-oxadiazol-3-yl)-5,7-dihydro-6H-pyrrolo[3,4-b]pyridin-6-yl)cyclohexyl)cyclopropanecarboxamide A) methyl 5-cyano-2-methylnicotinate A mixture of methyl 5-bromo-2-methylnicotinate (3.33 g), copper(I) cyanide (1.945 g) and DMF (15 ml) was stirred overnight at 150° C. under nitrogen atmosphere. To the reaction mixture was added ethyl acetate, and the mixture was filtered through Celite. To the filtrate was added saturated aqueous ammonium chloride solution, and the mixture was stirred for 30 min. The reaction mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (980 mg).

$^1$H NMR (300 MHz, CDCl$_3$) δ 2.92 (3H, s), 3.97 (3H, s), 8.47 (1H, d, J=2.3 Hz), 8.87 (1H, d, J=2.3 Hz).

B) methyl 5-(N'-hydroxycarbamimidoyl)-2-methylnicotinate

To a mixture of methyl 5-cyano-2-methylnicotinate (980 mg) and methanol (20 mL) was added 50% aqueous hydroxylamine solution (1.704 ml), and the mixture was stirred under nitrogen atmosphere at room temperature for 5 hr. The solvent was evaporated under reduced pressure, to the residue was added toluene, and the solvent was evaporated under reduced pressure to give the title compound. This compound was used in Step C without purification.

C) methyl 2-methyl-5-(5-(trifluoromethyl)-1,2,4-oxadiazol-3-yl)nicotinate

To a mixture of methyl 5-(N'-hydroxycarbamimidoyl)-2-methylnicotinate and THF (56 mL) was added trifluoroacetic anhydride (2.336 g), and the mixture was stirred overnight at 50° C. under nitrogen atmosphere. Trifluoroacetic anhydride (0.584 g) was added thereto, and the mixture was stirred for 4 hr. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (1.440 g).

$^1$H NMR (300 MHz, CDCl$_3$) δ 3.00 (3H, s), 4.01 (3H, s), 9.01 (1H, d, J=1.9 Hz), 9.40 (1H, d, J=1.9 Hz).

D) methyl 2-(bromomethyl)-5-(5-(trifluoromethyl)-1,2,4-oxadiazol-3-yl)nicotinate A mixture of methyl 2-methyl-5-(5-(trifluoromethyl)-1,2,4-oxadiazol-3-yl)nicotinate (300 mg), 1-bromopyrrolidine-2,5-dione (195 mg), 2,2'-azobis(isobutyronitrile) (17.15 mg) and (trifluoromethyl)benzene (10 mL) was stirred under nitrogen atmosphere at 80° C. for 3 hr. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (103.9 mg).

$^1$H NMR (300 MHz, CDCl$_3$) δ 4.04 (3H, s), 5.10 (2H, s), 8.96 (1H, d, J=1.9 Hz), 9.40 (1H, d, J=2.3 Hz).

E) tert-butyl ((1R,2R)-2-(5-oxo-3-(5-(trifluoromethyl)-1,2,4-oxadiazol-3-yl)-5,7-dihydro-6H-pyrrolo[3,4-b]pyridin-6-yl)cyclohexyl)carbamate A mixture of methyl 2-(bromomethyl)-5-(5-(trifluoromethyl)-1,2,4-oxadiazol-3-yl)nicotinate (103.9 mg), tert-butyl ((1R,2R)-2-aminocyclohexyl)carbamate (66.9 mg), DIEA (44.0 mg) and N,N-dimethylacetamide (1.4 mL) was heated under microwave irradiation at 100° C. for 2 hr. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (27.2 mg).

$^1$H NMR (300 MHz, CDCl$_3$) δ 1.09 (9H, s), 1.33-1.49 (3H, m), 1.61-1.76 (1H, m), 1.81-2.00 (3H, m), 2.07-2.17 (1H, m), 3.57-3.77 (1H, m), 4.19 (1H, td, J=11.3, 3.4 Hz), 4.45 (1H, d, J=18.1 Hz), 4.59 (1H, d, J=9.8 Hz), 4.89 (1H, d, J=18.1 Hz), 8.79 (1H, d, J=1.9 Hz), 9.45 (1H, d, J=1.9 Hz).

F) 6-((1R,2R)-2-aminocyclohexyl)-3-(5-(trifluoromethyl)-1,2,4-oxadiazol-3-yl)-6,7-dihydro-5H-pyrrolo[3,4-b]pyridin-5-one hydrochloride To a mixture of tert-butyl ((1R,2R)-2-(5-oxo-3-(5-(trifluoromethyl)-1,2,4-oxadiazol-3-yl)-5,7-dihydro-6H-pyrrolo[3,4-b]pyridin-6-yl)cyclohexyl)carbamate (27.2 mg) and methanol (1.0 mL) was added 4 M hydrogen chloride-CPME solution (0.25 mL), and the mixture was stirred overnight at room temperature. The solvent was evaporated under reduced pressure, and the residue was dried under reduced pressure to give the title compound. This compound was used in Step G without purification.

G) N-((1R,2R)-2-(5-oxo-3-(5-(trifluoromethyl)-1,2,4-oxadiazol-3-yl)-5,7-dihydro-6H-pyrrolo[3,4-b]pyridin-6-yl)cyclohexyl)cyclopropanecarboxamide A mixture of 6-((1R,2R)-2-aminocyclohexyl)-3-(5-(trifluoromethyl)-1,2,4-oxadiazol-3-yl)-6,7-dihydro-5H-pyrrolo[3,4-b]pyridin-5-one hydrochloride (24.2 mg), cyclopropanecarbonyl chloride (9.4 mg), TEA (18.19 mg) and THF (0.3 mL) was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (8.6 mg).

$^1$H NMR (300 MHz, CDCl$_3$) δ 0.14-0.28 (1H, m), 0.36-0.50 (1H, m), 0.53-0.65 (1H, m), 0.69-0.82 (1H, m), 1.11-1.24 (1H, m), 1.37-1.54 (3H, m), 1.62-1.78 (1H, m), 1.82-2.02 (3H, m), 2.08-2.22 (1H, m), 3.96-4.15 (1H, m), 4.19-4.33 (1H, m), 4.44 (1H, d, J=18.1 Hz), 4.76 (1H, d, J=18.5 Hz), 5.84 (1H, d, J=9.4 Hz), 8.78 (1H, s), 9.47 (1H, brs).

Example 85 tert-butyl ((1S,2R)-2-(1-oxo-6-(5-(trifluoromethyl)-1,2,4-oxadiazol-3-yl)-1,3-dihydro-2H-isoindol-2-yl)cyclohexyl)carbamate A) tert-butyl ((1S,2R)-2-(6-cyano-1-oxo-1,3-dihydro-2H-isoindol-2-yl)cyclohexyl)carbamate A mixture of methyl 2-(bromomethyl)-5-cyanobenzoate (226 mg), tert-butyl ((1S,2R)-2-aminocyclohexyl)carbamate (229 mg) and THF (10 ml) was stirred overnight at room temperature under nitrogen atmosphere. To the reaction mixture was added DIEA (0.186 ml), and the mixture was stirred overnight at room temperature, and then overnight at 50° C., under nitrogen atmosphere. The reaction mixture was concentrated under reduced pressure, to the residue was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (205 mg).

MS (API–), found: 354.1.

B) tert-butyl ((1S,2R)-2-(1-oxo-6-(5-(trifluoromethyl)-1,2,4-oxadiazol-3-yl)-1,3-dihydro-2H-isoindol-2-yl)cyclohexyl)carbamate To a mixture of tert-butyl ((1S,2R)-2-(6-cyano-1-oxo-1,3-dihydro-2H-isoindol-2-yl)cyclohexyl)carbamate (205 mg), methanol (3 ml) and ethanol (3 ml) was added 50% aqueous hydroxylamine solution (0.177 ml), and the mixture was stirred at 50° C. for 3 hr, and then overnight at room temperature, under nitrogen atmosphere. The reaction mixture was concentrated under reduced pressure, to the residue was added water, and the mixture was extracted with ethyl acetate. The organic layer was washed with saturated brine, dried over anhydrous sodium sulfate, and concentrated under reduced pressure to give a residue. To a mixture of the obtained residue and THF (6 ml) was added trifluoroacetic anhydride (0.162 ml), and the mixture was stirred overnight at 50° C. under nitrogen atmosphere. The reaction mixture was concentrated under reduced pressure, water was added thereto, and the mixture was extracted with ethyl acetate. The organic layer was washed with saturated brine, dried over anhydrous sodium sulfate, and concentrated under reduced pressure. The residue was washed with diisopropyl ether to give the title compound (90 mg). The mother liquor was concentrated, and the residue was purified by silica gel column chromatography (hexane/ethyl acetate) to give the title compound (110 mg).

$^1$H NMR (300 MHz, CDCl$_3$) δ 0.81-1.36 (1 0H, m), 1.38-1.52 (1H, m), 1.62-1.75 (1H, m), 1.76-2.02 (5H, m), 4.22-4.40 (2H, m), 4.44-5.17 (3H, m), 7.47-7.64 (1H, m), 8.19-8.35 (1H, m), 8.63 (1H, S).

Example 86

N-((1S,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide To a mixture of 2-((1R,2S)-2-aminocyclohexyl)-6-(5-(trifluoromethyl)-1,2,4-oxadiazol-3-yl)isoindolin-1-one hydrochloride (35 mg) (obtained using tert-butyl ((1S,2R)-2-(1-oxo-6-(5-(trifluoromethyl)-1,2,4-oxadiazol-3-yl)-1,3-dihydro-2H-isoindol-2-yl)cyclohexyl)carbamate by a method similar to Step F of Example 84), TEA (0.036 ml), 4,4-dimethylaminopyridine (3.2 mg) and THF (2 ml) was added cyclopropanecarbonyl chloride (0.011 ml) at 0° C., and the mixture was stirred at room temperature for 30 min. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate), and the fraction was concentrated under reduced pressure to give the title compound (33.4 mg).

$^1$H NMR (300 MHz, CDCl$_3$) δ 0.58-0.80 (3H, m), 0.85-0.96 (1H, m), 1.38-1.44 (1H, m), 1.45-1.53 (2H, m), 1.60-1.72 (2H, m), 1.83-2.09 (3H, m), 2.39-2.58 (1H, m), 3.94 (1H, dt, J=12.6, 3.7 Hz), 4.44-4.55 (2H, m), 4.56-4.65 (1H, m), 7.00 (1H, d, J=7.2 Hz), 7.54-7.62 (1H, m), 8.29 (1H, dd, J=7.9, 1.5 Hz), 8.59 (1H, d, J=1.5 Hz).

Example 87

N-((1R,2R)-4,4-difluoro-2-(1-oxo-6-(5-(trifluoromethyl)-1,2,4-oxadiazol-3-yl)-1,3-dihydro-2H-isoindol-2-yl)cyclohexyl)-3-methyloxetane-3-carboxamide A) ethyl (1R,2R)-2-((tert-butoxycarbonyl)amino)-5,5-difluorocyclohexanecarboxylate A mixture of ethyl (1R,2R)-2-(((benzyloxy)carbonyl)amino)-5,5-difluorocyclohexanecarboxylate (184 mg), ethanol (10 ml) and 10% palladium-carbon (50% wet, 28.7 mg) was stirred overnight at room temperature under hydrogen atmosphere. The insoluble substance was filtered off, and the filtrate was concentrated under reduced pressure. To a mixture of the obtained residue and THF (4 ml) were added TEA (0.226 ml) and di-tert-butyl dicarbonate (0.151 ml) at 0° C., and the mixture was stirred at room temperature for 3 days. The reaction mixture was concentrated under reduced pressure, to the residue was added water, and the mixture was extracted with ethyl acetate. The organic layer was washed with saturated brine, dried over anhydrous sodium sulfate, and concentrated under reduced pressure to give the title compound (166 mg).

$^1$H NMR (300 MHz, CDCl$_3$) δ 1.27 (3H, t, J=6.9 Hz), 1.42 (9H, s), 1.70-2.37 (6H, m), 2.51-2.69 (1H, m), 3.65-3.89 (1H, m), 4.16 (2H, q, J=6.9 Hz), 4.39-4.70 (1H, m).

B) tert-butyl ((1R,2R)-4,4-difluoro-2-(1-oxo-6-(5-(trifluoromethyl)-1,2,4-oxadiazol-3-yl)-1,3-dihydro-2H-isoindol-2-yl)cyclohexyl)carbamate To a mixture of ethyl (1R,2R)-2-((tert-butoxycarbonyl)amino)-5,5-difluorocyclohexanecarboxylate (166 mg), THF (3 ml) and ethanol (3 ml) was added 1 M aqueous sodium hydroxide solution (3 ml), and the mixture was stirred overnight at room temperature. The reaction mixture was diluted with water, and acidified with 1 M hydrochloric acid, and the mixture was extracted with ethyl acetate. The organic layer was washed with saturated brine, dried over anhydrous sodium sulfate, and concentrated under reduced pressure. To a mixture of the obtained residue and toluene (1.8 ml) were added diphenylphosphoryl azide (0.231 ml) and TEA (0.150 ml), and the mixture was stirred at room temperature for 2 hr under nitrogen atmosphere. To the reaction mixture was added benzyl alcohol (0.261 ml), and the mixture was stirred under nitrogen atmosphere at 80° C. for 3 hr. To the reaction mixture was added water, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate), and the fraction was concentrated under reduced pressure. A mixture of the obtained residue, ethanol (10 ml) and 10% palladium-carbon (50% wet, 26.7 mg) was stirred overnight at room temperature under hydrogen atmosphere. The insoluble substance was filtered off, and the filtrate was concentrated under reduced pressure. To a mixture of the obtained residue and THF (5 ml) were added methyl 2-(bromomethyl)-5-(5-(trifluoromethyl)-1,2,4-oxadiazol-3-yl)benzoate (85 mg) and DIEA (0.065 ml), and the mixture was stirred overnight at 60° C., and then at 70° C. for 4 hr, under nitrogen atmosphere. The reaction mixture was concentrated under reduced pressure, water was added thereto, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (36 mg).

MS (API+), found: 403.2 (M+1-Boc).

C) N-((1R,2R)-4,4-difluoro-2-(1-oxo-6-(5-(trifluoromethyl)-1,2,4-oxadiazol-3-yl)-1,3-dihydro-2H-isoindol-2-yl)cyclohexyl)-3-methyloxetane-3-carboxamide To a mixture of tert-butyl ((1R,2R)-4,4-difluoro-2-(1-oxo-6-(5-(trifluoromethyl)-1,2,4-oxadiazol-3-yl)-1,3-dihydro-2H-isoindol-2-yl)cyclohexyl)carbamate (36 mg) and methanol (1.5 ml) was added 4 M hydrogen chloride-CPME solution (1 ml), the mixture was stirred overnight at room temperature, and the reaction mixture was concentrated under reduced pressure. To a mixture of the obtained residue and DMF (1 ml) were added TEA (0.029 ml), 3-methyloxetane-3-carboxylic acid (11 mg) and HATU (41.6 mg) at 0° C., and the mixture was stirred at room temperature for 1 hr. To the reaction mixture was added water, and the mixture was extracted with ethyl acetate. The organic layer was washed with saturated aqueous sodium carbonate solution and saturated brine, dried over anhydrous sodium sulfate, and concentrated under reduced pressure. The residue was purified by Diol (3-(2,3-dihydroxypropoxy)propylsilane-bonded silica gel) silica gel column chromatography (hexane/ethyl acetate), and the fraction was concentrated under reduced pressure to give the title compound (28.2 mg).

$^1$H NMR (300 MHz, CDCl$_3$) δ 1.34 (3H, s), 1.67-1.82 (1H, m), 1.83-2.02 (1H, m), 2.08-2.32 (3H, m), 2.37-2.53 (1H, m), 4.10-4.28 (3H, m), 4.34-4.49 (2H, m), 4.55-4.73 (3H, m), 6.06 (1H, d, J=9.4 Hz), 7.65 (1H, d, J=8.7 Hz), 8.30-8.37 (1H, m), 8.56 (1H, d, J=0.8 Hz).

Example 88 tert-butyl (3R,4R)-4-(5-oxo-3-(5-(trifluoromethyl)-1,2,4-oxadiazol-3-yl)-5,7-dihydro-6H-pyrrolo[3,4-b]pyridin-6-yl)-3-phenylpiperidine-1-carboxylate A mixture of methyl 2-(bromomethyl)-5-(5-(trifluoromethyl)-1,2,4-oxadiazol-3-yl)nicotinate (73 mg), tert-butyl (3R,4R)-4-amino-3-phenylpiperidine-1-carboxylate (89 mg), DIEA (56.7 mg) and 4-methylbenzenesulfonate THF (4 mL) was stirred overnight at 50° C., and then at 70° C. for 5 hr. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate), and recrystallized from ethyl acetate-hexane to give the title compound (17.9 mg).

$^1$H NMR (300 MHz, CDCl$_3$) δ 1.50 (9H, s), 1.81-2.10 (2H, m), 2.72-3.21 (3H, m), 4.16-4.48 (4H, m), 4.85 (1H, td, J=11.6, 4.3 Hz), 7.10-7.36 (5H, m), 8.69 (1H, d, J=1.9 Hz), 9.36 (1H, d, J=1.9 Hz).

Example 89

N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanesulfonamide To a mixture of 2-((1R,2R)-2-aminocyclohexyl)-6-(5-(trifluoromethyl)-1,2,4-oxadiazol-3-yl)isoindolin-1-one hydrochloride (35 mg), TEA (0.036 ml), 4,4-dimethylaminopyridine (3.2 mg) and THF (2 ml) was added cyclopropanesulfonyl chloride (0.126 ml) at 0° C., and the mixture was stirred at room temperature for 2 hr. To the reaction mixture were added TEA (0.072 ml) and cyclopropanesulfonyl chloride (0.126 ml) at 0° C., and the mixture was stirred at room temperature for 5 hr. To the reaction mixture was added water, and the mixture was extracted with ethyl acetate. The organic layer was washed with saturated brine, dried over anhydrous sodium sulfate, and concentrated under reduced pressure. The residue was purified by Diol (3-(2,3-dihydroxypropoxy)propylsilane-bonded silica gel) silica gel column chromatography (hexane/ethyl acetate) to give the title compound (40 mg).

$^1$H NMR (300 MHz, CDCl$_3$) δ 0.67-0.81 (2H, m), 0.93-1.06 (2H, m), 1.29-1.54 (3H, m), 1.62-1.77 (1H, m), 1.80-1.94 (2H, m), 1.95-2.08 (1H, m), 2.11-2.23 (1H, m), 2.24-2.37 (1H, m), 3.41-3.62 (1H, m), 4.23 (1H, td, J=11.5, 3.8 Hz), 4.40-4.52 (1H, m), 4.62-4.71 (1H, m), 4.79 (1H, d, J=8.7 Hz), 7.63 (1H, d, J=7.9 Hz), 8.30 (1H, dd, J=7.9, 1.1 Hz), 8.61 (1H, s).

Example 90

(2S)—N-((1R,2R)-2-(1-oxo-6-(5-(trifluoromethyl)-1,2,4-oxadiazol-3-yl)-1,3-dihydro-2H-isoindol-2-yl)cyclohexyl)tetrahydrofuran-2-carboxamide A mixture of 2-((1R,2R)-2-aminocyclohexyl)-6-(5-(trifluoromethyl)-1,2,4-oxadiazol-3-yl)isoindolin-1-one hydrochloride (32 mg), (S)-tetrahydro-2-furancarboxylic acid (11 mg), DIEA (0.034 ml), HATU (37 mg) and DMF (1 ml) was stirred overnight at room temperature. To the reaction mixture was added water, and the mixture was extracted with ethyl acetate. The organic layer was concentrated, and the residue was purified by preparative HPLC (column: YMC Triart C18, mobile phase: acetonitrile/10 mM aqueous ammonium carbonate solution). The solvent of the obtained fraction was evaporated by air-blowing while warming to 60° C. to give the title compound (16.6 mg).

Alternative Step

To a solution of (S)-tetrahydro-2-furancarboxylic acid (21.57 ml) and DMF (0.673 ml) in anhydrous THF (490 ml) was added thionyl chloride (16.49 ml) at room temperature, and the mixture was stirred for 2 hr. The obtained reaction mixture was added to a solution of 2-((1R,2R)-2-aminocyclohexyl)-6-(5-(trifluoromethyl)-1,2,4-oxadiazol-3-yl)isoindolin-1-one hydrochloride (70 g) and TEA (121 ml) in THF (700 ml) over 30 min under ice-cooling, and the mixture was stirred at room temperature for 1.5 hr. To the reaction mixture was added saturated aqueous sodium hydrogencarbonate solution (500 ml) under ice-cooling, and then water (500 ml) was added thereto. The same procedure was repeated in another batch. The mixtures obtained from the two batches were combined, and extracted with ethyl acetate (4200 ml), and the organic layer was washed with water (500 ml) and saturated brine (500 ml), dried over anhydrous sodium sulfate, and concentrated under reduced pressure. The residue was purified by silica gel column chromatography (hexane/ethyl acetate), and the fraction was concentrated under reduced pressure. The residue was crystallized from methyl tert-butyl ether/heptane to give the title compound (133 g).

melting point: 132° C.

$^1$H NMR (300 MHz, DMSO-$d_6$) δ 0.97-1.13 (1H, m), 1.17-1.55 (4H, m), 1.58-1.88 (7H, m), 3.53-3.64 (1H, m), 3.67-3.78 (1H, m), 3.84-4.05 (2H, m), 4.07-4.21 (1H, m), 4.46-4.69 (2H, m), 7.47 (1H, d, J=9.82 Hz), 7.86 (1H, d, J=7.93 Hz), 8.21 (1H, s), 8.27 (1H, dd, J=7.93, 1.51 Hz).

elemental analysis: Anal. for $C_{22}H_{23}F_3N_4O_4$
calculated value C, 56.89; H, 4.99; N, 12.06.
actual measured value C, 56.95; H, 5.05; N, 12.02.

Examples 91-94

The compounds of Examples 91 to 94 were obtained using the corresponding carboxylic acid by a method similar to Example 90.

Example 95

2-hydroxy-2-methyl-N-((1R,2R)-2-(1-oxo-6-(5-(trifluoromethyl)-1,2,4-oxadiazol-3-yl)-1,3-dihydro-2H-isoindol-2-yl)cyclohexyl)propanamide A mixture of 2-((1R,2R)-2-aminocyclohexyl)-6-(5-(trifluoromethyl)-1,2,4-oxadiazol-3-yl)isoindolin-1-one hydrochloride (200 mg), 2-hydroxy-2-methylpropanoic acid (72.4 mg), HATU (302 mg), TEA (151 mg) and DMF (5 mL) was stirred at room temperature for 5 hr. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate), and then preparative HPLC (column: L-Column 2 ODS, mobile phase: acetonitrile/0.1% aqueous trifluoroacetic acid solution) to give the title compound (157.5 mg).

$^1$H NMR (300 MHz, CDCl$_3$) δ 0.94 (3H, s), 1.18-2.16 (11H, m), 3.87-4.05 (1H, m), 4.12-4.27 (1H, m), 4.40 (1H, d, J=17.4 Hz), 4.75 (1H, d, J=17.4 Hz), 6.89 (1H, d, J=9.8 Hz), 7.63 (1H, d, J=7.9 Hz), 8.29 (1H, dd, J=7.9, 1.5 Hz), 8.54 (1H, d, J=1.1 Hz).

Alternative Step

To a mixture of 2-((1R,2R)-2-aminocyclohexyl)-6-(5-(trifluoromethyl)-1,2,4-oxadiazol-3-yl)isoindolin-1-one hydrochloride (100 g), 2-hydroxy-2-methylpropanoic acid (38.8 g) and DMF (1167 ml) was added DIEA (91 ml) at 5° C., and the mixture was stirred for 15 min. To the reaction mixture were added EDCI hydrochloride (95 g) and HOBt monohydrate (76 g) at 5° C., and the mixture was stirred at room temperature for 1.5 hr. The reaction mixture was poured into water, and the mixture was extracted with ethyl acetate. The organic layer was washed with water, aqueous sodium hydrogencarbonate solution and saturated brine, dried over anhydrous sodium sulfate, and concentrated under reduced pressure. The residue was purified by silica gel column chromatography (ethyl acetate/hexane) to give the title compound (96 g).

$^1$H NMR (300 MHz, DMSO-$d_6$) δ 0.70 (3H, s), 1.06 (3H, s), 1.35 (2H, brs), 1.54-1.71 (2H, m), 1.72-1.83 (4H, m), 3.81-3.95 (1H, m), 4.07-4.20 (1H, m), 4.52 (1H, d, J=1.00 Hz), 4.64 (1H, d, J=1.00 Hz), 5.19 (1H, s), 7.43 (1H, d, J=9.82 Hz), 7.84 (1H, d, J=7.93 Hz), 8.19 (1H, s), 8.25 (1H, d, J=7.74 Hz).

Example 96

3-hydroxy-3-methyl-N-((1R,2R)-2-(1-oxo-6-(5-(trifluoromethyl)-1,2,4-oxadiazol-3-yl)-1,3-dihydro-2H-isoindol-2-yl)cyclohexyl)butanamide A mixture of 2-((1R,2R)-2-aminocyclohexyl)-6-(5-(trifluoromethyl)-1,2,4-oxadiazol-3-yl)isoindolin-1-one hydrochloride (200 mg), 3-hydroxy-3-methylbutanoic acid (82 mg), 4-(4,6-dimethoxy-1,3,5-triazin-2-yl)-4-methylmorpholin-4-ium (206 mg), TEA (201 mg) and ethanol (5 mL) was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (47.7 mg).

$^1$H NMR (300 MHz, CDCl$_3$) δ 0.82 (3H, s), 1.02 (3H, s), 1.32-1.53 (3H, m), 1.64-1.78 (1H, m), 1.81-2.02 (3H, m), 2.04-2.27 (3H, m), 3.92-4.30 (3H, m), 4.38-4.54 (1H, m), 4.60-4.78 (1H, m), 6.23 (1H, d, J=9.1 Hz), 7.63 (1H, d, J=8.7 Hz), 8.30 (1H, dd, J=7.9, 1.5 Hz), 8.55 (1H, d, J=0.8 Hz).

Examples 97-124

The compounds of Examples 97 to 124 were obtained using the corresponding carboxylic acid by a method similar to Example 90.

Example 125

3,3-difluoro-N-((1R,2R)-2-(1-oxo-6-(5-(trifluoromethyl)-1,2,4-oxadiazol-3-yl)-1,3-dihydro-2H-isoindol-2-yl)cyclohexyl)cyclobutanecarboxamide A mixture of 2-((1R,2R)-2-aminocyclohexyl)-6-(5-(trifluoromethyl)-1,2,4-oxadiazol-3-yl)isoindolin-1-one hydrochloride (200 mg), 3,3-difluorocyclobutanecarboxylic acid (95 mg), HATU (302 mg), TEA (151 mg) and DMF (5 mL) was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (197.4 mg).

$^1$H NMR (300 MHz, CDCl$_3$) δ 1.31-1.54 (3H, m), 1.67-1.78 (1H, m), 1.80-2.02 (3H, m), 2.04-2.25 (2H, m), 2.28-2.48 (1H, m), 2.49-2.73 (3H, m), 3.90-4.12 (1H, m), 4.15-4.28 (1H, m), 4.35-4.48 (1H, m), 4.59-4.76 (1H, m), 5.95 (1H, d, J=9.4 Hz), 7.64 (1H, d, J=7.9 Hz), 8.32 (1H, dd, J=7.9, 1.5 Hz), 8.54 (1H, d, J=0.8 Hz).

Examples 126-133

The compounds of Examples 126 to 133 were obtained using the corresponding carboxylic acid by a method similar to Example 90.

Example 134

N-((1R,2R)-2-(1-oxo-6-(5-(trifluoromethyl)-1,2,4-oxadiazol-3-yl)-1,3-dihydro-2H-isoindol-2-yl)cyclohexyl)-3-phenyloxetane-3-carboxamide To a mixture of 2-((1R,2R)-2-aminocyclohexyl)-6-(5-(trifluoromethyl)-1,2,4-oxadiazol-3-yl)isoindolin-1-one hydrochloride (31 mg), TEA (0.032 ml), 3-phenyloxetane-3-carboxylic acid (19.2 mg) and DMF (3 ml) was added HATU (46.8 mg) at 0° C., and the mixture was stirred at room temperature for 2 hr. To the reaction mixture was added water, and the mixture was extracted with ethyl acetate. The organic layer was washed with saturated aqueous sodium hydrogencarbonate solution and saturated brine, dried over anhydrous sodium sulfate, and concentrated under reduced pressure. The residue was purified by silica gel column chromatography (hexane/ethyl acetate), and the fraction was concentrated under reduced pressure to give the title compound (38 mg).

$^1$H NMR (300 MHz, CDCl$_3$) δ 1.06-1.49 (4H, m), 1.68-2.08 (4H, m), 3.87-4.18 (2H, m), 4.30-4.42 (1H, m), 4.52-4.61 (1H, m), 4.63 (1H, d, J=5.7 Hz), 4.74 (1H, d, J=6.0 Hz), 4.84 (1H, d, J=5.7 Hz), 5.08 (1H, d, J=5.7 Hz), 5.57 (1H, d, J=8.7 Hz), 7.00-7.08 (2H, m), 7.11-7.25 (3H, m), 7.60 (1H, d, J=7.9 Hz), 8.31 (1H, dd, J=7.9, 1.5 Hz), 8.53 (1H, s).

Example 135

The compound of Example 135 was obtained using the corresponding amine by a method similar to Example 24.

$^1$H NMR (300 MHz, CDCl$_3$) δ 1.50 (9H, s), 1.76-2.03 (2H, m), 2.72-2.91 (1H, m), 3.05 (2H, td, J=11.3, 4.2 Hz), 4.12-4.22 (1H, m), 4.24-4.46 (3H, m), 4.81 (1H, td, J=11.6, 4.3 Hz), 7.11-7.19 (1H, m), 7.20-7.32 (4H, m), 7.88 (1H, d, J=7.9 Hz), 8.09 (1H, s), 8.16 (1H, dd, J=7.9, 1.1 Hz).

Example 136

The compound of Example 136 was obtained using the compound obtained in Example 135 by a method similar to Example 15.

Example 137

The compound of Example 137 was obtained using the compound obtained in Example 136 by a method similar to Example 20.

Example 138

3-ethyl-N-((1R,2R)-2-(1-oxo-6-(5-(trifluoromethyl)-1,2,4-oxadiazol-3-yl)-1,3-dihydro-2H-isoindol-2-yl)cyclohexyl)oxetane-3-carboxamide To a mixture of 2-((1R,2R)-2-aminocyclohexyl)-6-(5-(trifluoromethyl)-1,2,4-oxadiazol-3-yl)isoindolin-1-one hydrochloride (33 mg), TEA (0.034 ml), 3-ethyloxetane-3-carboxylic acid (0.013 ml) and DMF (1.5 ml) was added HATU (49.8 mg) at 0° C., and the mixture was stirred overnight at room temperature. To the reaction mixture was added water, and the mixture was extracted with ethyl acetate. The organic layer was washed with saturated aqueous sodium hydrogencarbonate solution and saturated brine, dried over anhydrous sodium sulfate, and concentrated under reduced pressure. The residue was purified by Diol (3-(2,3-dihydroxypropoxy)propylsilane-bonded silica gel) silica gel column chromatography (hexane/ethyl acetate), and the fraction was concentrated under reduced pressure to give the title compound (39 mg).

$^1$H NMR (300 MHz, CDCl$_3$) δ 0.49 (3H, t, J=7.4 Hz), 1.36-1.52 (3H, m), 1.69-1.85 (4H, m), 1.90-2.03 (2H, m), 2.08-2.22 (1H, m), 4.02-4.17 (1H, m), 4.21-4.34 (3H, m), 4.39-4.70 (4H, m), 6.08 (1H, d, J=8.7 Hz), 7.63 (1H, d, J=7.9 Hz), 8.30 (1H, dd, J=8.1, 0.8 Hz), 8.56 (1H, d, J=0.8 Hz).

Example 139

N-((1R,2R)-2-(1-oxo-6-(5-(trifluoromethyl)-, 2,4-oxadiazol-3-yl)-1,3-dihydro-2H-isoindol-2-yl)cyclohexyl)morpholine-4-carboxamide To a mixture of 2-((1R,2R)-2-aminocyclohexyl)-6-(5-(trifluoromethyl)-1,2,4-oxadiazol-3-yl)isoindolin-1-one hydrochloride (50 mg), TEA (0.069 ml), 4,4-dimethylaminopyridine (4.6 mg) and THF (3 ml) was added morpholine-4-carbonyl chloride (0.028 ml) at 0° C., and the mixture was stirred at room temperature for 15 min, and then at 45° C. for 20 min under nitrogen atmosphere. To the reaction mixture was added water, and the mixture was extracted with ethyl acetate. The organic layer was washed with saturated brine, dried over anhydrous sodium sulfate, and concentrated under reduced pressure. The residue was purified by Diol (3-(2,3-dihydroxypropoxy)propylsilane-bonded silica gel) silica gel column chromatography (hexane/ethyl acetate), and the fraction was concentrated under reduced pressure to give the title compound (56 mg).

$^1$H NMR (300 MHz, CDCl$_3$) δ 1.25-1.46 (3H, m), 1.64-1.79 (1H, m), 1.80-2.06 (3H, m), 2.12-2.27 (1H, m), 3.11 (4H, t, J=4.9 Hz), 3.37-3.54 (4H, m), 3.82-3.98 (1H, m), 4.20 (1H, td, J=11.6, 3.6 Hz), 4.37-4.70 (2H, m), 4.95 (1H, d, J=8.3 Hz), 7.64 (1H, d, J=7.9 Hz), 8.31 (1H, dd, J=7.9, 0.8 Hz), 8.57 (1H, d, J=0.8 Hz).

Examples 140-141

The compounds of Examples 140 to 141 were obtained using the corresponding amine by a method similar to Example 26.

Examples 142-143

The compounds of Examples 142 to 143 were obtained using the compounds obtained in Examples 140 to 141 by a method similar to Example 7.

Example 144

N-((1R,2R)-2-(1-oxo-6-(5-(trifluoromethyl)-1,2,4-oxadiazol-3-yl)-1,3-dihydro-2H-isoindol-2-yl)cyclohexyl)-3-oxa-6-azabicyclo[3.1.1]heptane-6-carboxamide

A) tert-butyl ((1R,2R)-2-(1-oxo-6-(5-(trifluoromethyl)-1,2,4-oxadiazol-3-yl)-1,3-dihydro-2H-isoindol-2-yl)cyclohexyl)carbamate To a mixture of methyl 2-(bromomethyl)-5-(5-(trifluoromethyl)-1,2,4-oxadiazol-3-yl)benzoate (13.14 g), DIEA (10.06 mL) and THF (300 mL) was added tert-butyl ((1R,2R)-2-aminocyclohexyl)carbamate (8.10 g) at room temperature, and the mixture was stirred overnight at 60° C. under nitrogen atmosphere, and the reaction mixture was concentrated under reduced pressure. To the residue was added water, and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (13.79 g).

$^1$H NMR (300 MHz, CDCl$_3$) δ 1.07 (9H, s), 1.31-1.54 (3H, m), 1.61-1.73 (1H, m), 1.78-2.01 (3H, m), 2.10 (1H, d, J=7.2 Hz), 3.66 (1H, td, J=10.7, 7.0 Hz), 4.06-4.23 (1H, m), 4.38 (1H, d, J=17.4 Hz), 4.62 (1H, d, J=10.2 Hz), 4.78 (1H, d, J=17.4 Hz), 7.62 (1H, d, J=7.9 Hz), 8.28 (1H, dd, J=7.9, 1.5 Hz), 8.59 (1H, d, J=0.8 Hz).

B) 2-((1R,2R)-2-aminocyclohexyl)-6-(5-(trifluoromethyl)-1,2,4-oxadiazol-3-yl)isoindolin-1-one hydrochloride To a mixture of tert-butyl ((1R,2R)-2-(1-oxo-6-(5-(trifluoromethyl)-1,2,4-oxadiazol-3-yl)-1,3-dihydro-2H-isoindol-2-yl)cyclohexyl)carbamate (13.79 g) in methanol (220 mL) was added 4 M hydrogen chloride-CPME solution (222 mL), and the mixture was stirred at room temperature for 2 hr. The reaction mixture was concentrated, and the residue was washed with diisopropyl ether to give the title compound (11.1 g).

$^1$H NMR (300 MHz, DMSO-d$_6$) δ 1.22-1.58 (3H, m), 1.79 (4H, brs), 2.11 (1H, d, J=12.5 Hz), 3.44 (1H, td, J=11.1, 4.2 Hz), 4.02-4.18 (1H, m), 4.51-4.68 (2H, m), 7.83-8.02 (4H, m), 8.27 (1H, d, J=1.1 Hz), 8.31 (1H, dd, J=7.9, 1.5 Hz).

C) 4-nitrophenyl ((1R,2R)-2-(1-oxo-6-(5-(trifluoromethyl)-1,2,4-oxadiazol-3-yl)-1,3-dihydro-2H-isoindol-2-yl)cyclohexyl)carbamate A mixture of 2-((1R,2R)-2-aminocyclohexyl)-6-(5-(trifluoromethyl)-1,2,4-oxadiazol-3-yl)isoindolin-1-one hydrochloride (2000 mg), 4-nitrophenyl chlorocarbonate (1101 mg), pyridine (0.420 mL) and DIEA (0.867 mL) in THF (40 mL) was stirred at room temperature for 2 hr. To the reaction mixture was added water, and the mixture was extracted with ethyl acetate. The organic layer was washed with saturated brine, dried over anhydrous sodium sulfate, and concentrated under reduced pressure to give the title compound (2389 mg).

D) N-((1R,2R)-2-(1-oxo-6-(5-(trifluoromethyl)-1,2,4-oxadiazol -3-yl)-1,3-dihydro-2H-isoindol-2-yl)cyclohexyl)-3-oxa-6-azabicyclo[3.1.1]heptane-6-carboxamide A mixture of 4-nitrophenyl ((1R,2R)-2-(1-oxo-6-(5-(trifluoromethyl)-1,2,4-oxadiazol-3-yl)-1,3-dihydro-2H-isoindol -2-yl)cyclohexyl)carbamate (203 mg), 3-oxa-6-azabicyclo[3.1.1]heptane trifluoroacetate (1:1) (81 mg) and DIEA (0.267 mL) in DMF (4 mL) was stirred at room temperature for 1 hr. To the reaction mixture was added water, and the mixture was extracted with ethyl acetate. The organic layer was washed with water and saturated brine, dried over anhydrous sodium sulfate, and concentrated under reduced pressure. The residue was purified by silica gel column chromatography (ethyl acetate/methanol) to give the title compound (117 mg).

$^1$H NMR (300 MHz, CDCl$_3$) δ 1.31-1.55 (3H, m), 1.59-1.78 (2H, m), 1.81-2.02 (3H, m), 2.20 (1H, d, J=9.1 Hz), 2.37-2.49 (1H, m), 3.48 (2H, ddd, J=10.6, 5.1, 1.3 Hz), 3.85 (1H, d, J=10.6 Hz), 3.89-4.02 (4H, m), 4.15-4.27 (1H, m), 4.43 (1H, d, J=17.4 Hz), 4.65-4.82 (2H, m), 7.63 (1H, d, J=8.3 Hz), 8.30 (1H, dd, J=7.9, 1.5 Hz), 8.58 (1H, s).

Example 145

N-((1R,2R)-2-(1-oxo-6-(5-(trifluoromethyl)-1,2,4-oxadiazol-3-yl)-1,3-dihydro-2H-isoindol-2-yl)cyclohexyl)-3-oxa-8-azabicyclo[3.2.1]octane-8-carboxamide A mixture of 4-nitrophenyl ((1R,2R)-2-(1-oxo-6-(5-(trifluoromethyl)-1,2,4-oxadiazol-3-yl)-1,3-dihydro-2H-isoindol -2-yl)cyclohexyl)carbamate (182 mg), 3-oxa-8-azabicyclo[3.2.1]octane hydrochloride (51 mg) and DIEA (0.239 mL) in DMF (4 mL) was stirred at room temperature for 1.5 hr. To the reaction mixture was added water, and the mixture was extracted with ethyl acetate. The organic layer was washed with water and saturated brine, dried over anhydrous sodium sulfate, and concentrated under reduced pressure. The residue was purified by silica gel column chromatography (ethyl acetate/methanol) to give the title compound (107 mg).

$^1$H NMR (300 MHz, CDCl$_3$) δ 1.30-2.03 (11H, m), 2.20 (1H, d, J=9.4 Hz), 3.23-3.48 (4H, m), 3.79-4.00 (3H, m), 4.16-4.27 (1H, m), 4.43 (1H, d, J=17.8 Hz), 4.72 (1H, d, J=17.8 Hz), 4.88 (1H, d, J=7.9 Hz), 7.63 (1H, d, J=7.9 Hz), 8.30 (1H, dd, J=7.9, 1.5 Hz), 8.55 (1H, s).

Example 146

N-((1R,2R)-2-(1-oxo-6-(5-(trifluoromethyl)-1,2,4-oxadiazol-3-yl)-1,3-dihydro-2H-isoindol-2-yl)cyclohexyl)-8-oxa-3-azabicyclo[3.2.1]octane-3-carboxamide A mixture of 4-nitrophenyl ((1R,2R)-2-(1-oxo-6-(5-(trifluoromethyl)-1,2,4-oxadiazol-3-yl)-1,3-dihydro-2H-isoindol -2-yl)cyclohexyl)carbamate (188 mg), 8-oxa-3-azabicyclo[3.2.1]octane (40 mg) and DIEA (0.185 mL) in DMF (4 mL) was stirred at room temperature for 2 hr. To the reaction mixture was added water, and the mixture was extracted with ethyl acetate. The organic layer was washed with water and saturated brine, dried over anhydrous sodium sulfate, and concentrated under reduced pressure. The residue was purified by silica gel column chromatography (ethyl acetate/methanol) to give the title compound (104 mg).

$^1$H NMR (300 MHz, CDCl$_3$) δ 1.08-1.22 (1H, m), 1.31-2.03 (10H, m), 2.14 (1H, d, J=9.4 Hz), 2.81-2.92 (2H, m), 3.20 (1H, d, J=12.1 Hz), 3.31 (1H, d, J=12.5 Hz), 3.83-4.01 (1H, m), 4.15-4.26 (3H, m), 4.40 (1H, d, J=17.8 Hz), 4.70 (1H, d, J=17.4 Hz), 4.80 (1H, d, J=8.7 Hz), 7.63 (1H, d, J=7.9 Hz), 8.30 (1H, dd, J=7.9, 1.1 Hz), 8.57 (1H, s).

Example 147

(1S)-2,2-difluoro-N-((1R,2R)-2-(1-oxo-6-(5-(trifluoromethyl) -1,2,4-oxadiazol-3-yl)-1,3-dihydro-2H-isoindol-2-yl)cyclohexyl)cyclopropanecarboxamide A) (4R)-3-(((1S)-2,2-difluorocyclopropyl)carbonyl)-4-phenyl -1,3-oxazolidin-2-one and (4R)-3-(((1R)-2,2-difluorocyclopropyl)carbonyl)-4-phenyl-1,3-oxazolidin-2-one To a mixture of 2,2-difluorocyclopropanecarboxylic acid (1.0 g), DMF (2 drops) and THF (15 ml) was added oxalyl chloride (0.753 ml) at 0° C., and the mixture was stirred at room temperature for 2 hr. To the reaction mixture were added THF (20 ml), lithium chloride (1.736 g), (4R)-4-phenyl-1,3-oxazolidin-2-one (1.404 g) and TEA (5.71 ml) at 0° C., and the mixture was stirred overnight at room temperature. To the reaction mixture was added 1 M hydrochloric acid, and the mixture was extracted with ethyl acetate. The organic layer was washed with 0.1 M hydrochloric acid and saturated brine, dried over anhydrous sodium sulfate, and concentrated under reduced pressure. The residue was purified by silica gel column chromatography (hexane/ethyl acetate), and the fraction was concentrated under reduced pressure to give (4R)-3-(((1S) -2,2-difluorocyclopropyl)carbonyl)-4-phenyl-1,3-oxazolidin-2-one (0.645 g, one having a larger Rf value) and (4R)-3-(((1R)-2,2-difluorocyclopropyl)carbonyl)-4-phenyl-1,3-oxazolidin-2-one (0.770 g, one having a smaller Rf value).

(4R)-3-(((1S)-2,2-difluorocyclopropyl)carbonyl)-4-phenyl-1,3-oxazolidin-2-one: $^1$H NMR (300 MHz, CDCl$_3$) δ 1.66-1.81 (1H, m), 2.08-2.24 (1H, m), 3.82-3.95 (1H, m), 4.34 (1H, dd, J=8.9, 4.0 Hz), 4.74 (1H, t, J=8.9 Hz), 5.47 (1H, dd, J=8.9, 4.0 Hz), 7.29-7.47 (5H, m).

(4R)-3-(((1R)-2,2-difluorocyclopropyl)carbonyl)-4-phenyl-1,3-oxazolidin-2-one: $^1$H NMR (300 MHz, CDCl$_3$) δ 1.70-1.82 (1H, m), 2.10-2.23 (1H, m), 3.84-3.97 (1H, m), 4.27-4.32 (1H, m), 4.73 (1H, t, J=8.9 Hz), 5.45 (1H, dd, J=8.7, 3.8 Hz), 7.26-7.43 (5H, m).

B) (1S)-2,2-difluorocyclopropanecarboxylic acid

To a mixture of (4R)-3-(((1S)-2,2-difluorocyclopropyl) carbonyl)-4-phenyl-1,3-oxazolidin-2-one (611 mg), THF (24 ml) and water (8 ml) were added 35% hydrogen peroxide water (1.333 ml) and lithium hydroxide monohydrate (192 mg) at 0° C., and the mixture was stirred for 10 min, and then at room temperature for 2 hr. To the reaction mixture was added a mixture of sodium sulfite (2017 mg) and water (20 ml) at room temperature, and the mixture was stirred for 10 min. The reaction mixture was concentrated under reduced pressure, to the obtained residue was added water, and the mixture was washed with ethyl acetate. The aqueous layer was acidified with 6 M hydrochloric acid, and the mixture was extracted with ethyl acetate. The organic layer was washed with saturated brine, dried over anhydrous sodium sulfate, and concentrated under reduced pressure. To the residue was added toluene, and the mixture was concentrated under reduced pressure to give the title compound (260 mg).

$^1$H NMR (300 MHz, CDCl$_3$) δ 1.74-1.89 (1H, m), 2.01-2.17 (1H, m), 2.36-2.54 (1H, m).

C) (1S)-2,2-difluoro-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide To a mixture of 2-((1R,2R)-2-aminocyclohexyl)-6-(5-(trifluoromethyl)-1,2,4-oxadiazol-3-yl)isoindolin-1-one hydrochloride (40 mg), 4-methylmorpholine (0.033 ml), (1S)-2,2-difluorocyclopropanecarboxylic acid (17 mg) and DMF (2 ml) was added HATU (60.4 mg) at 0° C., and the mixture was stirred for 10 min, and then at room temperature for 2 hr. To the reaction mixture was added water, and the mixture was extracted with a mixture of ethyl acetate-THF. The organic layer was washed with saturated aqueous sodium hydrogencarbonate solution and saturated brine, dried over anhydrous sodium sulfate, and concentrated under reduced pressure. The residue was purified by silica gel column chromatography (hexane/ethyl acetate), and the fraction was concentrated under reduced pressure to give the title compound (40.8 mg).

$^1$H NMR (300 MHz, CDCl$_3$) δ 1.34-1.55 (4H, m), 1.69-1.76 (1H, m), 1.79-2.02 (4H, m), 2.04-2.18 (2H, m), 4.01-4.17 (1H, m), 4.19-4.31 (1H, m), 4.33-4.64 (2H, m), 6.22 (1H, d, J=9.1 Hz), 7.59 (1H, d, J=7.9 Hz), 8.29 (1H, dd, J=7.9, 1.9 Hz), 8.57 (1H, d, J=0.8 Hz).

Example 148

(1R)-2,2-difluoro-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide A) (1R)-2,2-difluorocyclopropanecarboxylic acid To a mixture of (4R)-3-(((1R)-2,2-difluorocyclopropyl) carbonyl)-4-phenyl-1,3-oxazolidin-2-one (718 mg), THF (24 ml) and water (8 ml) were added 35% hydrogen peroxide water (1.567 ml) and lithium hydroxide monohydrate (225 mg) at 0° C., and the mixture was stirred for 10 min, and then at room temperature for 2 hr. To the reaction mixture was added a mixture of sodium sulfite (2371 mg) and water (24 ml) at room temperature, and the mixture was stirred for 10 min. The reaction mixture was concentrated under reduced pressure, to the obtained residue was added water, and the mixture was washed with ethyl acetate. The aqueous layer was acidified with 6 M hydrochloric acid, and the mixture was extracted with ethyl acetate. The organic layer was washed with saturated brine, dried over anhydrous sodium sulfate, and concentrated under reduced pressure. To the residue was added toluene, and the mixture was concentrated under reduced pressure to give the title compound (290 mg).

$^1$H NMR (300 MHz, CDCl$_3$) δ 1.75-1.89 (1H, m), 2.05-2.16 (1H, m), 2.40-2.52 (1H, m).

B) (1R)-2,2-difluoro-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide To a mixture of 2-((1R,2R)-2-aminocyclohexyl)-6-(5-(trifluoromethyl)-1,2,4-oxadiazol-3-yl)isoindolin-1-one hydrochloride (40 mg), 4-methylmorpholine (0.033 ml), (1R)-2,2-difluorocyclopropanecarboxylic acid (17 mg) and DMF (2 ml) was added HATU (60.4 mg) at 0° C., and the mixture was stirred for 10 min, and then at room temperature for 2 hr. To the reaction mixture was added water, and the mixture was extracted with a mixture of ethyl acetate-THF. The organic layer was washed with saturated aqueous sodium hydrogencarbonate solution and saturated brine, dried over anhydrous sodium sulfate, and concentrated under reduced pressure. The residue was purified by silica gel column chromatography (hexane/ethyl acetate), and the fraction was concentrated under reduced pressure to give the title compound (38.4 mg).

$^1$H NMR (300 MHz, CDCl$_3$) δ 1.31-1.51 (4H, m), 1.62-1.76 (2H, m), 1.79-2.02 (3H, m), 2.04-2.21 (2H, m), 3.94-4.12 (1H, m), 4.17-4.29 (1H, m), 4.33-4.66 (2H, m), 6.10-6.21 (1H, m), 7.62 (1H, d, J=7.9 Hz), 8.31 (1H, dd, J=7.9, 1.5 Hz), 8.56 (1H, d, J=1.5 Hz).

Example 149

(1S)-2,2-difluoro-N-((3S,4R)-4-(1-oxo-6-(5-(trifluoromethyl) -1,2,4-oxadiazol-3-yl)-1,3-dihydro-2H-isoindol-2-yl)tetrahydro-2H-pyran-3-yl)cyclopropanecarboxamide To a mixture of 2-((3S,4R)-3-aminotetrahydro-2H-pyran-4-yl)-6-(5-(trifluoromethyl)-1,2,4-oxadiazol-3-yl)isoindolin-1-one hydrochloride (30 mg), 4-methylmorpholine (0.024 ml), (1S) -2,2-difluorocyclopropanecarboxylic acid (12.7 mg) and DMF (1.5 ml) was added HATU (45.1 mg) at 0° C., and the mixture was stirred for 10 min, and then at room temperature for 2 hr. To the reaction mixture was added water, and the mixture was extracted with a mixture of ethyl acetate-THF. The organic layer was washed with saturated aqueous sodium hydrogencarbonate solution and saturated brine, dried over anhydrous sodium sulfate, and concentrated under reduced pressure. The residue was purified by silica gel column chromatography (hexane/ethyl acetate), and the fraction was concentrated under reduced pressure to give the title compound (32.5 mg).

$^1$H NMR (300 MHz, CDCl$_3$) δ 1.47-1.61 (1H, m), 1.87-1.97 (2H, m), 2.02-2.11 (1H, m), 2.12-2.29 (1H, m), 3.29 (1H, t, J=10.8 Hz), 3.51-3.64 (1H, m), 4.09-4.22 (2H, m), 4.24-4.38 (1H, m), 4.39-4.70 (3H, m), 6.48-6.77 (1H, m), 7.62 (1H, d, J=7.9 Hz), 8.30 (1H, d, J=7.9 Hz), 8.52 (1H, s).

Example 150

(1R)-2,2-difluoro-N-((3S,4R)-4-(1-oxo-6-(5-(trifluoromethyl) -1,2,4-oxadiazol-3-yl)-1,3-dihydro-2H-isoindol-2-yl)tetrahydro-2H-pyran-3-yl)cyclopropanecarboxamide To a mixture of 2-((3S,4R)-3-aminotetrahydro-2H-pyran-4-yl)-6-(5-(trifluoromethyl)-1,2,4-oxadiazol-3-yl)isoindolin-1-one hydrochloride (30 mg), 4-methylmorpholine (0.024 ml), (1R) -2,2-difluorocyclopropanecarboxylic acid (12.7 mg) and DMF (1.5 ml) was added HATU (45.1 mg) at 0° C., and the mixture was stirred for 10 min, and then at room temperature for 2 hr. To the reaction mixture was added water, and the mixture was extracted with a mixture of ethyl acetate-THF. The organic layer was washed with saturated aqueous sodium hydrogencarbonate solution and saturated brine, dried over anhydrous sodium sulfate, and concentrated under reduced pressure. The residue was purified by Diol (3-(2,3-dihydroxypropoxy)propylsilane-bonded silica gel) silica gel column chromatography (hexane/ethyl acetate), and the fraction was concentrated under reduced pressure to give the title compound (32.5 mg).

$^1$H NMR (300 MHz, CDCl$_3$) δ 1.40-1.55 (1H, m), 1.73-1.86 (1H, m), 1.89-1.99 (1H, m), 2.01-2.26 (2H, m), 3.18-3.32 (1H, m), 3.50-3.63 (1H, m), 4.08-4.31 (3H, m), 4.42-4.66 (3H, m), 6.50 (1H, d, J=7.9 Hz), 7.65 (1H, d, J=7.9 Hz), 8.33 (1H, dd, J=7.9, 1.5 Hz), 8.54 (1H, d, J=1.5 Hz).

Examples 151-152

The compounds of Examples 151 to 152 were obtained using the corresponding carbonyl chloride by a method similar to Example 32.

Example 153

1-(hydroxymethyl)-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide A mixture of 2-((1R,2R)-2-aminocyclohexyl)-6-(5-(trifluoromethyl)-1,2,4-oxadiazol-3-yl)isoindolin-1-one hydrochloride (100 mg), 1-(hydroxymethyl)cyclopropanecarboxylic acid (34.6 mg), 4-(4,6-dimethoxy-1,3,5-triazin-2-yl)-4-methylmorpholin-4-ium (103 mg), TEA (100 mg) and ethanol (2 mL) was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (30.9 mg).

$^1$H NMR (300 MHz, CDCl$_3$) δ 0.27 (1H, ddd, J=9.5, 5.8, 4.3 Hz), 0.31-0.40 (1H, m), 0.41-0.51 (1H, m), 0.96 (1H, ddd, J=9.7, 6.3, 4.0 Hz), 1.21-1.78 (4H, m), 1.82-2.15 (4H, m), 3.09 (1H, brs), 3.29 (1H, d, J=12.1 Hz), 3.64-3.77 (1H, m), 3.97-4.25 (2H, m), 4.39 (1H, d, J=17.4 Hz), 4.69 (1H, d, J=17.4 Hz), 7.18 (1H, d, J=9.4 Hz), 7.62 (1H, d, J=8.7 Hz), 8.31 (1H, dd, J=7.9, 1.5 Hz), 8.57 (1H, d, J=0.8 Hz).

Example 154

1-cyclopropyl-3-((1R,2R)-2-(1-oxo-6-(5-(trifluoromethyl)-1,2,4-oxadiazol-3-yl)-1,3-dihydro-2H-isoindol-2-yl)cyclohexyl)urea To a mixture of 2-((1R,2R)-2-aminocyclohexyl)-6-(5-(trifluoromethyl)-1,2,4-oxadiazol-3-yl)isoindolin-1-one hydrochloride (100 mg), TEA (50.2 mg) and THF (3 mL) was added bis(trichloromethyl) carbonate (25.8 mg) at 0° C., and the mixture was stirred at room temperature for 1 hr. To the reaction mixture were added cyclopropanamine (28.3 mg) and TEA (25.1 mg), and the mixture was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (18.9 mg).

$^1$H NMR (300 MHz, CDCl$_3$) δ 0.27-0.42 (2H, m), 0.58-0.73 (2H, m), 1.32-1.50 (3H, m), 1.63-1.78 (1H, m), 1.80-2.03 (3H, m), 2.14-2.32 (2H, m), 3.80-4.00 (1H, m), 4.24 (1H, td, J=11.4, 3.6 Hz), 4.41 (2H, d, J=17.8 Hz), 4.71 (1H, d, J=17.8 Hz), 5.16 (1H, d, J=9.4 Hz), 7.62 (1H, d, J=8.3 Hz), 8.29 (1H, dd, J=7.9, 1.5 Hz), 8.57 (1H, d, J=0.8 Hz).

Example 155

1-cyclopropyl-1-methyl-3-((1R,2R)-2-(1-oxo-6-(5-(trifluoromethyl)-1,2,4-oxadiazol-3-yl)-1,3-dihydro-2H-isoindol-2-yl)cyclohexyl)urea To a mixture of 2-((1R,2R)-2-aminocyclohexyl)-6-(5-(trifluoromethyl)-1,2,4-oxadiazol-3-yl)isoindolin-1-one hydrochloride (100 mg), TEA (50.2 mg) and THF (1.3 mL) was added bis(trichloromethyl) carbonate (25.8 mg) at 0° C., and the mixture was stirred at room temperature for 1 hr. To the reaction mixture were added N-methylcyclopropanamine hydrochloride (53.4 mg) and TEA (50.2 mg), and the mixture was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate), and then preparative HPLC (column: YMC Triart C18, mobile phase: acetonitrile/10 mM aqueous ammonium carbonate solution) to give the title compound (18.4 mg).

$^1$H NMR (300 MHz, CDCl$_3$) δ 0.32-0.61 (2H, m), 0.66-0.89 (2H, m), 1.29-1.58 (3H, m), 1.69 (1H, qd, J=12.1, 3.0 Hz), 1.80-2.02 (3H, m), 2.11-2.22 (1H, m), 2.25-2.39 (1H, m), 2.58 (3H, s), 3.78-4.01 (1H, m), 4.25 (1H, td, J=11.6, 3.6 Hz), 4.40 (1H, d, J=17.8 Hz), 4.70 (1H, d, J=17.8 Hz), 5.35 (1H, d, J=9.1 Hz), 7.63 (1H, d, J=7.9 Hz), 8.29 (1H, dd, J=7.9, 1.5 Hz), 8.57 (1H, d, J=0.8 Hz).

Example 156

N-((1R,2R)-2-(1-oxo-6-(5-(trifluoromethyl)-1,2,4-oxadiazol-3-yl)-1,3-dihydro-2H-isoindol-2-yl)cyclohexyl)-2-oxa-5-azabicyclo[2.2.1]heptane-5-carboxamide To a mixture of 2-((1R,2R)-2-aminocyclohexyl)-6-(5-(trifluoromethyl)-1,2,4-oxadiazol-3-yl)isoindolin-1-one hydrochloride (50 mg), DIEA (0.106 mL) and THF (5 mL) was added bis(trichloromethyl) carbonate (12.9 mg) at room temperature, and the mixture was stirred at room temperature for 2 hr. To the reaction mixture was added (1S,4S)-2-oxa-5-azabicyclo[2.2.1]heptane hydrochloride (25.2 mg), and the mixture was stirred overnight at room temperature. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (36 mg).

$^1$H NMR (300 MHz, CDCl$_3$) δ 1.32-1.55 (3H, m), 1.61-1.78 (3H, m), 1.81-2.03 (3H, m), 2.08-2.20 (1H, m), 2.85-2.97 (1H, m), 3.05-3.14 (1H, m), 3.16-3.25 (1H, m), 3.33-3.41 (1H, m), 3.85-4.01 (1H, m), 4.14-4.27 (1H, m), 4.29-4.54 (4H, m), 4.67-4.77 (1H, m), 7.58-7.66 (1H, m), 8.29 (1H, dd, J=7.9, 1.5 Hz), 8.59-8.64 (1H, m).

Example 157

N-((1R,2R)-2-(1-oxo-6-(5-(trifluoromethyl)-1,2,4-oxadiazol-3-yl)-1,3-dihydro-2H-isoindol-2-yl)cyclohexyl)-2-oxa-5-azabicyclo[2.2.1]heptane-5-carboxamide To a mixture of 4-nitrophenyl ((1R,2R)-2-(1-oxo-6-(5-(trifluoromethyl)-1,2,4-oxadiazol-3-yl)-1,3-dihydro-2H-isoindol-2-yl)cyclohexyl)carbamate (63.8 mg), DIEA (0.103 mL) and THF (5 mL) was added 2-oxa-5-azabicyclo[2.2.1]heptane hydrochloride (4.4 mg) at 0° C., and the mixture was stirred overnight at room temperature. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (46 mg).

$^1$H NMR (300 MHz, CDCl$_3$) δ 1.31-1.55 (3H, m), 1.63-1.79 (3H, m), 1.80-2.04 (3H, m), 2.09-2.19 (1H, m), 2.85-2.97 (1H, m), 3.05-3.13 (1H, m), 3.16-3.24 (1H, m), 3.33-3.41 (1H, m), 3.84-4.01 (1H, m), 4.14-4.27 (1H, m), 4.29-4.55 (4H, m), 4.66-4.78 (1H, m), 7.58-7.66 (1H, m), 8.30 (1H, dd, J=7.9, 1.5 Hz), 8.59-8.64 (1H, m).

Example 158

N-((1R,2R)-2-(1-oxo-6-(5-(trifluoromethyl)-1,2,4-oxadiazol-3-yl)-1,3-dihydro-2H-isoindol-2-yl)cyclohexyl)pyrrolidine-1-carboxamide To a mixture of 2-((1R,2R)-2-aminocyclohexyl)-6-(5-(trifluoromethyl)-1,2,4-oxadiazol-3-yl)isoindolin-1-one hydrochloride (63.8 mg), 1-pyrrolidinecarbonyl chloride (0.055 mL) and THF (5 mL) were added TEA (0.138 mL) and 4,4-dimethylaminopyridine (9.1 mg) at 0° C., and the mixture was stirred at room temperature for 15 min, and then overnight at 45° C. To the reaction mixture were added 1-pyrrolidinecarbonyl chloride (0.055 mL) and TEA (0.138 mL), and the mixture was stirred with heating at 45° C. for 3 hr. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (47 mg).

$^1$H NMR (300 MHz, CDCl$_3$) δ 1.31-1.51 (3H, m), 1.61-2.01 (8H, m), 2.11-2.22 (1H, m), 2.89-3.01 (2H, m), 3.10-3.21 (2H, m), 3.85-4.00 (1H, m), 4.14-4.25 (1H, m), 4.34-4.49 (2H, m), 4.70-4.80 (1H, m), 7.60-7.66 (1H, m), 8.29 (1H, dd, J=7.9, 1.5 Hz), 8.54-8.57 (1H, m).

Example 159

N-((1R,2R)-2-(1-oxo-6-(5-(trifluoromethyl)-1,2,4-oxadiazol-3-yl)-1,3-dihydro-2H-isoindol-2-yl)cyclohexyl) azetidine-1-carboxamide To a mixture of 2-((1R,2R)-2-aminocyclohexyl)-6-(5-(trifluoromethyl)-1,2,4-oxadiazol-3-yl)isoindolin-1-one hydrochloride (100 mg), DIEA (0.212 mL) and THF (5 mL) was added bis(trichloromethyl) carbonate (25.8 mg) at room temperature, and the mixture was stirred at room temperature for 2 hr. To the reaction mixture was added azetidine hydrochloride (34.8 mg), and the mixture was stirred overnight at room temperature. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate), and recrystallized from ethyl acetate/hexane to give the title compound (40 mg).

$^1$H NMR (300 MHz, CDCl$_3$) δ 1.29-1.53 (3H, m), 1.63-1.76 (1H, m), 1.79-2.16 (6H, m), 3.53-3.65 (2H, m), 3.72-3.93 (3H, m), 4.10-4.30 (2H, m), 4.34-4.44 (1H, m), 4.68-4.79 (1H, m), 7.61-7.67 (1H, m), 8.30 (1H, dd, J=7.9, 1.5 Hz), 8.59-8.63 (1H, m).

Example 160

3-cyano-N-((1R,2R)-2-(1-oxo-6-(5-(trifluoromethyl)-1,2,4-oxadiazol-3-yl)-1,3-dihydro-2H-isoindol-2-yl)cyclohexyl)bicyclo[1.1.1]pentane-1-carboxamide A mixture of crude 2-((1R,2R)-2-aminocyclohexyl)-6-(5-(trifluoromethyl)-1,2,4-oxadiazol-3-yl)isoindolin-1-one hydrochloride (133 mg), methyl 3-cyanobicyclo[1.1.1]pentane-1-carboxylate (50 mg), bis(trimethylaluminium)-1,4-diazabicyclo[2.2.2]octane adduct (67.8 mg) and THF (3.0 mL) was heated under microwave irradiation at 110° C. for 60 min. To the reaction mixture was added saturated aqueous potassium sodium tartrate, and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate) to give the title compound (44 mg).

$^1$H NMR (300 MHz, CDCl$_3$) δ 1.34-1.51 (3H, m), 1.62-1.79 (1H, m), 1.79-2.14 (4H, m), 2.14-2.28 (6H, m), 3.85-4.03 (1H, m), 4.14-4.24 (1H, m), 4.35-4.45 (1H, m), 4.49-4.62 (1H, m), 5.99 (1H, d, J=9.1 Hz), 7.63 (1H, d, J=7.6 Hz), 8.33 (1H, dd, J=7.9, 1.5 Hz), 8.57 (1H, d, J=0.8 Hz).

Example 161

The compound of Example 161 was obtained using 2-oxa-6-azaspiro[3.3]heptane by a method similar to Example 156.

Example 162

3,3-difluoro-N-((1R,2R)-2-(1-oxo-6-(5-(trifluoromethyl)-1,2,4-oxadiazol-3-yl)-1,3-dihydro-2H-isoindol-2-yl)cyclohexyl)azetidine-1-carboxamide A solution of 4-nitrophenyl ((1R,2R)-2-(1-oxo-6-(5-(trifluoromethyl)-1,2,4-oxadiazol-3-yl)-1,3-dihydro-2H-isoindol-2-yl)cyclohexyl)carbamate (159 mg) in THF (3 mL) was added to a suspension of DIEA (0.256 mL) and 3,3-difluoroazetidine hydrochloride (58.3 mg) in THF (2 mL) at room temperature, and the mixture was stirred overnight at room temperature. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (45 mg).

$^1$H NMR (300 MHz, CDCl$_3$) δ 1.31-1.55 (3H, m), 1.62-1.78 (1H, m), 1.81-2.04 (3H, m), 2.08-2.20 (1H, m), 3.77-3.97 (3H, m), 4.04-4.25 (3H, m), 4.36-4.46 (1H, m), 4.59-4.73 (2H, m), 7.60-7.67 (1H, m), 8.32 (1H, dd, J=7.9, 1.9 Hz), 8.57-8.62 (1H, m).

Example 163

The compound of Example 163 was obtained using 3-methoxyazetidine by a method similar to Example 157.

Example 164

N-((1R,2R)-2-(1-oxo-6-(5-(trifluoromethyl)-1,2,4-oxadiazol-3-yl)-1,3-dihydro-2H-isoindol-2-yl)cyclohexyl)-6-oxa-3-azabicyclo[3.1.1]heptane-3-carboxamide A solution of 4-nitrophenyl ((1R,2R)-2-(1-oxo-6-(5-(trifluoromethyl)-1,2,4-oxadiazol-3-yl)-1,3-dihydro-2H-isoindol-2-yl)cyclohexyl)carbamate (159 mg) in THF (3 mL) was added to a suspension of DIEA (0.256 mL) and 6-oxa-3-azabicyclo[3.1.1]heptane (61 mg) in THF (2 mL) at room temperature, and the mixture was stirred overnight at room temperature. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (60 mg).

$^1$H NMR (300 MHz, CDCl$_3$) δ 1.32-1.60 (4H, m), 1.65-2.03 (4H, m), 2.16-2.28 (1H, m), 3.00-3.23 (2H, m), 3.31-3.51 (3H, m), 3.89-4.05 (1H, m), 4.17-4.29 (1H, m), 4.37-4.57 (3H, m), 4.67-4.77 (1H, m), 4.82 (1H, d, J=8.7 Hz), 7.63 (1H, d, J=7.9 Hz), 8.29 (1H, dd, J=7.9, 1.5 Hz), 8.50-8.55 (1H, m).

Example 165

1-(oxetan-3-yl)-3-((1R,2R)-2-(1-oxo-6-(5-(trifluoromethyl)-1,2,4-oxadiazol-3-yl)-1,3-dihydro-2H-isoindol-2-yl)cyclohexyl)urea A mixture of 4-nitrophenyl ((1R,2R)-2-(1-oxo-6-(5-(trifluoromethyl)-1,2,4-oxadiazol-3-yl)-1,3-dihydro-2H-isoindol-2-yl)cyclohexyl)carbamate (80 mg), THF (0.2 ml), oxetan-3-amine (21.93 mg), DIEA (103 mg) and THF (1.0 mL) was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (45.2 mg).

$^1$H NMR (300 MHz, CDCl$_3$) δ 1.31-1.56 (3H, m), 1.68-1.78 (1H, m), 1.81-2.02 (3H, m), 2.13-2.27 (1H, m, J=9.4 Hz), 3.78-3.97 (1H, m), 4.00-4.19 (2H, m), 4.28-4.52 (3H, m), 4.52-4.65 (1H, m), 4.66-4.79 (2H, m), 5.22 (1H, d, J=9.4 Hz), 5.42 (1H, d, J=7.2 Hz), 7.62 (1H, d, J=7.9 Hz), 8.26 (1H, dd, J=7.9, 1.5 Hz), 8.41 (1H, d, J=0.8 Hz).

Example 166

1,1-diisopropyl-3-((1R,2R)-2-(1-oxo-6-(5-(trifluoromethyl)-1,2,4-oxadiazol-3-yl)-1,3-dihydro-2H-isoindol-2-yl)cyclohexyl)urea A mixture of 4-nitrophenyl ((1R,2R)-2-(1-oxo-6-(5-(trifluoromethyl)-1,2,4-oxadiazol-3-yl)-1,3-dihydro-2H-isoindol-2-yl)cyclohexyl)carbamate (80 mg), THF (0.2 ml), N,N-diisopropylamine (30.4 mg), DIEA (103 mg) and THF (1.0 mL) was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (62.1 mg).

¹H NMR (300 MHz, CDCl₃) δ 0.85 (6H, d, J=6.8 Hz), 1.06 (6H, d, J=6.8 Hz), 1.32-1.52 (3H, m), 1.62-1.76 (1H, m), 1.80-2.00 (3H, m), 2.07-2.22 (1H, m), 3.47 (2H, spt, J=6.7 Hz), 3.92-4.07 (1H, m), 4.12-4.26 (1H, m), 4.31-4.44 (2H, m), 4.86 (1H, d, J=17.8 Hz), 7.53-7.65 (1H, m), 8.26 (1H, dd, J=7.9, 1.5 Hz), 8.54 (1H, d, J=1.1 Hz).

Example 167

N-((1R,2R)-2-(1-oxo-6-(5-(trifluoromethyl)-1,2,4-oxadiazol-3-yl)-1,3-dihydro-2H-isoindol-2-yl)cyclohexyl)-3-oxa-9-azabicyclo[3.3.1]nonane-9-carboxamide A mixture of 4-nitrophenyl ((1R,2R)-2-(1-oxo-6-(5-(trifluoromethyl)-1,2,4-oxadiazol-3-yl)-1,3-dihydro-2H-isoindol-2-yl)cyclohexyl)carbamate (159 mg), THF (3.0 ml), 3-oxa-9-azabicyclo[3.3.1]nonane hydrochloride (49.1 mg) and DIEA (0.157 mL) was stirred overnight at room temperature. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (hexane/ethyl acetate) to give the title compound (133 mg).

¹H NMR (300 MHz, CDCl₃) δ 1.16-1.81 (9H, m), 1.82-2.03 (3H, m), 2.10-2.22 (1H, m), 2.31 (1H, td, J=9.4, 5.7 Hz), 3.42 (1H, d, J=10.6 Hz), 3.56 (2H, d, J=10.6 Hz), 3.71 (3H, q, J=11.7 Hz), 3.90-4.07 (1H, m), 4.14-4.26 (1H, m), 4.42 (1H, d, J=17.4 Hz), 4.71-4.87 (2H, m), 7.64 (1H, dd, J=7.9, 0.8 Hz), 8.29 (1H, dd, J=7.9, 1.5 Hz), 8.55 (1H, d, J=1.1 Hz).

Example 168

N-((1R,2R)-2-(1-oxo-6-(5-(trifluoromethyl)-1,2,4-oxadiazol-3-yl)-1,3-dihydro-2H-isoindol-2-yl)cyclohexyl)thiomorpholine-4-carboxamide 1,1-dioxide A mixture of 4-nitrophenyl ((1R,2R)-2-(1-oxo-6-(5-(trifluoromethyl)-1,2,4-oxadiazol-3-yl)-1,3-dihydro-2H-isoindol-2-yl)cyclohexyl)carbamate (159 mg), THF (3.0 ml), thiomorpholine 1,1-dioxide (40.6 mg) and DIEA (0.052 mL) was stirred overnight at room temperature. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (hexane/ethyl acetate) to give the title compound (95 mg).

¹H NMR (300 MHz, CDCl₃) δ 1.22-1.33 (1H, m), 1.34-1.56 (3H, m), 1.72-2.03 (3H, m), 2.11-2.25 (1H, m), 2.49-2.63 (2H, m), 2.76-2.91 (2H, m), 3.59 (2H, ddd, J=14.9, 7.7, 2.6 Hz), 3.73-3.95 (3H, m), 4.15-4.26 (1H, m), 4.39-4.51 (1H, m), 4.63-4.76 (1H, m), 5.37 (1H, d, J=7.9 Hz), 7.66 (1H, d, J=7.9 Hz), 8.34 (1H, dd, J=7.9, 1.5 Hz), 8.59 (1H, d, J=0.8 Hz).

Example 169

3,3-difluoro-N-((1R,2R)-2-(1-oxo-6-(5-(trifluoromethyl)-1,2,4-oxadiazol-3-yl)-1,3-dihydro-2H-isoindol-2-yl)cyclohexyl)pyrrolidine-1-carboxamide A mixture of 4-nitrophenyl ((1R,2R)-2-(1-oxo-6-(5-(trifluoromethyl)-1,2,4-oxadiazol-3-yl)-1,3-dihydro-2H-isoindol-2-yl)cyclohexyl)carbamate (159 mg), THF (3.0 ml), 3,3-difluoropyrrolidine hydrochloride (43.1 mg) and DIEA (0.157 mL) was stirred overnight at room temperature. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (hexane/ethyl acetate) to give the title compound (118 mg).

¹H NMR (300 MHz, CDCl₃) δ 1.30-2.04 (7H, m), 2.10-2.32 (3H, m), 3.18-3.63 (4H, m), 3.80-3.98 (1H, m), 4.21 (1H, td, J=11.6, 3.6 Hz), 4.37-4.47 (1H, m), 4.69 (1H, d, J=17.4 Hz), 4.76 (1H, d, J=9.1 Hz), 7.64 (1H, d, J=7.9 Hz), 8.31 (1H, dd, J=7.9, 1.5 Hz), 8.56 (1H, s).

Example 170

2,2-difluoro-1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide (optically active compound having a shorter retention time)

A) 2,2-difluoro-1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide To a mixture of 2-((1R,2R)-2-aminocyclohexyl)-6-(5-(trifluoromethyl)-1,2,4-oxadiazol-3-yl)isoindolin-1-one hydrochloride (105 mg), 4-methylmorpholine (0.086 ml), 2,2-difluoro-1-methylcyclopropanecarboxylic acid (49.7 mg) and DMF (3 ml) was added HATU (159 mg) at 0° C., and the mixture was stirred for 10 min, and then overnight at room temperature. To the reaction mixture was added water, and the mixture was extracted with a mixture of ethyl acetate-THF. The organic layer was washed with saturated aqueous sodium hydrogencarbonate solution and saturated brine, dried over anhydrous sodium sulfate, and concentrated under reduced pressure. The residue was purified by Diol (3-(2,3-dihydroxypropoxy)propylsilane-bonded silica gel) silica gel column chromatography (hexane/ethyl acetate), and the fraction was concentrated under reduced pressure to give the title compound (120 mg).

¹H NMR (300 MHz, CDCl₃) δ 0.94-1.13 (1H, m), 1.20-1.31 (3H, m), 1.32-1.55 (4H, m), 1.73-2.03 (4H, m), 2.07-2.22 (1H, m), 3.93-4.16 (1H, m), 4.19-4.32 (1H, m), 4.35-4.66 (2H, m), 6.14-6.35 (1H, m), 7.55-7.67 (1H, m), 8.23-8.36 (1H, m), 8.53-8.62 (1H, m).

B) 2,2-difluoro-1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide (optically active compound having a shorter retention time)

A diastereomer mixture (120 mg) of 2,2-difluoro-1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide was resolved by HPLC (column: CHIRALPAK AD (RC042), 4.6 mmID×250 mmL, manufactured by Daicel Chemical Industries, mobile phase: hexane/methanol=95/5 (v/v)) under the following condition to give the title compound (45.6 mg) having a shorter retention time.

column: CHIRALPAK AD (RC042), 4.6 mmID×250 mmL, manufactured by Daicel Chemical Industries, mobile phase: hexane/methanol=95/5 (v/v)
flow rate: 1.0 ml/min
temperature: 30° C.
detection: UV 220 nm
concentration: 0.5 mg/ml
injected amount: 0.010 ml
$^1$H NMR (300 MHz, CDCl$_3$) δ 1.02-1.13 (1H, m), 1.27-1.30 (3H, m), 1.36-1.51 (3H, m), 1.61-1.77 (1H, m), 1.80-2.04 (4H, m), 2.06-2.22 (1H, m), 3.99-4.12 (1H, m), 4.25 (1H, td, J=11.5, 3.8 Hz), 4.34-4.60 (2H, m), 6.12 (1H, d, J=9.1 Hz), 7.55-7.63 (1H, m), 8.29 (1H, dd, J=7.9, 1.5 Hz), 8.59 (1H, d, J=0.8 Hz).

Example 171

2,2-difluoro-1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide (optically active compound having a longer retention time)

A diastereomer mixture (120 mg) of 2,2-difluoro-1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide was resolved by HPLC (column: CHIRALPAK AD (RC042), 4.6 mmID×250 mmL, manufactured by Daicel Chemical Industries, mobile phase: hexane/methanol=95/5 (v/v)) under the following condition to give the title compound (54.2 mg) having a longer retention time.
$^1$H NMR (300 MHz, CDCl$_3$) δ 0.97-1.06 (1H, m), 1.23-1.25 (3H, m), 1.36-1.51 (4H, m), 1.75-2.01 (4H, m), 2.07-2.20 (1H, m), 3.90-4.11 (1H, m), 4.21-4.33 (1H, m), 4.37-4.63 (2H, m), 6.12 (1H, d, J=9.1 Hz), 7.57-7.67 (1H, m), 8.31 (1H, dd, J=7.9, 1.5 Hz), 8.57 (1H, d, J=0.8 Hz).

Example 172

(1S)-2,2-difluoro-N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide A) tert-butyl ((3S,4R)-4-aminotetrahydro-2H-pyran-3-yl)carbamate A mixture of benzyl tert-butyl (3S,4R)-tetrahydro-2H-pyran-3,4-diylbiscarbamate (727 mg), ethanol (30 ml) and 10% palladium-carbon (50% wet, 110 mg) was stirred overnight at room temperature under hydrogen atmosphere. The insoluble substance was filtered off, and the filtrate was concentrated under reduced pressure to give the title compound (449 mg).
$^1$H NMR (300 MHz, CDCl$_3$) δ 1.45 (9H, s), 1.82-2.01 (1H, m), 2.63 (1H, td, J=9.4, 4.2 Hz), 2.96-3.10 (1H, m), 3.20-3.53 (3H, m), 3.82-4.10 (3H, m), 4.30-5.06 (2H, m).

B) (1S)-2,2-difluoro-N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide To a mixture of tert-butyl ((3S,4R)-4-aminotetrahydro-2H-pyran-3-yl)carbamate (77.7 mg), (1S)-2,2-difluorocyclopropanecarboxylic acid (61.4 mg), TEA (0.150 ml) and DMF (2 ml) was added HATU (219 mg) at 0° C., and the mixture was stirred at room temperature for 30 min. To the reaction mixture was added water, and the mixture was extracted with ethyl acetate. The organic layer was washed with saturated aqueous sodium hydrogencarbonate solution and saturated brine, dried over anhydrous sodium sulfate, and concentrated under reduced pressure. The residue was purified by silica gel column chromatography (ethyl acetate), and the fraction was concentrated under reduced pressure. To a mixture of the obtained residue and ethyl acetate (2 ml) and THF (2 ml) was added 4 M hydrogen chloride-ethyl acetate solution (2 ml), and the mixture was stirred overnight at room temperature, and concentrated under reduced pressure. To a mixture of the obtained residue, THF (5 ml) and methyl 2-(bromomethyl)-5-(5-(trifluoromethyl)-1,2,4-oxadiazol-3-yl)benzoate (131 mg) was added DIEA (0.163 ml) at room temperature, and the mixture was stirred overnight under nitrogen atmosphere at 60° C. The reaction mixture was concentrated under reduced pressure, water was added thereto, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) and Diol (3-(2,3-dihydroxypropoxy)propylsilane-bonded silica gel) silica gel column chromatography (hexane/ethyl acetate), and the fraction was concentrated under reduced pressure. The obtained residue was purified by preparative HPLC (column: L-Column 2 ODS, mobile phase: acetonitrile/0.1% aqueous trifluoroacetic acid solution), and the obtained fraction was neutralize with saturated aqueous sodium hydrogencarbonate solution, and the mixture was extracted with ethyl acetate. The organic layer was dried over anhydrous magnesium sulfate, and concentrated under reduced pressure to give the title compound (13.2 mg).
$^1$H NMR (300 MHz, CDCl$_3$) δ 1.46-1.57 (1H, m), 1.76-1.95 (2H, m), 2.09-2.20 (2H, m), 3.46-3.63 (2H, m), 4.04-4.12 (2H, m), 4.27-4.40 (2H, m), 4.40-4.54 (1H, m), 4.65 (1H, d, J=17.0 Hz), 6.28 (1H, d, J=8.7 Hz), 7.59 (1H, d, J=7.6 Hz), 8.29 (1H, dd, J=7.5, 1.5 Hz), 8.56 (1H, d, J=1.5 Hz).

Alternative Step

To a mixture of tert-butyl ((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)carbamate (106 g) and 2-propanol (500 ml) was added 4 M hydrogen chloride-CPME solution (600 ml), and the mixture was stirred at room temperature for 22 hr. To the reaction mixture was added 4 M hydrogen chloride-CPME solution (100 ml), and the mixture was stirred at room temperature for 5 hr. To the reaction mixture was added CPME (800 ml) at room temperature, and the mixture was stirred at room temperature for 1 hr. The precipitate was collected by filtration, washed twice with CPME (250 ml), and dried. The same procedure was repeated in another batch. The products obtained from two batches were combined to give 2-((3S,4R)-4-aminotetrahydro-2H-pyran-3-yl)-6-(5-(trifluoromethyl)-1,2,4-oxadiazol-3-yl)isoindolin-1-one hydrochloride (164 g). To a mixture of the obtained 2-((3S,4R)-4-aminotetrahydro-2H-pyran-3-yl)-6-(5-(trifluoromethyl)-1,2,4-oxadiazol-3-yl)isoindolin-1-one hydrochloride (160 g) and DMF (1600 ml) were added DIEA (138 ml), EDCI hydrochloride (114 g) and HOBt monohydrate (91 g) at 0° C., and the mixture was stirred at room temperature for 1.5 hr. The reaction mixture was poured into water, and the mixture was extracted with ethyl acetate. The organic layer was washed with aqueous sodium hydrogencarbonate solution and saturated brine, dried over anhydrous sodium sulfate, and concentrated under reduced pressure. The residue was purified by silica gel column chromatography (hexane/ethyl acetate and ethyl acetate). The obtained fraction was crystallized from ethanol/water to give the title compound (167 g).

$^1$H NMR (400 MHz, DMSO-d$_6$) δ 1.61-1.77 (3H, m), 1.82-1.91 (1H, m), 2.33-2.47 (1H, m), 3.43-3.62 (2H, m), 3.82 (1H, dd, J=11.00, 4.65 Hz), 3.92 (1H, dd, J=11.37, 4.28 Hz), 4.14 (1H, td, J=10.88, 4.65 Hz), 4.21-4.32 (1H, m), 4.52 (1H, d, J=18.10 Hz), 4.64 (1H, d, J=18.10 Hz), 7.82 (1H, d, J=8.07 Hz), 8.23 (1H, s), 8.25 (1H, d, J=8.22 Hz), 8.56 (1H, d, J=9.05 Hz).

elemental analysis: Anal. for C$_{20}$H$_{17}$F$_5$N$_4$O$_4$
calculated value C, 50.85; H, 3.63; N, 11.86.
actual measured value C, 50.86; H, 3.65; N, 11.84.

Example 173

1-hydroxy-N-((1R,2R)-2-(1-oxo-6-(5-(trifluoromethyl)-1,2,4-oxadiazol-3-yl)-1,3-dihydro-2H-isoindol-2-yl)cyclohexyl)cyclobutanecarboxamide To a mixture of 2-((1R,2R)-2-aminocyclohexyl)-6-(5-(trifluoromethyl)-1,2,4-oxadiazol-3-yl)isoindolin-1-one hydrochloride (100 mg), TEA (0.104 ml), 1-hydroxycyclobutanecarboxylic acid (40.4 mg) and DMF (3 ml) was added HATU (151 mg) at 0° C., and the mixture was stirred overnight at room temperature. To the reaction mixture was added water, and the mixture was extracted with ethyl acetate. The organic layer was washed with saturated aqueous sodium hydrogencarbonate solution and saturated brine, dried over anhydrous sodium sulfate, and concentrated under reduced pressure. The residue was purified by silica gel column chromatography (hexane/ethyl acetate), and the fraction was concentrated under reduced pressure. The obtained residue was crystallized from a mixture of diethyl ether-THF/a mixture of hexane-diisopropyl ether to give the title compound (23.8 mg).

$^1$H NMR (300 MHz, CDCl$_3$) δ 1.36-1.55 (3H, m), 1.59-1.82 (5H, m), 1.84-2.12 (5H, m), 2.22-2.37 (1H, m), 3.14 (1H, s), 3.89-4.24 (2H, m), 4.40 (1H, d, J=17.8 Hz), 4.72 (1H, d, J=17.4 Hz), 6.68 (1H, d, J=10.2 Hz), 7.64 (1H, d, J=7.9 Hz), 8.30 (1H, dd, J=7.9, 1.5 Hz), 8.51 (1H, d, J=0.8 Hz).

Example 174

1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)cyclobutanecarboxamide To a mixture of 2-((1R,2R)-2-aminocyclohexyl)-6-(5-(trifluoromethyl)-1,2,4-oxadiazol-3-yl)isoindolin-1-one hydrochloride (50 mg), TEA (0.052 ml), 1-methylcyclobutanecarboxylic acid (19.8 mg) and DMF (2 ml) was added HATU (76 mg) at 0° C., and the mixture was stirred overnight at room temperature. To the reaction mixture was added water, and the mixture was extracted with ethyl acetate. The organic layer was washed with saturated aqueous sodium hydrogencarbonate solution and saturated brine, dried over anhydrous sodium sulfate, and concentrated under reduced pressure. The residue was purified by silica gel column chromatography (hexane/ethyl acetate) to give the title compound (53.2 mg).

$^1$H NMR (300 MHz, CDCl$_3$) δ 1.10 (3H, s), 1.35-2.18 (14H, m), 3.97-4.14 (1H, m), 4.15-4.28 (1H, m), 4.39 (1H, d, J=17.4 Hz), 4.70 (1H, d, J=17.4 Hz), 5.60 (1H, d, J=9.4 Hz), 7.62 (1H, d, J=7.9 Hz), 8.29 (1H, dd, J=7.9, 1.5 Hz), 8.56 (1H, d, J=1.5 Hz).

Example 175

1-methoxy-N-((1R,2R)-2-(1-oxo-6-(5-(trifluoromethyl)-1,2,4-oxadiazol-3-yl)-1,3-dihydro-2H-isoindol-2-yl)cyclohexyl)cyclobutanecarboxamide To a mixture of 2-((1R,2R)-2-aminocyclohexyl)-6-(5-(trifluoromethyl)-1,2,4-oxadiazol-3-yl)isoindolin-1-one hydrochloride (50 mg), TEA (0.052 ml), 1-methoxycyclobutanecarboxylic acid (22.6 mg) and DMF (2 ml) was added HATU (76 mg) at 0° C., and the mixture was stirred at room temperature for 3 hr. To the reaction mixture was added water, and the mixture was extracted with ethyl acetate. The organic layer was washed with saturated aqueous sodium hydrogencarbonate solution and saturated brine, dried over anhydrous sodium sulfate, and concentrated under reduced pressure. The residue was purified by silica gel column chromatography (hexane/ethyl acetate) to give the title compound (54.1 mg).

$^1$H NMR (300 MHz, CDCl$_3$) δ 1.39-1.56 (4H, m), 1.61-2.11 (9H, m), 2.19-2.32 (1H, m), 2.98 (3H, s), 3.96-4.15 (1H, m), 4.20-4.31 (1H, m), 4.41 (1H, d, J=17.4 Hz), 4.76 (1H, d, J=17.4 Hz), 6.45 (1H, d, J=9.4 Hz), 7.63 (1H, d, J=7.9 Hz), 8.28 (1H, dd, J=7.9, 1.5 Hz), 8.54 (1H, s).

Example 176

2-((1R,2S)-2-aminocyclohexyl)-6-(5-(trifluoromethyl)-1,2,4-oxadiazol-3-yl)isoindolin-1-one hydrochloride To a mixture of tert-butyl ((1S,2R)-2-(1-oxo-6-(5-(trifluoromethyl)-1,2,4-oxadiazol-3-yl)-1,3-dihydro-2H-isoindol-2-yl)cyclohexyl)carbamate (105 mg) and methanol (3 ml) was added 4 M hydrogen chloride-CPME solution (2 ml), and the mixture was stirred overnight at room temperature. The reaction mixture was concentrated under reduced pressure to give the title compound (91 mg).

Examples 177-179

The compounds of Examples 177 to 179 were obtained using methyl 2-(bromomethyl)-5-(5-(trifluoromethyl)-1,2,4-oxadiazol-3-yl)benzoate and the corresponding amine by a method similar to Step C of Example 24.

Example 180

2-((3S,4R)-3-(2-oxopyrrolidin-1-yl)tetrahydro-2H-pyran-4-yl)-6-(5-(trifluoromethyl)-1,2,4-oxadiazol-3-yl)isoindolin-1-one A) tert-butyl ((3S,4R)-3-aminotetrahydro-2H-pyran-4-yl)carbamate A mixture of benzyl tert-butyl (3S,4R)-tetrahydro-2H-pyran-3,4-diylbiscarbamate (20 g), ethanol (200 ml) and 10% palladium-carbon (50% wet, 2 g) was stirred under hydrogen atmosphere at room temperature for 3 hr. The insoluble substance was filtered off, and the filtrate was concentrated under reduced pressure to give the title compound (10.3 g).

MS (API+), found: 217.3.

B) tert-butyl ((3S,4R)-3-(2-oxopyrrolidin-1-yl)tetrahydro-2H-pyran-4-yl)carbamate To a solution of tert-butyl ((3S,4R)-3-aminotetrahydro-2H-pyran-4-yl)carbamate (1.0 g) and TEA (0.77 ml) in THF (20 ml) was added 4-chlorobutanoyl chloride (0.57 ml) at 0° C. The mixture was stirred at the same temperature for 30 min, and potassium tert-butoxide (1621 mg) was added thereto. The mixture was stirred at the same temperature for 1 hr, ice water was added thereto, and the mixture was extracted twice with ethyl acetate. The organic layer was washed with 0.1M hydrochloric acid and brine, dried over sodium sulfate, and concentrated under reduced pressure to give the title compound (1.2 g).

$^1$H NMR (300 MHz, DMSO-$d_6$) δ 1.35 (9H, s), 1.50-1.95 (4H, m), 2.14 (2H, m, J=8.69 Hz), 3.17 (1H, q, J=7.55 Hz), 3.25-3.32 (2H, m), 3.44-3.85 (5H, m), 6.85 (1H, d, J=9.06 Hz).

C) 1-((3S,4R)-4-aminotetrahydro-2H-pyran-3-yl)pyrrolidin-2-one hydrochloride

To a solution of tert-butyl ((3S,4R)-3-(2-oxopyrrolidin-1-yl)tetrahydro-2H-pyran-4-yl)carbamate (1.19 g) in ethyl acetate (5 ml) was added 4 M hydrogen chloride-ethyl acetate solution (10.5 ml), and the mixture was stirred at room temperature for 8 hr. The reaction mixture was concentrated under reduced pressure to give the title compound (860 mg).

$^1$H NMR (300 MHz, DMSO-$d_6$) δ 1.53-1.78 (1H, m), 1.80-2.09 (3H, m), 2.11-2.39 (2H, m), 3.16-3.29 (1H, m), 3.29-3.36 (1H, m), 3.37-3.49 (2H, m), 3.51-3.62 (1H, m), 3.62-3.73 (1H, m), 3.78-3.96 (2H, m), 8.18 (3H, brs).

D) 2-((3S,4R)-3-(2-oxopyrrolidin-1-yl)tetrahydro-2H-pyran-4-yl)-6-(5-(trifluoromethyl)-1,2,4-oxadiazol-3-yl)isoindolin-1-one To a solution of 1-((3S,4R)-4-aminotetrahydro-2H-pyran-3-yl)pyrrolidin-2-one hydrochloride (3.0 g) and DIEA (12 ml) in acetonitrile (60 ml) was added methyl 2-(bromomethyl)-5-(5-(trifluoromethyl)-1,2,4-oxadiazol-3-yl)benzoate (5.5 g) at 80° C. The mixture was refluxed for 10 hr. To the reaction mixture was added 1 M hydrochloric acid at room temperature, and the mixture was stirred for 1 hr. The obtained solid was collected by filtration to give the title compound (3.8 g).

$^1$H NMR (300 MHz, DMSO-$d_6$) δ 1.65-1.93 (4H, m), 1.95-2.16 (2H, m), 3.19-3.30 (1H, m), 3.42-3.68 (3H, m), 3.80 (1H, dd, J=10.8, 4.7 Hz), 3.96 (1H, dd, J=11.4, 3.8 Hz), 4.05-4.19 (1H, m), 4.44-4.69 (3H, m), 7.84-7.91 (1H, m), 8.22-8.25 (1H, m), 8.25-8.31 (1H, m).

Example 181

The compound of Example 181 was obtained using methyl 2-(bromomethyl)-5-(5-(trifluoromethyl)-1,2,4-oxadiazol-3-yl)benzoate and the corresponding amine by a method similar to Step C of Example 24 and Example 34.

Example 182

The compound of Example 182 was obtained using the compound of Example 178 by a method similar to Example 34.

Example 183

The compound of Example 183 was obtained using the compound of Example 178 by a method similar to Example 35.

Example 184

The compound of Example 184 was obtained using methyl 2-(bromomethyl)-5-cyanobenzoate and the corresponding amine by a method similar to Steps C, D, F and G of Example 1.

Example 185

The compound of Example 185 was obtained using methyl 2-(bromomethyl)-5-(5-(trifluoromethyl)-1,2,4-oxadiazol-3-yl)benzoate and the corresponding amine by a method similar to Steps C and D of Example 1.

Example 186

The compound of Example 186 was obtained using methyl 2-(bromomethyl)-5-(5-(trifluoromethyl)-1,2,4-oxadiazol-3-yl)nicotinate and the corresponding amine by a method similar to Step E of Example 84.

Example 187

The compound of Example 187 was obtained using 2-((1R,2R)-2-aminocyclohexyl)-6-(5-(trifluoromethyl)-1,2,4-oxadiazol-3-yl)isoindolin-1-one hydrochloride and the corresponding amine by a method similar to Example 156.

Example 188

N,N-dimethyl-2-(1-oxo-6-(5-(trifluoromethyl)-1,2,4-oxadiazol-3-yl)-1,3-dihydro-2H-isoindol-2-yl)benzamide A) methyl 5-cyano-2-(((2-(dimethylcarbamoyl)phenyl)amino)methyl)benzoate To a solution of methyl 2-(bromomethyl)-5-cyanobenzoate (300 mg) and 2-amino-N,N-dimethylbenzamide (194 mg) in DMF (5 ml) was added DIEA (458 mg) at room temperature. The mixture was stirred under nitrogen atmosphere at 50° C. for 15 hr, and concentrated under reduced pressure. To the residue was added water, and the mixture was extracted with ethyl acetate. The organic layer was washed with brine, dried over magnesium sulfate, and concentrated under reduced pressure. The residue was purified by silica gel column chromatography (hexane/ethyl acetate) to give the title compound (262 mg).

$^1$H NMR (300 MHz, DMSO-$d_6$) δ 2.95 (6H, brs), 3.89 (3H, s), 4.71 (2H, d, J=6.1 Hz), 6.03 (1H, t, J=6.2 Hz), 6.39 (1H, d, J=8.3 Hz), 6.60 (1H, td, J=7.4, 1.1 Hz), 7.00-7.14 (2H, m), 7.65 (1H, d, J=8.0 Hz), 8.00 (1H, dd, J=8.0, 1.9 Hz), 8.24 (1H, d, J=1.9 Hz).

B) 2-(6-cyano-1-oxo-1,3-dihydro-2H-isoindol-2-yl)-N,N-dimethylbenzamide

To a solution of methyl 5-cyano-2-(((2-(dimethylcarbamoyl)phenyl)amino)methyl)benzoate (258 mg) in methanol (5 ml) was added 1 M aqueous sodium hydroxide solution (1.5 ml) at room temperature. The mixture was stirred for 1 hr, 1 M hydrochloric acid was added thereto, and the mixture was concentrated under reduced pressure. To the residue were added DMF (5 ml), TEA (0.32 ml) and HATU (436 mg), and the mixture was stirred at room temperature for 15 hr. To the reaction mixture was added aqueous sodium hydrogencarbonate solution, and the mixture was extracted with ethyl acetate. The organic layer was washed with brine, dried over anhydrous magnesium sulfate, and concentrated under reduced pressure. The residue was purified by silica gel column chromatography (hexane/ethyl acetate) to give the title compound (158 mg).

$^1$H NMR (300 MHz, DMSO-d) δ 2.84 (3H, s), 2.91 (3H, s), 4.95 (2H, s), 7.37-7.51 (2H, m), 7.53-7.63 (2H, m), 7.82-7.93 (1H, m), 8.05-8.18 (1H, m), 8.24 (1H, s).

C) N,N-dimethyl-2-(1-oxo-6-(5-(trifluoromethyl)-1,2,4-oxadiazol-3-yl)-1,3-dihydro-2H-isoindol-2-yl) benzamide To a solution of 2-(6-cyano-1-oxo-1,3-dihydro-2H-isoindol-2-yl)-N,N-dimethylbenzamide (150 mg) in methanol (3 ml) was added 50% aqueous hydroxylamine solution (0.15 ml) at room temperature. The mixture was stirred at room temperature for 5 hr, and concentrated under reduced pressure. To the residue was added THF (3 ml), and to the mixture was added trifluoroacetic anhydride (0.21 ml) at room temperature. The mixture was stirred under nitrogen atmosphere at 50° C. for 15 hr. To the reaction mixture was added brine, and the mixture was extracted with ethyl acetate. The organic layer was washed with brine, dried over anhydrous magnesium sulfate, and concentrated under reduced pressure. The residue was purified by silica gel column chromatography (hexane/ethyl acetate) to give the title compound (160 mg).

$^1$H NMR (300 MHz, DMSO-d$_6$) δ 2.85 (3H, s), 2.93 (3H, s), 4.98 (2H, brs), 7.40-7.49 (2H, m), 7.51-7.64 (2H, m), 7.94 (1H, d, J=8.3 Hz), 8.31 (1H, s), 8.33-8.40 (1H, m).

Example 189

2-((3S,4R)-4-aminotetrahydro-2H-pyran-3-yl)-6-(5-(trifluoromethyl)-1,2,4-oxadiazol-3-yl)isoindolin-1-one hydrochloride

A) ethyl 4-(((1R)-1-phenylethyl)amino)-5,6-dihydro-2H-pyran-3-carboxylate

To a mixture of tetrahydro-4H-pyran-4-one (500 g) and toluene (6600 ml) was added 1 M lithium 1,1,1,3,3,3-hexamethyldisilazan-2-ide THF solution (5500 ml) at −70° C. The mixture was stirred at −70° C. for 30 min, ethyl carbonochloridate (611 g) was added thereto, and the mixture was stirred at room temperature for 20 min. To the reaction mixture were added acetic acid (777 g) and water (1100 ml), and the organic layer was washed with saturated brine, dried over anhydrous sodium sulfate, and concentrated under reduced pressure. To the residue was added toluene (1300 ml) and (1R)-1-phenylethanamine (153 g) and p-toluenesulfonic acid (24 g) were added thereto, and the mixture was heated under reflux overnight. To the mixture was added ethyl acetate, and the mixture was washed with saturated aqueous sodium hydrogencarbonate solution and saturated brine, dried over anhydrous sodium sulfate, and concentrated under reduced pressure. The residue was purified by silica gel column chromatography (petroleum ether/ethyl acetate) to give the title compound (189 g)

$^1$H NMR (400 MHz, CDCl$_3$) δ 1.29 (3H, t, J=7.2 Hz), 1.51 (3H, d, J=6.8 Hz), 2.02-2.06 (1H, m), 2.35-2.40 (1H, m), 3.60-3.71 (2H, m), 4.13-4.19 (2H, m), 4.30 (2H, s), 4.59-4.62 (1H, m), 7.21-7.26 (3H, m), 7.30-7.34 (2H, m), 9.10-9.11 (1H, m).

B) ethyl (3R,4R)-4-(((1R)-1-phenylethyl)amino) tetrahydro-2H-pyran-3-carboxylate To a mixture of ethyl 4-(((1R)-1-phenylethyl)amino)-5,6-dihydro-2H-pyran-3-carboxylate (189 g) and toluene (1300 ml) was added magnesium sulfate (329 g), and the mixture was stirred at room temperature for 20 min. Acetic acid (216 ml) and sodium triacetoxyborohydride (216 g) were added thereto at 0° C., and the mixture was stirred at room temperature for 5 hr.

To the mixture was added water, the pH of the mixture was adjusted to 8 with conc. aqueous ammonia, and the mixture was extracted with ethyl acetate. The organic layer was washed with saturated brine, dried over anhydrous sodium sulfate, and concentrated under reduced pressure. The residue was purified by silica gel column chromatography (petroleum ether/ethyl acetate) to give the title compound (162 g).

$^1$H NMR (400 MHz, CDCl$_3$) δ 1.27-1.34 (6H, m), 1.56-1.64 (1H, m), 1.81-1.98 (1H, m), 2.18 (1H, brs), 2.78-2.85 (2H, m), 3.31-3.47 (2H, m), 3.85-3.96 (2H, m), 4.14-4.26 (3H, m), 7.20-7.27 (1H, m), 7.29-7.38 (4H, m).

C) ethyl (3R,4R)-4-aminotetrahydro-2H-pyran-3-carboxylate

A mixture of ethyl (3R,4R)-4-(((1R)-1-phenylethyl)amino)tetrahydro-2H-pyran-3-carboxylate (80 g), 10% palladium-carbon (50% wet, 15 g) and ethanol (1000 ml) was stirred under hydrogen atmosphere (3.4 atm) at 45° C. for 12 hr. The mixture was filtered, and the filtrate was concentrated under reduced pressure to give the title compound (48 g).

D) ethyl (3R,4R)-4-((tert-butoxycarbonyl)amino) tetrahydro-2H-pyran-3-carboxylate A mixture of ethyl (3R,4R)-4-aminotetrahydro-2H-pyran-3-carboxylate (95 g), di-tert-butyl dicarbonate (127 g), TEA (141.7 g) and methanol/dichloromethane (1/1) mixture (2000 ml) was stirred overnight at room temperature. The mixture was concentrated under reduced pressure, and to the residue was added ethyl acetate. The mixture was washed with saturated brine, dried over anhydrous sodium sulfate, and concentrated under reduced pressure. The residue was purified by silica gel column chromatography (petroleum ether/ethyl acetate) to give the title compound (148.3 g).

$^1$H NMR (400 MHz, CDCl$_3$) δ 1.21 (3H, d, J=7.2 Hz), 1.43 (9H, s), 1.70 (1H, d, J=13.6 Hz), 1.96-2.10 (1H, m), 2.74 (1H, d, J=2.8 Hz), 3.40-3.52 (1H, m), 3.57 (1H, dd, J=11.80, 2.4 Hz), 3.88-4.02 (2H, m), 4.19 (2H, q, J=7.2 Hz), 4.24-4.36 (1H, m), 5.60 (1H, d, J=8.8 Hz).

E) ethyl (3S,4R)-4-((tert-butoxycarbonyl)amino) tetrahydro-2H-pyran-3-carboxylate Sodium (18.6 g) was added to ethanol (715 ml) at 0° C., and the mixture was stirred at 0° C. until the sodium was dissolved to prepare sodium ethanolate. A mixture of ethyl (3R,4R)-4-((tert-butoxycarbonyl)amino)tetrahydro-2H-pyran-3-carboxylate (148.3 g) and ethanol (382 ml) was added to the prepared sodium ethanolate, and the mixture was stirred overnight at room temperature. To the mixture was added 0.5 M hydrochloric acid, and the mixture was extracted with ethyl acetate. The organic layer was washed with saturated brine, dried over anhydrous sodium sulfate, and concentrated under reduced pressure. The residue was purified by silica gel column chromatography (petroleum ether/ethyl acetate) to give the title compound (89.0 g).

$^1$H NMR (400 MHz, CDCl$_3$) δ 1.25 (3H, t, J=7.2 Hz), 1.42 (9H, s), 1.97-2.07 (1H, m), 2.48 (1H, m), 3.42-3.61 (2H, m), 3.86-3.97 (2H, m), 4.03 (1H, dd, J=11.6, 4.0 Hz), 4.14 (2H, m), 4.64 (1H, brs).

F) (3S,4R)-4-((tert-butoxycarbonyl)amino)tetrahydro-2H-pyran-3-carboxylic acid

To a mixture of ethyl (3S,4R)-4-((tert-butoxycarbonyl)amino)tetrahydro-2H-pyran-3-carboxylate (30 g), THF (300 ml) and ethanol (300 ml) was added 2 M aqueous sodium hydroxide solution (300 ml), and the mixture was stirred at room temperature for 1 hr, and concentrated under reduced pressure. To the mixture was added water, and the mixture was washed with diethyl ether. The pH of the aqueous layer was adjusted to about 5 with 2 M hydrochloric acid, and the mixture was extracted with ethyl acetate. The organic layer was washed with saturated brine, dried over anhydrous sodium sulfate, and concentrated under reduced pressure to give the title compound (25 g).

$^1$H NMR (400 MHz, CDCl$_3$) δ 1.44 (9H, s), 2.04 (1H, m), 2.54 (1H, s), 3.43-3.65 (2H, m), 3.96 (2H, d, J=11.6 Hz), 4.03-4.14 (1H, m), 4.75 (1H, s).

G) benzyl tert-butyl (3S,4R)-tetrahydro-2H-pyran-3,4-diylbiscarbamate

A mixture of (3S,4R)-4-((tert-butoxycarbonyl)amino)tetrahydro-2H-pyran-3-carboxylic acid (75.8 g), diphenylphosphoryl azide (80 ml), TEA (51.6 ml) and toluene (1000 ml) was stirred at room temperature for 2 hr under nitrogen atmosphere. To the reaction mixture was added benzyl alcohol (160 ml), and the mixture was stirred under nitrogen atmosphere at 80° C. for 3 hr. To the reaction mixture was added water at room temperature, and the mixture was extracted with ethyl acetate. The organic layer was washed with water and saturated brine, dried over anhydrous sodium sulfate, and concentrated under reduced pressure. The residue was purified by silica gel column chromatography (hexane/ethyl acetate), and the fraction was concentrated under reduced pressure. The obtained residue was crystallized from petroleum ether/ethyl acetate to give the title compound (32.5 g).

$^1$H NMR (400 MHz, CDCl$_3$) δ 1.41 (9H, s), 1.95 (1H, m), 3.04 (1H, t, J=10.4 Hz), 3.33-3.44 (1H, m), 3.46-3.63 (2H, m), 3.97 (1H, m), 4.12 (1H, m), 4.67 (1H, d, J=7.2 Hz), 5.04-5.14 (2H, m), 5.38 (1H, d, J=5.0 Hz), 7.33 (5H, m).

H) tert-butyl ((3S,4R)-3-aminotetrahydro-2H-pyran-4-yl)carbamate

A mixture of benzyl tert-butyl (3S,4R)-tetrahydro-2H-pyran-3,4-diylbiscarbamate (32.5 g), 10% palladium-carbon (50% wet, 6 g) and ethanol (320 ml) was stirred under hydrogen atmosphere (3.4 atm) at 45° C. for 12 hr. The mixture was filtered, and the filtrate was concentrated under reduced pressure to give the title compound (20 g).

$^1$H NMR (400 MHz, CDCl$_3$) δ 1.46 (9H, s), 1.96-2.09 (1H, m), 2.51-2.65 (1H, m), 3.05 (1H, t, J=10.0 Hz), 3.29-3.48 (2H, m), 3.72 (1H, m), 3.87-4.01 (2H, m), 4.61 (1H, brs).

I) tert-butyl ((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)carbamate A mixture of tert-butyl ((3S,4R)-3-aminotetrahydro-2H-pyran-4-yl)carbamate (20 g), methyl 2-(bromomethyl)-5-(5-(trifluoromethyl)-1,2,4-oxadiazol-3-yl)benzoate (33.8 g), DIEA (19.3 ml) and THF (1500 ml) was stirred overnight under nitrogen atmosphere at 60° C., and the mixture was concentrated under reduced pressure. To the mixture was added water, and the mixture was extracted with ethyl acetate. The organic layer was washed with saturated brine, dried over anhydrous so sodium sulfate, and concentrated under reduced pressure. The residue was purified by silica gel column chromatography (hexane/ethyl acetate) to give the title compound (28.8 g).

$^1$H NMR (400 MHz, CDCl$_3$) δ 1.13 (9H, s), 2.05-2.10 (1H, m), 3.46-3.57 (2H, m), 3.90-3.99 (1H, m), 4.03-4.13 (2H, m), 4.30-4.39 (2H, m), 4.70-4.85 (2H, m), 7.62 (1H, d, J=8.0 Hz), 8.29 (1H, d, J=8.0 Hz), 8.60 (1H, s).

J) 2-((3S,4R)-4-aminotetrahydro-2H-pyran-3-yl)-6-(5-(trifluoromethyl)-1,2,4-oxadiazol-3-yl)isoindolin-1-one hydrochloride A mixture of tert-butyl ((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)carbamate (4.9 g) and 4 M hydrogen chloride-dioxane solution (50 ml) was stirred overnight at room temperature, and concentrated under reduced pressure to give the title compound (4.3 g).

$^1$H NMR (400 MHz, DMSO-d$_6$): δ 1.72-1.82 (1H, m), 2.11-2.14 (1H, m), 3.35 (1H, brs), 3.43 (1H, t, J=11.2 Hz), 3.62 (1H, t, J=11.2 Hz), 3.82-3.95 (3H, m), 4.17-4.24 (1H, m), 4.54-4.72 (2H, m), 7.89 (1H, d, J=8.0 Hz), 8.26-8.32 (5H, m).

Example 190

(1R)-2,2-difluoro-N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide To a mixture of 2-((3S,4R)-4-aminotetrahydro-2H-pyran-3-yl)-6-(5-(trifluoromethyl)-1,2,4-oxadiazol-3-yl)isoindolin-1-one hydrochloride (2.8 g), 4-methylmorpholine (2.0 g), 2,2-difluorocyclopropanecarboxylic acid (1.05 g) and DMF (35 ml) was added HATU (3.76 g) at 0° C., and the mixture was stirred overnight at room temperature. To the mixture was added water, and the mixture was extracted with ethyl acetate. The organic layer was washed with saturated aqueous sodium hydrogencarbonate solution and saturated brine, dried over anhydrous sodium sulfate, and concentrated under reduced pressure. The residue was purified by silica gel column chromatography (petroleum ether/ethyl acetate) to give the title compound (1.15 g).

$^1$H NMR (400 MHz, DMSO-d$_6$) δ 1.53-1.74 (3H, m), 1.84-1.90 (1H, m), 2.34-2.43 (1H, m), 3.46 (1H, t, J=11.6 Hz), 3.55 (1H, t, J=11.2 Hz), 3.81 (1H, dd, J=11.2, 4.8 Hz), 3.90 (1H, dd, J=11.2, 4.4 Hz), 4.12 (1H, td, J=10.8, 4.8 Hz), 4.22-4.31 (1H, m), 4.54-4.65 (2H, m), 7.86 (2H, d, J=7.6 Hz), 8.23 (1H, s), 8.27 (1H, dd, J=7.6, 1.2 Hz), 8.50 (1H, d, J=8.8 Hz).

Example 191

2-((1R,2R)-2-(2-oxopyrrolidin-1-yl)cyclohexyl)-6-(5-(trifluoromethyl)-1,2,4-oxadiazol-3-yl)isoindolin-1-one The compound of Example 191 was obtained using methyl 2-(bromomethyl)-5-(5-(trifluoromethyl)-1,2,4-oxadiazol-3-yl)benzoate and the corresponding amine by a method similar to Step C of Example 24.

Example 192

3-methyl-N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)oxetane-3-carboxamide To a mixture of 2-((3S,4R)-4-aminotetrahydro-2H-pyran-3-yl)-6-(5-(trifluoromethyl)-1,2,4-oxadiazol-3-yl)isoindolin-1-one hydrochloride (100 mg), TEA (0.103 ml), 3-methyloxetane-3-carboxylic acid (34.4 mg) and DMF (5 ml) was added HATU (150 mg) at 0° C., and the mixture was stirred at room temperature for 3 hr. To the mixture was added water, and the mixture was extracted with ethyl acetate. The organic layer was washed with saturated aqueous sodium hydrogencarbonate solution and saturated brine, dried over anhydrous sodium sulfate, and concentrated under reduced pressure. The residue was purified by silica gel column chromatography (hexane/ethyl acetate) to give the title compound (80 mg).

Example 193

3-methyl-N-((1S,2S)-2-(1-oxo-6-(5-(trifluoromethyl)-1,2,4-oxadiazol-3-yl)-1,3-dihydro-2H-isoindol-2-yl)cyclohexyl)oxetane-3-carboxamide The compound of Example 193 was obtained using 2-((1S,2S)-2-aminocyclohexyl)-6-(5-(trifluoromethyl)-1,2,4-oxadiazol-3-yl)isoindolin-1-one hydrochloride and 3-methyloxetane-3-carboxylic acid by a method similar to Example 42.

Example 194

3-methyl-N-((1R,2R)-2-(1-oxo-6-(5-(trifluoromethyl)-1,2,4-oxadiazol-3-yl)-1,3-dihydro-2H-isoindol-2-yl)cyclohexyl)azetidine-3-carboxamide hydrochloride To a solution of tert-butyl 3-methyl-3-(((1R,2R)-2-(1-oxo-6-(5-(trifluoromethyl)-1,2,4-oxadiazol-3-yl)-1,3-dihydro-2H-isoindol-2-yl)cyclohexyl)carbamoyl)azetidine-1-carboxylate (450 mg) in methanol (6 mL) was added 4 M hydrochloric acid-CPME solution (6.0 mL, 24.0 mmol), and the mixture was stirred at room temperature for 3 hr. The reaction mixture was concentrated. The residue was suspended in hexane, and the solid was collected by filtration to give the title compound (389 mg).

Example 195

1-acetyl-3-methyl-N-((1R,2R)-2-(1-oxo-6-(5-(trifluoromethyl)-1,2,4-oxadiazol-3-yl)-1,3-dihydro-2H-isoindol-2-yl)cyclohexyl)azetidine-3-carboxamide To a solution of 3-methyl-N-((1R,2R)-2-(1-oxo-6-(5-(trifluoromethyl)-1,2,4-oxadiazol-3-yl)-1,3-dihydro-2H-isoindol-2-yl)cyclohexyl)azetidine-3-carboxamide hydrochloride (100 mg) in tetrahydrofuran (2.0 mL) were added acetic anhydride (20 μL) and DIEA (70 μL), and the mixture was stirred at room temperature for 3 hr. To the reaction mixture was added saturated aqueous sodium hydrogencarbonate solution, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/methanol) to give the title compound (88 mg).

Example 196

1,3-dimethyl-N-((1R,2R)-2-(1-oxo-6-(5-(trifluoromethyl)-1,2,4-oxadiazol-3-yl)-1,3-dihydro-2H-isoindol-2-yl)cyclohexyl)azetidine-3-carboxamide To a solution of 3-methyl-N-((1R,2R)-2-(1-oxo-6-(5-(trifluoromethyl)-1,2,4-oxadiazol-3-yl)-1,3-dihydro-2H-isoindol-2-yl)cyclohexyl)azetidine-3-carboxamide hydrochloride (270 mg) in methanol (3.0 mL) were added sodium triacetoxyborohydride (343 mg), 37% formaldehyde solution (80 μL) and DIEA (94 μL), and the mixture was stirred overnight at room temperature. To the reaction mixture was added saturated aqueous sodium hydrogencarbonate solution, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/methanol) to give the title compound (165 mg).

Example 197 tert-butyl 3-methyl-3-(((1R,2R)-2-(1-oxo-6-(5-(trifluoromethyl)-1,2,4-oxadiazol-3-yl)-1,3-dihydro-2H-isoindol-2-yl)cyclohexyl)carbamoyl)azetidine-1-carboxylate The compound of Example 197 was obtained using 2-((1R,2R)-2-aminocyclohexyl)-6-(5-(trifluoromethyl)-1,2,4-oxadiazol-3-yl)isoindolin-1-one hydrochloride and 1-(tert-butoxycarbonyl)-3-methylazetidine-3-carboxylic acid by a method similar to Example 42.

Example 198 tert-butyl (cis-2-(1-oxo-6-(5-(trifluoromethyl)-1,2,4-oxadiazol-3-yl)-1,3-dihydro-2H-isoindol-2-yl)cyclohexyl)carbamate A mixture of methyl 2-(bromomethyl)-5-(5-(trifluoromethyl)-1,2,4-oxadiazol-3-yl)benzoate (500 mg), cis-N1-(tert-butoxycarbonyl)-1,2-cyclohexanediamine (308 mg), DIEA (0.383 mL) and THF (6 mL) was stirred overnight under nitrogen atmosphere at 60° C. To the reaction mixture was added water, and the mixture was extracted with ethyl acetate. The organic layer was washed with saturated brine, dried over anhydrous sodium sulfate, and concentrated under reduced pressure to give the title compound (172 mg).

Example 199

2-(cis-2-aminocyclohexyl)-6-(5-(trifluoromethyl)-1,2,4-oxadiazol-3-yl)isoindolin-1-one hydrochloride The compound of Example 199 was obtained using tert-butyl (cis-2-(1-oxo-6-(5-(trifluoromethyl)-1,2,4-oxadiazol-3-yl)-1,3-dihydro-2H-isoindol-2-yl)cyclohexyl)carbamate by a method similar to Example 194.

Example 200

3-methyl-N-(cis-2-(1-oxo-6-(5-(trifluoromethyl)-1,2,4-oxadiazol-3-yl)-1,3-dihydro-2H-isoindol-2-yl)cyclohexyl)oxetane-3-carboxamide A mixture of 3-methyloxetane-3-carboxylic acid (38.1 mg), 2-(cis-2-aminocyclohexyl)-6-(5-(trifluoromethyl)-1,2,4-oxadiazol-3-yl)isoindolin-1-one hydrochloride (120 mg), HATU (136 mg), DIEA (0.156 mL) and DMF (3 mL) was stirred at room temperature for 5 hr. The reaction mixture was diluted with saturated aqueous sodium hydrogencarbonate solution, and the mixture was extracted with ethyl acetate. The extract was washed with water and saturated brine, and dried over anhydrous sodium sulfate, and the solvent was evaporated under reduced pressure. The residue was recrystallized from hexane-ethyl acetate to give the title compound (116 mg).

Examples 201-202

(1S)-2,2-difluoro-N-((3R,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide (1R)-2,2-difluoro-N-((3R,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide The compounds of Examples 201-202 were obtained using tert-butyl ((3R,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)carbamate by a method similar to Example 7 and Step C of Example 147.

Example 203-204

3-chloro-2-(hydroxymethyl)-2-methyl-N-(trans-2-(1-oxo-6-(5-(trifluoromethyl)-1,2,4-oxadiazol-3-yl)-1,3-dihydro-2H-isoindol-2-yl)cyclohexyl)propanamide (Example 203: less polar), and 3-chloro-2-(hydroxymethyl)-2-methyl-N-(trans-2-(1-oxo-6-(5-(trifluoromethyl)-1,2,4-oxadiazol-3-yl)-1,3-dihydro-2H-isoindol-2-yl)cyclohexyl)propanamide (Example 204: more polar)

A) tert-butyl (trans-6-aminocyclohex-3-en-1-yl)carbamate

To a mixture of trans-cyclohex-4-ene-1,2-diamine dihydrochloride (200 mg) in methanol (3 mL) was added 8 M aqueous sodium hydroxide solution (0.135 mL) under ice-cooling. The reaction mixture was stirred at room temperature for 10 min, a solution of di-tert-butyl dicarbonate (0.251 ml) in methanol (1 mL) was added thereto, and the mixture was stirred overnight at room temperature. The reaction mixture was neutralized with 1 M aqueous sodium hydroxide solution, and the mixture was extracted with ethyl acetate. The organic layer was washed with saturated brine, dried over anhydrous sodium sulfate, and concentrated under reduced pressure to give the title compound (231 mg).
$^1$H NMR (400 MHz, DMSO-d$_6$) δ 1.37-1.49 (11H, m), 1.85-2.03 (2H, m), 2.38-2.58 (2H, m), 2.78 (1H, td, J=8.9, 5.4 Hz), 3.35-3.75 (1H, m), 4.35-5.03 (1H, m), 5.52-5.66 (2H, m).

B) tert-butyl (trans-6-(((3-methyloxetan-3-yl)carbonyl)amino)cyclohex-3-en-1-yl)carbamate A mixture of tert-butyl (trans-6-aminocyclohex-3-en-1-yl)carbamate (228 mg), 3-methyloxetane-3-carboxylic acid (137 mg), EDCI hydrochloride (247 mg), HOBt monohydrate (181 mg) and DMF (5.0 mL) was stirred overnight at room temperature. To the reaction mixture was added saturated aqueous sodium hydrogencarbonate solution, and the mixture was extracted with ethyl acetate. The extract was washed with water and saturated brine, and dried over anhydrous sodium sulfate, and the solvent was evaporated under reduced pressure. The residue was recrystallized from heptane-ethyl acetate to give the title compound (157 mg).
$^1$H NMR (400 MHz, DMSO-d$_6$) δ 1.43 (9H, s), 1.59 (3H, s), 1.89-2.10 (2H, m), 2.47 (1H, d, J=17.1 Hz), 2.65 (1H, d, J=16.6 Hz), 3.68-3.82 (1H, m), 3.87-4.00 (1H, m), 4.37 (2H, dd, J=5.9, 3.4 Hz), 4.62 (1H, d, J=8.1 Hz), 4.90 (2H, dd, J=12.2, 5.9 Hz), 5.60 (2H, brs), 6.56 (1H, d, J=4.6 Hz).

C) N-(trans-6-aminocyclohex-3-en-1-yl)-3-chloro-2-(hydroxymethyl)-2-methylpropanamide To a solution of tert-butyl (trans-6-(((3-methyloxetan-3-yl)carbonyl)amino)cyclohex-3-en-1-yl)carbamate (157 mg) in methanol (4 mL) was added 4 M hydrochloric acid-CPME solution (3.8 mL, 15.2 mmol), and the mixture was stirred at room temperature for 3 hr. The reaction mixture was neutralized with 1M aqueous sodium hydroxide solution, and the mixture was extracted with ethyl acetate. The organic layer was washed with saturated brine, dried over anhydrous sodium sulfate, and concentrated under reduced pressure to give the title compound (99 mg).
MS (API+), found: 247.3.

D) N-(trans-2-aminocyclohexyl)-3-chloro-2-(hydroxymethyl)-2-methylpropanamide

A mixture of N-(trans-6-aminocyclohex-3-en-1-yl)-3-chloro-2-(hydroxymethyl)-2-methylpropanamide (97 mg), methanol (5 mL) and 10% palladium-carbon (50% wet, 50 mg) was stirred under hydrogen atmosphere at room temperature for 3 hr. The insoluble substance was filtered off, and the filtrate was concentrated under reduced pressure to give the title compound (94 mg).
MS (API+), found: 249.3.

E) 3-chloro-2-(hydroxymethyl)-2-methyl-N-(trans-2-(1-oxo-6-(5-(trifluoromethyl)-1,2,4-oxadiazol-3-yl)-1,3-dihydro-2H-isoindol-2-yl)cyclohexyl)propanamide (Example 203: less polar), and 3-chloro-2-(hydroxymethyl)-2-methyl-N-(trans-2-(1-oxo-6-(5-(trifluoromethyl)-1,2,4-oxadiazol-3-yl)-1,3-dihydro-2H-isoindol-2-yl)cyclohexyl)propanamide (Example 204: more polar)

A mixture of N-(trans-2-aminocyclohexyl)-3-chloro-2-(hydroxymethyl)-2-methylpropanamide (94 mg), methyl 2-(bromomethyl)-5-(5-(trifluoromethyl)-1,2,4-oxadiazol-3-yl)benzoate (161 mg), DIEA (0.123 mL) and THF (5.0 mL) was stirred overnight under nitrogen atmosphere at 60° C. To the reaction mixture was added potassium carbonate (122 mg), and the mixture was stirred overnight under nitrogen atmosphere at 60° C. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give a less polar enantiomeric mixture (63 mg, Example 203) of 3-chloro-2-(hydroxymethyl)-2-methyl-N-(trans-2-(1-oxo-6-(5-(trifluoromethyl)-1,2,4-oxadiazol-3-yl)-1,3-dihydro-2H-isoindol-2-yl)cyclohexyl)propanamide, and a more polar enantiomeric mixture (41 mg, Example 204) of 3-chloro-2-(hydroxymethyl)-2-methyl-N-(trans-2-(1-oxo-6-(5-(trifluoromethyl)-1,2,4-oxadiazol-3-yl)-1,3-dihydro-2H-isoindol-2-yl)cyclohexyl)propanamide.

Example 205

N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)tetrahydrofuran-3-carboxamide The compound of Example 205 (containing the 3R,4S-form derived the raw material compound) was obtained using 2-((3S,4R)-4-aminotetrahydro-2H-pyran-3-yl)-6-(5-(trifluoromethyl)-1,2,4-oxadiazol-3-yl)isoindolin-1-one hydrochloride and tetrahydrofuran-3-carboxylic acid by a method similar to Step B of Example 203.

Example 206

(3R)—N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)tetrahydrofuran-3-carboxamide N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)tetrahydrofuran-3-carboxamide (120 mg, containing the 3R,4S-form derived the raw material compound) was resolved by HPLC (column: CHIRALPAK AD (SL013), 4.6 mmID×250 mmL, manufactured by Daicel Chemical Industries, mobile phase: hexane/isopropyl alcohol=60/40) to give the compound having a shortest retention time of peak (tR1-1,2), and the obtained compound was resolved by HPLC (column: CHIRALPAK IC(KK012), 4.6 mmID×250 mmL, manufactured by Daicel Chemical Industries, mobile phase: hexane/ethanol=45/55) to give the title compound (52 mg) having a longer retention time of peak (IC-tR2).

Example 207 tert-butyl ((3R,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)carbamate A) ethyl 4-(((1S)-1-phenylethyl)amino)-5,6-dihydro-2H-pyran-3-carboxylate To a mixture of tetrahydro-4H-pyran-4-one (15 g) and toluene (300 ml) was added 1M lithium 1,1,1,3,3,3-hexamethyldisilazan-2-ide THF solution (121 ml) under argon at 0° C., and the mixture was stirred for 5 min. Ethyl carbonochloridate (14.99 ml) was added thereto at 0° C., and the mixture was stirred for 5 min. To the reaction mixture were added acetic acid (50 ml) and water (50 ml) at 0° C., and the mixture was extracted with ethyl acetate. The extract was washed with saturated brine, and dried over anhydrous magnesium sulfate, and the solvent was evaporated under reduced pressure. To the residue were added (1S)-1-phenylethanamine (19.99 ml) and toluene (300 ml), and the mixture was heated under reflux for 2 hr. The solvent was evaporated under reduced pressure, and the residue was purified by silica gel column chromatography (hexane/ethyl acetate) to give the title compound (13.32 g).
$^1$H NMR (400 MHz, CDCl$_3$) δ 1.28 (3H, t, J=7.2 Hz), 1.50 (3H, d, J=6.8 Hz), 1.99-2.11 (1H, m), 2.33-2.43 (1H, m), 3.56-3.75 (2H, m), 4.16 (2H, qd, J=7.1, 1.8 Hz), 4.30 (2H, s), 4.61 (1H, quin, J=7.0 Hz), 7.18-7.26 (3H, m), 7.30-7.37 (2H, m), 9.11 (1H, d, J=7.3 Hz).

B) ethyl (3S,4S)-4-(((1S)-1-phenylethyl)amino)tetrahydro-2H-pyran-3-carboxylate

A mixture of ethyl 4-(((1S)-1-phenylethyl)amino)-5,6-dihydro-2H-pyran-3-carboxylate (25.28 g), anhydrous magnesium sulfate (44.2 g) and toluene (180 ml) was stirred at room temperature for 30 min, sodium triacetoxyborohydride (29.2 g) and acetic acid (30.0 ml) were added thereto at 0° C., and the mixture was stirred overnight at room temperature. To the reaction mixture was added water, the pH of the mixture was adjusted to 8 with conc. aqueous ammonia, and the mixture was extracted with ethyl acetate. The organic layer was washed with saturated brine, and dried over anhydrous magnesium sulfate, and the solvent was evaporated under reduced pressure. The residue was purified by silica gel column chromatography (hexane/ethyl acetate) to give the title compound (14.76 g).
$^1$H NMR (400 MHz, CDCl$_3$) δ 1.27-1.36 (6H, m), 1.55-1.65 (1H, m), 1.82-2.01 (2H, m), 2.78-2.87 (2H, m), 3.36 (1H, ddd, J=11.5, 10.0, 3.2 Hz), 3.44 (1H, dd, J=11.7, 2.9 Hz), 3.84-3.96 (2H, m), 4.14-4.19 (1H, m), 4.22 (2H, q, J=7.2 Hz), 7.21-7.26 (1H, m), 7.29-7.37 (4H, m).

C) ethyl (3S,4S)-4-aminotetrahydro-2H-pyran-3-carboxylate

A mixture of ethyl (3S,4S)-4-(((1S)-1-phenylethyl)amino)tetrahydro-2H-pyran-3-carboxylate (14.76 g), 10% palladium-carbon (2.83 g) and ethanol (140 ml) was stirred overnight under hydrogen atmosphere at 50° C. The insoluble substance was filtered off, and the filtrate was concentrated under reduced pressure to give the title compound (8.90 g).
$^1$H NMR (400 MHz, CDCl$_3$) δ 1.28 (3H, t, J=7.2 Hz), 1.73-1.93 (2H, m), 2.73 (1H, dt, J=7.1, 3.8 Hz), 3.29-3.39 (1H, m), 3.56 (1H, ddd, J=11.3, 6.5, 4.4 Hz), 3.72 (1H, dd, J=11.6, 3.8 Hz), 3.87 (1H, ddd, J=11.4, 7.2, 4.2 Hz), 4.09 (1H, dd, J=11.7, 6.8 Hz), 4.18 (2H, q, J=7.3 Hz).

D) ethyl (3S,4S)-4-((tert-butoxycarbonyl)amino)tetrahydro-2H-pyran-3-carboxylate A mixture of ethyl (3S,4S)-4-aminotetrahydro-2H-pyran-3-carboxylate (8.9 g), di-tert-butyl dicarbonate (14.32 ml), TEA (14.32 ml) and THF (120 ml) was stirred overnight at room temperature. The solvent was evaporated under reduced pressure, and the residue was extracted with ethyl acetate. The organic layer was washed with saturated brine, dried over anhydrous magnesium sulfate, and concentrated under reduced pressure. The residue was purified by silica gel column chromatography (hexane/ethyl acetate) to give the title compound (12.48 g).
$^1$H NMR (400 MHz, CDCl$_3$) δ 1.29 (3H, t, J=7.1 Hz), 1.44 (9H, s), 1.65-1.74 (1H, m), 1.94-2.14 (1H, m), 2.70-2.81 (1H, m), 3.48 (1H, td, J=11.6, 2.8 Hz), 3.58 (1H, dd, J=11.9, 3.1 Hz), 3.87-4.03 (2H, m), 4.20 (2H, q, J=7.1 Hz), 4.31 (1H, dd, J=11.9, 1.6 Hz), 5.60 (1H, d, J=9.0 Hz).

E) ethyl (3R,4S)-4-((tert-butoxycarbonyl)amino) tetrahydro-2H-pyran-3-carboxylate To a mixture of ethyl (3S,4S)-4-((tert-butoxycarbonyl) amino)tetrahydro-2H-pyran-3-carboxylate (5.78 g) and ethanol (60 ml) was added sodium ethanolate (20% ethanol solution) (16.19 ml) at room temperature, and the mixture was stirred at room temperature for 3 hr. To the reaction mixture was added 0.1 M hydrochloric acid, and the mixture was extracted with ethyl acetate. The organic layer was washed with saturated brine, and dried over anhydrous magnesium sulfate, and the solvent was evaporated under reduced pressure. The residue was purified by silica gel column chromatography (hexane/ethyl acetate) to give the title compound (3.85 g).
$^1$H NMR (400 MHz, CDCl$_3$) δ 1.26 (3H, t, J=7.2 Hz), 1.43 (9H, s), 1.45-1.56 (1H, m), 1.98-2.09 (1H, m), 2.48 (1H, td, J=10.4, 4.2 Hz), 3.49 (1H, td, J=11.7, 2.4 Hz), 3.57 (1H, t, J=11.0 Hz), 3.95 (2H, dt, J=11.7, 3.3 Hz), 4.04 (1H, dd, J=11.6, 4.3 Hz), 4.09-4.20 (2H, m), 4.57 (1H, brs).

F) ((3R,4S))-4-((tert-butoxycarbonyl) amino)tetrahydro-2H-pyran-3-carboxylic acid To a mixture of ethyl (3R,4S)-4-((tert-butoxycarbonyl) amino)tetrahydro-2H-pyran-3-carboxylate (4.44 g), THF (20 ml) and ethanol (20 ml) was added 2 M aqueous sodium hydroxide solution (40.6 ml), and the mixture was stirred at room temperature for 2 hr. To the reaction mixture was added hydrochloric acid (40.6 ml), and the mixture was extracted with ethyl acetate. The organic layer was washed with saturated brine, and dried over anhydrous magnesium sulfate, and the solvent was evaporated under reduced pressure to give the title compound (3.84 g).
$^1$H NMR (400 MHz, CDCl$_3$) δ 1.44 (10H, s), 1.95-2.08 (1H, m), 2.54 (1H, td, J=10.0, 4.2 Hz), 3.43-3.67 (2H, m), 3.95 (2H, dt, J=11.6, 3.4 Hz), 4.09 (1H, dd, J=11.5, 4.4 Hz), 4.66 (1H, brs).

G) benzyl tert-butyl (3R,4S)-tetrahydro-2H-pyran-3,4-diylbiscarbamate

A mixture of (3R,4S)-4-((tert-butoxycarbonyl)amino)tetrahydro-2H-pyran-3-carboxylic acid (4 g), diphenyl phosphoramidate (4.21 ml), TEA (2.73 ml) and toluene (65 ml) was stirred at room temperature for 3 hr under nitrogen atmosphere. To the reaction mixture was added phenylmethanol (8.48 ml), and the mixture was stirred under nitrogen atmosphere at 80° C. for 3 hr. To the reaction mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (hexane/ethyl acetate) to give the title compound (3.18 g).
$^1$H NMR (400 MHz, CDCl$_3$) δ 1.41 (9H, s), 1.51-1.69 (1H, m), 1.95 (1H, d, J=12.0 Hz), 3.03 (1H, t, J=10.5 Hz), 3.39 (1H, td, J=11.9, 2.2 Hz), 3.46-3.66 (2H, m), 3.91-4.02 (1H, m), 4.05-4.16 (1H, m), 4.64 (1H, d, J=7.8 Hz), 4.97-5.15 (2H, m), 5.36 (1H, d, J=5.6 Hz), 7.28-7.40 (5H, m).

H) tert-butyl ((3R,4S)-3-aminotetrahydro-2H-pyran-4-yl)carbamate

A mixture of benzyl tert-butyl (3R,4S)-tetrahydro-2H-pyran-3,4-diylbiscarbamate (1 g), 10% palladium-carbon (0.304 g) and ethanol (30 ml) was stirred overnight at room temperature under hydrogen atmosphere. The insoluble substance was filtered off, and the filtrate was concentrated under reduced pressure to give the title compound (0.630 g).

I) tert-butyl ((3R,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)carbamate A mixture of tert-butyl ((3R,4S)-3-aminotetrahydro-2H-pyran-4-yl)carbamate (600 mg), methyl 2-(bromomethyl)-5-(5-(trifluoromethyl)-1,2,4-oxadiazol-3-yl)benzoate (1013 mg), DIEA (0.727 ml) and anhydrous THF (14 ml) was stirred overnight under nitrogen atmosphere at 60° C. To the reaction mixture was added water, and the mixture was extracted with ethyl acetate. The organic layer was washed with water and saturated brine, and dried over anhydrous magnesium sulfate, and the solvent was evaporated under reduced pressure. The residue was crystallized from ethyl acetate/hexane to give the title compound (327.2 mg). The filtrate was concentrated under reduced pressure, and the residue was purified by silica gel column chromatography (hexane/ethyl acetate) to give the title compound (921 mg).
$^1$H NMR (400 MHz, CDCl$_3$) δ 1.13 (9H, s), 1.73 (1H, qd, J=12.4, 4.6 Hz), 2.09 (1H, d, J=13.0 Hz), 3.43-3.65 (2H, m), 3.94 (1H, qd, J=10.8, 4.4 Hz), 4.02-4.10 (2H, m), 4.26-4.43 (2H, m), 4.67 (1H, d, J=9.5 Hz), 4.83 (1H, d, J=16.9 Hz), 7.63 (1H, d, J=8.1 Hz), 8.30 (1H, dd, J=7.9, 1.6 Hz), 8.61 (1H, s).

Example 208

(3S)—N-((3S,4R)-3-(1-oxo-6-(5-(trifluoromethyl)-1,2,4-oxadiazol-3-yl)-1,3-dihydro-2H-isoindol-2-yl) tetrahydro-2H-pyran-4-yl)tetrahydrofuran-3-carboxamide N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)tetrahydrofuran-3-carboxamide (120 mg, containing the 3R,4S-form derived the raw material compound) was resolved by HPLC (column: CHIRALPAK AD (SL013), 4.6 mmID×250 mmL, manufactured by Daicel Chemical Industries, mobile phase: hexane/isopropyl alcohol=60/40) to give the compound having a shortest retention time of peak (tR1-1,2), and the obtained compound was resolved by HPLC (column: CHIRALPAK IC(KK012), 4.6 mmID×250 mmL, manufactured by Daicel Chemical Industries, mobile phase: hexane/ethanol=45/55) to give the title compound (46.7 mg) having a longer retention time of peak (IC-tR1).

Example 209

(3R)—N-((3S,4R)-3-(1-oxo-6-(5-(trifluoromethyl)-1,2,4-oxadiazol-3-yl)-1,3-dihydro-2H-isoindol-2-yl) tetrahydro-2H-pyran-4-yl)tetrahydrofuran-3-carboxamide N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)tetrahydrofuran-3-carboxamide (120 mg, containing the 3R,4S-form derived the raw material compound) was resolved by HPLC (column: CHIRALPAK AD (SL013), 4.6 mmID×250 mmL, manufactured by Daicel Chemical Industries, mobile phase: hexane/isopropyl alcohol=60/40) to give the title compound (7.6 mg) having a second shortest retention time of peak (tR2).

Example 210

(3S)—N-(((3R,4S))-3-(1-oxo-6-(5-(trifluoromethyl)-1,2,4-oxadiazol-3-yl)-1,3-dihydro-2H-isoindol-2-yl)tetrahydro-2H-pyran-4-yl)tetrahydrofuran-3-carboxamide N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)tetrahydrofuran-3-carboxamide (120 mg, containing the 3R,4S-form derived the raw material compound) was resolved by HPLC (column: CHIRALPAK AD (SL013), 4.6 mmID×250 mmL, manufactured by Daicel Chemical Industries, mobile phase: hexane/isopropyl alcohol=60/40) to give the title compound (11.8 mg) having a largest retention time of peak (tR3).

Example 211

(1R)- or (1S)-2,2-difluoro-N-((3R,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide A) 1,5-anhydro-2-((tert-butoxycarbonyl)amino)-2,4-dideoxy-L-threo-pentitol To a mixture of 2-amino-1,5-anhydro-2,4-dideoxy-L-threo-pentitol (120 g), methanol (1200 mL) and TEA (124 g) was added a mixture of di-tert-butyl dicarbonate (240 g) and methanol (530 mL) over 35 min or longer, the container used for addition was washed with methanol (30 ml), and the mixture was stirred overnight at room temperature. The solvent was evaporated under reduced pressure, and dichloromethane (1000 ml) was added thereto. The mixture was washed with 1 M hydrochloric acid (500 ml) and saturated brine, and dried over anhydrous magnesium sulfate, and the solvent was evaporated under reduced pressure to give the title compound (200 g).
$^1$HNMR (400 MHz, DMSO-$d_6$): δ 1.34-1.38 (10H, m), 1.80-1.84 (1H, m), 2.86-2.91 (1H, m), 3.15-3.26 (2H, m), 3.35-3.41 (1H, m), 3.67-3.77 (2H, m), 4.80 (1H, s), 6.64 (1H, d, J=8.0 Hz).

B) 1,5-anhydro-2-((tert-butoxycarbonyl)amino)-2,4-dideoxy-3-O-(methylsulfonyl)-L-threo-pentitol To a mixture of 1,5-anhydro-2-((tert-butoxycarbonyl)amino)-2,4-dideoxy-L-threo-pentitol (197 g), TEA (137 g) and dichloromethane (900 mL) was added dropwise a mixture of methanesulfonyl chloride (114 g) and dichloromethane (100 mL) at 0° C., and the mixture was stirred for 30 min, and then at room temperature for 2 hr. The reaction mixture was washed with 1 M hydrochloric acid (500 ml), the organic layer was dried, and the solvent was evaporated under reduced pressure to give the title compound (270 g).
$^1$H NMR (400 MHz, CDCl$_3$) δ 1.45 (9H, s), 1.93-1.94 (1H, m), 2.17-2.19 (1H, m), 3.10 (3H, s), 3.43-3.46 (1H, m), 3.48-3.66 (2H, m), 3.83-3.88 (1H, m), 3.98-4.02 (1H, m), 4.75-4.73 (1H, m), 5.05 (1H, d, J=6.8 Hz).

C) tert-butyl ((3R,4R)-4-azidotetrahydro-2H-pyran-3-yl)carbamate

A mixture of 1,5-anhydro-2-((tert-butoxycarbonyl)amino)-2,4-dideoxy-3-O-(methylsulfonyl)-L-threo-pentitol (100 g), sodium acetate (55.0 g), sodium azide (43.0 g) and DMF (500 mL) was stirred overnight at 95° C. To the reaction mixture were added water (2 L) and ethyl acetate (1.5 L), and the mixture was stirred for 5 min, and extracted with ethyl acetate (1 L). The organic layer was washed twice with water (2 l), and the solvent was evaporated under reduced pressure to give the title compound (46 g).
$^1$H NMR (400 MHz, CDCl$_3$) δ 1.39 (9H, s), 1.84-1.85 (2H, m), 3.43-3.48 (1H, m), 3.54-3.56 (2H, m), 3.65-3.69 (1H, m), 3.84 (2H, m), 4.97 (1H, s).

D) tert-butyl ((3R,4R)-4-aminotetrahydro-2H-pyran-3-yl)carbamate

A mixture of tert-butyl ((3R,4R)-4-azidotetrahydro-2H-pyran-3-yl)carbamate (120 g), platinum oxide (15.0 g) and ethanol (1.2 l) was stirred overnight at room temperature under hydrogen atmosphere. The reaction mixture was filtered through Celite under nitrogen atmosphere, and the Celite was washed twice with ethanol (500 ml). The filtrate was concentrated under reduced pressure to give the title compound (105 g).
$^1$H NMR (400 MHz, CDCl$_3$) δ 1.33 (2H, s), 1.46-1.53 (10H, m), 1.68-1.72 (1H, m), 3.01-3.03 (1H, m), 3.41-3.52 (2H, m), 3.73-3.75 (1H, m), 3.79-3.82 (1H, m), 3.88-3.91 (1H, m), 5.16 (1H, d, J=7.2 Hz).

E) (1R)- or (1S)-2,2-difluoro-N-((3R,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide The compound of Example 211 was obtained using tert-butyl ((3R,4R)-4-aminotetrahydro-2H-pyran-3-yl)carbamate and methyl 2-(bromomethyl)-5-(5-(trifluoromethyl)-1,2,4-oxadiazol-3-yl)benzoate by a method similar to Example 172.

Example 212

(1R)- or (1S)-2,2-difluoro-N-((3R,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide The compound of Example 212 was obtained by a method similar to Example 211.

Examples 213-214

(1R)- or (1S)-2,2-difluoro-N-((3S,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide, and (1R)- or (1S)-2,2-difluoro-N-((3S,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide A) tert-butyl ((3S,4S)-3-azidotetrahydro-2H-pyran-4-yl)carbamate The title compound was obtained using the corresponding aminoalcohol by a method similar to Steps A-C of Example 211.

B) tert-butyl ((3S,4S)-3-aminotetrahydro-2H-pyran-4-yl)carbamate

A mixture of tert-butyl ((3S,4S)-3-azidotetrahydro-2H-pyran-4-yl)carbamate (3.91 g), 10% palladium-carbon (0.8 g), and methanol (60 ml) was stirred overnight at room temperature under hydrogen atmosphere. The insoluble substance was filtered off, and the filtrate was concentrated under reduced pressure to give the title compound (3.45 g).

C) (1R)- or (1S)-2,2-difluoro-N-((3S,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide, and (1R)- or (1S)-2,2-difluoro-N-((3S,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide The compounds of Examples 213-214 were obtained using tert-butyl ((3S,4S)-3-aminotetrahydro-2H-pyran-4-yl)carbamate, methyl 2-(bromomethyl)-5-(5-(trifluoromethyl)-1,2,4-oxadiazol-3-yl)benzoate and the corresponding carboxylic acid by a method similar to Step I of Example 207, Example 7 and Step C of Example 147.

Example 215

2-chloro-N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)acetamide A mixture of 2-((3S,4R)-4-aminotetrahydro-2H-pyran-3-yl)-6-(5-(trifluoromethyl)-1,2,4-oxadiazol-3-yl)isoindolin-1-one hydrochloride (50 mg), chloroacetyl chloride (14.76 µl), TEA (51.7 µl) and THF (600 µl) was stirred overnight at room temperature. To the reaction mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (hexane/ethyl acetate) to give the title compound (34.4 mg).
$^1$H NMR (400 MHz, CDCl$_3$) δ 1.84 (1H, qd, J=12.4, 4.9 Hz), 2.08-2.18 (1H, m), 3.46-3.66 (2H, m), 3.72-3.93 (2H, m), 4.10 (2H, dd, J=11.0, 4.6 Hz), 4.24-4.39 (2H, m), 4.50 (1H, td, J=10.9, 4.8 Hz), 4.67 (1H, d, J=17.1 Hz), 6.78 (1H, d, J=8.8 Hz), 7.63 (1H, d, J=7.8 Hz), 8.32 (1H, dd, J=7.9, 1.6 Hz), 8.61 (1H, d, J=1.0 Hz).

Example 216

2-chloro-N-((3R,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)acetamide The compound of Example 216 was obtained using tert-butyl ((3R,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)carbamate by a method similar to Example 215.

Example 217

(2S)—N-((1S,2S)-2-(1-oxo-6-(5-(trifluoromethyl)-1,2,4-oxadiazol-3-yl)-1,3-dihydro-2H-isoindol-2-yl)cyclohexyl)tetrahydrofuran-2-carboxamide A mixture of 2-((1S,2S)-2-aminocyclohexyl)-6-(5-(trifluoromethyl)-1,2,4-oxadiazol-3-yl)isoindolin-1-one hydrochloride (50 mg), (2S)-tetrahydrofuran-2-carboxylic acid (17.78 µl), EDCI hydrochloride (47.6 mg), HOBt (33.5 mg, 0.25 mmol), DIEA (64.2 mg) and DMF (700 µl) was stirred overnight at room temperature. To the reaction mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (hexane/ethyl acetate) to give the title compound (33.9 mg).
$^1$H NMR (400 MHz, DMSO-d$_6$) δ 1.28-1.39 (2H, m), 1.41-1.63 (4H, m), 1.66-1.81 (5H, m), 1.81-1.93 (1H, m), 3.50-3.65 (1H, m), 3.68-3.75 (1H, m), 3.83-3.97 (2H, m), 4.07-4.19 (1H, m), 4.51-4.70 (2H, m), 7.75 (1H, d, J=9.3 Hz), 7.85 (1H, d, J=7.8 Hz), 8.22 (1H, s), 8.27 (1H, dd, J=7.9, 1.6 Hz).

Examples 218-219

The compounds of Examples 218-219 were obtained using the corresponding carboxylic acid by a method similar to Example 217.

Examples 220-221

(1S)-2,2-difluoro-N-((3R,4S)-4-(1-oxo-6-(5-(trifluoromethyl)-1,2,4-oxadiazol-3-yl)-1,3-dihydro-2H-isoindol-2-yl)tetrahydro-2H-pyran-3-yl)cyclopropanecarboxamide (Example 220), and (1R)-2,2-difluoro-N-((3R,4S)-4-(1-oxo-6-(5-(trifluoromethyl)-1,2,4-oxadiazol-3-yl)-1,3-dihydro-2H-isoindol-2-yl)tetrahydro-2H-pyran-3-yl)cyclopropanecarboxamide (Example 221)

A) tert-butyl ((3R,4S)-3-(((2,2-difluorocyclopropyl)carbonyl)amino)tetrahydro-2H-pyran-4-yl)carbamate A mixture of tert-butyl ((3R,4S)-3-aminotetrahydro-2H-pyran-4-yl)carbamate (260 mg), 2,2-difluorocyclopropanecarboxylic acid (176 mg), 4-(4,6-dimethoxy-1,3,5-triazin-2-yl)-4-methylmorpholin-4-ium (398 mg), THF (3 ml) and 2-propanol (3 ml) was stirred at room temperature for 3 hr. To the reaction mixture was added water, and the precipitate was collected by filtration and washed with water to give the title compound (243 mg).

B) (1S)-2,2-difluoro-N-((3R,4S)-4-(1-oxo-6-(5-(trifluoromethyl)-1,2,4-oxadiazol-3-yl)-1,3-dihydro-2H-isoindol-2-yl)tetrahydro-2H-pyran-3-yl)cyclopropanecarboxamide (Example 220), and (1R)-2,2-difluoro-N-((3R,4S)-4-(1-oxo-6-(5-(trifluoromethyl)-1,2,4-oxadiazol-3-yl)-1,3-dihydro-2H-isoindol-2-yl)tetrahydro-2H-pyran-3-yl)cyclopropanecarboxamide (Example 221)

The compounds of Examples 220-221 were obtained using tert-butyl ((3R,4S)-3-(((2,2-difluorocyclopropyl)carbonyl)amino)tetrahydro-2H-pyran-4-yl)carbamate and methyl 2-(bromomethyl)-5-(5-(trifluoromethyl)-1,2,4-oxadiazol-3-yl)benzoate by a method similar to Step B of Example 172.

The compounds of Examples are shown in the following tables. MS in the tables means actual measured value.

TABLE 1-1

| EXAMPLE | IUPAC NAME | Structure | ADDITIVE | MS |
|---|---|---|---|---|
| 1 | 2-phenyl-5-(5-(trifluoromethyl)-1,2,4-oxadiazol-3-yl)isoindolin-1-one | 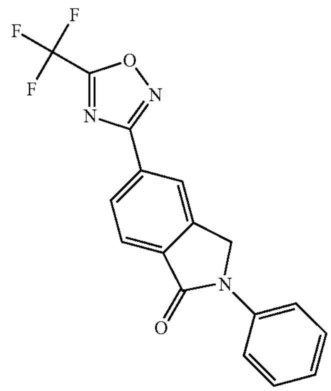 [SMILES: O=C1c2ccc(-c3noc(C(F)(F)F)n3)cc2CN1c1ccccc1] | | 346.1 |
| 2 | tert-butyl trans-3-(1-oxo-6-(5-(trifluoromethyl)-1,2,4-oxadiazol-3-yl)-1,3-dihydro-2H-isoindol-2-yl)-4-phenylpyrrolidine-1-carboxylate | 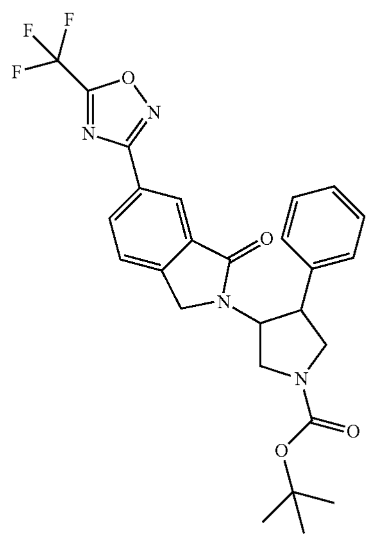 [SMILES: CC(C)(C)OC(=O)N1CC(c2ccccc2)C(N2Cc3ccc(-c4noc(C(F)(F)F)n4)cc3C2=O)C1] | | 513.2 |
| 3 | trans-2-(4-phenylpyrrolidin-3-yl)-6-(5-(trifluoromethyl)-1,2,4-oxadiazol-3-yl)isoindolin-1-one | 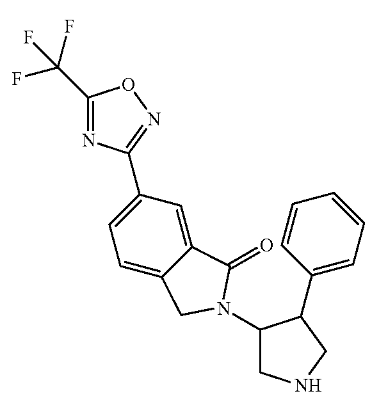 [SMILES: O=C1c2cc(-c3noc(C(F)(F)F)n3)ccc2CN1C1CNCC1c1ccccc1] | HCl | 415.0 |

TABLE 1-1-continued

| EXAMPLE | IUPAC NAME | Structure | ADDITIVE | MS |
|---|---|---|---|---|
| 4 | trans-2-(1-acetyl-4-phenylpyrrolidin-3-yl)-6-(5-(trifluoromethyl)-1,2,4-oxadiazol-3-yl)isoindolin-1-one | 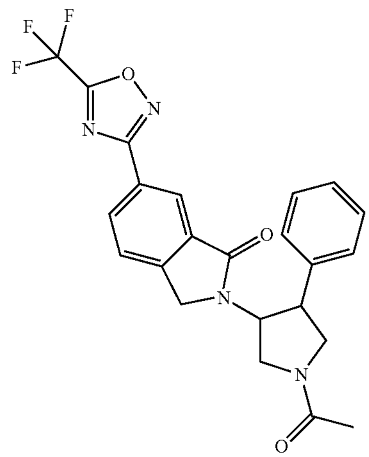 [SMILES: CC(=O)N1CC(c2ccccc2)C(N2Cc3ccc(-c4noc(C(F)(F)F)n4)cc3C2=O)C1] | | 457.1 |
| 5 | trans-2-(3-phenyltetrahydro-2H-pyran-4-yl)-6-(5-(trifluoromethyl)-1,2,4-oxadiazol-3-yl)isoindolin-1-one | 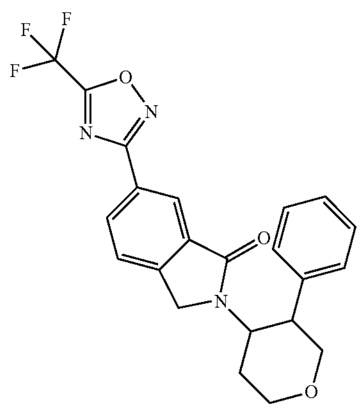 [SMILES: O=C1c2cc(-c3noc(C(F)(F)F)n3)ccc2CN1C1CCOCC1c1ccccc1] | | 430.0 |
| 6 | tert-butyl trans-(2-(1-oxo-6-(5-(trifluoromethyl)-1,2,4-oxadiazol-3-yl)-1,3-dihydro-2H-isoindol-2-yl)cyclohexyl)carbamate | 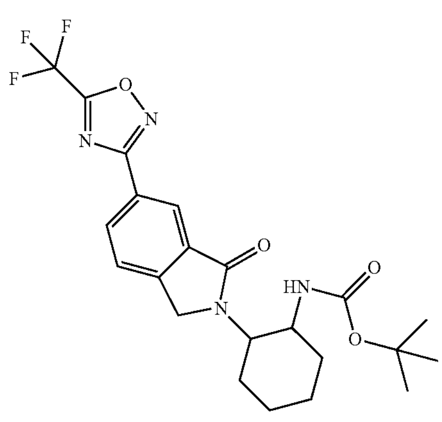 [SMILES: CC(C)(C)OC(=O)NC1CCCCC1N1Cc2ccc(-c3noc(C(F)(F)F)n3)cc2C1=O] | | 467.1 |

TABLE 1-1-continued

| EXAMPLE | IUPAC NAME | Structure | ADDITIVE | MS |
|---|---|---|---|---|
| 7 | trans-2-(2-aminocyclohexyl)-6-(5-(trifluoromethyl)-1,2,4-oxadiazol-3-yl)isoindolin-1-one | 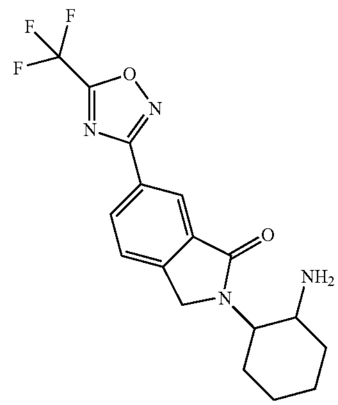 [SMILES: NC1CCCCC1N1Cc2ccc(-c3noc(C(F)(F)F)n3)cc2C1=O] | HCl | 367.6 |

TABLE 1-2

| EXAMPLE | IUPAC NAME | Structure | ADDITIVE | MS |
|---|---|---|---|---|
| 8 | N-(2-(1-oxo-6-(5-(trifluoromethyl)-1,2,4-oxadiazol-3-yl)-1,3-dihydro-2H-isoindol-2-yl)cyclohexyl)actamide | 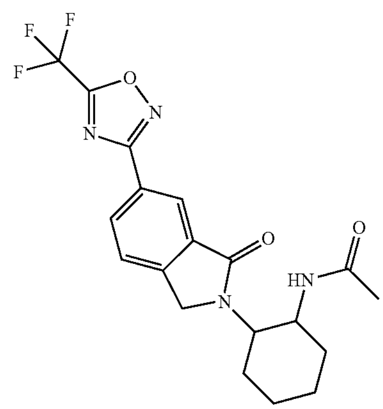 [SMILES: CC(=O)NC1CCCCC1N1Cc2ccc(-c3noc(C(F)(F)F)n3)cc2C1=O] | | 407.1 |
| 9 | trans-N-(2-(1-oxo-6-(5-(trifluoromethyl)-1,2,4-oxadiazol-3-yl)-1,3-dihydro-2H-isoindol-2-yl)cyclohexyl)benzamide | 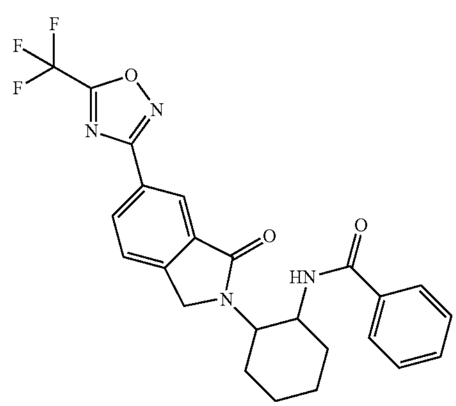 [SMILES: O=C(NC1CCCCC1N1Cc2ccc(-c3noc(C(F)(F)F)n3)cc2C1=O)c1ccccc1] | | 469.2 |

TABLE 1-2-continued

| EXAMPLE | IUPAC NAME | Structure | ADDITIVE | MS |
|---------|-----------|-----------|----------|-----|
| 10 | trans-2-(1-benzoyl-4-phenylpyrrolidin-3-yl)-6-(5-(trifluoromethyl)-1,2,4-oxadiazol-3-yl)isoindolin-1-one | 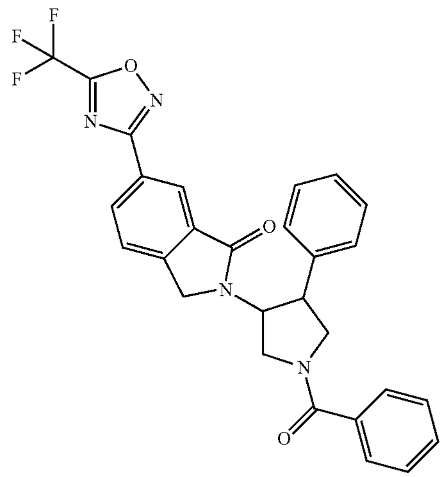 [SMILES: O=C(c1ccccc1)N1CC(c2ccccc2)C(N2Cc3ccc(-c4noc(C(F)(F)F)n4)cc3C2=O)C1] | | 519.1 |
| 11 | trans-2-(1-(cyclopropylcarbonyl)-4-phenylpyrrolidin-3-yl)-6-(5-(trifluoromethyl)-1,2,4-oxadiazol-3-yl)isoindolin-1-one | 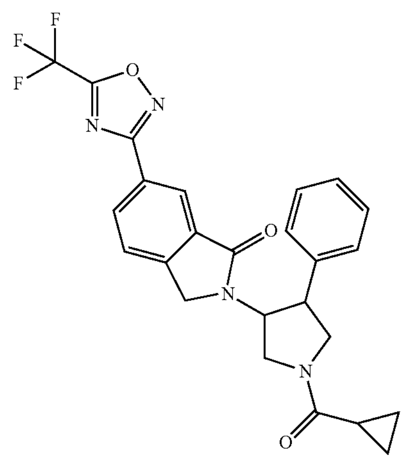 [SMILES: O=C(C1CC1)N1CC(c2ccccc2)C(N2Cc3ccc(-c4noc(C(F)(F)F)n4)cc3C2=O)C1] | | 483.0 |
| 12 | trans-N-(2-(1-oxo-6-(5-(trifluoromethyl)-1,2,4-oxadiazol-3-yl)-1,3-dihydro-2H-isoindol-2-yl)cyclohexyl)cyclopropanecarboxamide | 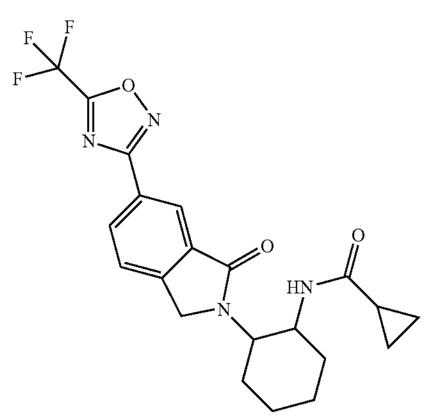 [SMILES: O=C(NC1CCCCC1N1Cc2ccc(-c3noc(C(F)(F)F)n3)cc2C1=O)C1CC1] | | 435.0 |

TABLE 1-2-continued

| EXAMPLE | IUPAC NAME | Structure | ADDITIVE | MS |
|---|---|---|---|---|
| 13 | tert-butyl (3R,4R)-4-(1-oxo-6-(5-(trifluoromethyl)-1,2,4-oxadiazol-3-yl)-1,3-dihydro-2H-isoindol-2-yl)-3-phenylpiperidine-1-carboxylate | 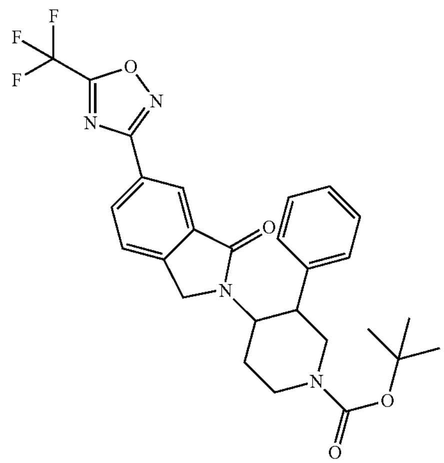 [SMILES: CC(C)(C)OC(=O)N1CCC(N2Cc3ccc(-c4noc(C(F)(F)F)n4)cc3C2=O)C(c2ccccc2)C1] | | 527.2 |
| 14 | tert-butyl (3R,4S)-4-(1-oxo-6-(5-(trifluoromethyl)-1,2,4-oxadiazol-3-yl)-1,3-dihydro-2H-isoindol-2-yl)-3-phenylpiperidine-1-carboxylate | 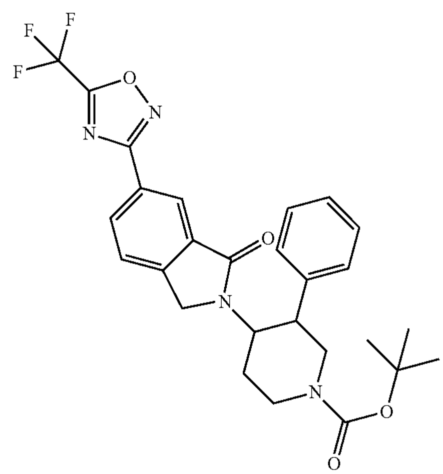 [SMILES: CC(C)(C)OC(=O)N1CCC(N2Cc3ccc(-c4noc(C(F)(F)F)n4)cc3C2=O)C(c2ccccc2)C1] | | 527.1 |

TABLE 1-3

| EXAMPLE | IUPAC NAME | Structure | ADDITIVE | MS |
|---|---|---|---|---|
| 15 | 2-((3R,4R)-3-phenylpiperidin-4-yl)-6-(5-(trifluoromethyl)-1,2,4-oxadiazol-3-yl)isoindolin-1-one | 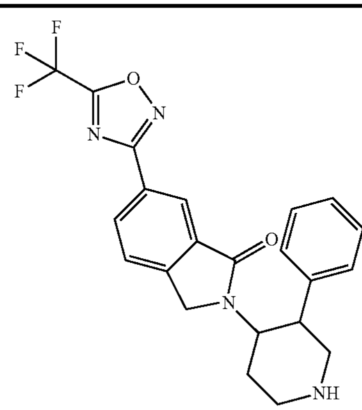 | HCl | 429.0 |

TABLE 1-3-continued

| EXAMPLE | IUPAC NAME | Structure | ADDITIVE | MS |
|---------|------------|-----------|----------|-----|
| 16 | 2-((3R,4S)-3-phenylpiperidin-4-yl)-6-(5-(trifluoromethyl)-1,2,4-oxadiazol-3-yl)isoindolin-1-one | 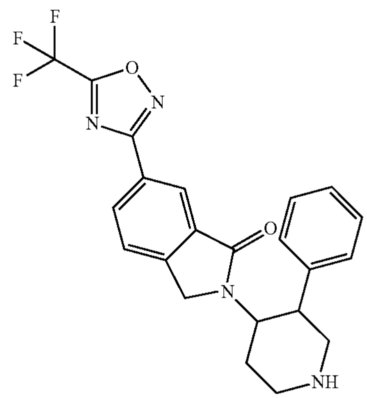 [SMILES: O=C1c2cc(-c3noc(C(F)(F)F)n3)ccc2CN1C1CCNCC1c1ccccc1] | HCl | 429.0 |
| 17 | trans-2-(2-phenylcyclohexyl)-6-(5-(trifluoromethyl)-1,2,4-oxadiazol-3-yl)isoindolin-1-one | 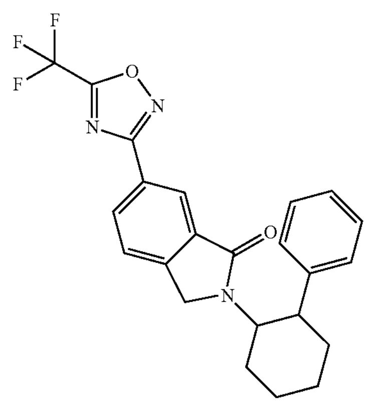 [SMILES: O=C1c2cc(-c3noc(C(F)(F)F)n3)ccc2CN1C1CCCCC1c1ccccc1] | | 428.0 |
| 18 | trans-2-(2-(2-oxopyrrolidin-1-yl)cyclohexyl)-6-(5-(trifluoromethyl)-1,2,4-oxadiazol-3-yl)isoindolin-1-one | | | 435.0 | ns
TABLE 1-3-continued

| EXAMPLE | IUPAC NAME | Structure | ADDITIVE | MS |
|---|---|---|---|---|
| 19 | tert-butyl (3S,4R)-4-(1-oxo-6-(5-(trifluoromethyl)-1,2,4-oxadiazol-3-yl)-1,3-dihydro-2H-isoindol-2-yl)-3-phenylpiperidine-1-carboxylate | 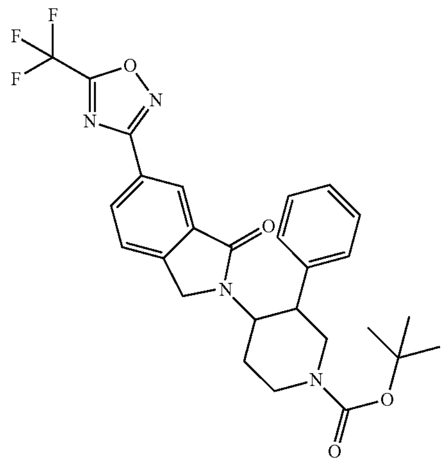 [SMILES: CC(C)(C)OC(=O)N1CCC(N2Cc3ccc(-c4noc(C(F)(F)F)n4)cc3C2=O)C(c2ccccc2)C1] | | 527.2 |
| 20 | 2-((3R,4R)-1-acetyl-3-phenylpiperidin-4-yl)-6-(5-(trifluoromethyl)-1,2,4-oxadiazol-3-yl)isoindolin-1-one | 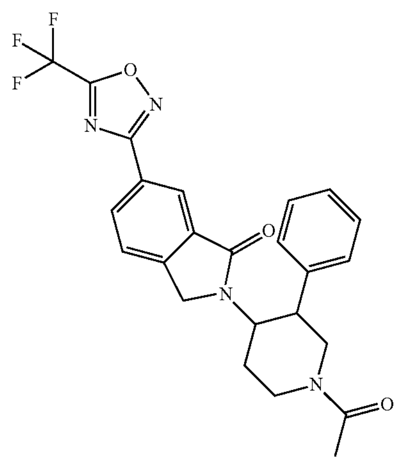 [SMILES: CC(=O)N1CCC(N2Cc3ccc(-c4noc(C(F)(F)F)n4)cc3C2=O)C(c2ccccc2)C1] | | 471.0 |
| 21 | 2-((3R,4S)-1-acetyl-3-phenylpiperidin-4-yl)-6-(5-(trifluoromethyl)-1,2,4-oxadiazol-3-yl)isoindolin-1-one | 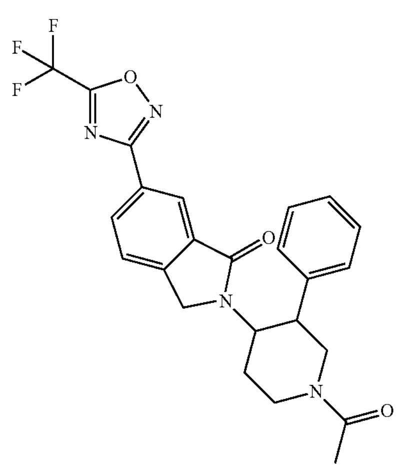 [SMILES: CC(=O)N1CCC(N2Cc3ccc(-c4noc(C(F)(F)F)n4)cc3C2=O)C(c2ccccc2)C1] | | 471.0 |

TABLE 1-4

| EXAMPLE | IUPAC NAME | Structure | ADDITIVE | MS |
|---|---|---|---|---|
| 22 | 2-((3S,4R)-3-phenyipiperidin-4-yl)-6-(5-(trifluoromethyl)-1,2,4-oxadiazol-3-yl)isoindolin-1-one | 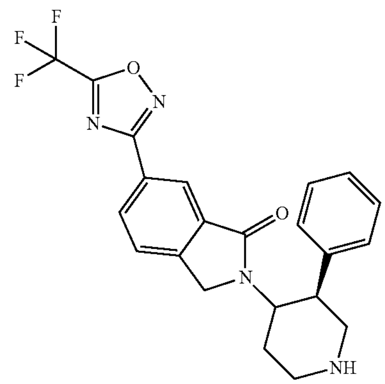 [SMILES: O=C1c2cc(-c3noc(C(F)(F)F)n3)ccc2CN1C1CCNC[C@@H]1c1ccccc1] | HCl | 429.0 |
| 23 | 2-((3S,4R)-1-acetyl-3-phenylpiperidin-4-yl)-6-(5-(trifluoromethyl)-1,2,4-oxadiazol-3-yl)isoindolin-1-one | 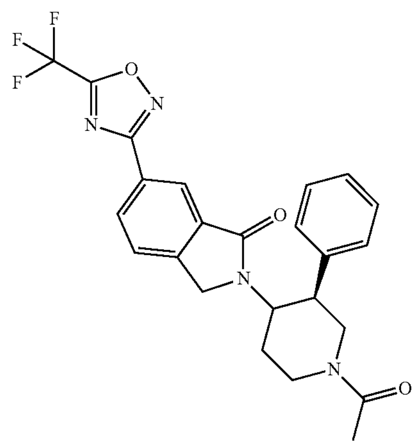 [SMILES: CC(=O)N1CCC(N2Cc3ccc(-c4noc(C(F)(F)F)n4)cc3C2=O)[C@@H](c2ccccc2)C1] | | 471.0 |
| 24 | 2-((1S)-2,3-dihydro-1H-inden-1-yl)-6-(5-(trifluoromethyl)-1,2,4-oxadiazol-3-yl)isoindolin-1-one | 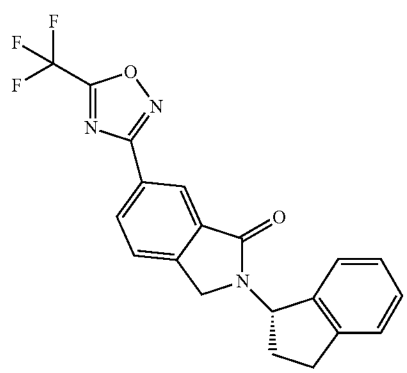 [SMILES: O=C1c2cc(-c3noc(C(F)(F)F)n3)ccc2CN1[C@H]1CCc2ccccc21] | | 386.0 |
| 25 | 2-((1R)-2,3-dihydro-1H-inden-1-yl)-6-(5-(trifluoromethyl)-1,2,4-oxadiazol-3-yl)isoindolin-1-one | 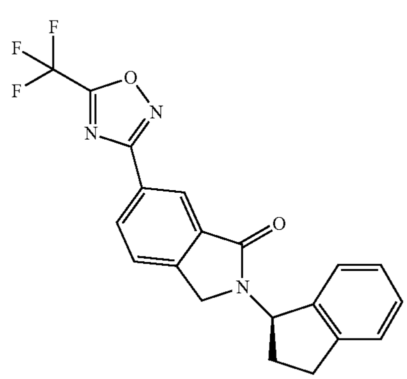 [SMILES: O=C1c2cc(-c3noc(C(F)(F)F)n3)ccc2CN1[C@@H]1CCc2ccccc21] | | 385.9 |

TABLE 1-4-continued

| EXAMPLE | IUPAC NAME | Structure | ADDITIVE | MS |
|---------|------------|-----------|----------|-----|
| 26 | tert-butyl ((1R,2R)-2-(1-oxo-6-(5-(trifluoromethyl)-1,2,4-oxadiazol-3-yl)-1,3-dihydro-2H-isoindol-2-yl)cyclohexyl)carbamate | 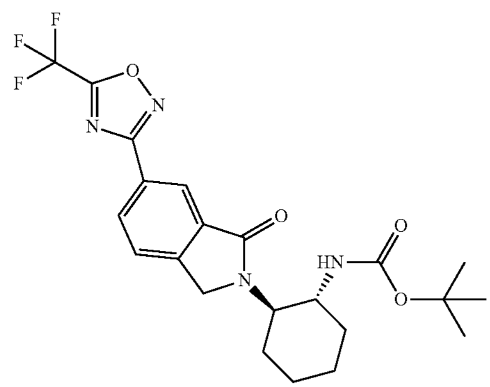 [SMILES: CC(C)(C)OC(=O)N[C@@H]1CCCC[C@H]1N1Cc2ccc(-c3noc(C(F)(F)F)n3)cc2C1=O] | | 467.1 |
| 27 | tert-butyl ((1S,2S)-2-(1-oxo-6-(5-(trifluoromethyl)-1,2,4-oxadiazol-3-yl)-1,3-dihydro-2H-isoindol-2-yl)cyclohexyl)carbamate | 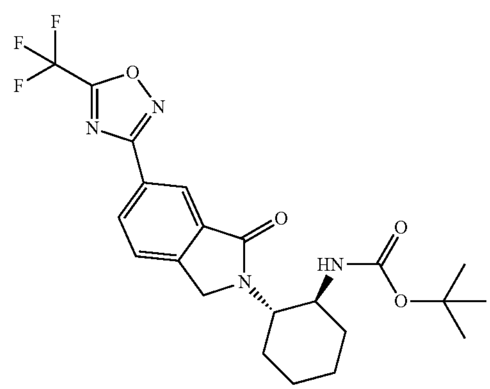 [SMILES: CC(C)(C)OC(=O)N[C@H]1CCCC[C@@H]1N1Cc2ccc(-c3noc(C(F)(F)F)n3)cc2C1=O] | | 467.0 |
| 28 | 2-((1R,2R)-2-aminocyclohexyl)-6-[5-(trifluoromethyl)-1,2,4-oxadiazol-3-yl]isoindolin-1-one | 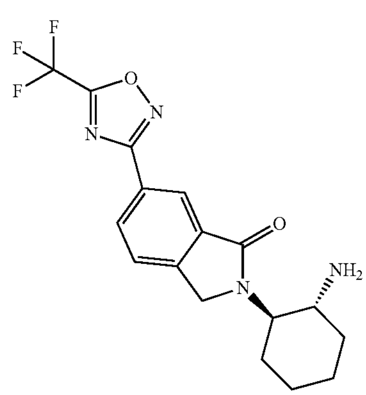 [SMILES: N[C@@H]1CCCC[C@H]1N1Cc2ccc(-c3noc(C(F)(F)F)n3)cc2C1=O] | HCl | 367.0 |

TABLE 1-5

| EXAMPLE | IUPAC NAME | Structure | ADDITIVE | MS |
|---|---|---|---|---|
| 29 | 2-((1S,2S)-2-aminocyclohexyl)-6-(5-(trifluoromethyl)-1,2,4-oxadiazol 3-yl)isoindolin-1-one | 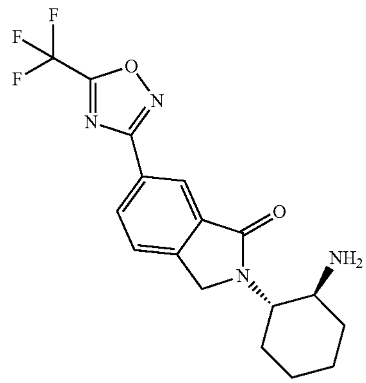 [SMILES: N[C@H]1CCCC[C@@H]1N1Cc2ccc(-c3noc(C(F)(F)F)n3)cc2C1=O] | HCl | 367.0 |
| 30 | tert-butyl (3S,4S)-4-(1-oxo-6-(5-(trifluoromethyl)-1,2,4-oxadiazol-3-yl)-1,3-dihydro-2H-isoindol-2-yl)-3-phenylpiperidine-1-carboxylate | 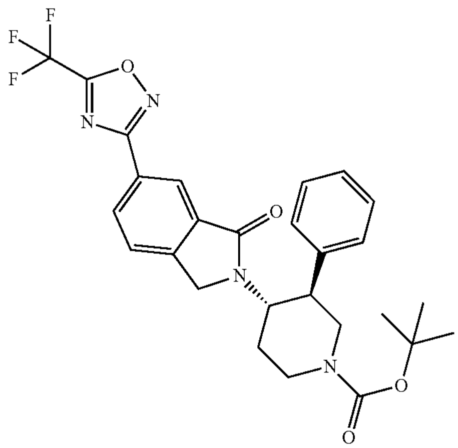 [SMILES: CC(C)(C)OC(=O)N1CC[C@H](N2Cc3ccc(-c4noc(C(F)(F)F)n4)cc3C2=O)[C@@H](c2ccccc2)C1] | | 527.1 |
| 31 | 2-((3S,4S)-3-phenylpiperidin-4-yl)-6-(5-(trifluoromethyl)-1,2,4-oxadiazol-3-yl)isoindolin-1-one | 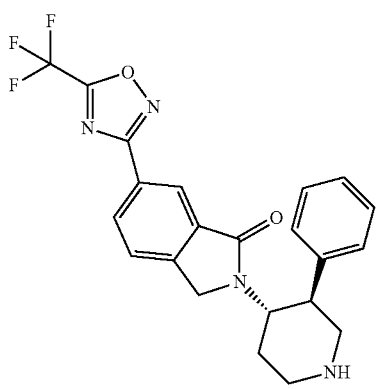 [SMILES: O=C1c2cc(-c3noc(C(F)(F)F)n3)ccc2CN1[C@H]1CCNC[C@@H]1c1ccccc1] | HCl | 429.0 |
| 32 | N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide | 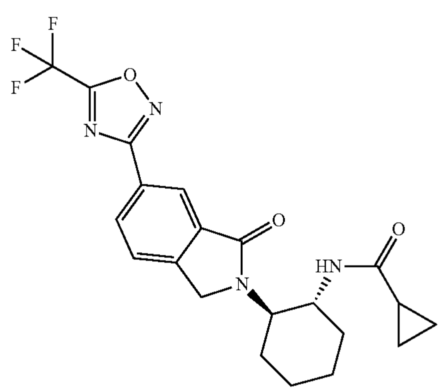 [SMILES: O=C(N[C@@H]1CCCC[C@H]1N1Cc2ccc(-c3noc(C(F)(F)F)n3)cc2C1=O)C1CC1] | | 435.0 |

TABLE 1-5-continued

| EXAMPLE | IUPAC NAME | Structure | ADDITIVE | MS |
|---|---|---|---|---|
| 33 | N-((1S,2S)-2-(1-oxo-6-(5-(trifluoromethyl)-1,2,4-oxadiazol-3-yl)-1,3-dihydro-2H-isoindol-2-yl)cyclohexyl)cyclopropanecarboxamide | 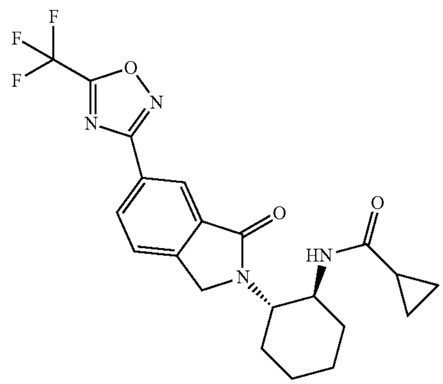 [SMILES: O=C(N[C@H]1CCCC[C@@H]1N1Cc2ccc(-c3noc(C(F)(F)F)n3)cc2C1=O)C1CC1] | | 435.0 |
| 34 | trans-2-(3-phenyltetrahydro-2H-pyran-4-yl)-6-(5-(trifluoromethyl)-1,2,4-oxadiazol-3-yl)isoindolin-1-one | 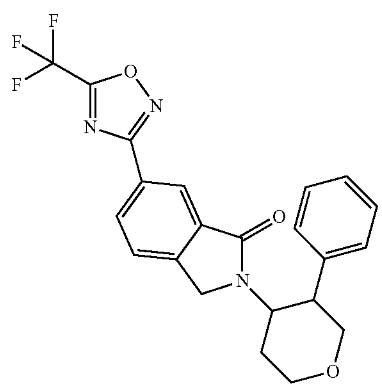 [SMILES: O=C1c2cc(-c3noc(C(F)(F)F)n3)ccc2CN1C1CCOCC1c1ccccc1] | | 429.9 |
| 35 | trans-2-(3-phenyltetrahydro-2H-pyran-4-yl)-6-(5-(trifluoromethyl)-1,2,4-oxadiazol-3-yl)isoindolin-1-one | 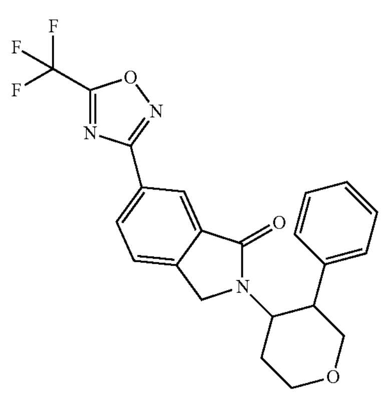 [SMILES: O=C1c2cc(-c3noc(C(F)(F)F)n3)ccc2CN1C1CCOCC1c1ccccc1] | | 430.0 |

TABLE 1-6

| EXAMPLE | IUPAC NAME | Structure | ADDITIVE | MS |
|---|---|---|---|---|
| 36 | 1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide | 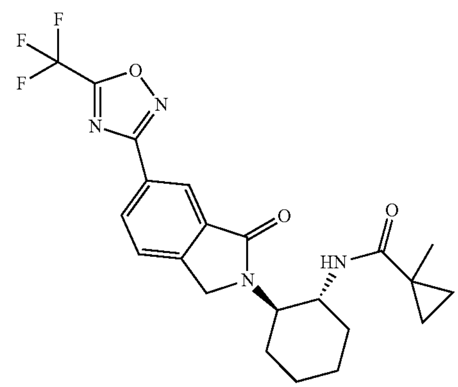 [SMILES: CC1(C(=O)N[C@@H]2CCCC[C@H]2N2Cc3ccc(-c4noc(C(F)(F)F)n4)cc3C2=O)CC1] | | 449.0 |
| 37 | N-((1R,2R)-2-(1-oxo-6-(5-(trifluoromethyl)-1,2,4-oxadiazol-3-yl)-1,3-dihydro-2H-isoindol-2-yl)cyclohexyl)tetrahydro-2H-pyran-4-carboxamide | 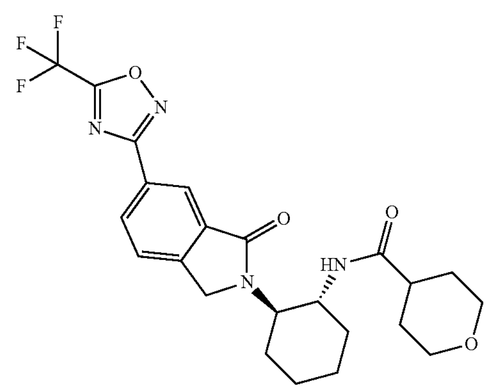 [SMILES: O=C(N[C@@H]1CCCC[C@H]1N1Cc2ccc(-c3noc(C(F)(F)F)n3)cc2C1=O)C1CCOCC1] | | 479.1 |
| 38 | 6-(1-acetylpiperidin-4-yl)-3-(5-(trifluoromethyl)-1,2,4-oxadiazol-3-yl)-6,7-dihydro-5H-pyrrolo[3,4-b]pyridin-5-one | 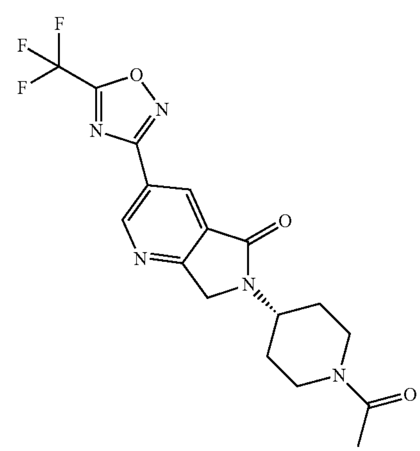 | | 396.1 |

TABLE 1-6-continued
| EXAMPLE | IUPAC NAME | Structure | ADDITIVE | MS |
|---|---|---|---|---|
| 39 | 6-(1-acetylpiperidin-3-yl)-3-(5-(trifluoromethyl)-1,2,4-oxadiazol-3-yl)-6,7-dihydro-5H-pyrrolo[3,4-b]pyridin-5-one | 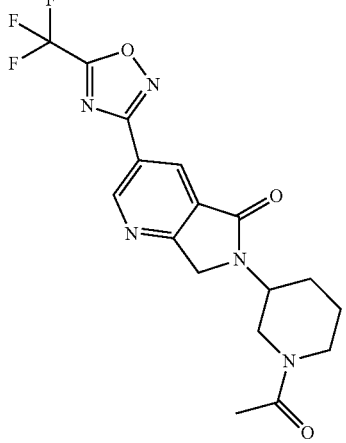 | | 396.0 |
| 40 | 6-(1-benzoylpiperidin-3-yl)-3-(5-(trifluoromethyl)-1,2,4-oxadiazol-3-yl)-6,7-dihydro-5H-pyrrolo[3,4-b]pyridin-5-one | 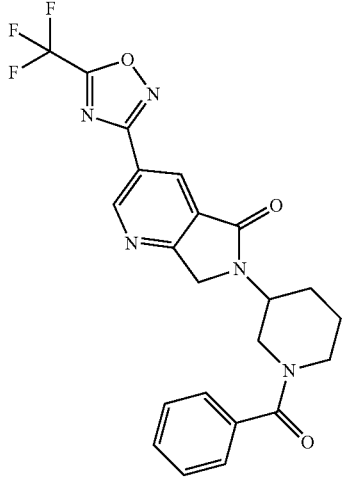 [SMILES: O=C(c1ccccc1)N1CCCC(N2Cc3ncc(-c4noc(C(F)(F)F)n4)cc3C2=O)C1] | | 458.0 |
| 41 | 6-(1-((4-fluorophenyl)acetyl)piperidin-3-yl)-3-(5-(trifluoromethyl)-1,2,4-oxadiazol-3-yl)-6,7-dihydro-5H-pyrrolo[3,4-b]pyridin-5-one | 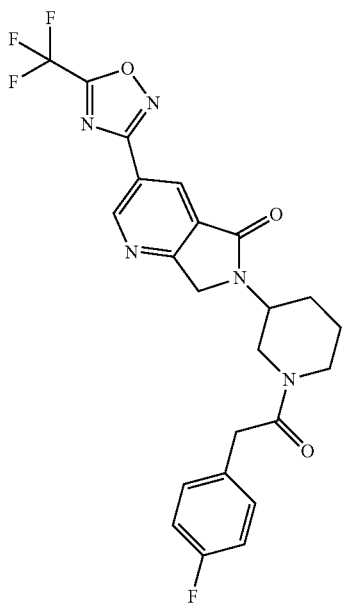 [SMILES: O=C(Cc1ccc(F)cc1)N1CCCC(N2Cc3ncc(-c4noc(C(F)(F)F)n4)cc3C2=O)C1] | | 490.1 |

TABLE 1-6-continued

| EXAMPLE | IUPAC NAME | Structure | ADDITIVE | MS |
|---|---|---|---|---|
| 42 | 3-methyl-N-((1R,2R)-2-(1-oxo-6-(5-(trifluoromethyl)-1,2,4-oxadiazol-3-yl)-1,3-dihydro-2H-isoindol-2-yl)cyclohexyl)oxetane-3-carboxamide | 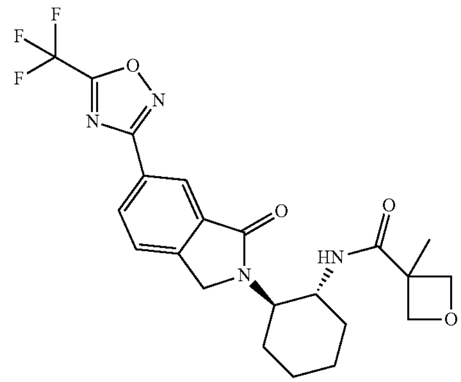 [SMILES: CC1(C(=O)N[C@@H]2CCCC[C@H]2N2Cc3ccc(-c4noc(C(F)(F)F)n4)cc3C2=O)COC1] | | 465.2 |

TABLE 1-7

| EXAMPLE | IUPAC NAME | Structure | ADDITIVE | MS |
|---|---|---|---|---|
| 43 | (3R,4R)-4-(1-oxo-6-(5-(trifluoromethyl)-1,2,4-oxadiazol-3-yl)-1,3-dihydro-2H-isoindol-2-yl)-3-phenylpiperidine-1-carboxamide | 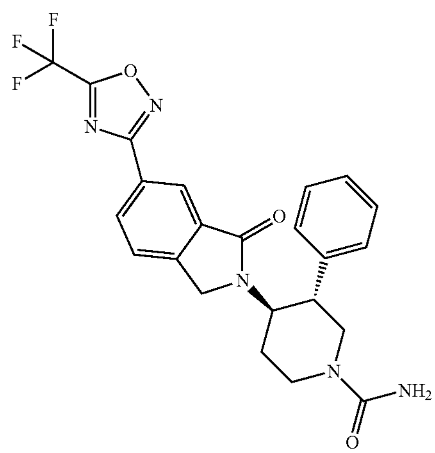 [SMILES: NC(=O)N1CC[C@@H](N2Cc3ccc(-c4noc(C(F)(F)F)n4)cc3C2=O)[C@H](c2ccccc2)C1] | | 472.0 |
| 44 | (3R,4R)-N-ethyl-4-(1-oxo-6-(5-(trifluoromethyl)-1,2,4-oxadiazol-3-yl)-1,3-dihydro-2H-isoindol-2-yl)-3-phenylpiperidine-1-carboxamide | 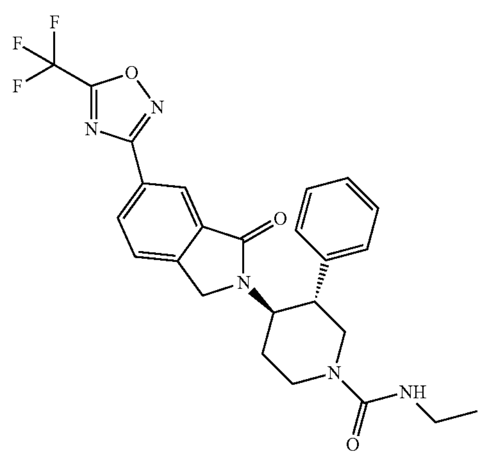 [SMILES: CCNC(=O)N1CC[C@@H](N2Cc3ccc(-c4noc(C(F)(F)F)n4)cc3C2=O)[C@H](c2ccccc2)C1] | | 500.1 |

TABLE 1-7-continued

| EXAMPLE | IUPAC NAME | Structure | ADDITIVE | MS |
|---|---|---|---|---|
| 45 | 2-(trans-3-(4-fluorophenyl)piperidin-4-yl)-6-(5-(trifluoromethyl)-1,2,4-oxadiazol-3-yl)isoindolin-1-one | 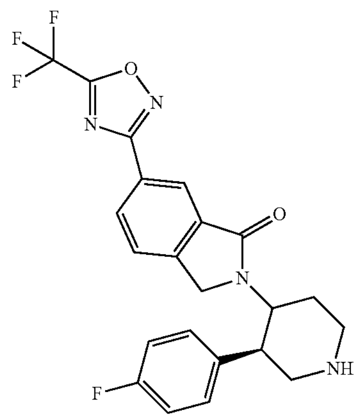 [SMILES: O=C1c2cc(-c3noc(C(F)(F)F)n3)ccc2CN1C1CCNC[C@H]1c1ccc(F)cc1] | HCl | 447.0 |
| 46 | 2-(trans-3-(3,4-difluorophenyl)piperidin-4-yl)-6-(5-(trifluoromethyl)-1,2,4-oxadiazol-3-yl)isoindolin-1-one | 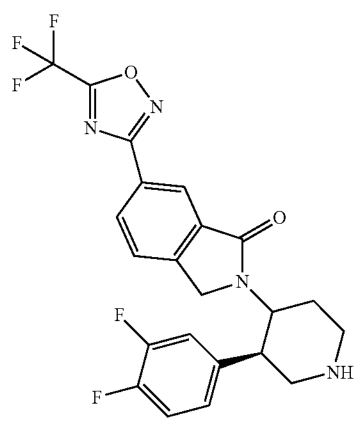 [SMILES: O=C1c2cc(-c3noc(C(F)(F)F)n3)ccc2CN1C1CCNC[C@H]1c1ccc(F)c(F)c1] | HCl | 465.0 |
| 47 | 2-(trans-3-(4-methylphenyl)piperidin-4-yl)-6-(5-(trifluoromethyl)-1,2,4-oxadiazol-3-yl)isoindolin-1-one | 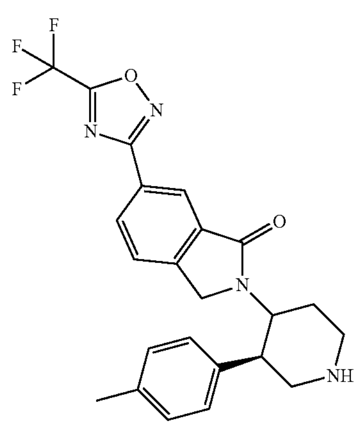 [SMILES: Cc1ccc([C@@H]2CNCCC2N2Cc3ccc(-c4noc(C(F)(F)F)n4)cc3C2=O)cc1] | HCl | 443.1 |

TABLE 1-7-continued

| EXAMPLE | IUPAC NAME | Structure | ADDITIVE | MS |
|---|---|---|---|---|
| 48 | 2-(trans-3-(3-fluoro-4-methylphenyl)piperidin-4-yl)-6-(5-(trifluoromethyl)-1,2,4-oxadiazol-3-yl)isoindolin-1-one | 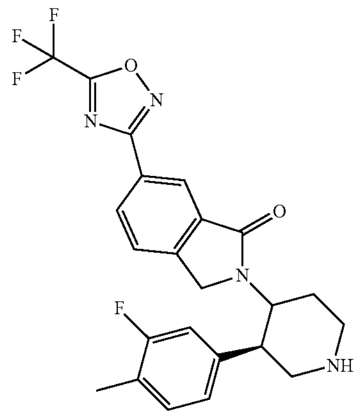 [SMILES: Cc1ccc([C@@H]2CNCCC2N2Cc3ccc(-c4noc(C(F)(F)F)n4)cc3C2=O)cc1F] | HCl | 461.0 |
| 49 | 2-(trans-3-(4-fluoro-3-methylphenyl)piperidin-4-yl)-6-(5-(trifluoromethyl)-1,2,4-oxadiazol-3-yl)isoindolin-1-one | 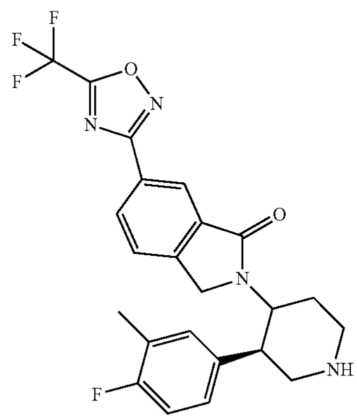 [SMILES: Cc1cc([C@@H]2CNCCC2N2Cc3ccc(-c4noc(C(F)(F)F)n4)cc3C2=O)ccc1F] | HCl | 461.0 |

TABLE 1-8

| EXAMPLE | IUPAC NAME | Structure | ADDITIVE | MS |
|---|---|---|---|---|
| 50 | 2-(trans-3-(4-fluoro-2-methylphenyl)piperidin-4-yl)-6-(5-(trifluoromethyl)-1,2,4-oxadiazol-3-yl)isoindolin-1-one | 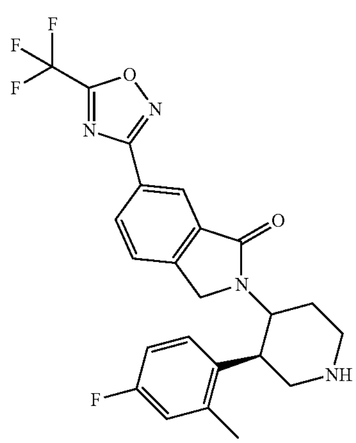 [SMILES: Cc1cc(F)ccc1[C@@H]1CNCCC1N1Cc2ccc(-c3noc(C(F)(F)F)n3)cc2C1=O] | HCl | 461.0 |

TABLE 1-8-continued

| EXAMPLE | IUPAC NAME | Structure | ADDITIVE | MS |
|---|---|---|---|---|
| 51 | 2-(trans-3-(4-chlorophenyl)piperidin-4-yl)-6-(5-(trifluoromethyl)-1,2,4-oxadiazol-3-yl)isoindolin-1-one | 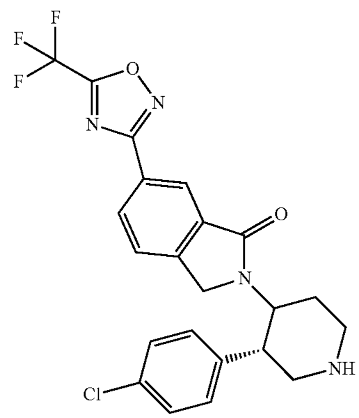 [SMILES: O=C1c2cc(-c3noc(C(F)(F)F)n3)ccc2CN1C1CCNC[C@@H]1c1ccc(Cl)cc1] | HCl | 462.9 |
| 52 | 2-(trans-3-(4-chloro-3-fluorophenyl)piperidin-4-yl)-6-(5-(trifluoromethyl)-1,2,4-oxadiazol-3-yl)isoindolin-1-one | 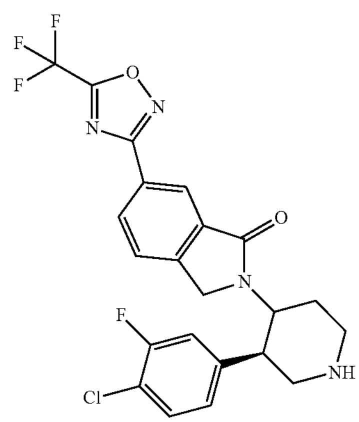 [SMILES: O=C1c2cc(-c3noc(C(F)(F)F)n3)ccc2CN1C1CCNC[C@H]1c1ccc(Cl)c(F)c1] | HCl | 481.0 |
| 53 | 2-(trans-3-(3-chlorophenyl)piperidin-4-yl)-6-(5-(trifluoromethyl)-1,2,4-oxadiazol-3-yl)isoindolin-1-one | 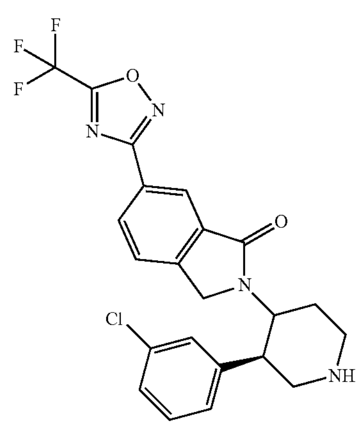 [SMILES: O=C1c2cc(-c3noc(C(F)(F)F)n3)ccc2CN1C1CCNC[C@H]1c1cccc(Cl)c1] | HCl | 463.0 |

TABLE 1-8-continued

| EXAMPLE | IUPAC NAME | Structure | ADDITIVE | MS |
|---|---|---|---|---|
| 54 | 2-(trans-3-(3-chloro-4-fluorophenyl)piperidin-4-yl)-6-(5-(trifluoromethyl)-1,2,4-oxadiazol-3-yl)isoindolin-1-one | 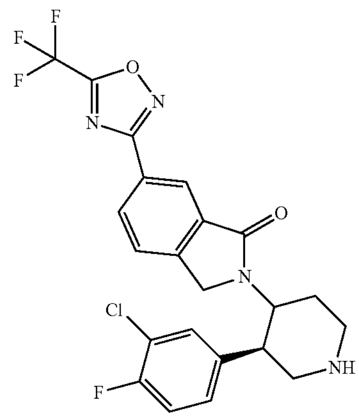 [SMILES: O=C1c2cc(-c3noc(C(F)(F)F)n3)ccc2CN1C1CCNC[C@H]1c1ccc(F)c(Cl)c1] | HCl | 480.9 |
| 55 | 2-(trans-3-(4-methoxyphenyl)piperidin-4-yl)-6-(5-(trifluoromethyl)-1,2,4-oxadiazol-3-yl)isoindolin-1-one | 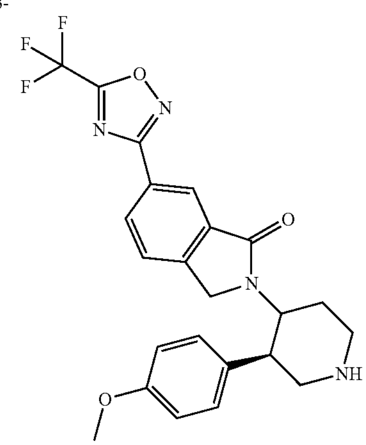 | HCl | 458.9 |
| 56 | 2-(trans-3-(3-chloro-4-methylphenyl)piperidin-4-yl)-6-(5-(trifluoromethyl)-1,2,4-oxadiazol-3-yl)isoindolin-1-one | 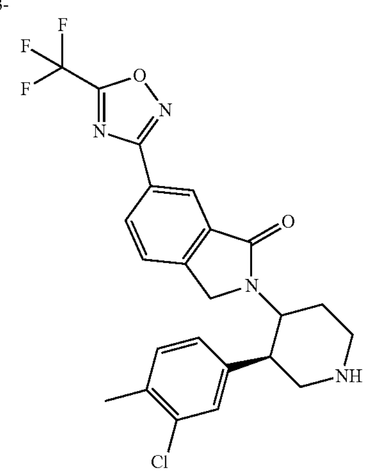 | HCl | 477.0 |

TABLE 1-9

| EXAMPLE | IUPAC NAME | Structure | ADDITIVE | MS |
|---|---|---|---|---|
| 57 | 2-(trans-3-(4-chloro-3-methylphenyl)piperidin-4-yl)-6-(5-(trifluoromethyl)-1,2,4-oxadiazol-3-yl)isoindolin-1-one | 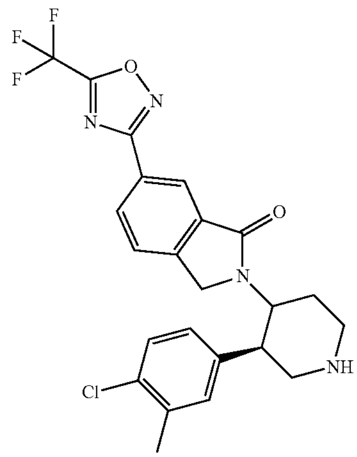 [SMILES: Cc1cc([C@@H]2CNCCC2N2Cc3ccc(-c4noc(C(F)(F)F)n4)cc3C2=O)ccc1Cl] | HCl | 477.0 |
| 58 | 2-(trans-3-(3,5-dichlorophenyl)piperidin-4-yl)-6-(5-(trifluoromethyl)-1,2,4-oxadiazol-3-yl)isoindolin-1-one | 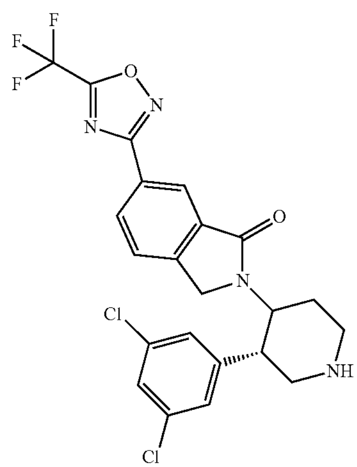 [SMILES: O=C1c2cc(-c3noc(C(F)(F)F)n3)ccc2CN1C1CCNC[C@@H]1c1cc(Cl)cc(Cl)c1] | HCl | 496.9 |
| 59 | 2-(trans-2-(morpholin-4-yl)cyclohexyl)-6-(5-(trifluoromethyl)-1,2,4-oxadiazol-3-yl)isoindolin-1-one | 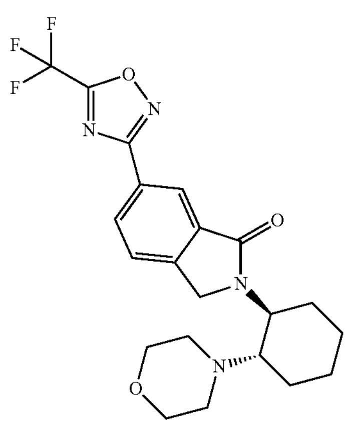 [SMILES: O=C1c2cc(-c3noc(C(F)(F)F)n3)ccc2CN1[C@H]1CCCC[C@@H]1N1CCOCC1] | | 437.0 |

TABLE 1-9-continued

| EXAMPLE | IUPAC NAME | Structure | ADDITIVE | MS |
|---|---|---|---|---|
| 60 | 2-(cis-2-benzylcyclobutyl)-6-(5-(trifluoromethyl)-1,2,4-oxadiazol-3-yl)isoindolin-1-one | 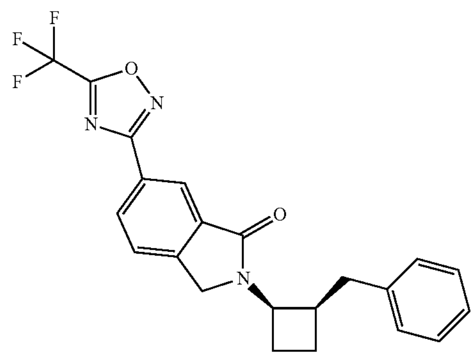 [SMILES: O=C1c2cc(-c3noc(C(F)(F)F)n3)ccc2CN1[C@@H]1CC[C@@H]1Cc1ccccc1] | | 414.0 |
| 61 | 2-((3S)-3-benzyl-5-oxopyrrolidin-3-yl)-6-(5-(trifluoromethyl)-1,2,4-oxadiazol-3-yl)isoindolin-1-one | 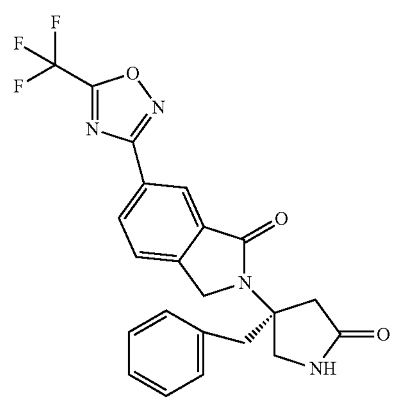 [SMILES: O=C1C[C@](Cc2ccccc2)(N2Cc3ccc(-c4noc(C(F)(F)F)n4)cc3C2=O)CN1] | | 443.0 |
| 62 | 2-((3aS,6R,6aR)-1-((1R)-1-phenylethyl)octahydrocyclopenta[b]pyrrol-6-yl)-6-(5-(trifluoromethyl)-1,2,4-oxadiazol-3-yl)isoindolin-1-one | 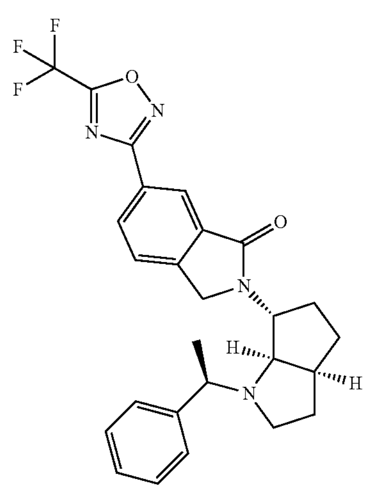 [SMILES: C[C@H](c1ccccc1)N1CC[C@@H]2CC[C@@H](N3Cc4ccc(-c5noc(C(F)(F)F)n5)cc4C3=O)[C@@H]21] | | 483.1 |

TABLE 1-9-continued

| EXAMPLE | IUPAC NAME | Structure | ADDITIVE | MS |
|---|---|---|---|---|
| 63 | 2-((3aR,6S,6aS)-1-((1R)-1-phenylethyl)octahydrocyclopenta[b]pyrrol-6-yl)-6-(5-(trifluoromethyl)-1,2,4-oxadiazol-3-yl)isoindolin-1-one | 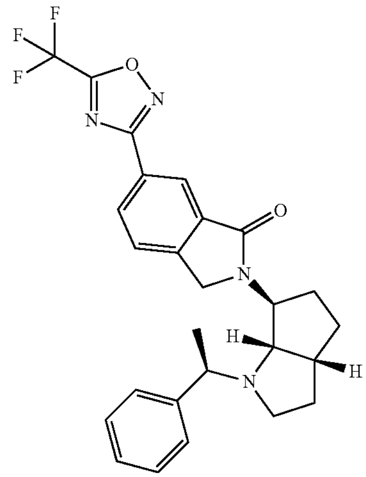 [SMILES: C[C@H](c1ccccc1)N1CC[C@H]2CC[C@H](N3Cc4ccc(-c5noc(C(F)(F)F)n5)cc4C3=O)[C@H]21] | | 483.1 |

TABLE 1-10

| EXAMPLE | IUPAC NAME | Structure | ADDITIVE | MS |
|---|---|---|---|---|
| 64 | (5r,8r)-8-(1-oxo-6-(5-(trifluoromethyl)-1,2,4-oxadiazol-3-yl)-1,3-dihydro-2H-isoindol-2-yl)-1-azaspiro[4.5]decan-2-one | 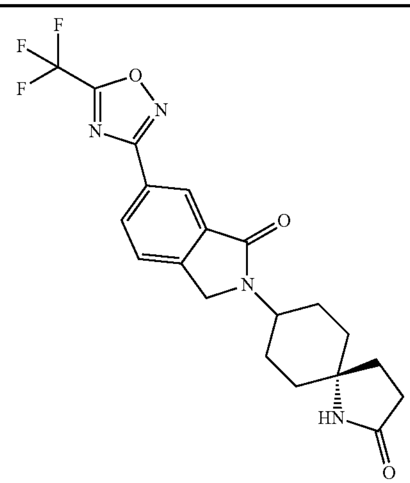 | | 421.0 |
| 65 | 3-(2-oxo-2-(4-(1-oxo-6-(5-(trifluoromethyl)-1,2,4-oxadiazol-3-yl)-1,3-dihydro-2H-isoindol-2-yl)piperidin-1-yl)ethyl)-1,3-benzoxazol-2(3H)-one | 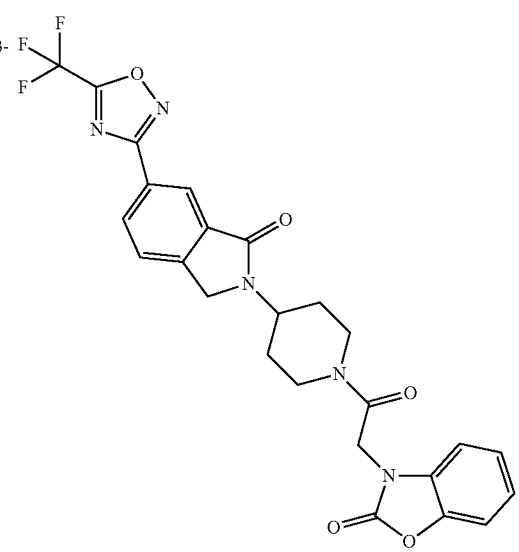 | | 528.1 |

TABLE 1-10-continued

| EXAMPLE | IUPAC NAME | Structure | ADDITIVE | MS |
|---|---|---|---|---|
| 66 | 2-(trans-2-phenylcyclopropyl)-6-(5-(trifluoromethyl)-1,2,4-oxadiazol-3-yl)isoindolin-1-one | 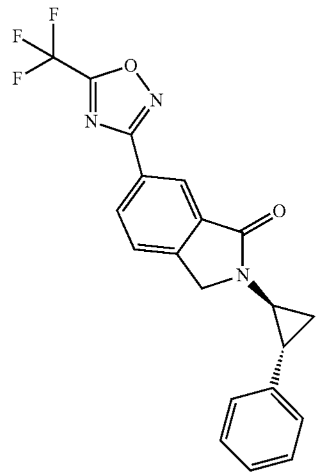 [SMILES: O=C1c2cc(-c3noc(C(F)(F)F)n3)ccc2CN1[C@H]1C[C@@H]1c1ccccc1] | | 386.0 |
| 67 | 6-(1-benzoylpiperidin-4-yl)-3-(5-(trifluoromethyl)-1,2,4-oxadiazol-3-yl)-6,7-dihydro-5H-pyrrolo[3,4-b]pyridin-5-one | 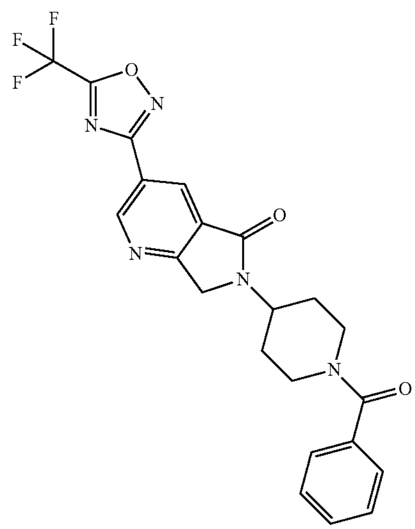 [SMILES: O=C(c1ccccc1)N1CCC(N2Cc3ncc(-c4noc(C(F)(F)F)n4)cc3C2=O)CC1] | | 458.0 |
| 68 | 6-(1-((4-fluorophenyl)acetyl)piperidin-4-yl)-3-(5-(trifluoromethyl)-1,2,4-oxadiazol-3-yl)-6,7-dihydro-5H-pyrrolo[3,4-b]pyridin-5-one | 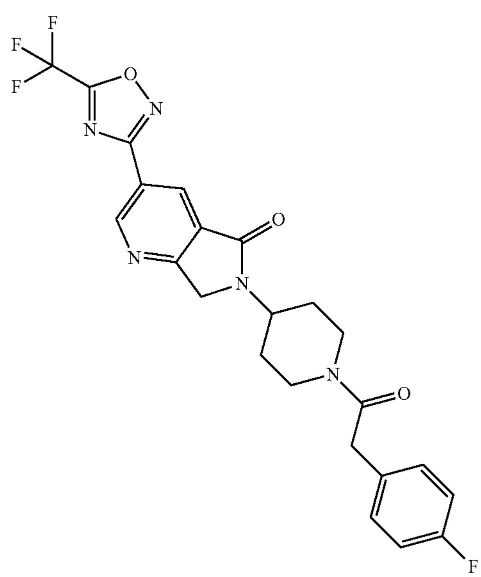 [SMILES: O=C(Cc1ccc(F)cc1)N1CCC(N2Cc3ncc(-c4noc(C(F)(F)F)n4)cc3C2=O)CC1] | | 490.0 |

TABLE 1-10-continued

| EXAMPLE | IUPAC NAME | Structure | ADDITIVE | MS |
|---|---|---|---|---|
| 69 | 6-(1-acetylpyrrolidin-3-yl)-3-(5-(trifluoromethyl)-1,2,4-oxadiazol-3-yl)-6,7-dihydro-5H-pyrrolo[3,4-b]pyridin-5-one | 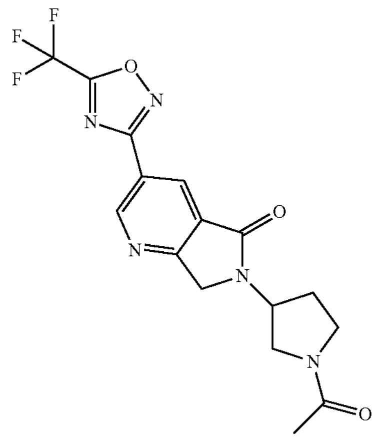 [SMILES: CC(=O)N1CCC(N2Cc3ncc(-c4noc(C(F)(F)F)n4)cc3C2=O)C1] | | 381.9 |
| 70 | 6-(1-benzoylpyrrolidin-3-yl)-3-(5-(trifluoromethyl)-1,2,4-oxadiazol-3-yl)-6,7-dihydro-5H-pyrrolo[3,4-b]pyridin-5-one | 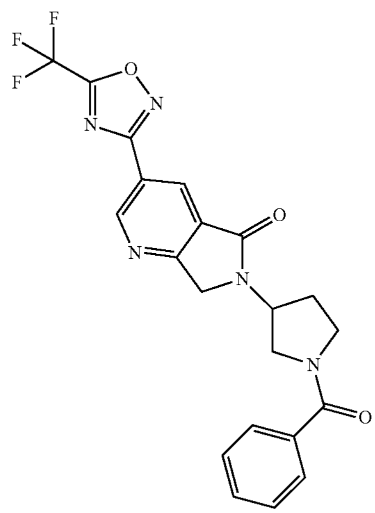 [SMILES: O=C(c1ccccc1)N1CCC(N2Cc3ncc(-c4noc(C(F)(F)F)n4)cc3C2=O)C1] | | 444.0 |

TABLE 1-11

| EXAMPLE | IUPAC NAME | Structure | ADDITIVE | MS |
|---|---|---|---|---|
| 71 | tert-butyl trans-3-(1-oxo-5-(5-(trifluoromethyl)-1,2,4-oxadiazol-3-yl)-1,3-dihydro-2H-isoindol-2-yl)-4-phenylpiperidine-1-carboxylate | 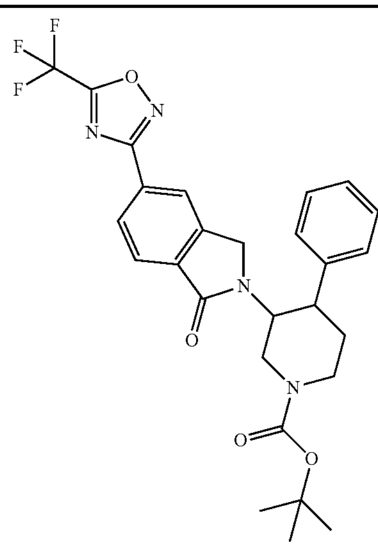 | | 527.1 |

TABLE 1-11-continued

| EXAMPLE | IUPAC NAME | Structure | ADDITIVE | MS |
|---|---|---|---|---|
| 72 | trans-2-(4-phenylpiperidin-3-yl)-5-(5-(trifluoromethyl)-1,2,4-oxadiazol-3-yl)isoindolin-1-one | 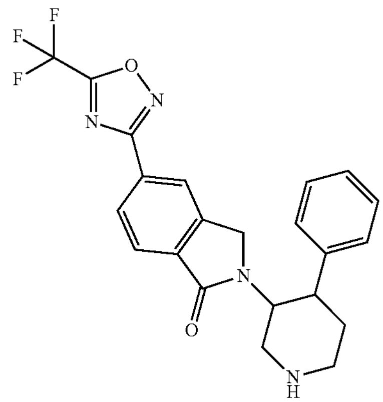 [SMILES: O=C1c2ccc(-c3noc(C(F)(F)F)n3)cc2CN1C1CNCCC1c1ccccc1] | | 429.0 |
| 73 | trans-2-(1-acetyl-4-phenylpiperidin-3-yl)-5-(5-(trifluoromethyl)-1,2,4-oxadiazol-3-yl)isoindolin-1-one | 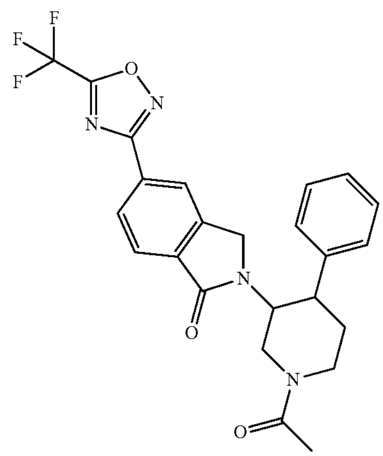 [SMILES: CC(=O)N1CCC(c2ccccc2)C(N2Cc3cc(-c4noc(C(F)(F)F)n4)ccc3C2=O)C1] | | 471.0 |
| 74 | 6-(1-((4-fluorophenyl)acetyl)pyrrolidin-3-yl)-3-(5-(trifluoromethyl)-1,2,4-oxadiazol-3-yl)-6,7-dihydro-5H-pyrrolo[3,4-b]pyridin-5-one | 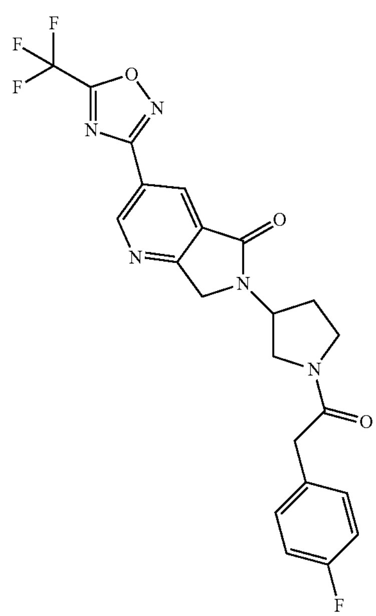 [SMILES: O=C(Cc1ccc(F)cc1)N1CCC(N2Cc3ncc(-c4noc(C(F)(F)F)n4)cc3C2=O)C1] | | 476.0 |

TABLE 1-11-continued
| EXAMPLE | IUPAC NAME | Structure | ADDITIVE | MS |
|---|---|---|---|---|
| 75 | 6-(1-acetylazetidin-3-yl)-3-(5-(trifluoromethyl)-1,2,4-oxadiazol-3-yl)-6,7-dihydro-5H-pyrrolo[3,4-b]pyridin-5-one | 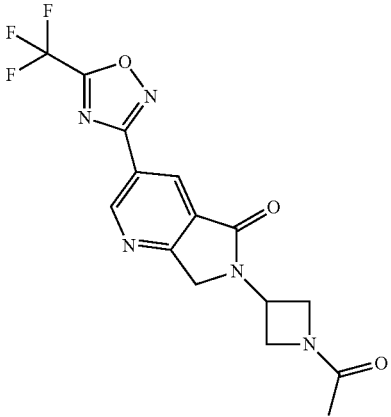 [SMILES: CC(=O)N1CC(N2Cc3ncc(-c4noc(C(F)(F)F)n4)cc3C2=O)C1] | | 367.9 |
| 76 | 6-(1-benzoylazetidin-3-yl)-3-(5-(trifluoromethyl)-1,2,4-oxadiazol-3-yl)-6,7-dihydro-5H-pyrrolo[3,4-b]pyridin-5-one | 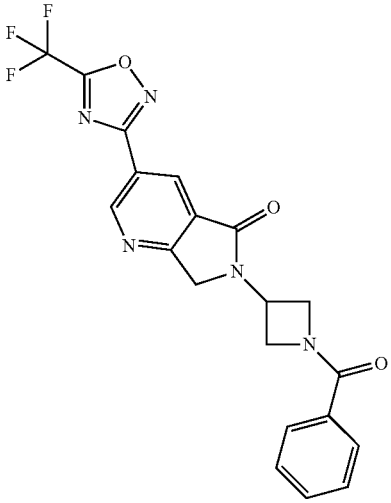 [SMILES: O=C(c1ccccc1)N1CC(N2Cc3ncc(-c4noc(C(F)(F)F)n4)cc3C2=O)C1] | | 429.9 |
| 77 | 6-(1-((4-fluorophenyl)acetyl)azetidin-3-yl)-3-(5-(trifluoromethyl)-1,2,4-oxadiazol-3-yl)-6,7-dihydro-5H-pyrrolo[3,4-b]pyridin-5-one | 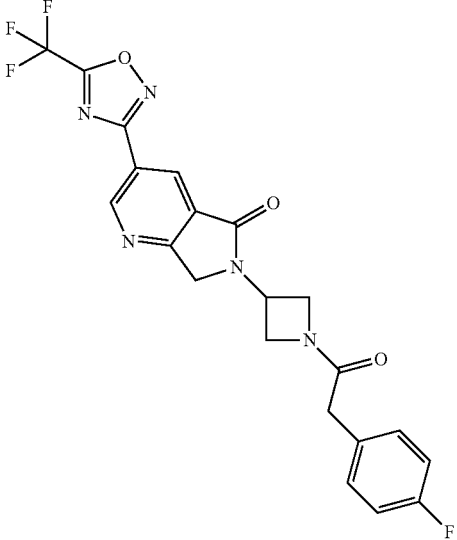 [SMILES: O=C(Cc1ccc(F)cc1)N1CC(N2Cc3ncc(-c4noc(C(F)(F)F)n4)cc3C2=O)C1] | | 462.0 |

TABLE 1-12

| EXAMPLE | IUPAC NAME | Structure | ADDITIVE | MS |
|---|---|---|---|---|
| 78 | tert-butyl cis-4-(1-oxo-5-(5-(trifluoromethyl)-1,2,4-oxadiazol-3-yl)-1,3-dihydro-2H-isoindol-2-yl)-3-phenylpiperidine-1-carboxylate | 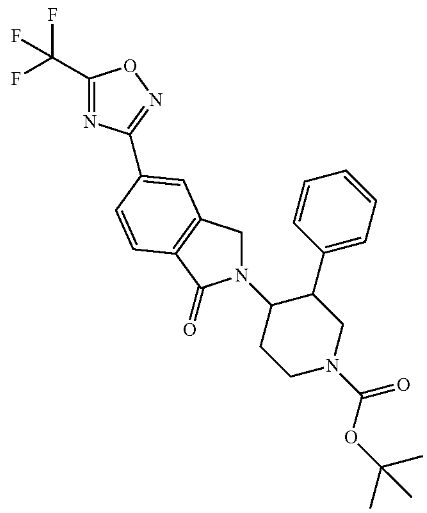 [SMILES: CC(C)(C)OC(=O)N1CCC(N2Cc3cc(-c4noc(C(F)(F)F)n4)ccc3C2=O)C(c2ccccc2)C1] | | |
| 79 | cis-2-(3-phenylpiperidin-4-yl)-5-(5-(trifluoromethyl)-1,2,4-oxadiazol-3-yl)isoindolin-1-one | 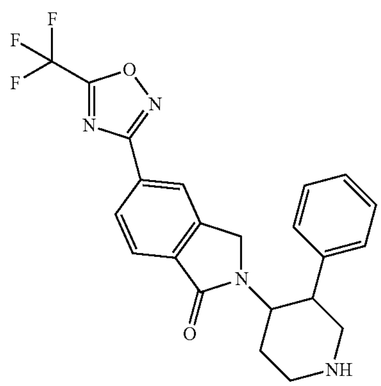 [SMILES: O=C1c2ccc(-c3noc(C(F)(F)F)n3)cc2CN1C1CCNCC1c1ccccc1] | HCl | 429.0 |
| 80 | cis-2-(1-acetyl-3-phenylpiperidin-4-yl)-5-(5-(trifluoromethyl)-1,2,4-oxadiazol-3-yl)isoindolin-1-one | 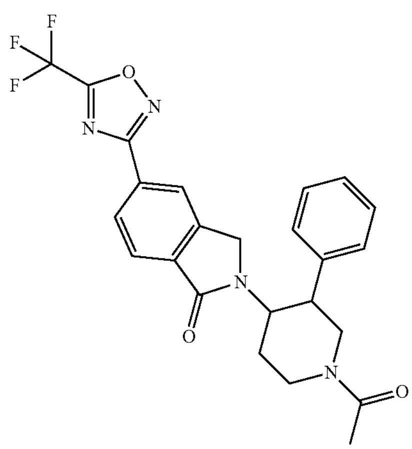 [SMILES: CC(=O)N1CCC(N2Cc3cc(-c4noc(C(F)(F)F)n4)ccc3C2=O)C(c2ccccc2)C1] | | 471.0 |

TABLE 1-12-continued

| EXAMPLE | IUPAC NAME | Structure | ADDITIVE | MS |
|---|---|---|---|---|
| 81 | tert-butyl ((3S,4R)-4-(1-oxo-6-(5-(trifluoromethyl)-1,2,4-oxadiazol-3-yl)-1,3-dihydro-2H-isoindol-2-yl)tetrahydro-2H-pyran-3-yl)carbamate | 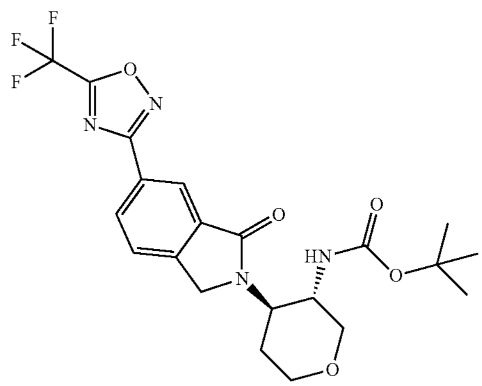 [SMILES: CC(C)(C)OC(=O)N[C@@H]1COCC[C@H]1N1Cc2ccc(-c3noc(C(F)(F)F)n3)cc2C1=O] | | 469.2 |
| 82 | N-((3S,4R)-4-(1-oxo-6-(5-(trifluoromethyl)-1,2,4-oxadiazol-3-yl)-1,3-dihydro-2H-isoindol-2-yl)tetrahydro-2H-pyran-3-yl)cyclopropanecarboxamide | 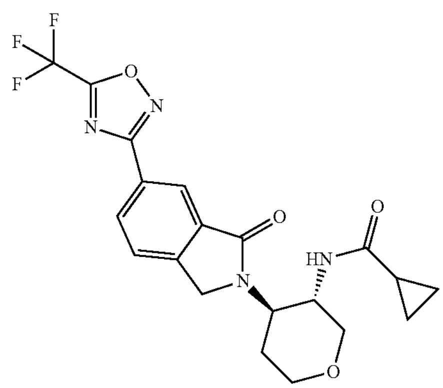 [SMILES: O=C(N[C@@H]1COCC[C@H]1N1Cc2ccc(-c3noc(C(F)(F)F)n3)cc2C1=O)C1CC1] | | 437.0 |
| 83 | 3-methyl-N-((3S,4R)-4-(1-oxo-6-(5-(trifluoromethyl)-1,2,4-oxadiazol-3-yl)-1,3-dihydro-2H-isoindol-2-yl)tetrahydro-2H-pyran-3-yl)oxetane-3-carboxamide | 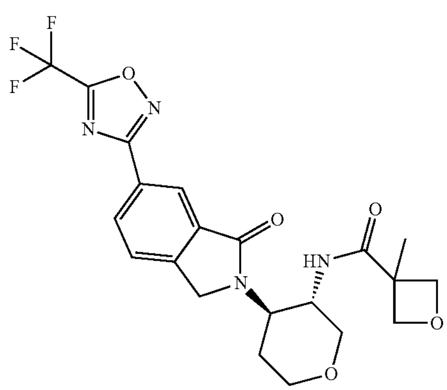 [SMILES: CC1(C(=O)N[C@@H]2COCC[C@H]2N2Cc3ccc(-c4noc(C(F)(F)F)n4)cc3C2=O)COC1] | | 465.0 |
| 84 | N-((1R,2R)-2-(5-oxo-3-(5-(trifluoromethyl)-1,2,4-oxadiazol-3-yl)-5,7-dihydro-6H-pyrrolo[3,4-b]pyridin-6-yl)cyclohexyl)cyclopropanecarboxamide | 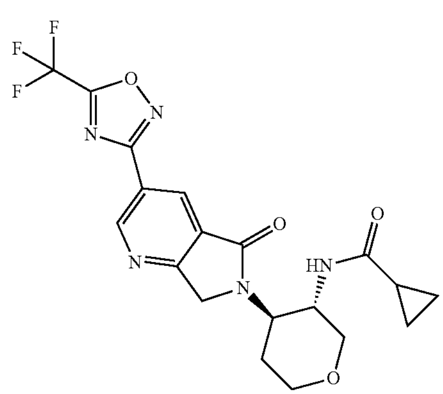 [SMILES: O=C(N[C@@H]1COCC[C@H]1N1Cc2ncc(-c3noc(C(F)(F)F)n3)cc2C1=O)C1CC1] | | 436.0 |

TABLE 1-13

| EXAMPLE | IUPAC NAME | Structure | ADDITIVE | MS |
|---|---|---|---|---|
| 85 | tert-butyl ((1S,2R)-2-(1-oxo-6-(5-(trifluoromethyl)-1,2,4-oxadiazol-3-yl)-1,3-dihydro-2H-isoindol-2-yl)cyclohexyl)carbamate | 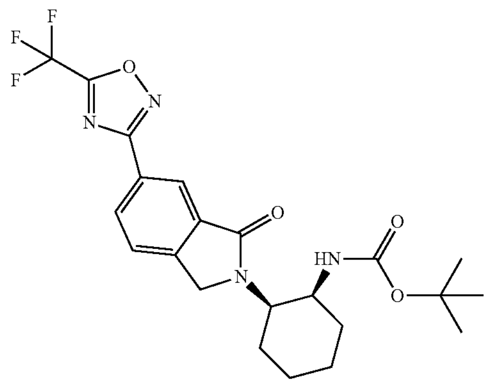 [SMILES: CC(C)(C)OC(=O)N[C@H]1CCCC[C@H]1N1Cc2ccc(-c3noc(C(F)(F)F)n3)cc2C1=O] | | 465.1 |
| 86 | N-((1S,2R)-2-(1-oxo-6-(5-(trifluoromethyl)-1,2,4-oxadiazol-3-yl)-1,3-dihydro-2H-isoindol-2-yl)cyclohexyl) cyclopropanecarboxamide | 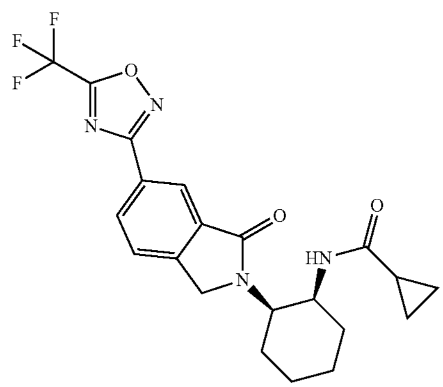 [SMILES: O=C(N[C@H]1CCCC[C@H]1N1Cc2ccc(-c3noc(C(F)(F)F)n3)cc2C1=O)C1CC1] | | 434.9 |
| 87 | N-((1R,2R)-4,4-difluoro-2-(1-oxo-6-(5-(trifluoromethyl)-1,2,4-oxadiazol-3-yl)-1,3-dihydro-2H-isoindol-2-yl)cyclohexyl)-3-methyloxetane-3-carboxamide | 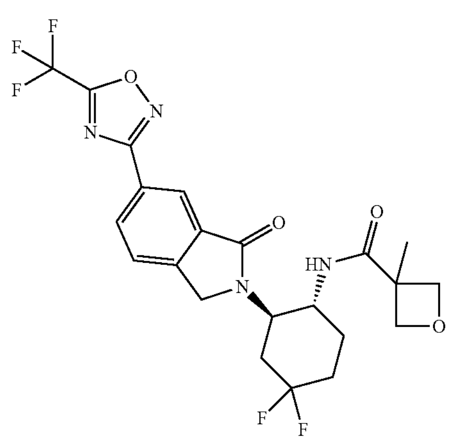 [SMILES: CC1(C(=O)N[C@@H]2CCC(F)(F)C[C@H]2N2Cc3ccc(-c4noc(C(F)(F)F)n4)cc3C2=O)COC1] | | 501.0 |

TABLE 1-13-continued

| EXAMPLE | IUPAC NAME | Structure | ADDITIVE | MS |
|---|---|---|---|---|
| 88 | tert-butyl (3R,4R)-4-(5-oxo-3-(5-(trifluoromethyl)-1,2,4-oxadiazol-3-yl)-5,7-dihydro-6H-pyrrolo[3,4-b]pyridin-6-yl)-3-phenylpiperidine-1-carboxylate | 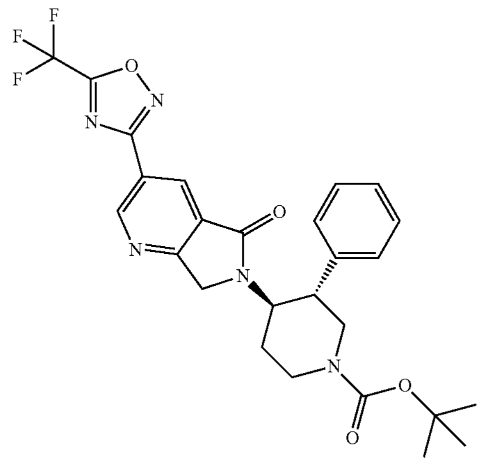 [SMILES: CC(C)(C)OC(=O)N1CC[C@@H](N2Cc3ncc(-c4noc(C(F)(F)F)n4)cc3C2=O)[C@H](c2ccccc2)C1] | | 528.1 |
| 89 | N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanesulfonamide | 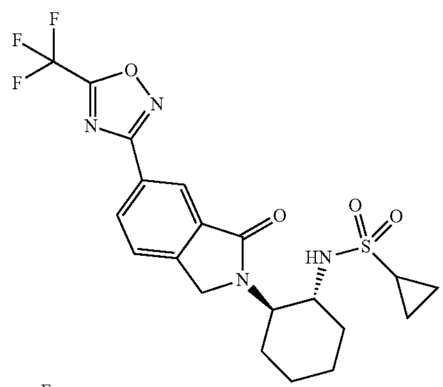 | | 471.0 |
| 90 | (2S)-N-((1R,2R)-2-(1-oxo-6-(5-(trifluoromethyl)-1,2,4-oxadiazol-3-yl)-1,3-dihydro-2H-isoindol-2-yl)cyclohexyl)tetrahydrofuran-2-carboxamide | 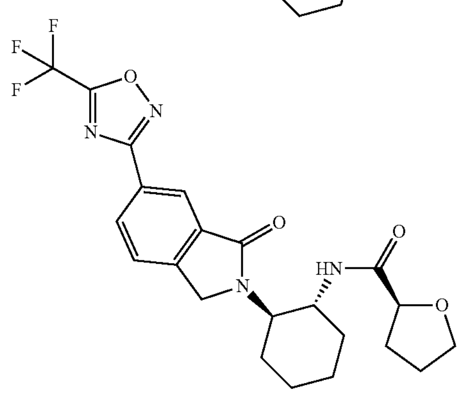 | | 465.3 |
| 91 | 2-(1-hydroxycyclopentyl)-N-((1R,2R)-2-(1-oxo-6-(5-(trifluoromethyl)-1,2,4-oxadiazol-3-yl)-1,3-dihydro-2H-isoindol-2-yl)cyclohexyl)acetamide | 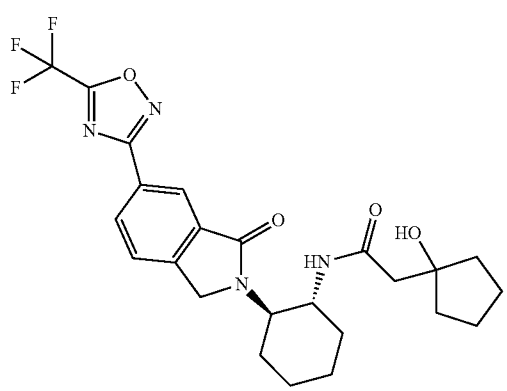 [SMILES: O=C(CC1(O)CCCC1)N[C@@H]1CCCC[C@H]1N1Cc2ccc(-c3noc(C(F)(F)F)n3)cc2C1=O] | | 493.1 |

TABLE 1-14

| EXAMPLE | IUPAC NAME | Structure | ADDITIVE | MS |
|---|---|---|---|---|
| 92 | 5-oxo-N-((1R,2R)-2-(1-oxo-6-(5-(trifluoromethyl)-1,2,4-oxadiazol-3-yl)-1,3-dihydro-2H-isoindol-2-yl)cyclohexyl)-D-prolinamide | 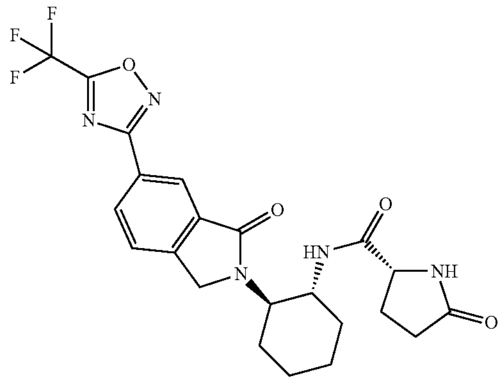 [SMILES: O=C1CC[C@H](C(=O)N[C@@H]2CCCC[C@H]2N2Cc3ccc(-c4noc(C(F)(F)F)n4)cc3C2=O)N1] | | 478.1 |
| 93 | (2S)-4-oxo-N-((1R,2R)-2-(1-oxo-6-(5-(trifluoromethyl)-1,2,4-oxadiazol-3-yl)-1,3-dihydro-2H-isoindol-2-yl)cyclohexyl)azetidine-2-carboxamide | 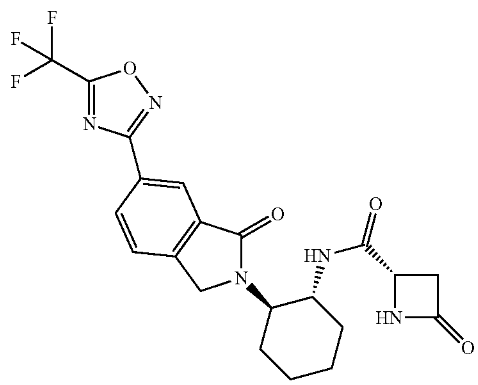 [SMILES: O=C1C[C@@H](C(=O)N[C@@H]2CCCC[C@H]2N2Cc3ccc(-c4noc(C(F)(F)F)n4)cc3C2=O)N1] | | 464.0 |
| 94 | 1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)-D-prolinamide | 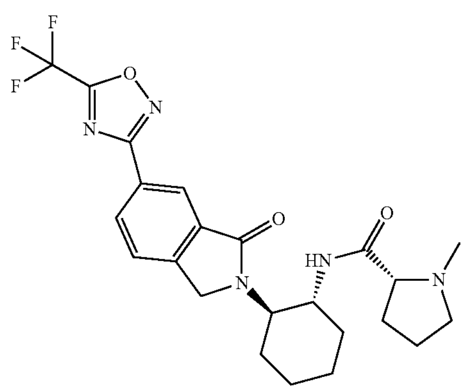 [SMILES: CN1CCC[C@@H]1C(=O)N[C@@H]1CCCC[C@H]1N1Cc2ccc(-c3noc(C(F)(F)F)n3)cc2C1=O] | | 478.0 |
| 95 | 2-hydroxy-2-methyl-N-((1R,2R)-2-(1-oxo-6-(5-(trifluoromethyl)-1,2,4-oxadiazol-3-yl)-1,3-dihydro-2H-isoindol-2-yl)cyclohexyl)propanamide | 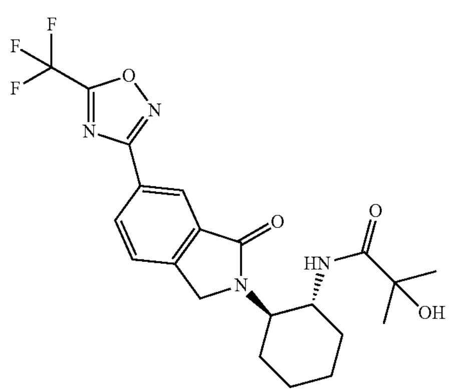 [SMILES: CC(C)(O)C(=O)N[C@@H]1CCCC[C@H]1N1Cc2ccc(-c3noc(C(F)(F)F)n3)cc2C1=O] | | 453.3 |

TABLE 1-14-continued

| EXAMPLE | IUPAC NAME | Structure | ADDITIVE | MS |
|---|---|---|---|---|
| 96 | 3-hydroxy-3-methyl-N-((1R,2R)-2-(1-oxo-6-(5-(trifluoromethyl)-1,2,4-oxadiazol-3-yl)-1,3-dihydro-2H-isoindol-2-yl)cyclohexyl)butanamide | 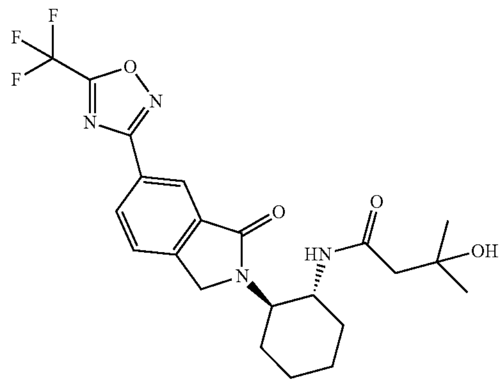 [SMILES: CC(C)(O)CC(=O)N[C@@H]1CCCC[C@H]1N1Cc2ccc(-c3noc(C(F)(F)F)n3)cc2C1=O] | | 467.1 |
| 97 | N-((1R,2R)-2-(1-oxo-6-(5-(trifluoromethyl)-1,2,4-oxadiazol-3-yl)-1,3-dihydro-2H-isoindol-2-yl)cyclohexyl)cyclobutanecarboxamide | 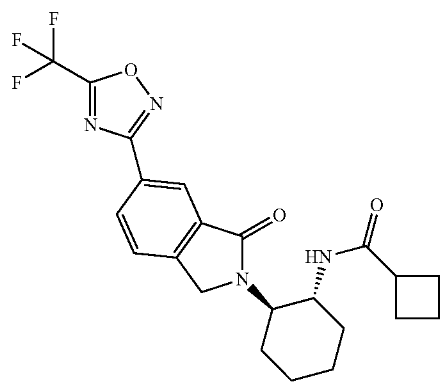 [SMILES: O=C(N[C@@H]1CCCC[C@H]1N1Cc2ccc(-c3noc(C(F)(F)F)n3)cc2C1=O)C1CCC1] | | 449.0 |
| 98 | 2-fluoro-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide | 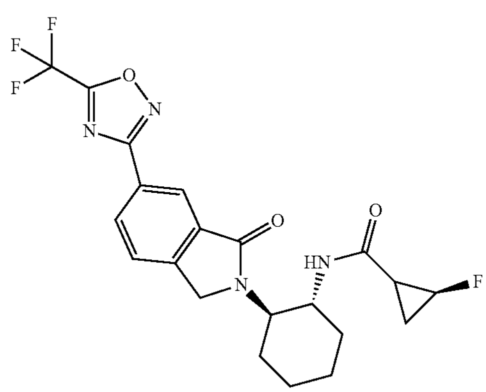 [SMILES: O=C(N[C@@H]1CCCC[C@H]1N1Cc2ccc(-c3noc(C(F)(F)F)n3)cc2C1=O)C1C[C@@H]1F] | | 453.1 |

TABLE 1-15

| EXAMPLE | IUPAC NAME | Structure | ADDITIVE | MS |
|---|---|---|---|---|
| 99 | 2,2,3,3-tetramethyl-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide | 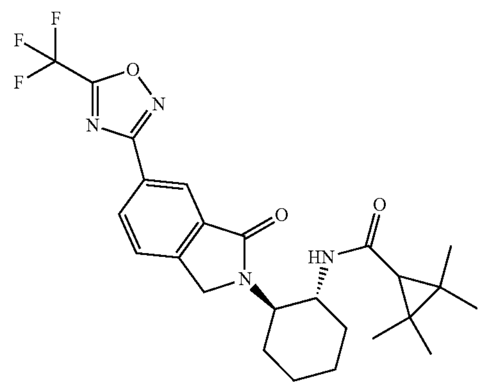 [SMILES: CC1(C)C(C(=O)N[C@@H]2CCCC[C@H]2N2Cc3ccc(-c4noc(C(F)(F)F)n4)cc3C2=O)C1(C)C] | | 491.1 |
| 100 | 2-cyano-2-methyl-N-((1R,2R)-2-(1-oxo-6-(5-(trifluoromethyl)-1,2,4-oxadiazol-3-yl)-1,3-dihydro-2H-isoindol-2-yl)cyclohexyl)propanamide | 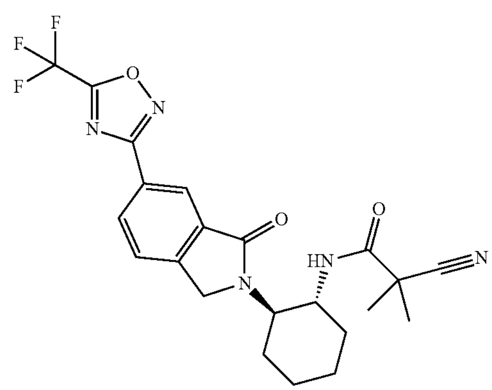 [SMILES: CC(C)(C#N)C(=O)N[C@@H]1CCCC[C@H]1N1Cc2ccc(-c3noc(C(F)(F)F)n3)cc2C1=O] | | 462.0 |
| 101 | 1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)-1H-imidazole-4-carboxamide | 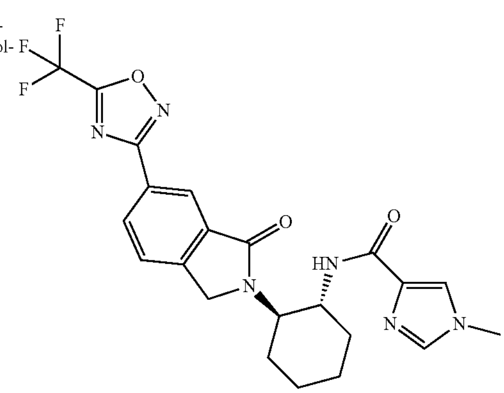 | | 475.1 |
| 102 | 2-methyl-N-((1R,2R)-2-(1-oxo-6-(5-(trifluoromethyl)-1,2,4-oxadiazo-3-yl)-1,3-dihydro-2H-isoindol-2-yl)cyclohexyl)cyclopropanecarboxamide | 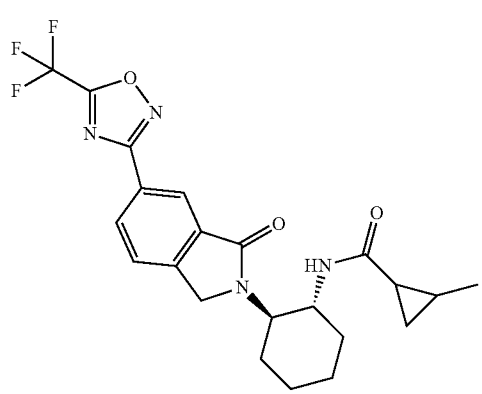 [SMILES: CC1CC1C(=O)N[C@@H]1CCCC[C@H]1N1Cc2ccc(-c3noc(C(F)(F)F)n3)cc2C1=O] | | 449.0 |

TABLE 1-15-continued

| EXAMPLE | IUPAC NAME | Structure | ADDITIVE | MS |
|---------|------------|-----------|----------|-----|
| 103 | N-((1R,2R)-2-(1-oxo-6-(5-(trifluoromethyl)-1,2,4-oxadiazol-3-yl)-1,3-dihydro-2H-isoindol-2-yl)cyclohexyl)-1,3-oxazole-4-carboxamide | 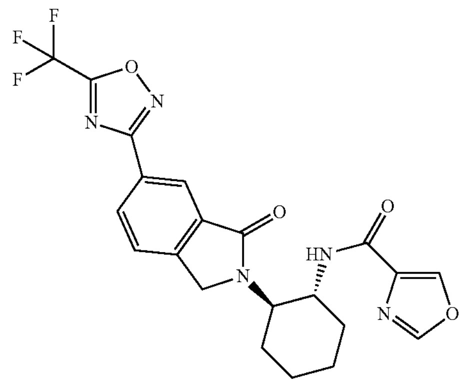 [SMILES: O=C(N[C@@H]1CCCC[C@H]1N1Cc2ccc(-c3noc(C(F)(F)F)n3)cc2C1=O)c1cocn1] | | 462.0 |
| 104 | 1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)-L-prolinamide | 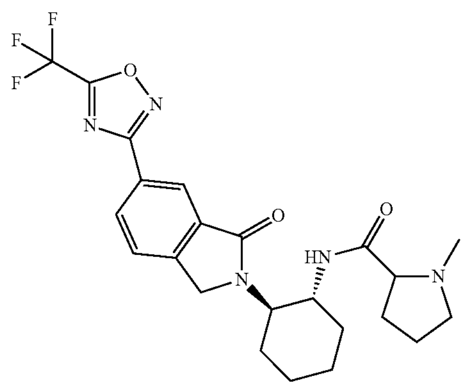 [SMILES: CN1CCCC1C(=O)N[C@@H]1CCCC[C@H]1N1Cc2ccc(-c3noc(C(F)(F)F)n3)cc2C1=O] | | 478.1 |
| 105 | 2,2-difluoro-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide | 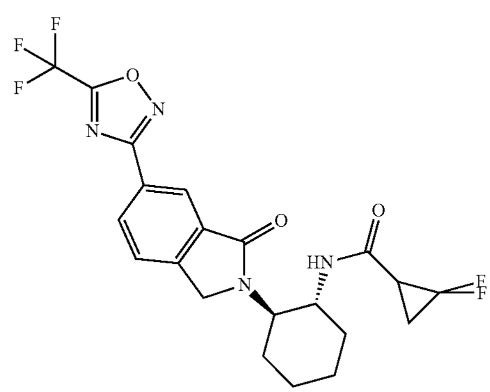 [SMILES: O=C(N[C@@H]1CCCC[C@H]1N1Cc2ccc(-c3noc(C(F)(F)F)n3)cc2C1=O)C1CC1(F)F] | | 471.0 |

TABLE 1-16

| EXAMPLE | IUPAC NAME | Structure | ADDITIVE | MS |
|---|---|---|---|---|
| 106 | 2-cyano-N-((1R,2R)-2-(1-oxo-6-(5-(trifluoromethyl)-1,2,4-oxadiazol-3-yl)-1,3-dihydro-2H-isoindol-2-yl)cyclohexyl)benzamide | 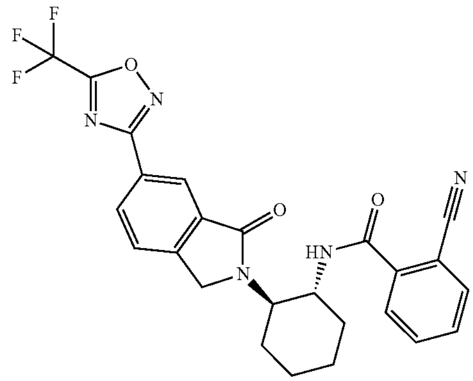 [SMILES: N#Cc1ccccc1C(=O)N[C@@H]1CCCC[C@H]1N1Cc2ccc(-c3noc(C(F)(F)F)n3)cc2C1=O] | | 496.0 |
| 107 | 2,2-dimethyl-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide | 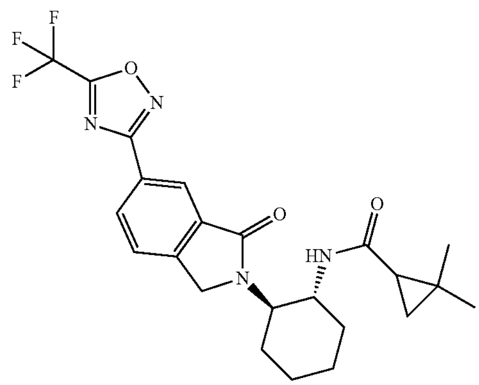 [SMILES: CC1(C)CC1C(=O)N[C@@H]1CCCC[C@H]1N1Cc2ccc(-c3noc(C(F)(F)F)n3)cc2C1=O] | | 463.1 |
| 108 | 2-oxo-N-((1Rr2R)-2-(1-oxo-6-(5-(trifluoromethyl)-1,2,4-oxadiazol-3-yl)-1,3-dihydro-2H-isoindol-2-yl)cyclohexyl)pyrrolidine-3-carboxamide | 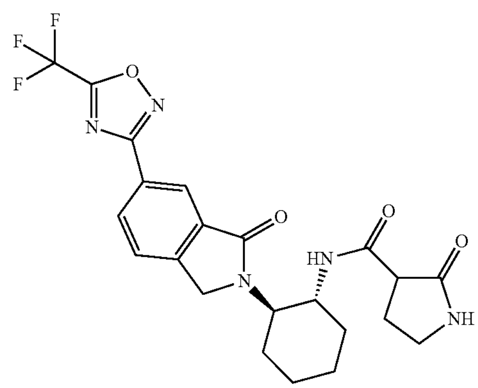 [SMILES: O=C1NCCC1C(=O)N[C@@H]1CCCC[C@H]1N1Cc2ccc(-c3noc(C(F)(F)F)n3)cc2C1=O] | | 478.1 |
| 109 | 2-oxo-N-((1R,2R)-2-(1-oxo-6-(5-(trifluoromethyl)-1,2,4-oxadiazol-3-yl)-1,3-dihydro-2H-isoindol-2-yl)cyclohexyl)imidazolidine-4-carboxamide | 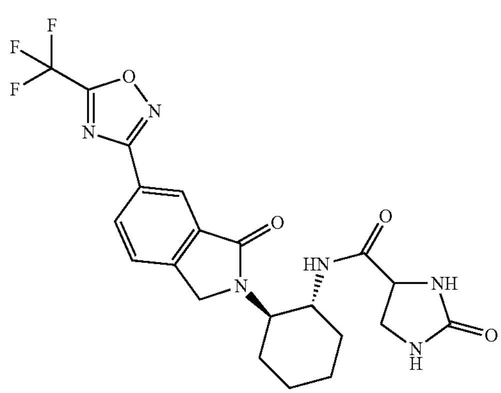 [SMILES: O=C1NCC(C(=O)N[C@@H]2CCCC[C@H]2N2Cc3ccc(-c4noc(C(F)(F)F)n4)cc3C2=O)N1] | | 479.0 |

TABLE 1-16-continued

| EXAMPLE | IUPAC NAME | Structure | ADDITIVE | MS |
|---|---|---|---|---|
| 110 | 1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)-1H-imidazole-5-carboxamide | 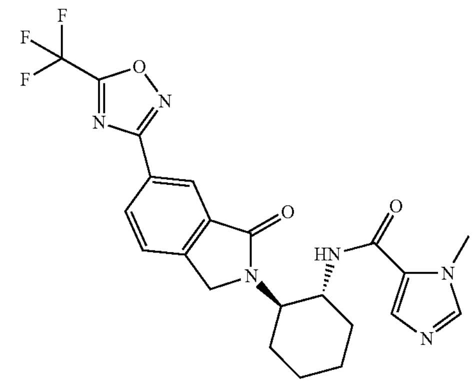 [SMILES: Cn1cncc1C(=O)N[C@@H]1CCCC[C@H]1N1Cc2ccc(-c3noc(C(F)(F)F)n3)cc2C1=O] | | 475.1 |
| 111 | 2,2-difluoro-1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide | 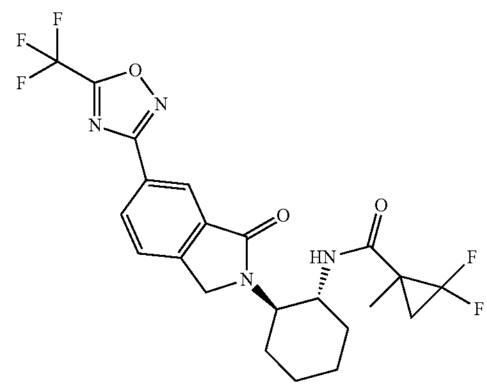 [SMILES: CC1(C(=O)N[C@@H]2CCCC[C@H]2N2Cc3ccc(-c4noc(C(F)(F)F)n4)cc3C2=O)CC1(F)F] | | 485.0 |
| 112 | 1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)-1H-pyrazole-4-carboxamide | 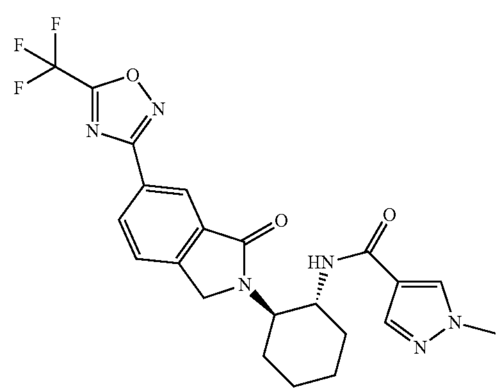 [SMILES: Cn1cc(C(=O)N[C@@H]2CCCC[C@H]2N2Cc3ccc(-c4noc(C(F)(F)F)n4)cc3C2=O)cn1] | | 475.1 |

TABLE 1-17

| EXAMPLE | IUPAC NAME | Structure | ADDITIVE | MS |
|---|---|---|---|---|
| 113 | 4-(hydroxymethyl)-N-((1R,2R)-2-(1-oxo-6-(5-(trifluoromethyl)-1,2,4-oxadiazol-3-yl)-1,3-dihydro-2H-isoindol-2-yl)cyclohexyl)tetrahydro-2H-pyran-4-carboxamide | 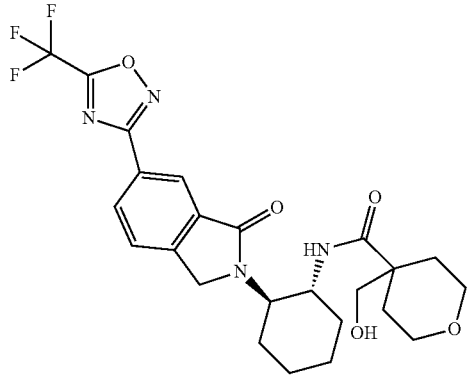 [SMILES: O=C1c2cc(-c3noc(C(F)(F)F)n3)ccc2CN1[C@@H]1CCCC[C@H]1NC(=O)C1(CO)CCOCC1] | | 509.2 |
| 114 | 1-tert-butyl-N-((1R,2R)-2-(1-oxo-6-(5-(trifluoromethyl)-1,2,4-oxadiazol-3-yl)-1,3-dihydro-2H-isoindol-2-yl)cyclohexyl)azetidine-3-carboxamide | 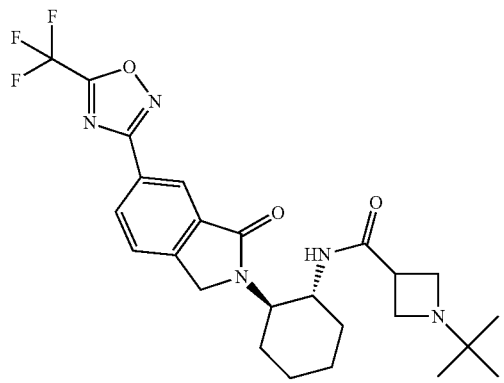 [SMILES: CC(C)(C)N1CC(C(=O)N[C@@H]2CCCC[C@H]2N2Cc3ccc(-c4noc(C(F)(F)F)n4)cc3C2=O)C1] | | 506.1 |
| 115 | N-((1R,2R)-2-(1-oxo-6-(5-(trifluoromethyl)-1,2,4-oxadiazol-3-yl)-1,3-dihydro-2H-isoindol-2-yl)cyclohexyl)pyrimidine-4-carboxamide | 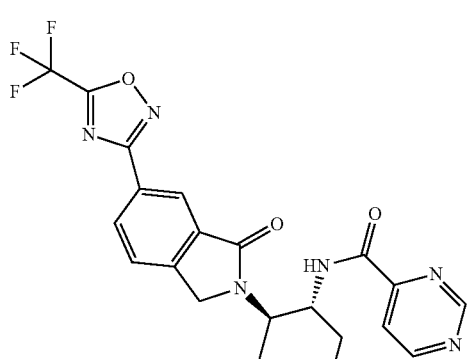 | | 473.0 |
| 116 | N-((1R,2R)-2-(1-oxo-6-(5-(trifluoromethyl)-1,2,4-oxadiazol-3-yl)-1,3-dihydro-2H-isoindol-2-yl)cyclohexyl)tetrahydrofuran-3-carboxamide | 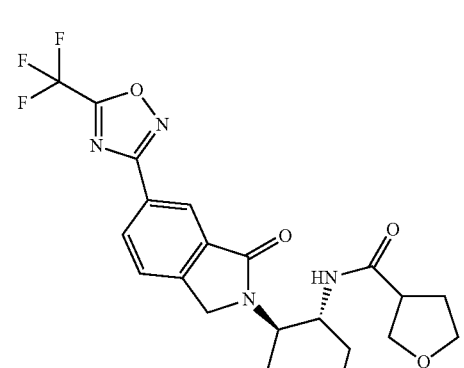 | | 465.0 |

TABLE 1-17-continued

| EXAMPLE | IUPAC NAME | Structure | ADDITIVE | MS |
|---|---|---|---|---|
| 117 | 2-(5-oxo-2,5-dihydro-1H-pyrazol-3-yl)-N-((1R,2R)-2-(1-oxo-6-(5-(trifluoromethyl)-1,2,4-oxadiazol-3-yl)-1,3-dihydro-2H-isoindol-2-yl)cyclohexyl)acetamide | 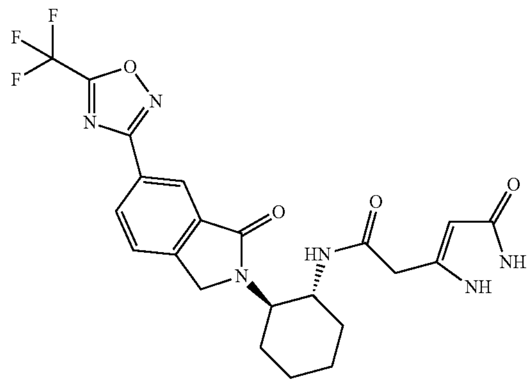 [SMILES: NC(=O)/C=C(\N)CC(=O)N[C@@H]1CCCC[C@H]1N1Cc2ccc(-c3noc(C(F)(F)F)n3)cc2C1=O] | | 491.1 |
| 118 | 6-oxo-N-((1R,2R)-2-(1-oxo-6-(5-(trifluoromethyl)-1,2,4-oxadiazol-3-yl)-1,3-dihydro-2H-isoindol-2-yl)cyclohexyl)-1,4,5,6-tetrahydropyridazine-3-carboxamide | 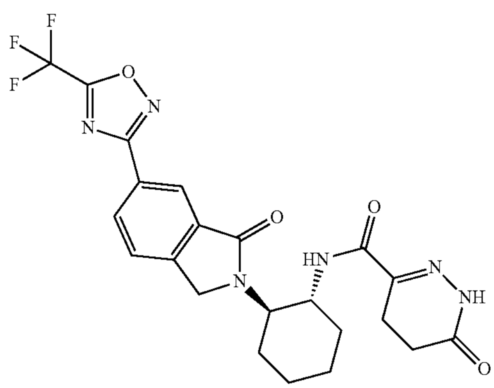 [SMILES: O=C1CCC(C(=O)N[C@@H]2CCCC[C@H]2N2Cc3ccc(-c4noc(C(F)(F)F)n4)cc3C2=O)=NN1] | | 491.0 |
| 119 | N-((1R,2R)-2-(1-oxo-6-(5-(trifluoromethyl)-1,2,4-oxadiazol-3-yl)-1,3-dihydro-2H-isoindol-2-yl)cyclohexyl)oxepane-2-carboxamide | 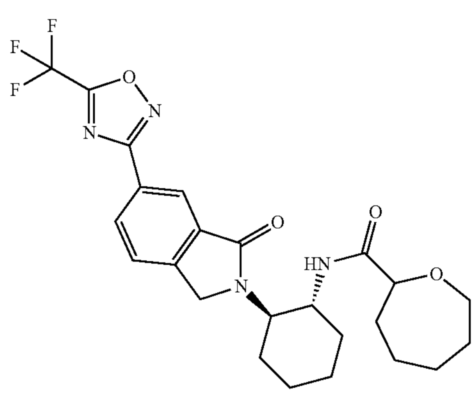 [SMILES: O=C(N[C@@H]1CCCC[C@H]1N1Cc2ccc(-c3noc(C(F)(F)F)n3)cc2C1=O)C1CCCCCO1] | | 493.2 |

TABLE 1-18

| EXAMPLE | IUPAC NAME | Structure | ADDITIVE | MS |
|---|---|---|---|---|
| 120 | 1-methyl-5-oxo-N-((1R,2R)-2-(1-oxo-6-(5-(trifluoromethyl)-1,2,4-oxadiazol-3-yl)-1,3-dihydro-2H-isoindol-2-yl)cyclohexyl)pyrrolidine-3-carboxamide | 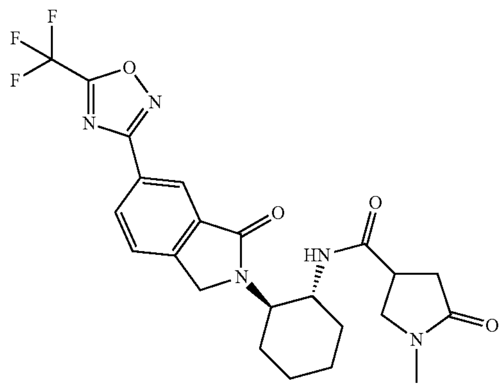 [SMILES: CN1CC(C(=O)N[C@@H]2CCCC[C@H]2N2Cc3ccc(-c4noc(C(F)(F)F)n4)cc3C2=O)CC1=O] | | 492.1 |
| 121 | 2-(2-oxopyrrolidin-1-yl)-N-((1R,2R)-2-(1-oxo-6-(5-(trifluoromethyl)-1,2,4-oxadiazol-3-yl)-1,3-dihydro-2H-isoindol-2-yl)cyclohexyl)acetamide | 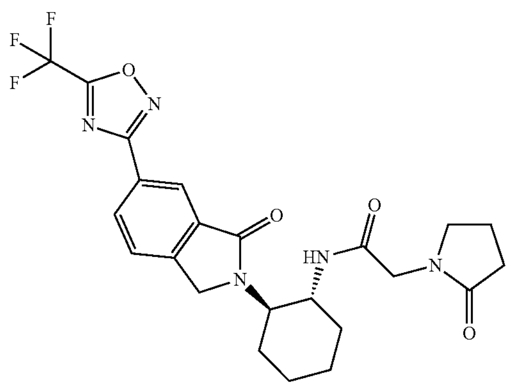 [SMILES: O=C(CN1CCCC1=O)N[C@@H]1CCCC[C@H]1N1Cc2ccc(-c3noc(C(F)(F)F)n3)cc2C1=O] | | 492.1 |
| 122 | 1-cyano-N-((1R,2R)-2-(1-oxo-6-(5-(trifluoromethyl)-1,2,4-oxadiazol-3-yl)-1,3-dihydro-2H-isoindol-2-yl)cyclohexyl) cyclopropanecarboxamide | 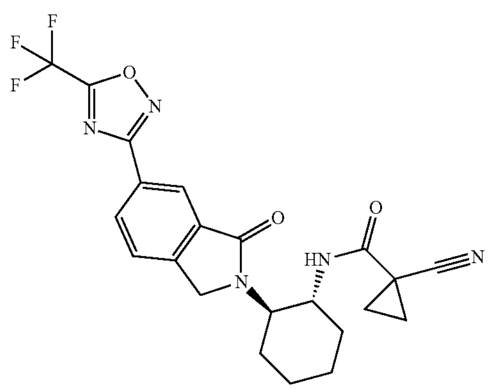 [SMILES: N#CC1(C(=O)N[C@@H]2CCCC[C@H]2N2Cc3ccc(-c4noc(C(F)(F)F)n4)cc3C2=O)CC1] | | 460.1 |
| 123 | 1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)piperidine-4-carboxamide | 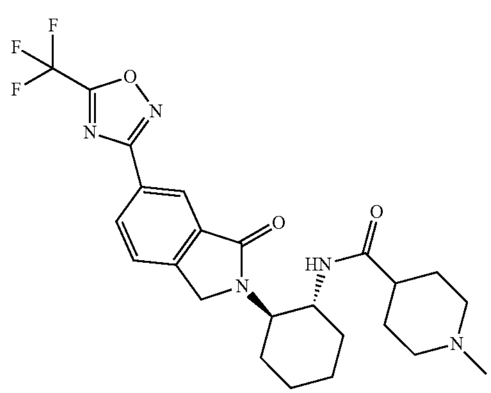 [SMILES: CN1CCC(C(=O)N[C@@H]2CCCC[C@H]2N2Cc3ccc(-c4noc(C(F)(F)F)n4)cc3C2=O)CC1] | | 492.1 |

TABLE 1-18-continued

| EXAMPLE | IUPAC NAME | Structure | ADDITIVE | MS |
|---|---|---|---|---|
| 124 | 1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)piperidine-2-carboxamide | 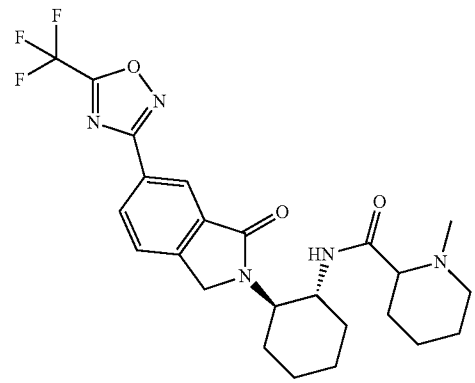 [SMILES: CN1CCCCC1C(=O)N[C@@H]1CCCC[C@H]1N1Cc2ccc(-c3noc(C(F)(F)F)n3)cc2C1=O] | | 492.2 |
| 125 | 3,3-difluoro-N-((1R,2R)-2-(1-oxo-6-(5-(trifluoromethyl)-1,2,4-oxadiazol-3-yl)-1,3-dihydro-2H-isoindol-2-yl)cyclohexyl)cyclobutanecarboxamide | 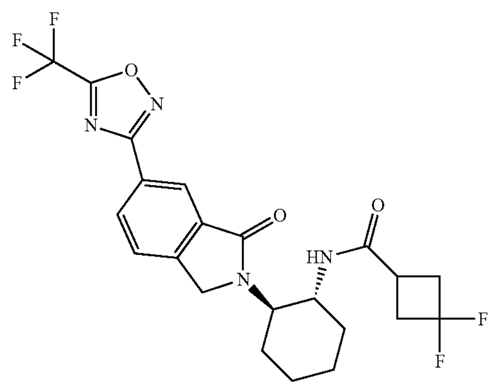 [SMILES: O=C(N[C@@H]1CCCC[C@H]1N1Cc2ccc(-c3noc(C(F)(F)F)n3)cc2C1=O)C1CC(F)(F)C1] | | 485.0 |
| 126 | 4,4-difluoro-N-((1R,2R)-2-(1-oxo-6-(5-(trifluoromethyl)-1,2,4-oxadiazol-3-yl)-1,3-dihydro-2H-isoindol-2-yl)cyclohexyl)butanamide | 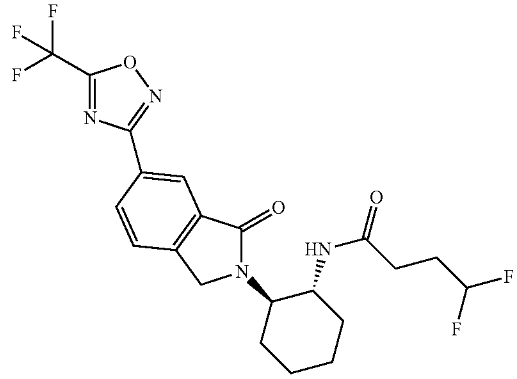 [SMILES: O=C(CCC(F)F)N[C@@H]1CCCC[C@H]1N1Cc2ccc(-c3noc(C(F)(F)F)n3)cc2C1=O] | | 473.0 |

TABLE 1-19

| EXAMPLE | IUPAC NAME | Structure | ADDITIVE | MS |
|---|---|---|---|---|
| 127 | N-((1R,2R)-2-(1-oxo-6-(5-(trifluoromethyl)-1,2,4-oxadiazol-3-yl)-1,3-dihydro-2H-isoindol-2-yl)cyclohexyl)oxetane-3-carboxamide | 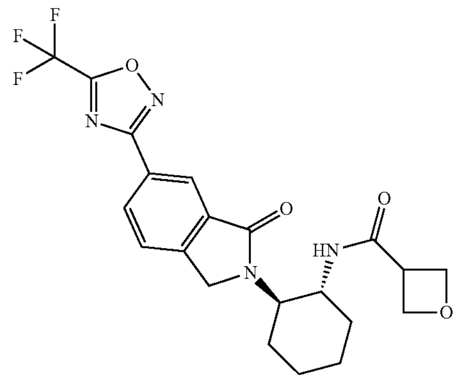 [SMILES: O=C(N[C@@H]1CCCC[C@H]1N1Cc2ccc(-c3noc(C(F)(F)F)n3)cc2C1=O)C1COC1] | | 451.0 |
| 128 | 5-oxo-N-((1R,2R)-2-(1-oxo-6-(5-(trifluoromethyl)-1,2,4-oxadiazol-3-yl)-1,3-dihydro-2H-isoindol-2-yl)cyclohexyl)-L-prolinamide | 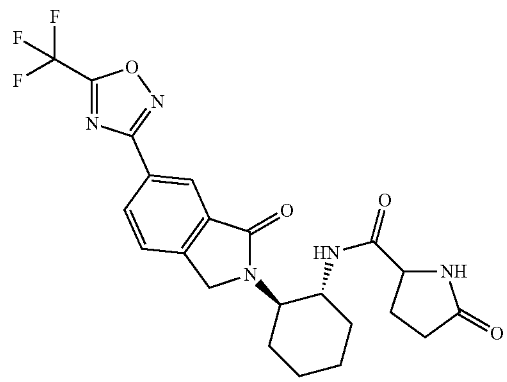 [SMILES: O=C1CCC(C(=O)N[C@@H]2CCCC[C@H]2N2Cc3ccc(-c4noc(C(F)(F)F)n4)cc3C2=O)N1] | | 478.1 |
| 129 | (2R)-N-((1R,2R)-2-(1-oxo-6-(5-(trifluoromethyl)-1,2,4-oxadiazol-3-yl)-1,3-dihydro-2H-isoindol-2-yl)cyclohexyl)tetrahydrofuran-2-carboxamide | 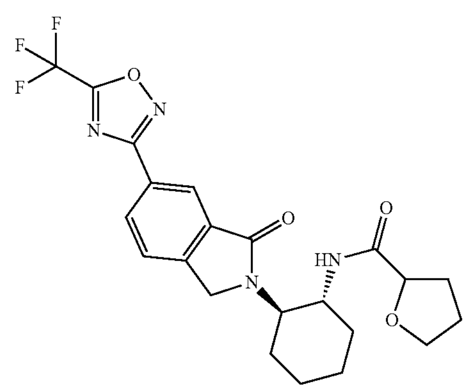 [SMILES: O=C(N[C@@H]1CCCC[C@H]1N1Cc2ccc(-c3noc(C(F)(F)F)n3)cc2C1=O)C1CCCO1] | | 465.3 |
| 130 | (3S)-5-oxo-N-((1R,2R)-2-(1-oxo-6-(5-(trifluoromethyl)-1,2,4-oxadiazol-3-yl)-1,3-dihydro-2H-isoindol-2-yl)cyclohexyl)pyrrolidine-3-carboxamide | 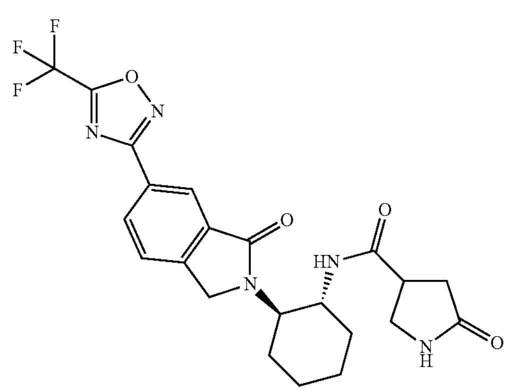 [SMILES: O=C1CC(C(=O)N[C@@H]2CCCC[C@H]2N2Cc3ccc(-c4noc(C(F)(F)F)n4)cc3C2=O)CN1] | | 478.0 |

TABLE 1-19-continued

| EXAMPLE | IUPAC NAME | Structure | ADDITIVE | MS |
|---|---|---|---|---|
| 131 | (3R)-5-oxo-N-((1R,2R)-2-(1-oxo-6-(5-(trifluoromethyl)-1,2,4-oxadiazol-3-yl)-1,3-dihydro-2H-isoindol-2-yl)cyclohexyl)pyrrolidine-3-carboxamide | 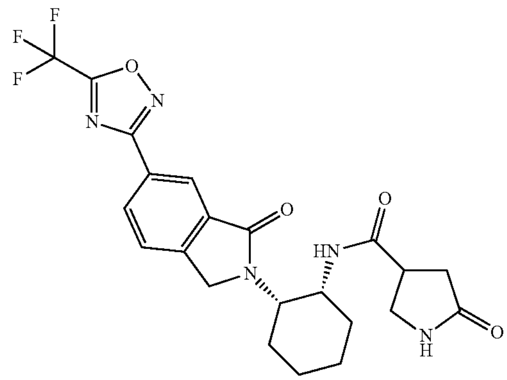 [SMILES: O=C1CC(C(=O)N[C@@H]2CCCC[C@@H]2N2Cc3ccc(-c4noc(C(F)(F)F)n4)cc3C2=O)CN1] | | 478.1 |
| 132 | 2-fluoro-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide | 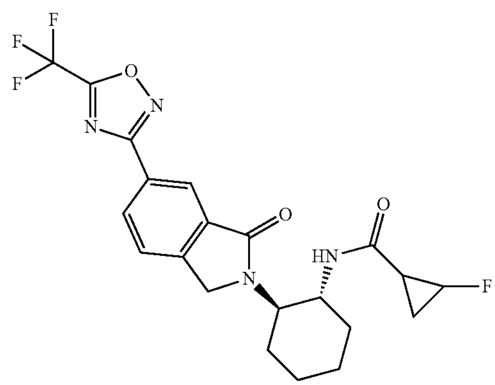 [SMILES: O=C(N[C@@H]1CCCC[C@H]1N1Cc2ccc(-c3noc(C(F)(F)F)n3)cc2C1=O)C1CC1F] | | 453.0 |
| 133 | N-((1R,2R)-2-(1-oxo-6-(5-(trifluoromethyl)-1,2,4-oxadiazol-3-yl)-1,3-dihydro-2H-isoindol-2-yl)cyclohexyl)oxepane-2-carboxamide | 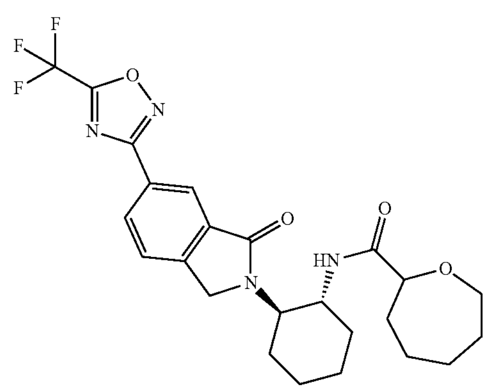 [SMILES: O=C(N[C@@H]1CCCC[C@H]1N1Cc2ccc(-c3noc(C(F)(F)F)n3)cc2C1=O)C1CCCCCO1] | | 493.2 |

TABLE 1-20

| EXAMPLE | IUPAC NAME | Structure | ADDITIVE | MS |
|---------|-----------|-----------|----------|-----|
| 134 | N-((1R,2R)-2-(1-oxo-6-(5-(trifluoromethyl)-1,2,4-oxadiazol-3-yl)-1,3-dihydro-2H-isoindol-2-yl)cyclohexyl)-3-phenyloxetane-3-carboxamide | 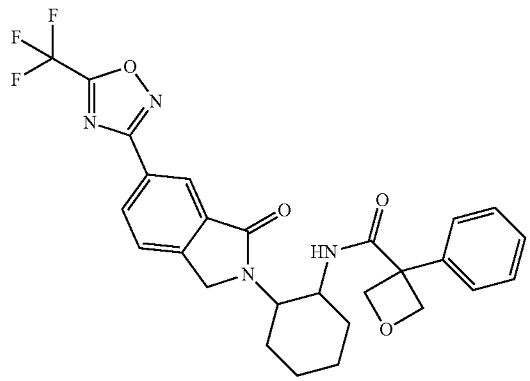 [SMILES: O=C1c2cc(-c3noc(C(F)(F)F)n3)ccc2CN1C1CCCCC1NC(=O)C1(c2ccccc2)COC1] | | 527.1 |
| 135 | tert-butyl-trans-4-(1-oxo-5-(5-(trifluoromethyl)-1,2,4-oxadiazol-3-yl)-1,3-dihydro-2H-isoindol-2-yl)-3-phenylpiperidine-1-carboxylate | 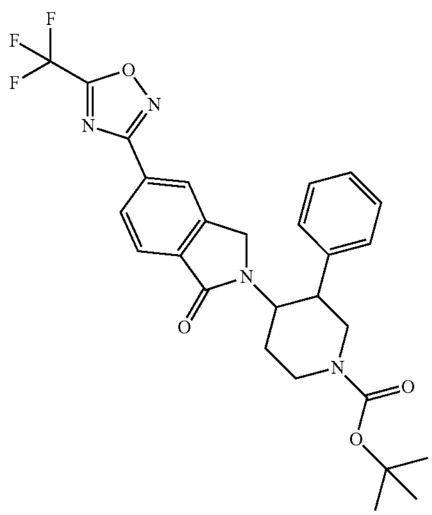 [SMILES: CC(C)(C)OC(=O)N1CCC(N2Cc3cc(-c4noc(C(F)(F)F)n4)ccc3C2=O)C(c2ccccc2)C1] | | |
| 136 | trans-2-(3-phenylpiperidin-4-yl)-5-(5-(trifluoromethyl)-1,2,4-oxadiazol-3-yl)isoindolin-1-one | 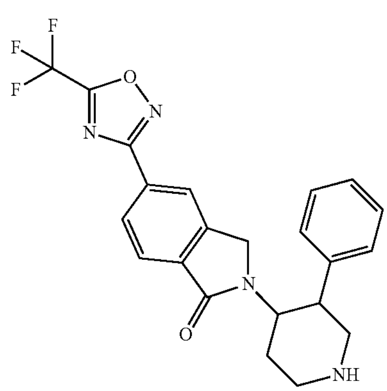 [SMILES: O=C1c2ccc(-c3noc(C(F)(F)F)n3)cc2CN1C1CCNCC1c1ccccc1] | HCl | 429.1 |

TABLE 1-20-continued

| EXAMPLE | IUPAC NAME | Structure | ADDITIVE | MS |
|---------|------------|-----------|----------|-----|
| 137 | trans-2-(1-acetyl-3-phenylpiperidin-4-yl)-5-(5-(trifluoromethyl)-1,2,4-oxadiazol-3-yl)isoindolin-1-one | 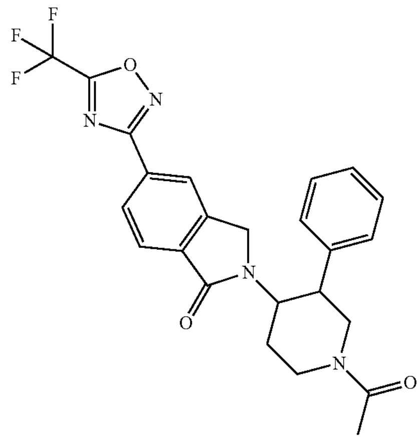 [SMILES: CC(=O)N1CCC(N2Cc3cc(-c4noc(C(F)(F)F)n4)ccc3C2=O)C(c2ccccc2)C1] | | 471.1 |
| 138 | 3-ethyl-N-((1R,2R)-2-(1-oxo-6-(5-(trifluoromethyl)-1,2,4-oxadiazol-3-yl)-1,3-dihydro-2H-isoindol-2-yl)cyclohexyl)oxetane-3-carboxamide | 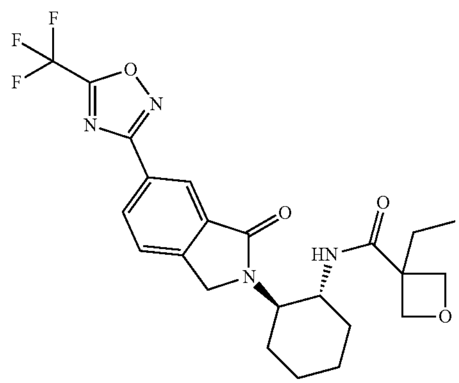 [SMILES: CCC1(C(=O)N[C@@H]2CCCC[C@H]2N2Cc3ccc(-c4noc(C(F)(F)F)n4)cc3C2=O)COC1] | | 479.1 |
| 139 | N-((1R,2R)-2-(1-oxo-6-(5-(trifluoromethyl)-1,2,4-oxadiazol-3-yl)-1,3-dihydro-2H-isoindol-2-yl)cyclohexyl)morpholine-4-carboxamide | 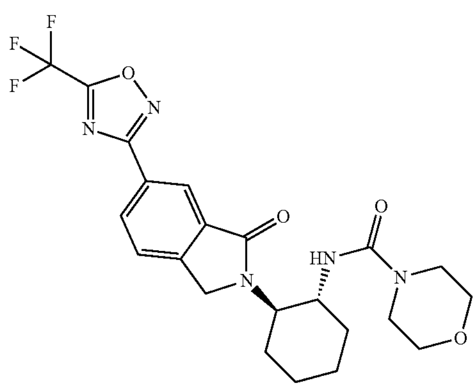 [SMILES: O=C(N[C@@H]1CCCC[C@H]1N1Cc2ccc(-c3noc(C(F)(F)F)n3)cc2C1=O)N1CCOCC1] | | 480.1 |
| 140 | tert-butyl ((1R,2R)-2-(1-oxo-6-(5-(trifluoromethyl)-1,2,4-oxadiazol-3-yl)-1,3-dihydro-2H-isoindol-2-yl)cyclopentyl)carbamate | 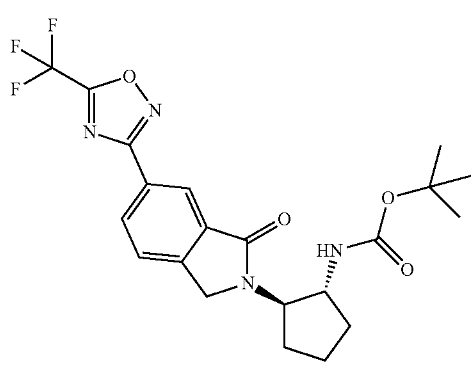 [SMILES: CC(C)(C)OC(=O)N[C@@H]1CCC[C@H]1N1Cc2ccc(-c3noc(C(F)(F)F)n3)cc2C1=O] | | 453.0 |

TABLE 1-21

| EXAMPLE | IUPAC NAME | Structure | ADDITIVE | MS |
|---|---|---|---|---|
| 141 | tert-butyl ((1S,2S)-2-(1-oxo-6-(5-(trifluoromethyl)-1,2,4-oxadiazol-3-yl)-1,3-dihydro-2H-isoindol-2-yl)cyclopentyl)carbamate | 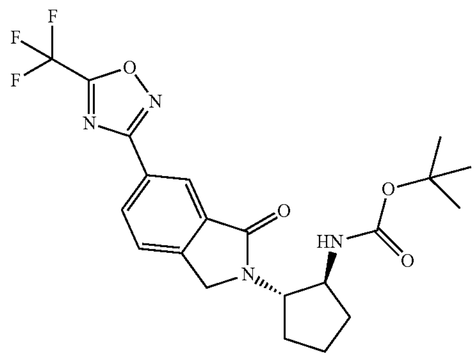 [SMILES: CC(C)(C)OC(=O)N[C@H]1CCC[C@@H]1N1Cc2ccc(-c3noc(C(F)(F)F)n3)cc2C1=O] | | 453.0 |
| 142 | 2-((1R,2R)-2-aminocyclopentyl)-6-(5-(trifluoromethyl)-1,2,4-oxadiazol-3-yl)isoindolin-1-one | 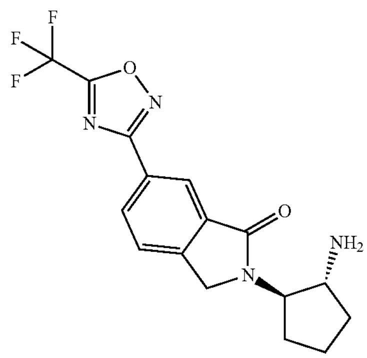 [SMILES: N[C@@H]1CCC[C@H]1N1Cc2ccc(-c3noc(C(F)(F)F)n3)cc2C1=O] | HCl | 353.0 |
| 143 | 2-((1S,2S)-2-aminocyclopentyl)-6-(5-(trifluoromethyl)-1,2,4-oxadiazol-3-yl)isoindolin-1-one | 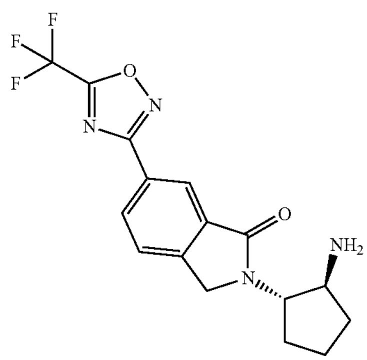 [SMILES: N[C@H]1CCC[C@@H]1N1Cc2ccc(-c3noc(C(F)(F)F)n3)cc2C1=O] | HCl | 353.0 |
| 144 | N-((1R,2R)-2-(1-oxo-6-(5-(trifluoromethyl)-1,2,4-oxadiazol-3-yl)-1,3-dihydro-2H-isoindol-2-yl)cyclohexyl)-3-oxa-6-azabicyclo[3.1.1]heptane-6-carboxamide | 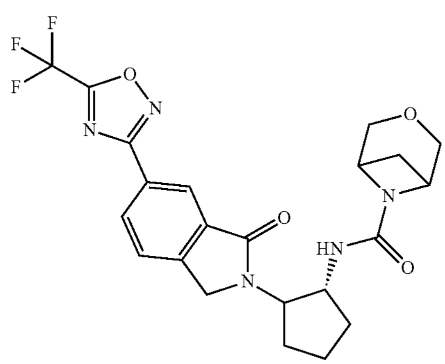 [SMILES: O=C1c2cc(-c3noc(C(F)(F)F)n3)ccc2CN1C1CCC[C@H]1NC(=O)N1C2COCC1C2] | | 492.1 |

TABLE 1-21-continued

| EXAMPLE | IUPAC NAME | Structure | ADDITIVE | MS |
|---------|------------|-----------|----------|-----|
| 145 | N-((1R,2R)-2-(1-oxo-6-(5-(trifluoromethyl)-1,2,4-oxadiazol-3-yl)-1,3-dihydro-2H-isoindol-2-yl)cyclohexyl)-3-oxa-8-azabicyclo[3.2.1]octane-8-carboxamide | 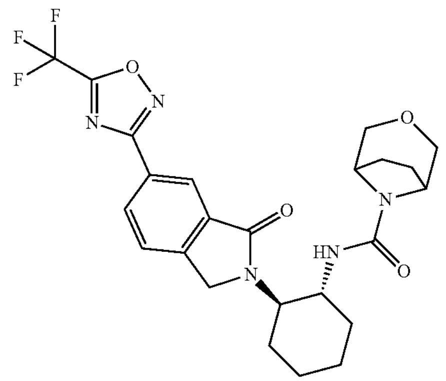 [SMILES: O=C(N[C@@H]1CCCC[C@H]1N1Cc2ccc(-c3noc(C(F)(F)F)n3)cc2C1=O)N1C2CCC1COC2] | | 506.1 |
| 146 | N-((1R,2R)-2-(1-oxo-6-(5-(trifluoromethyl)-1,2,4-oxadiazol-3-yl)-1,3-dihydro-2H-isoindol-2-yl)cyclohexyl)-8-oxa-3-azabicyclo[3.2.1]octane-3-carboxamide | 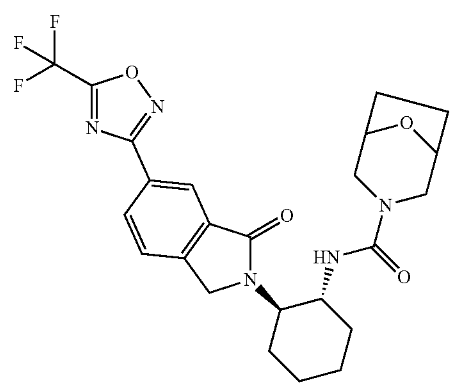 [SMILES: O=C(N[C@@H]1CCCC[C@H]1N1Cc2ccc(-c3noc(C(F)(F)F)n3)cc2C1=O)N1CC2CCC(C1)O2] | | 506.1 |
| 147 | 2,2-difluoro-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide | 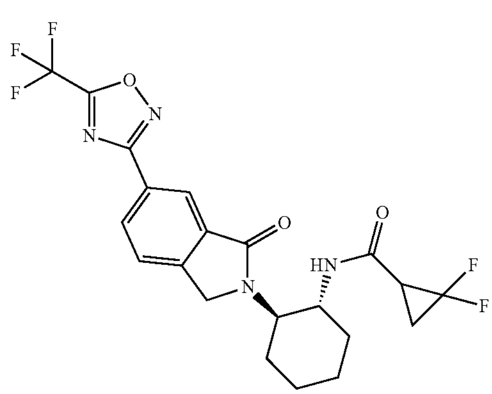 [SMILES: O=C(N[C@@H]1CCCC[C@H]1N1Cc2ccc(-c3noc(C(F)(F)F)n3)cc2C1=O)C1CC1(F)F] | | 471.0 |

TABLE 1-22

| EXAMPLE | IUPAC NAME | Structure | ADDITIVE | MS |
|---|---|---|---|---|
| 148 | (1R)-2,2-difluoro-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide | 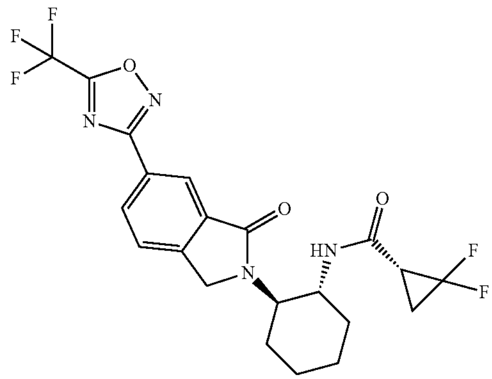 | | 471.0 |
| 149 | (1S)-2,2-difluoro-N-((3S,4R)-4-(1-oxo-6-(5-(trifluoromethyl)-1,2,4-oxadiazol-3-yl)-1,3-dihydro-2H-isoindol-2-yl)tetrahydro-2H-pyran-3-yl)cyclopropanecarboxamide | 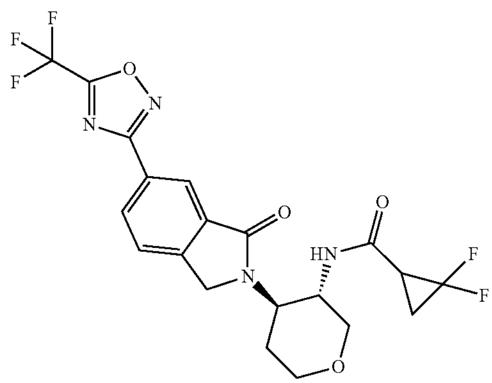 | | 471.0 |
| 150 | (1R)-2,2-difluoro-N-((3S,4R)-4-(1-oxo-6-(5-(trifluoromethyl)-1,2,4-oxadiazol-3-yl)-1,3-dihydro-2H-isoindol-2-yl)tetrahydro-2H-pyran-3-yl)cyclopropanecarboxamide | 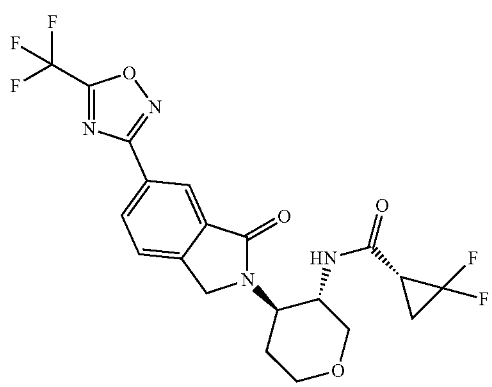 [SMILES: O=C(N[C@@H]1CCCC[C@H]1N1Cc2ccc(-c3noc(C(F)(F)F)n3)cc2C1=O)[C@H]1CC1(F)F] | | 473.0 |
| 151 | 3-methyl-N-((1R,2R)-2-(1-oxo-6-(5-(trifluoromethyl)-1,2,4-oxadiazol-3-yl)-1,3-dihydro-2H-isoindol-2-yl)cyclopentyl)oxetane-3-carboxamide | 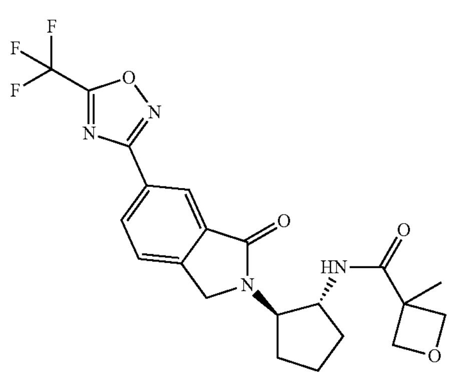 [SMILES: CC1(C(=O)N[C@@H]2CCC[C@H]2N2Cc3ccc(-c4noc(C(F)(F)F)n4)cc3C2=O)COC1] | | 450.9 |

TABLE 1-22-continued

| EXAMPLE | IUPAC NAME | Structure | ADDITIVE | MS |
|---|---|---|---|---|
| 152 | 3-methyl-N-((1S,2S)-2-(1-oxo-6-(5-(trifluoromethyl)-1,2,4-oxadiazol-3-yl)-1,3-dihydro-2H-isoindol-2-yl)cyclopentyl)oxetane-3-carboxamide | 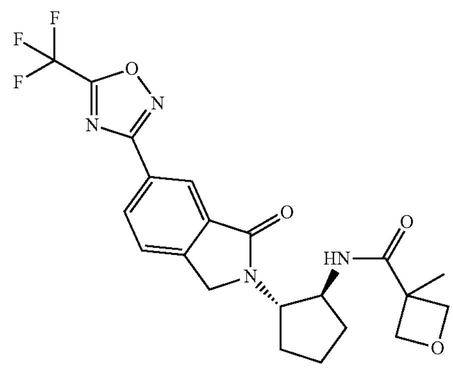 [SMILES: CC1(C(=O)N[C@H]2CCC[C@@H]2N2Cc3ccc(-c4noc(C(F)(F)F)n4)cc3C2=O)COC1] | | 451.0 |
| 153 | 1-(hydroxymethyl)-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide | 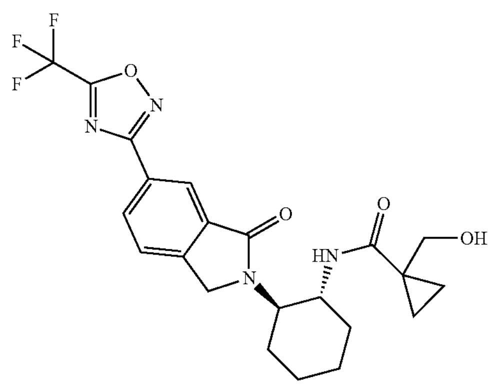 [SMILES: O=C1c2cc(-c3noc(C(F)(F)F)n3)ccc2CN1[C@@H]1CCCC[C@H]1NC(=O)C1(CO)CC1] | | 465.0 |
| 154 | 1-cyclopropyl-3-((1R,2R)-2-(1-oxo-6-(5-(trifluoromethyl)-1,2,4-oxadiazol-3-yl)-1,3-dihydro-2H-isoindol-2-yl)cyclohexyl)urea | 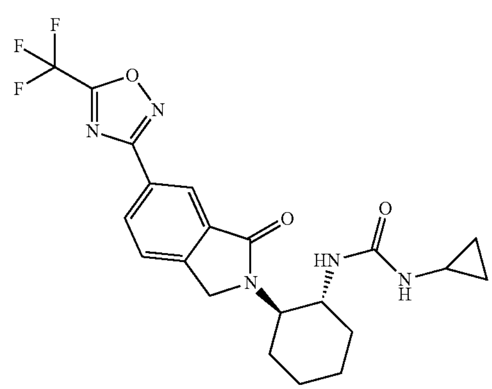 [SMILES: O=C(NC1CC1)N[C@@H]1CCCC[C@H]1N1Cc2ccc(-c3noc(C(F)(F)F)n3)cc2C1=O] | | 450.0 |

TABLE 1-23

| EXAMPLE | IUPAC NAME | Structure | ADDITIVE | MS |
|---|---|---|---|---|
| 155 | 1-cyclopropyl-1-methyl-3-((1R,2R)-2-(1-oxo-6-(5-(trifluoromethyl)-1,2,4-oxadiazol-3-yl)-1,3-dihydro-2H-isoindol-2-yl)cyclohexyl)urea | 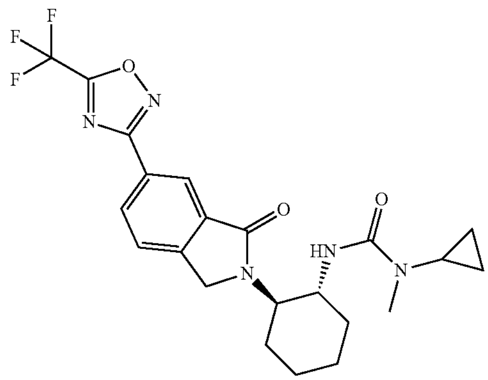 [SMILES: CN(C(=O)N[C@@H]1CCCC[C@H]1N1Cc2ccc(-c3noc(C(F)(F)F)n3)cc2C1=O)C1CC1] | | 464.1 |
| 156 | N-((1R,2R)-2-(1-oxo-6-(5-(trifluoromethyl)-1,2,4-oxadiazol-3-yl)-1,3-dihydro-2H-isoindol-2-yl)cyclohexyl)-2-oxa-5-azabicyclo[2.2.1]heptane-5-carboxamide | 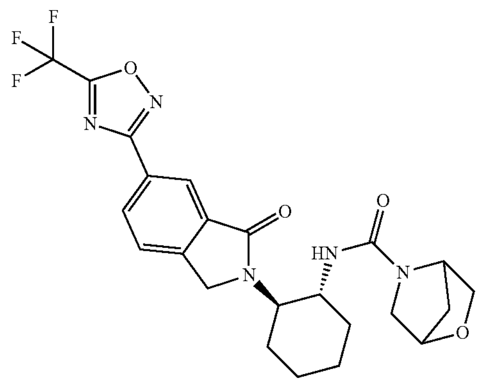 [SMILES: O=C(N[C@@H]1CCCC[C@H]1N1Cc2ccc(-c3noc(C(F)(F)F)n3)cc2C1=O)N1CC2CC1CO2] | | 492.1 |
| 157 | N-((1R,2R)-2-(1-oxo-6-(5-(trifluoromethyl)-1,2,4-oxadiazol-3-yl)-1,3-dihydro-2H-isoindol-2-yl)cyclohexyl)-2-oxa-5-azabicyclo[2.2.1]heptane-5-carboxamide | 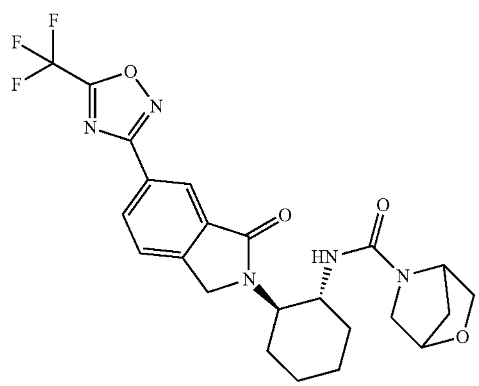 [SMILES: O=C(N[C@@H]1CCCC[C@H]1N1Cc2ccc(-c3noc(C(F)(F)F)n3)cc2C1=O)N1CC2CC1CO2] | | 492.1 |
| 158 | N-((1R,2R)-2-(1-oxo-6-(5-(trifluoromethyl)-1,2,4-oxadiazol-3-yl)-1,3-dihydro-2H-isoindol-2-yl)cyclohexyl)pyrrolidine-1-carboxamide | 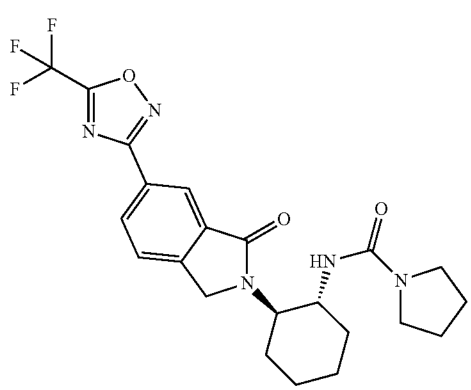 [SMILES: O=C(N[C@@H]1CCCC[C@H]1N1Cc2ccc(-c3noc(C(F)(F)F)n3)cc2C1=O)N1CCCC1] | | 464.1 |

TABLE 1-23-continued

| EXAMPLE | IUPAC NAME | Structure | ADDITIVE | MS |
|---|---|---|---|---|
| 159 | N-((1R,2R)-2-(1-oxo-6-(5-(trifluoromethyl)-1,2,4-oxadiazol-3-yl)-1,3-dihydro-2H-isoindol-2-yl)cyclohexyl)azetidine-1-carboxamide | 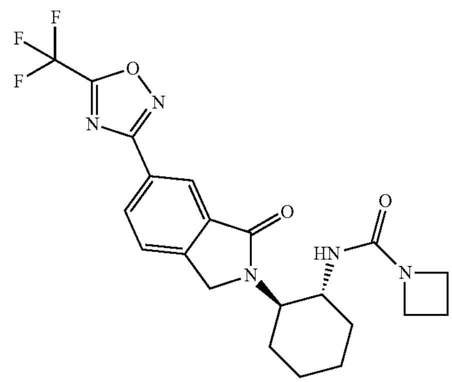 [SMILES: O=C(N[C@@H]1CCCC[C@H]1N1Cc2ccc(-c3noc(C(F)(F)F)n3)cc2C1=O)N1CCC1] | | 450.0 |
| 160 | 3-cyano-N-((1R,2R)-2-(1-oxo-6-(5-(trifluoromethyl)-1,2,4-oxadiazol-3-yl)-1,3-dihydro-2H-isoindol-2-yl)cyclohexyl)bicyclo[1.1.1]pentane-1-carboxamide | 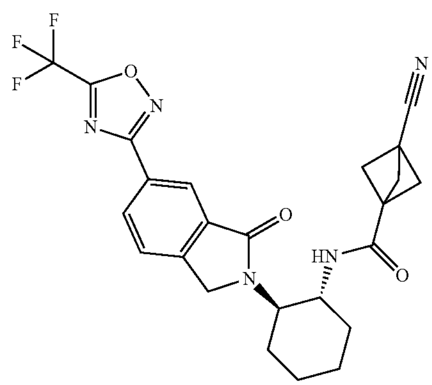 [SMILES: N#CC12CC(C(=O)N[C@@H]3CCCC[C@H]3N3Cc4ccc(-c5noc(C(F)(F)F)n5)cc4C3=O)(C1)C2] | | 486.0 |
| 161 | N-((1R,2R)-2-(1-oxo-6-(5-(trifluoromethyl)-1,2,4-oxadiazol-3-yl)-1,3-dihydro-2H-isoindol-2-yl)cyclohexyl)-2-oxa-6-azaspiro[3.3]heptane-6-carboxamide | 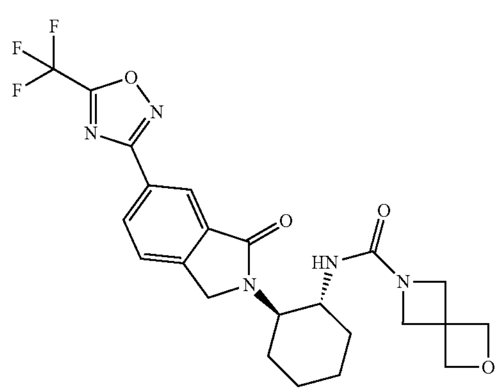 [SMILES: O=C(N[C@@H]1CCCC[C@H]1N1Cc2ccc(-c3noc(C(F)(F)F)n3)cc2C1=O)N1CC2(COC2)C1] | | 492.1 |

TABLE 1-24

| EXAMPLE | IUPAC NAME | Structure | ADDITIVE | MS |
|---|---|---|---|---|
| 162 | 3,3-difluoro-N-((1R,2R)-2-(1-oxo-6-(5-(trifluoromethyl)-1,2,4-oxadiazol-3-yl)-1,3-dihydro-2H-isoindol-2-yl)cyclohexyl)azetidine-1-carboxamide | 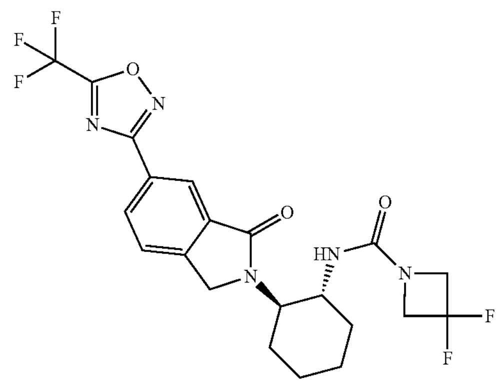 [SMILES: O=C(N[C@@H]1CCCC[C@H]1N1Cc2ccc(-c3noc(C(F)(F)F)n3)cc2C1=O)N1CC(F)(F)C1] | | 486.0 |
| 163 | 3-methoxy-N-((1R,2R)-2-(1-oxo-6-(5-(trifluoromethyl)-1,2,4-oxadiazol-3-yl)-1,3-dihydro-2H-isoindol-2-yl)cyclohexyl)azetidine-1-carboxamide | 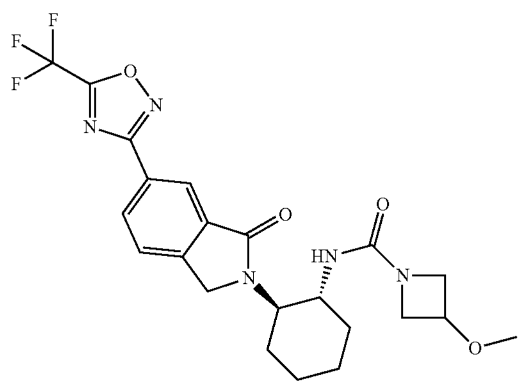 [SMILES: COC1CN(C(=O)N[C@@H]2CCCC[C@H]2N2Cc3ccc(-c4noc(C(F)(F)F)n4)cc3C2=O)C1] | | 480.0 |
| 164 | N-((1R,2R)-2-(1-oxo-6-(5-(trifluoromethyl)-1,2,4-oxadiazol-3-yl)-1,3-dihydro-2H-isoindol-2-yl)cyclohexyl)-6-oxa-3-azabicyclo[3.1.1]heptane-3-carboxamide | 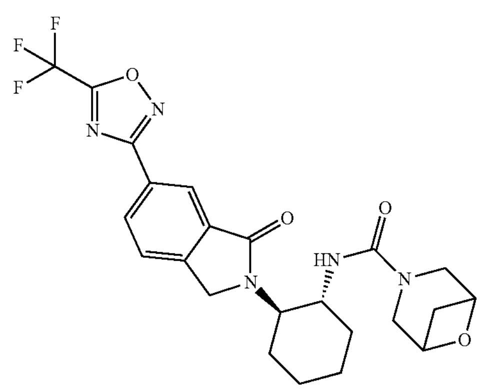 [SMILES: O=C(N[C@@H]1CCCC[C@H]1N1Cc2ccc(-c3noc(C(F)(F)F)n3)cc2C1=O)N1CC2CC(C1)O2] | | 492.1 |
| 165 | 1-oxetan-3-yl-3-((1R,2R)-2-(1-oxo-6-(5-(trifluoromethyl)-1,2,4-oxadiazol-3-yl)-1,3-dihydro-2H-isoindol-2-yl)cyclohexyl)urea | 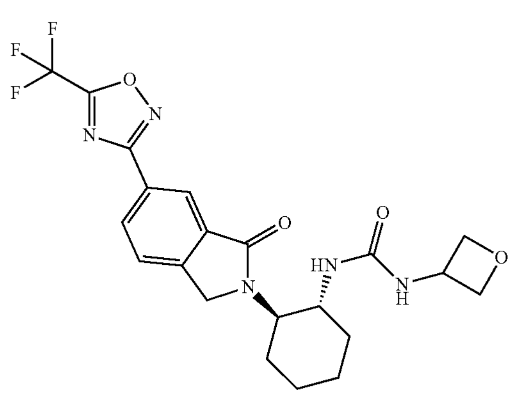 [SMILES: O=C(NC1COC1)N[C@@H]1CCCC[C@H]1N1Cc2ccc(-c3noc(C(F)(F)F)n3)cc2C1=O] | | 466.0 |

TABLE 1-24-continued

| EXAMPLE | IUPAC NAME | Structure | ADDITIVE | MS |
|---|---|---|---|---|
| 166 | 1,1-diisopropyl-3-((1R,2R)-2-(1-oxo-6-(5-(trifluoromethyl)-1,2,4-oxadiazol-3-yl)-1,3-dihydro-2H-isoindol-2-yl)cyclohexyl)urea | 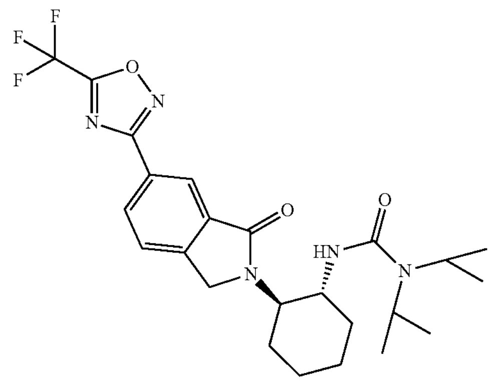 [SMILES: CC(C)N(C(=O)N[C@@H]1CCCC[C@H]1N1Cc2ccc(-c3noc(C(F)(F)F)n3)cc2C1=O)C(C)C] | | 494.1 |
| 167 | N-((1R,2R)-2-(1-oxo-6-(5-(trifluoromethyl)-1,2,4-oxadiazol-3-yl)-1,3-dihydro-2H-isoindol-2-yl)cyclohexyl)-3-oxa-9-azabicyclo[3.3.1]nonane-9-carboxamide | 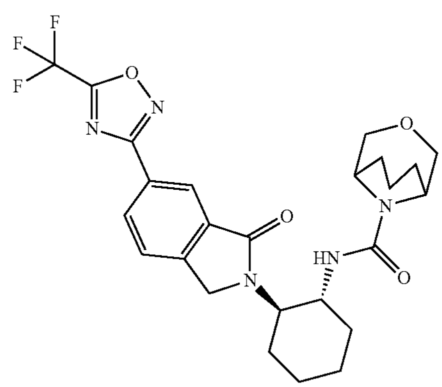 [SMILES: O=C(N[C@@H]1CCCC[C@H]1N1Cc2ccc(-c3noc(C(F)(F)F)n3)cc2C1=O)N1C2CCCC1COC2] | | 520.1 |
| 168 | N-((1R,2R)-2-(1-oxo-6-(5-(trifluoromethyl)-1,2,4-oxadiazol-3-yl)-1,3-dihydro-2H-isoindol-2-yl)cyclohexyl)thiomorpholine-4-carboxamide 1,1-dioxide | 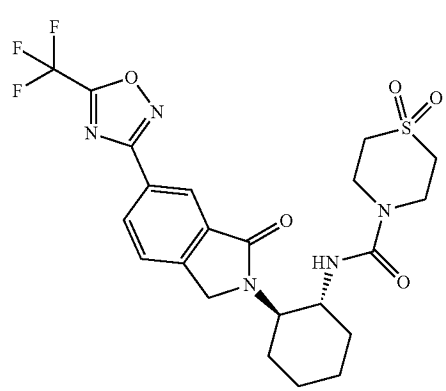 [SMILES: O=C(N[C@@H]1CCCC[C@H]1N1Cc2ccc(-c3noc(C(F)(F)F)n3)cc2C1=O)N1CCS(=O)(=O)CC1] | | 528.0 |

TABLE 1-25

| EXAMPLE | IUPAC NAME | Structure | ADDITIVE | MS |
|---|---|---|---|---|
| 169 | 3,3-difluoro-N-((1R,2R)-2-(1-oxo-6-(5-(trifluoromethyl)-1,2,4-oxadiazol-3-yl)-1,3-dihydro-2H-isoindol-2-yl)cyclohexyl)pyrrolidine-1-carboxamide | 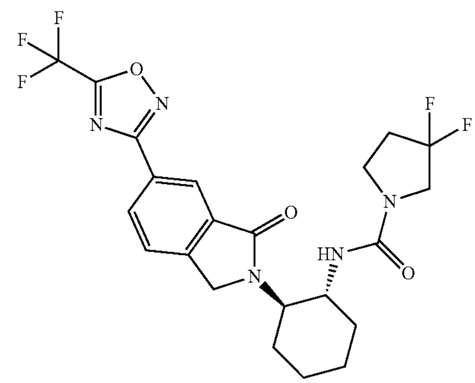 [SMILES: O=C(N[C@@H]1CCCC[C@H]1N1Cc2ccc(-c3noc(C(F)(F)F)n3)cc2C1=O)N1CCC(F)(F)C1] | | 500.3 |
| 170 | 2,2-difluoro-1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)cyclopropanecarboxamide | 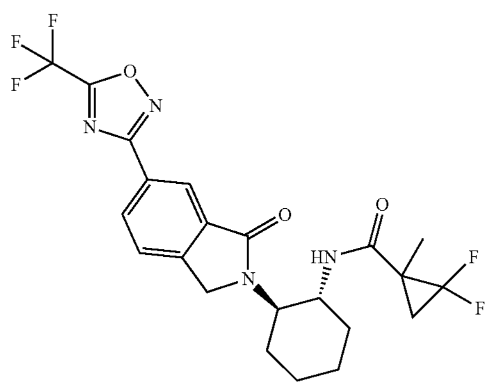 [SMILES: CC1(C(=O)N[C@@H]2CCCC[C@H]2N2Cc3ccc(-c4noc(C(F)(F)F)n4)cc3C2=O)CC1(F)F] | | 485.0 |
| 171 | 2,2-difluoro-1-methyl-N-((1R,2R)2-(1-oxo-6-(5-(trifluoromethyl)-1,2,4-oxadiazol-3-yl)-1,3-dihydro-2H-isoindol-2-yl)cyclohexyl)cyclopropanecarboxamide | 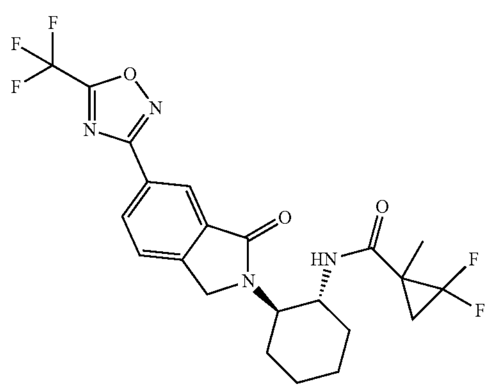 [SMILES: CC1(C(=O)N[C@@H]2CCCC[C@H]2N2Cc3ccc(-c4noc(C(F)(F)F)n4)cc3C2=O)CC1(F)F] | | 485.0 |
| 172 | (1S)-2,2-difluoro-N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide | 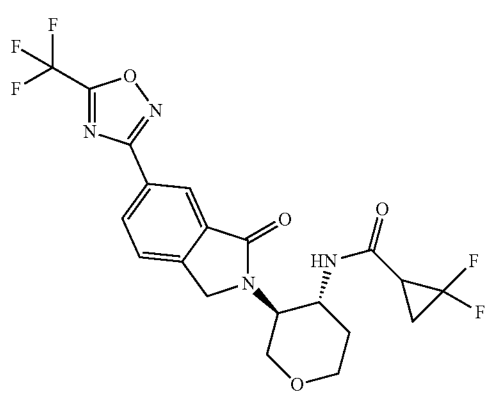 [SMILES: O=C(N[C@@H]1CCOC[C@H]1N1Cc2ccc(-c3noc(C(F)(F)F)n3)cc2C1=O)C1CC1(F)F] | | 473.1 |

TABLE 1-25-continued

| EXAMPLE | IUPAC NAME | Structure | ADDITIVE | MS |
|---|---|---|---|---|
| 173 | 1-hydroxy-N-((1R,2R)-2-(1-oxo-6-(5-(trifluoromethyl)-1,2,4-oxadiazol-3-yl)-1,3-dihydro-2H-isoindol-2-yl)cyclohexyl)cyclobutanecarboxamide | 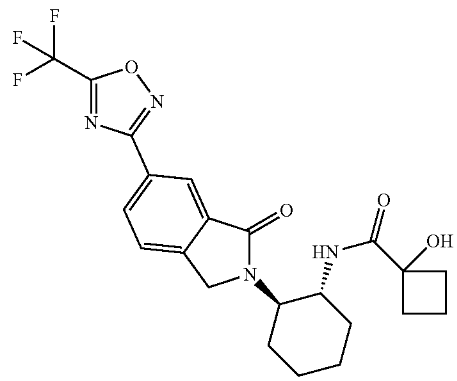 [SMILES: O=C1c2cc(-c3noc(C(F)(F)F)n3)ccc2CN1[C@@H]1CCCC[C@H]1NC(=O)C1(O)CCC1] | | 465.0 |
| 174 | 1-methyl-N-((1R,2R)-2-(1-oxo-6-(5-(trifluoromethyl)-1,2,4-oxadiazol-3-yl)-1,3-dihydro-2H-isoindol-2-yl)cyclohexyl)cyclobutanecarboxamide | 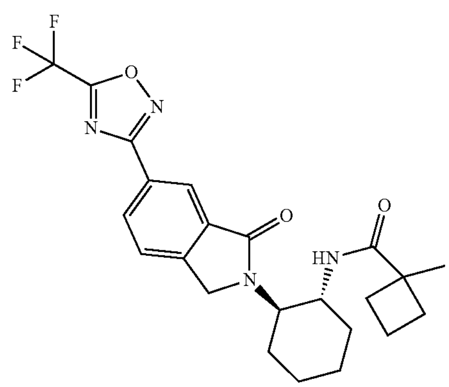 [SMILES: CC1(C(=O)N[C@@H]2CCCC[C@H]2N2Cc3ccc(-c4noc(C(F)(F)F)n4)cc3C2=O)CCC1] | | 463.0 |
| 175 | 1-methoxy-N-((1R,2R)-2-(1-oxo-6-(5-(trifluoromethyl)-1,2,4-oxadiazol-3-yl)-1,3-dihydro-2H-isoindol-2-yl)cyclohexyl)cyclobutanecarboxamide | 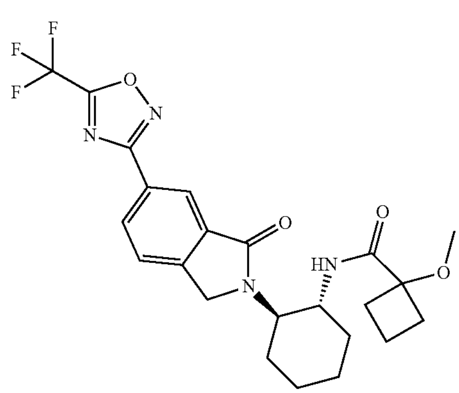 [SMILES: COC1(C(=O)N[C@@H]2CCCC[C@H]2N2Cc3ccc(-c4noc(C(F)(F)F)n4)cc3C2=O)CCC1] | | 479.1 |

TABLE 1-26

| EXAMPLE | IUPAC NAME | Structure | ADDITIVE | MS |
|---|---|---|---|---|
| 176 | 2-((1R,2S)-2-aminocyclohexyl)-6-(5-(trifluoromethyl)-1,2,4-oxadiazol-3-yl)isoindolin-1-one | 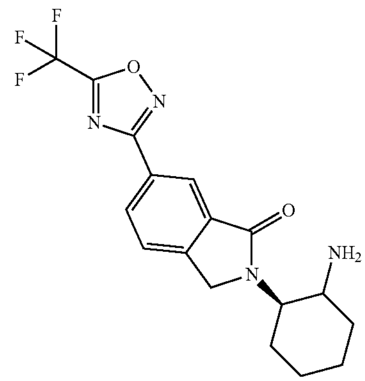 [SMILES: NC1CCCC[C@H]1N1Cc2ccc(-c3noc(C(F)(F)F)n3)cc2C1=O] | HCl | 367.0 |

TABLE 1-27

| EXAMPLE | IUPAC NAME | Structure | ADDITIVE | MS |
|---|---|---|---|---|
| 177 | 2-((3S,4R)-3-(2-oxopyrrolidin-1-yl)tetrahydro-2H-pyran-4-yl)-6-(5-(trifluoromethyl)-1,2,4-oxadiazol-3-yl)isoindolin-1-one | 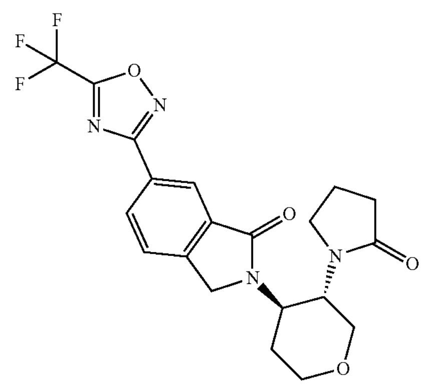 [SMILES: O=C1CCCN1[C@@H]1COCC[C@H]1N1Cc2ccc(-c3noc(C(F)(F)F)n3)cc2C1=O] | | 437.1 |
| 178 | 2-((3S,4R)-4-(2-oxopyrrolidin-1-yl)tetrahydro-2H-pyran-3-yl)-6-(5-(trifluoromethyl)-1,2,4-oxadiazol-3-yl)isoindolin-1-one | 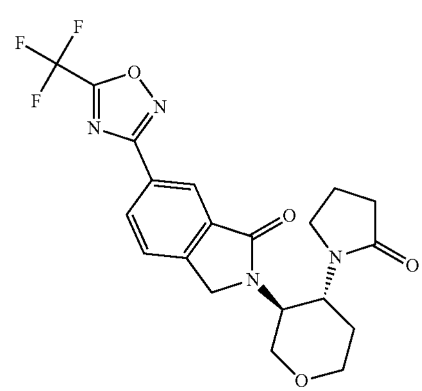 [SMILES: O=C1CCCN1[C@@H]1CCOC[C@H]1N1Cc2ccc(-c3noc(C(F)(F)F)n3)cc2C1=O] | | 437.2 |

TABLE 1-27-continued

| EXAMPLE | IUPAC NAME | Structure | ADDITIVE | MS |
|---|---|---|---|---|
| 179 | 1,5-anhydro-2,4-dideoxy-2-(1-oxo-6-(5-(trifluoromethyl)-1,2,4-oxadiazol-3-yl)-1,3-dihydro-2H-isoindol-2-yl)-D-threo-pentitol | 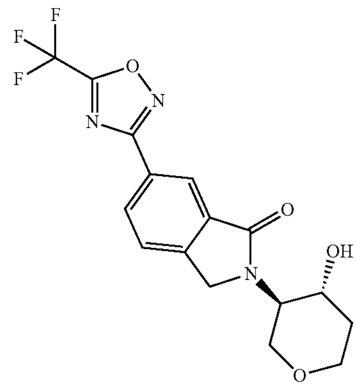 [SMILES: O=C1c2cc(-c3noc(C(F)(F)F)n3)ccc2CN1[C@@H]1COCC[C@H]1O] | | 370.0 |
| 180 | 2-((3S,4R)-3-(2-oxopyrrolidin-1-yl)tetrahydro-2H-pyran-4-yl)-6-(5-(trifluoromethyl)-1,2,4-oxadiazol-3-yl)isoindolin-1-one | 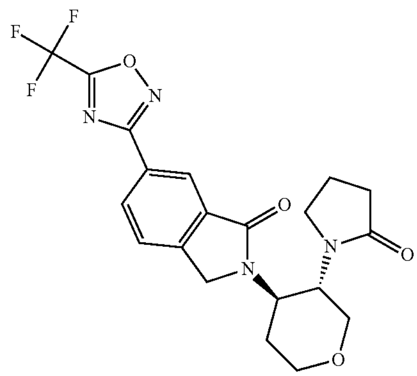 [SMILES: O=C1CCCN1[C@@H]1COCC[C@H]1N1Cc2ccc(-c3noc(C(F)(F)F)n3)cc2C1=O] | | 437.1 |
| 181 | 2-((3R,4S)-3-(2-oxopyrrolidin-1-yl)tetrahydro-2H-pyran-4-yl)-6-(5-(trifluoromethyl)-1,2,4-oxadiazol-3-yl)isoindolin-1-one | 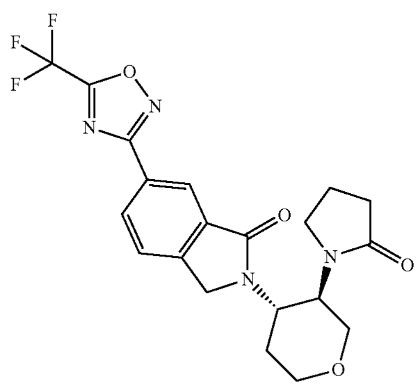 [SMILES: O=C1CCCN1[C@H]1COCC[C@@H]1N1Cc2ccc(-c3noc(C(F)(F)F)n3)cc2C1=O] | | 437.1 |
| 182 | 2-((3S,4R)-4-(2-oxopyrrolidin-1-yl)tetrahydro-2H-pyran-3-yl)-6-(5-(trifluoromethyl)-1,2,4-oxadiazol-3-yl)isoindolin-1-one | 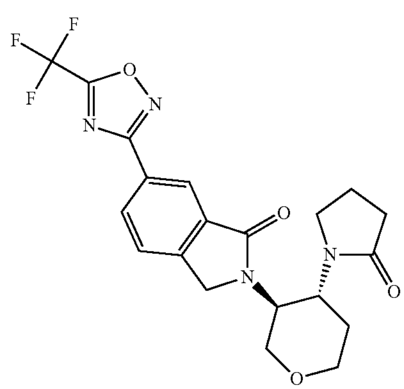 [SMILES: O=C1CCCN1[C@@H]1CCOC[C@H]1N1Cc2ccc(-c3noc(C(F)(F)F)n3)cc2C1=O] | | 437.0 |

TABLE 1-27-continued

| EXAMPLE | IUPAC NAME | Structure | ADDITIVE | MS |
|---|---|---|---|---|
| 183 | 2-((3S,4R)-4-(2-oxopyrrolidin-1-yl)tetrahydro-2H-pyran-3-yl)-6-(5-(trifluoromethyl)-1,2,4-oxadiazol-3-yl)isoindolin-1-one | 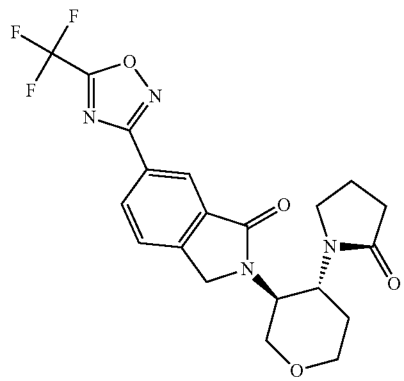 | | 437.1 |

TABLE 1-28

| EXAMPLE | IUPAC NAME | Structure | ADDITIVE | MS |
|---|---|---|---|---|
| 184 | 2-(2-(2-oxopyrrolidin-1-yl)phenyl)-6-(5-(trifluoromethyl)-1,2,4-oxadiazol-3-yl)isoindolin-1-one | 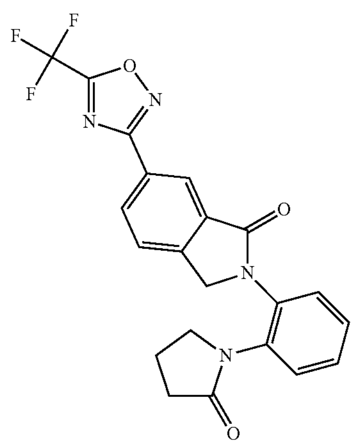 [SMILES: O=C1CCCN1c1ccccc1N1Cc2ccc(-c3noc(C(F)(F)F)n3)cc2C1=O] | | 429.1 |
| 185 | 2-(2-chloro-6-(2-oxopyrrolidin-1-yl)phenyl)-6-(5-(trifluoromethyl)-1,2,4-oxadiazol-3-yl)isoindolin-1-one | 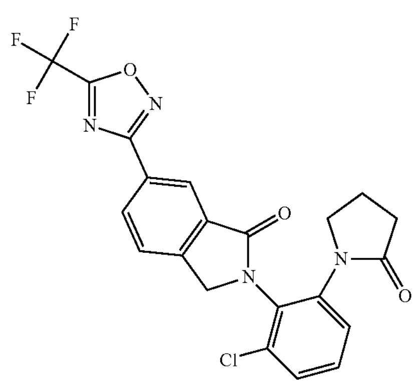 [SMILES: O=C1CCCN1c1cccc(Cl)c1N1Cc2ccc(-c3noc(C(F)(F)F)n3)cc2C1=O] | | 463.1 |

TABLE 1-28-continued

| EXAMPLE | IUPAC NAME | Structure | ADDITIVE | MS |
|---|---|---|---|---|
| 186 | 6-((1R,2R)-2-(2-oxopyrrolidin-1-yl)cyclohexyl)-3-(5-(trifluoromethyl)-1,2,4-oxadiazol-3-yl)-6,7-dihydro-5H-pyrrolo[3,4-b]pyridin-5-one | 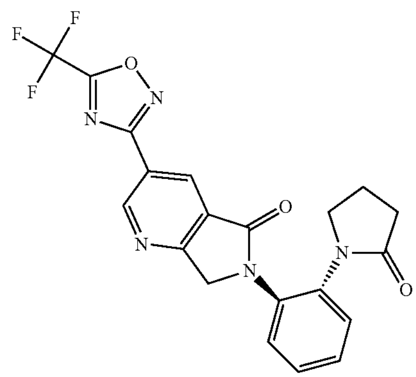 | | 436.2 |
| 187 | 3-fluoro-N-((1R,2R)-2-(1-oxo-6-(5-(trifluoromethyl)-1,2,4-oxadiazol-3-yl)-1,3-dihydro-2H-isoindol-2-yl)cyclohexyl)azetidine-1-carboxamide | 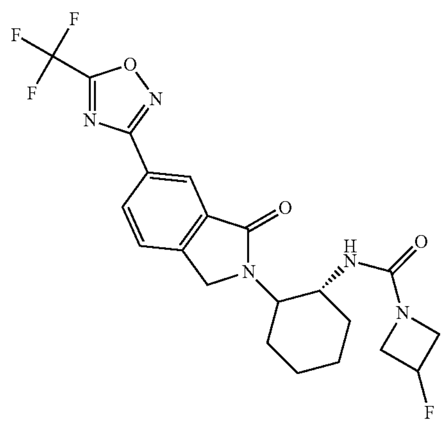 [SMILES: O=C(N[C@@H]1CCCCC1N1Cc2ccc(-c3noc(C(F)(F)F)n3)cc2C1=O)N1CC(F)C1] | | 468.2 |
| 188 | N,N-dimethyl-2-(1-oxo-6-(5-(trifluoromethyl)-1,2,4-oxadiazol-3-yl)-1,3-dihydro-2H-isoindol-2-yl)benzamide | 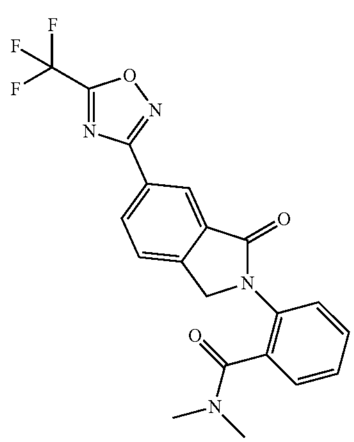 [SMILES: CN(C)C(=O)c1ccccc1N1Cc2ccc(-c3noc(C(F)(F)F)n3)cc2C1=O] | | 417.0 |

TABLE 1-29

| EXAMPLE | IUPAC NAME | Structure | ADDITIVE | MS |
|---------|------------|-----------|----------|-----|
| 189 | 2-((3S,4R)-4-aminotetrahydro-2H-pyran-3-yl)-6-(5-(trifluoromethyl)-1,2,4-oxadiazol-3-yl)isoindolin-1-one | 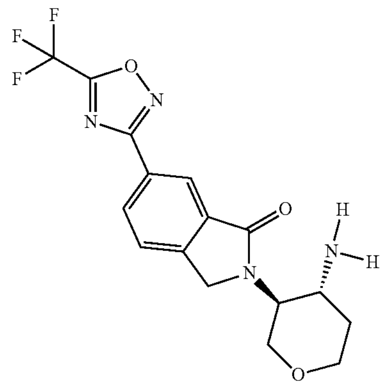 [SMILES: N[C@@H]1CCOC[C@H]1N1Cc2ccc(-c3noc(C(F)(F)F)n3)cc2C1=O] | HCl | |
| 190 | (1R)-2,2-difluoro-N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide | 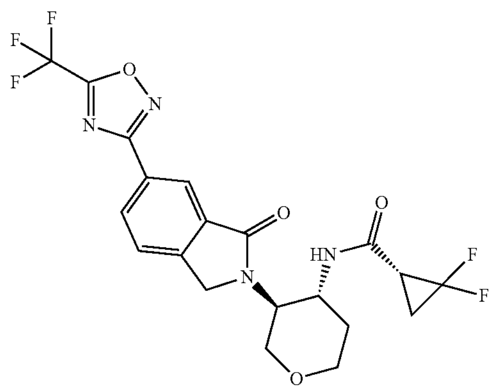 [SMILES: O=C(N[C@@H]1CCOC[C@H]1N1Cc2ccc(-c3noc(C(F)(F)F)n3)cc2C1=O)[C@H]1CC1(F)F] | | 473.1 |
| 191 | 2-((1R,2R)-2-(2-oxopyrrolidin-1-yl)cyclohexyl)-6-(5-(trifluoromethyl)-1,2,4-oxadiazol-3-yl)isoindolin-1-one | 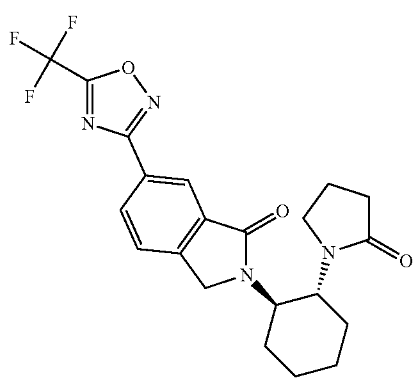 [SMILES: O=C1CCCN1[C@@H]1CCCC[C@H]1N1Cc2ccc(-c3noc(C(F)(F)F)n3)cc2C1=O] | | 435.1 |
| 192 | 3-methyl-N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)oxetane-3-carboxamide | 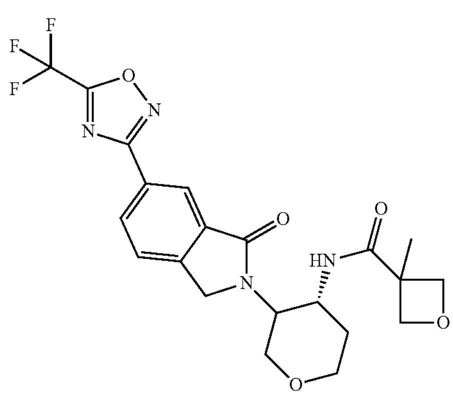 [SMILES: CC1(C(=O)N[C@@H]2CCOCC2N2Cc3ccc(-c4noc(C(F)(F)F)n4)cc3C2=O)COC1] | | 467.1 |

TABLE 1-29-continued

| EXAMPLE | IUPAC NAME | Structure | ADDITIVE | MS |
|---|---|---|---|---|
| 193 | 3-methyl-N-((1S,2S)-2-(1-oxo-6-(5-(trifluoromethyl)-1,2,4-oxadiazol-3-yl)-1,3-dihydro-2H-isoindol-2-yl)cyclohexyl)oxetane-3-carboxamide | 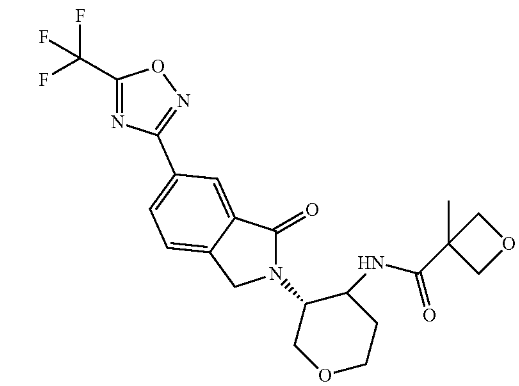 [SMILES: CC1(C(=O)NC2CCOC[C@@H]2N2Cc3ccc(-c4noc(C(F)(F)F)n4)cc3C2=O)COC1] | | 465.1 |
| 194 | 3-methyl-N-((1R,2R)-2-(1-oxo-6-(5-(trifluoromethyl)-1,2,4-oxadiazol-3-yl)-1,3-dihydro-2H-isoindol-2-yl)cyclohexyl)azetidine-3-carboxamide | 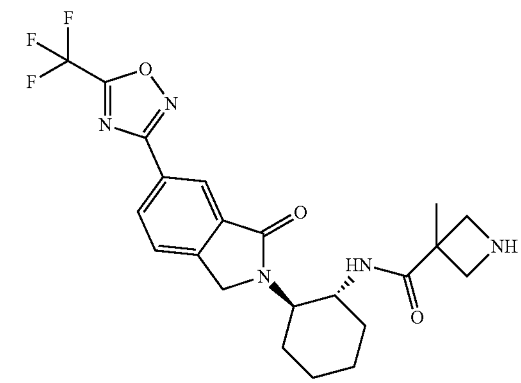 [SMILES: CC1(C(=O)N[C@@H]2CCCC[C@H]2N2Cc3ccc(-c4noc(C(F)(F)F)n4)cc3C2=O)CNC1] | HCl | 464.2 |
| 195 | 1-acetyl-3-methyl-N-((1R,2R)-2-(1-oxo-6-(5-(trifluoromethyl)-1,2,4-oxadiazol-3-yl)-1,3-dihydro-2H-isoindol-2-yl)cyclohexyl)azetidine-3-carboxamide | 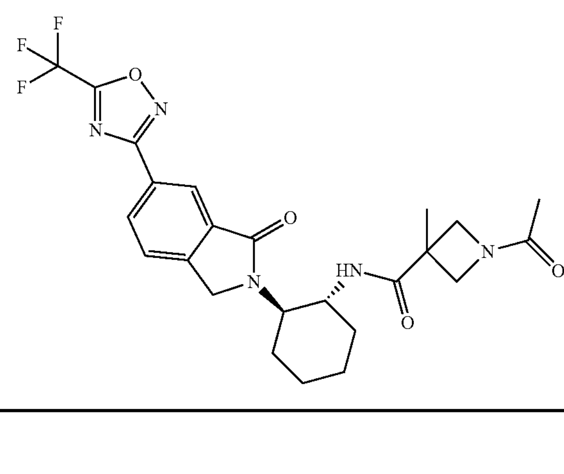 | | 506.2 |

TABLE 1-30

| EXAMPLE | IUPAC NAME | Structure | ADDITIVE | MS |
|---|---|---|---|---|
| 196 | 1,3-dimethyl-N-((1R,2R)-2-(1-oxo-6-(5-(trifluoromethyl)-1,2,4-oxadiazol-3-yl)-1,3-dihydro-2H-isoindol-2-yl)cyclohexyl)azetidine-3-carboxamide | 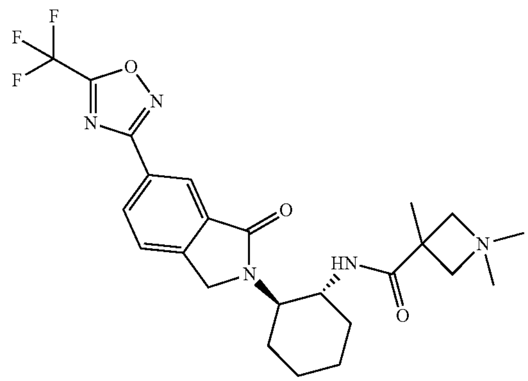 | | 478.2 |
| 197 | tert-butyl 3-methyl-3-(((1R,2R)-2-(1-oxo-6-(5-(trifluoromethyl)-1,2,4-oxadiazol-3-yl)-1,3-dihydro-2H-isoindol-2-yl)cyclohexyl)carbamoyl)azetidine-1-carboxylate | 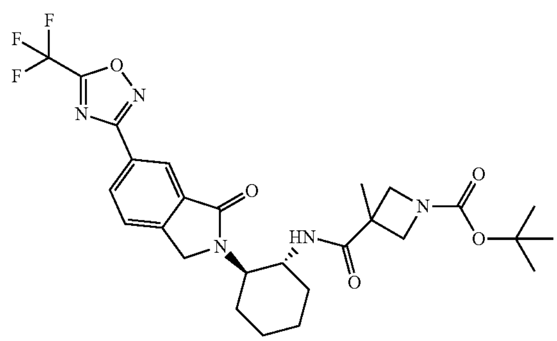 [SMILES: CC(C)(C)OC(=O)N1CC(C)(C(=O)N[C@@H]2CCCC[C@H]2N2Cc3ccc(-c4noc(C(F)(F)F)n4)cc3C2=O)C1] | | 562.3 |
| 198 | tert-butyl (cis-2-(1-oxo-6-(5-(trifluoromethyl)-1,2,4-oxadiazol-3-yl)-1,3-dihydro-2H-isoindol-2-yl)cyclohexyl)carbamate | 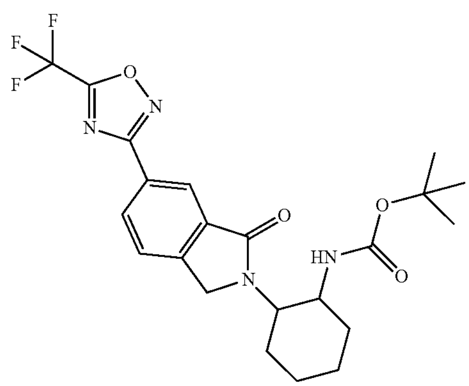 [SMILES: CC(C)(C)OC(=O)NC1CCCCC1N1Cc2ccc(-c3noc(C(F)(F)F)n3)cc2C1=O] | | 465.2 |
| 199 | 2-(cis-2-aminocyclohexyl)-6-(5-(trifluoromethyl)-1,2,4-oxadiazol-3-yl)isoindolin-1-one | 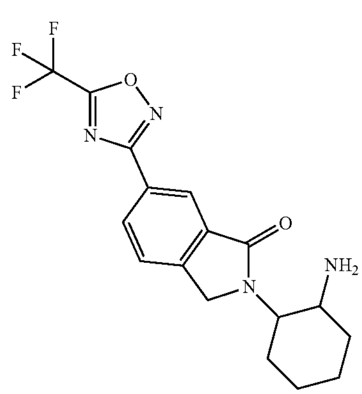 [SMILES: NC1CCCCC1N1Cc2ccc(-c3noc(C(F)(F)F)n3)cc2C1=O] | HCl | 367.1 |

TABLE 1-30-continued

| EXAMPLE | IUPAC NAME | Structure | ADDITIVE | MS |
|---|---|---|---|---|
| 200 | 3-methyl-N-(cis-2-(1-oxo-6-(5-(trifluoromethyl)-1,2,4-oxadiazol-3-yl)-1,3-dihydro-2H-isoindol-2-yl)cyclohexyl)oxetane-3-carboxamide | 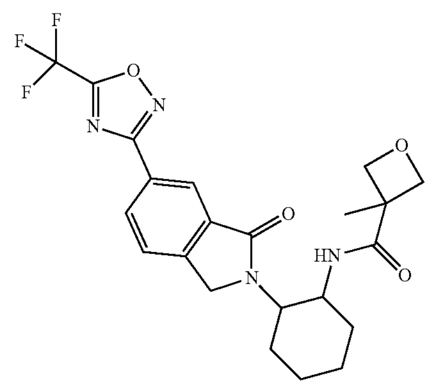 [SMILES: CC1(C(=O)NC2CCCCC2N2Cc3ccc(-c4noc(C(F)(F)F)n4)cc3C2=O)COC1] | | 465.2 |
| 201 | (1S)-2,2-difluoro-N-((3R,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide | 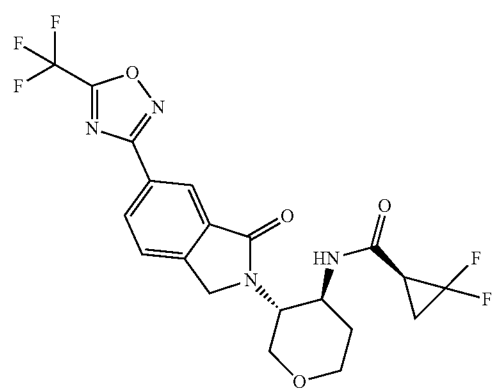 [SMILES: O=C(N[C@H]1CCOC[C@@H]1N1Cc2ccc(-c3noc(C(F)(F)F)n3)cc2C1=O)[C@@H]1CC1(F)F] | | 473.2 |
| 202 | (1R)-2,2-difluoro-N-((3R,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide | 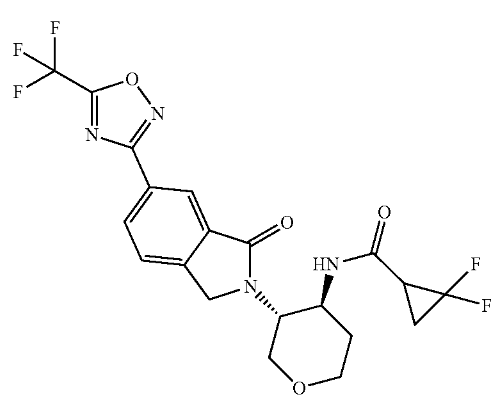 [SMILES: O=C(N[C@H]1CCOC[C@@H]1N1Cc2ccc(-c3noc(C(F)(F)F)n3)cc2C1=O)C1CC1(F)F] | | 472.1 |

TABLE 1-31

| EXAMPLE | IUPAC NAME | Structure | ADDITIVE | MS |
|---|---|---|---|---|
| 203 | 3-chloro-2-(hydroxymethyl)-2-methyl-N-(trans-2-(1-oxo-6-(5-(trifluoromethyl)-1,2,4-oxadiazol-3-yl)-1,3-dihydro-2H-isoindol-2-yl)cyclohexyl)propanamide | 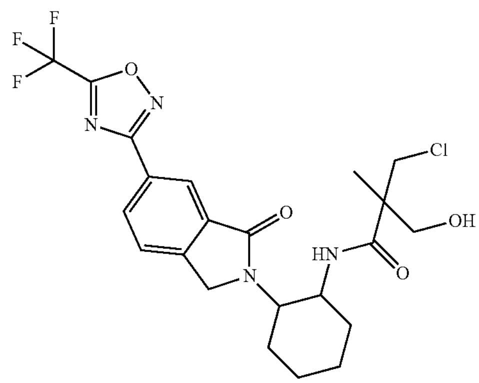 [SMILES: CC(CO)(CCl)C(=O)NC1CCCCC1N1Cc2ccc(-c3noc(C(F)(F)F)n3)cc2C1=O] | | 501.3 |
| 204 | 3-chloro-2-(hydroxymethyl)-2-methyl-N-(trans-2-(1-oxo-6-(5-(trifluoromethyl)-1,2,4-oxadiazol-3-yl)-1,3-dihydro-2H-isoindol-2-yl)cyclohexyl)propanamide | 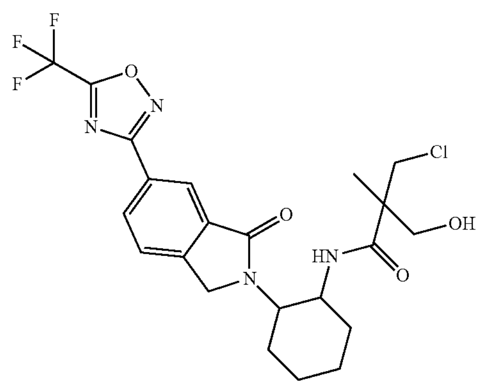 [SMILES: CC(CO)(CCl)C(=O)NC1CCCCC1N1Cc2ccc(-c3noc(C(F)(F)F)n3)cc2C1=O] | | 501.3 |
| 205 | N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)tetrahydrofuran-3-carboxamide | 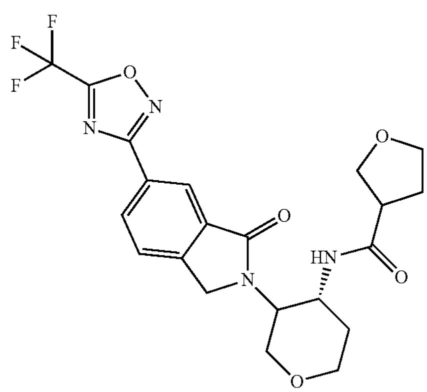 [SMILES: O=C(N[C@@H]1CCOCC1N1Cc2ccc(-c3noc(C(F)(F)F)n3)cc2C1=O)C1CCOC1] | | 465.2 |
| 206 | (3R)-N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)tetrahydrofuran-3-carboxamide | 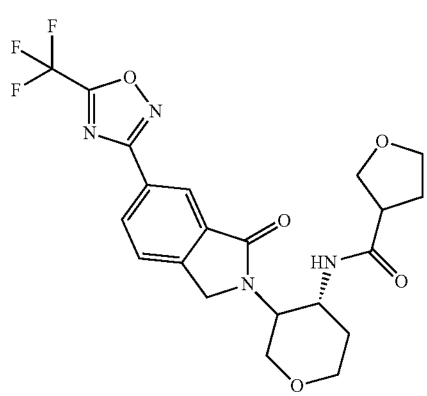 [SMILES: O=C(N[C@@H]1CCOCC1N1Cc2ccc(-c3noc(C(F)(F)F)n3)cc2C1=O)C1CCOC1] | | 467.3 |

TABLE 1-31-continued

| EXAMPLE | IUPAC NAME | Structure | ADDITIVE | MS |
|---------|------------|-----------|----------|-----|
| 207 | tert-butyl((3R,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)carbamate | 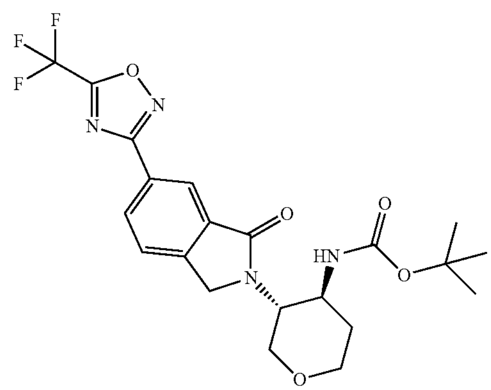 [SMILES: CC(C)(C)OC(=O)N[C@H]1CCOC[C@@H]1N1Cc2ccc(-c3noc(C(F)(F)F)n3)cc2C1=O] | | |
| 208 | (3S)-N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)tetrahydrofuran-3-carboxamide | 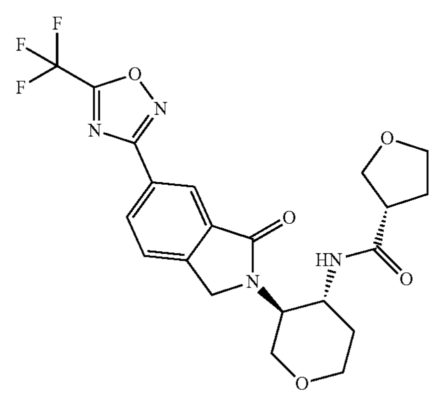 [SMILES: O=C(N[C@@H]1CCOC[C@H]1N1Cc2ccc(-c3noc(C(F)(F)F)n3)cc2C1=O)[C@H]1CCOC1] | | 467.1 |
| 209 | (3R)-N-((3R,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)tetrahydrofuran-3-carboxamide | 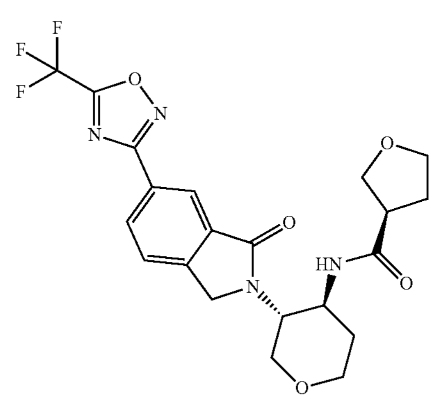 [SMILES: O=C(N[C@H]1CCOC[C@@H]1N1Cc2ccc(-c3noc(C(F)(F)F)n3)cc2C1=O)[C@@H]1CCOC1] | | 467.0 |

TABLE 1-32

| EXAMPLE | IUPAC NAME | Structure | ADDITIVE | MS |
|---|---|---|---|---|
| 210 | (3S)-N-((3R,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)tetrahydrofuran-3-carboxamide | 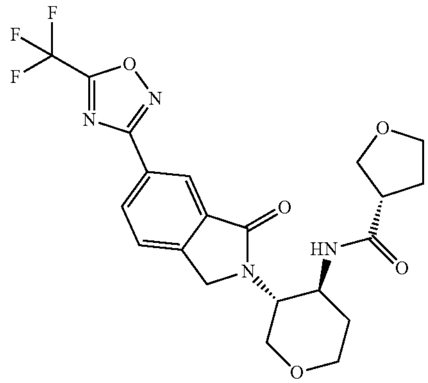 [SMILES: O=C(N[C@H]1CCOC[C@@H]1N1Cc2ccc(-c3noc(C(F)(F)F)n3)cc2C1=O)[C@H]1CCOC1] | | 466.2 |
| 211 | (1R) or (1S)-2,2-difluoro-N-((3R,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide | 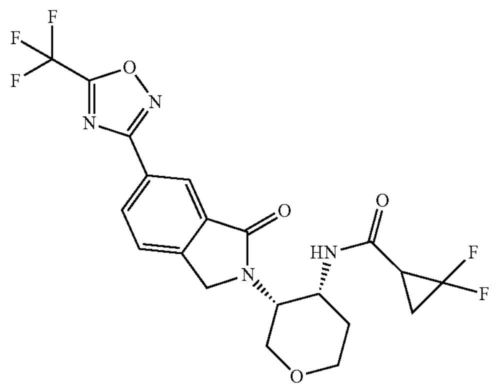 [SMILES: O=C(N[C@@H]1CCOC[C@@H]1N1Cc2ccc(-c3noc(C(F)(F)F)n3)cc2C1=O)C1CC1(F)F] | | 473.1 |
| 212 | (1R) or (1S)-2,2-difluoro-N-((3R,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide | 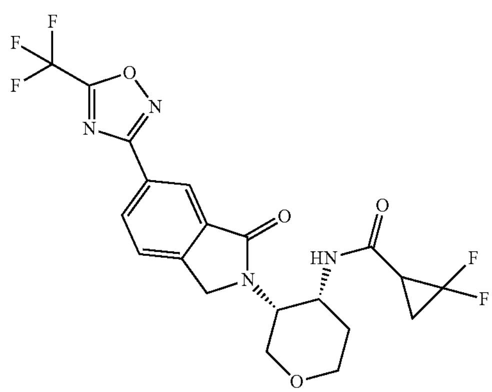 [SMILES: O=C(N[C@@H]1CCOC[C@@H]1N1Cc2ccc(-c3noc(C(F)(F)F)n3)cc2C1=O)C1CC1(F)F] | | 471.1 |
| 213 | (1R) or (1S)-2,2-difluoro-N-((3S,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide | 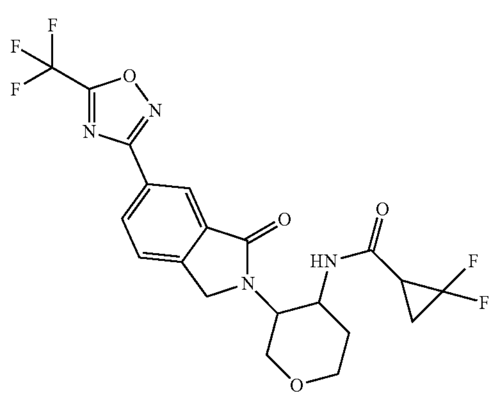 [SMILES: O=C(NC1CCOCC1N1Cc2ccc(-c3noc(C(F)(F)F)n3)cc2C1=O)C1CC1(F)F] | | 473.1 |

TABLE 1-32-continued

| EXAMPLE | IUPAC NAME | Structure | ADDITIVE | MS |
|---|---|---|---|---|
| 214 | (1R) or (1S)-2,2-difluoro-N-((3S,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide | 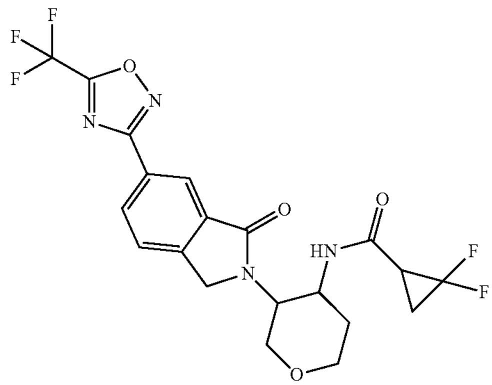 [SMILES: O=C(NC1CCOCC1N1Cc2ccc(-c3noc(C(F)(F)F)n3)cc2C1=O)C1CC1(F)F] | | 473.2 |
| 215 | 2-chloro-N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)acetamide | 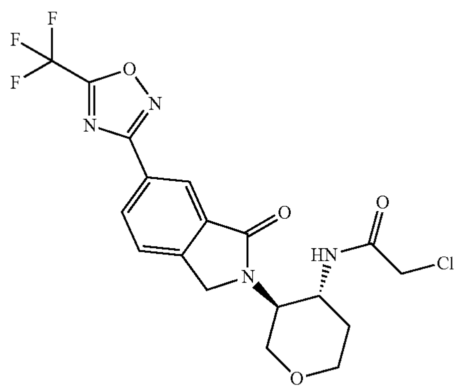 [SMILES: O=C(CCl)N[C@@H]1CCOC[C@H]1N1Cc2ccc(-c3noc(C(F)(F)F)n3)cc2C1=O] | | 445.0 |
| 216 | 2-chloro-N-((3R,4S)-3-(1-oxo-6-(5-(trifluoromethyl)-1,2,4-oxadiazol-3-yl)-1,3-dihydro-2H-isoindol-2-yl)tetrahydro-2H-pyran-4-yl)acetamide | 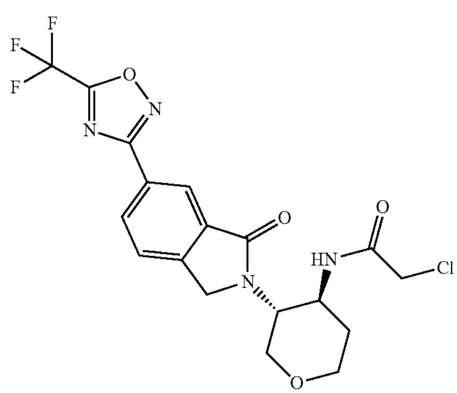 [SMILES: O=C(CCl)N[C@H]1CCOC[C@@H]1N1Cc2ccc(-c3noc(C(F)(F)F)n3)cc2C1=O] | | 445.1 |

TABLE 1-33

| EXAMPLE | IUPAC NAME | Structure | ADDITIVE | MS |
|---|---|---|---|---|
| 217 | (2S)-N-((1S,2S)-2-(1-oxo-6-(5-(trifluoromethyl)-1,2,4-oxadiazol-3-yl)-1,3-dihydro-2H-isoindol-2-yl)cyclohexyl)tetrahydrofuran-2-carboxamide | 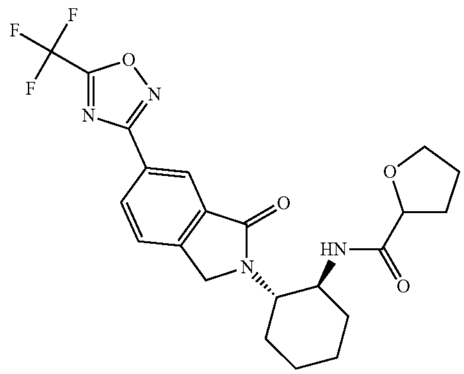 [SMILES: O=C(N[C@H]1CCCC[C@@H]1N1Cc2ccc(-c3noc(C(F)(F)F)n3)cc2C1=O)C1CCCO1] | | 465.2 |
| 218 | (2R)-N-((1S,2S)-2-(1-oxo-6-(5-(trifluoromethyl)-1,2,4-oxadiazol-3-yl)-1,3-dihydro-2H-isoindol-2-yl)cyclohexyl)tetrahydrofuran-2-carboxamide | 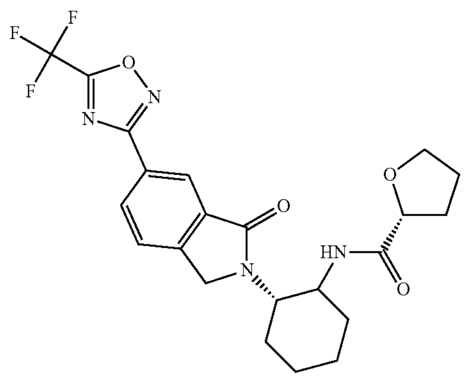 [SMILES: O=C(NC1CCCC[C@@H]1N1Cc2ccc(-c3noc(C(F)(F)F)n3)cc2C1=O)[C@H]1CCCO1] | | 465.2 |
| 219 | 2-hydroxy-2-methyl-N-((1S,2S)-2-(1-oxo-6-(5-(trifluoromethyl)-1,2,4-oxadiazol-3-yl)-1,3-dihydro-2H-isoindol-2-yl)cyclohexyl)propanamide | 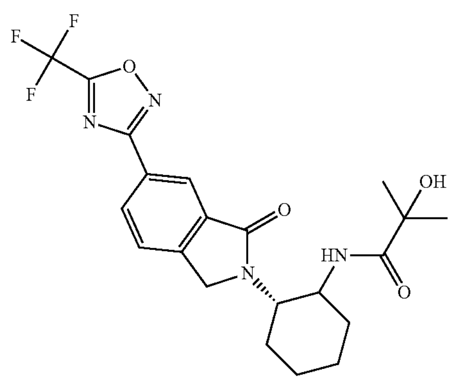 [SMILES: CC(C)(O)C(=O)NC1CCCC[C@@H]1N1Cc2ccc(-c3noc(C(F)(F)F)n3)cc2C1=O] | | 451.1 |
| 220 | (1S)-2,2-difluoro-N-((3R,4S)-4-(1-oxo-6-(5-(trifluoromethyl)-1,2,4-oxadiazol-3-yl)-1,3-dihydro-2H-isoindol-2-yl)tetrahydro-2H-pyran-3-yl)cyclopropanecarboxamide | 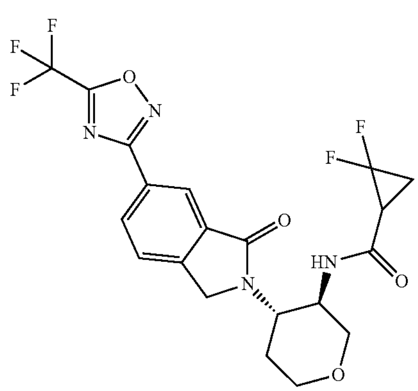 [SMILES: O=C(N[C@H]1COCC[C@@H]1N1Cc2ccc(-c3noc(C(F)(F)F)n3)cc2C1=O)C1CC1(F)F] | | 471.0 |

TABLE 1-33-continued

| EXAMPLE | IUPAC NAME | Structure | ADDITIVE | MS |
|---|---|---|---|---|
| 221 | (1R)-2,2-difluoro-N-((3R,4S)-4-(1-oxo-6-(5-(trifluoromethyl)-1,2,4-oxadiazol-3-yl)-1,3-dihydro-2H-isoindol-2-yl)tetrahydro-2H-pyran-3-yl)cyclopropanecarboxamide | 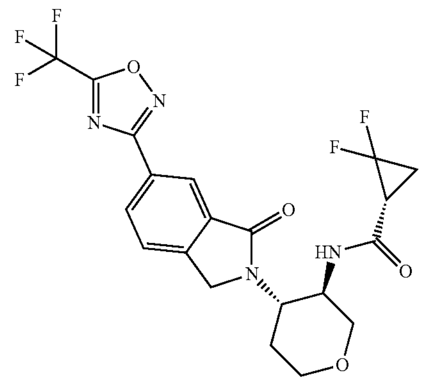 | | 471.0 |

Experimental Example 1

HDAC1/6 Enzyme Inhibitory Assay

HDAC1 enzyme and HDAC6 enzyme each prepared by transducing full length HDAC1 and HDAC6 genes into Sf-9 insect cells and purifying by GST affinity column were purchased from SignalChem. Using these enzymes, HDAC1 and/or HDAC6 enzyme inhibitory activities of the compound of the present invention were evaluated. Enzymes were used after preserved at −70° C. HDAC1 or HDAC6 enzyme inhibitory activity of the compound of the present invention was measured using HDAC-Glo™ I/II Assay kit (Promega) according to the following experimental method. The test compound diluted with assay buffer (24 mM Tris-HCl (pH 7.5), 1 mM $MgCl_2$, 0.35 mM KCl, 135 mM NaCl, 0.6 mM Glutathione, 0.01% Tween-20) was added to a 384-well plate by each 2 μL. Then, HDAC1 or HDAC6 enzyme solution diluted with assay buffer was added thereto by each 4 μL, and the plate was incubated at room temperature for 60 min. After incubated, HDAC substrate-Developer solution prepared according to Promega protocol attached to the assay kit was added to the 384-well plate by each 2 μL, and the enzyme reaction was started. After reacting at room temperature for 20 min, luminescence level was measured using plate reader Envision (PerkinElmer). The inhibitory activity of each compound was calculated as a relative activity value when luminescence level in wells without enzyme is considered as 100% inhibition. The results are shown in Table 2.

HDAC9 Enzyme Inhibitory Assay

Enzyme was prepared by transducing full length HDAC9 gene into Sf-9 insect cells and purifying by Ni-NTA affinity column, and HDAC9 enzyme inhibitory activity was evaluated. Enzymes were used after preserved at −70° C. HDAC9 enzyme inhibitory activity of the test compound was measured using HDAC-Glo class IIa (Promega) according to the following experimental method. The test compound diluted with assay buffer (24 mM Tris-HCl (pH 7.5), 1 mM $MgCl_2$, 0.35 mM KCl, 135 mM NaCl, 0.6 mM Glutathione, 0.01% Tween-20) was added to a 384-well plate by each 2 μL. Then, HDAC9 enzyme solution diluted with assay buffer was added thereto by each 2 μL, and the plate was incubated at room temperature for 60 min. After incubated, HDAC substrate-Developer solution prepared according to Promega protocol was added to the 384-well plate by each 4 μL, and the enzyme reaction was started. After reacting at room temperature for 20 min, luminescence level was measured using plate reader Envision (PerkinElmer). The inhibitory activity of each compound was calculated as a relative activity value when luminescence level in wells without enzyme is considered as 100% inhibition. The results are shown in Table 2.

TABLE 2

| Ex. No. | HDAC6 inhibitory rate (%) (1 μM) | HDAC1 inhibitory rate (%) (1 μM) | HDAC9 inhibitory rate (%) (1 μM) |
|---|---|---|---|
| 1 | 8 | | 55 |
| 2 | 98 | 33 | 90 |
| 3 | 96 | 87 | 98 |
| 4 | 99 | 69 | 96 |
| 5 | 99 | 78 | 95 |
| 6 | 95 | 9 | 65 |
| 7 | 76 | 6 | 72 |
| 8 | 98 | 10 | 43 |
| 9 | 97 | 54 | 89 |
| 10 | 96 | 63 | 96 |
| 11 | 100 | 70 | 95 |
| 12 | 98 | 9 | 48 |
| 13 | 101 | 53 | 84 |
| 14 | 68 | 0 | 48 |
| 15 | 98 | 97 | 99 |
| 16 | 98 | 49 | 87 |
| 17 | 98 | 52 | 85 |
| 18 | 99 | 5 | 47 |
| 19 | 99 | 18 | 48 |
| 20 | 98 | 87 | 96 |
| 21 | 93 | 8 | 80 |
| 22 | 100 | 85 | 96 |
| 23 | 98 | 58 | 84 |
| 24 | 95 | 6 | 52 |
| 25 | 92 | 7 | 39 |
| 26 | 98 | 11 | 47 |
| 27 | 36 | 16 | 76 |
| 28 | 89 | 3 | 78 |
| 29 | 34 | −2 | 45 |
| 30 | 97 | 30 | 84 |
| 31 | 99 | 78 | 97 |
| 32 | 99 | 5 | 52 |
| 33 | 83 | 7 | 46 |
| 34 | 99 | 90 | 96 |
| 35 | 99 | 50 | 91 |
| 36 | 98 | 12 | 66 |
| 37 | 96 | 1 | 19 |
| 38 | 90 | 25 | 82 |
| 39 | 91 | 23 | 86 |
| 40 | 95 | 56 | 97 |
| 41 | 93 | 37 | 94 |
| 42 | 100 | 15 | 41 |
| 43 | 99 | 90 | 96 |
| 44 | 98 | 88 | 95 |

TABLE 2-continued

| Ex. No. | HDAC6 inhibitory rate (%) (1 μM) | HDAC1 inhibitory rate (%) (1 μM) | HDAC9 inhibitory rate (%) (1 μM) |
|---|---|---|---|
| 45 | 100 | 94 | 99 |
| 46 | 99 | 94 | 99 |
| 47 | 95 | 90 | 99 |
| 48 | 99 | 90 | 98 |
| 49 | 100 | 96 | 99 |
| 50 | 98 | 93 | 99 |
| 51 | 98 | 94 | 99 |
| 52 | 97 | 97 | 99 |
| 53 | 97 | 98 | 99 |
| 54 | 100 | 93 | 99 |
| 55 | 96 | 95 | 99 |
| 56 | 97 | 93 | 99 |
| 57 | 94 | 93 | 99 |
| 58 | 98 | 99 | 99 |
| 59 | 97 | 60 | 91 |
| 60 | 92 | 37 | 77 |
| 61 | 99 | 41 | 93 |
| 62 | 98 | 46 | 89 |
| 63 | 90 | 15 | 82 |
| 64 | 93 | 6 | 70 |
| 65 | 89 | 7 | 73 |
| 66 | 90 | 17 | 54 |
| 67 | 99 | 13 | 81 |
| 68 | 90 | 35 | 90 |
| 69 | 91 | 15 | 81 |
| 70 | 96 | 52 | 95 |
| 71 | 36 | 9 | 73 |
| 72 | 90 | 32 | 80 |
| 73 | 77 | 19 | 81 |
| 74 | 86 | 33 | 90 |
| 75 | 87 | 11 | 79 |
| 76 | 85 | 31 | 89 |
| 77 | 92 | 30 | 90 |
| 78 | 11 | −3 | 76 |
| 79 | 78 | 17 | 88 |
| 80 | 76 | 13 | 97 |
| 81 | 100 | 16 | 62 |
| 82 | 99 | 10 | 61 |
| 83 | 101 | 5 | 52 |
| 84 | 102 | 18 | 85 |
| 85 | 98 | 41 | 67 |
| 86 | 98 | 80 | 92 |
| 87 | 99 | 1 | 45 |
| 88 | 98 | 79 | 97 |
| 89 | 98 | 37 | 85 |
| 90 | 97 | 5 | 37 |
| 91 | 99 | 11 | 44 |
| 92 | 96 | 0 | 23 |
| 93 | 95 | 2 | 42 |
| 94 | 99 | 5 | 24 |
| 95 | 100 | 3 | 37 |
| 96 | 101 | 10 | 50 |
| 97 | 99 | 14 | 59 |
| 98 | 99 | 4 | 55 |
| 99 | 100 | 13 | 51 |
| 100 | 100 | 9 | 73 |
| 101 | 98 | 12 | 68 |
| 102 | 99 | 7 | 52 |
| 103 | 102 | 14 | 55 |
| 104 | 98 | 3 | 43 |
| 105 | 100 | 7 | 50 |
| 106 | 101 | 58 | 88 |
| 107 | 99 | 11 | 57 |
| 108 | 97 | 2 | 35 |
| 109 | 71 | −2 | 19 |
| 110 | 99 | 18 | 73 |
| 111 | 99 | 14 | 69 |
| 112 | 96 | 13 | 57 |
| 113 | 97 | 0 | 32 |
| 114 | 39 | 1 | 11 |
| 115 | 99 | 16 | 64 |
| 116 | 98 | 4 | 45 |
| 117 | 97 | 4 | 27 |
| 118 | 98 | 5 | 46 |
| 119 | 100 | 4 | 38 |
| 120 | 79 | −3 | 37 |
| 121 | 89 | 3 | 40 |
| 122 | 97 | 6 | 67 |
| 123 | 56 | −4 | 5 |
| 124 | 96 | 3 | 32 |
| 125 | 99 | 11 | 55 |
| 126 | 100 | 10 | 59 |
| 127 | 99 | 5 | 47 |
| 128 | 92 | −3 | 39 |
| 129 | 100 | 9 | 45 |
| 130 | 86 | 0 | 30 |
| 131 | 88 | 0 | 31 |
| 132 | 99 | 5 | 55 |
| 133 | 99 | 9 | 38 |
| 134 | 99 | −5 | 36 |
| 135 | 40 | −5 | 58 |
| 136 | 94 | 39 | 82 |
| 137 | 89 | 25 | 94 |
| 138 | 97 | 2 | 55 |
| 139 | 98 | 5 | 25 |
| 140 | 39 | 27 | 41 |
| 141 | 42 | 28 | 43 |
| 142 | −3 | −6 | 54 |
| 143 | −4 | −1 | 52 |
| 144 | 100 | 3 | 31 |
| 145 | 98 | 0 | 35 |
| 146 | 99 | 2 | 23 |
| 147 | 99 | 6 | 51 |
| 148 | 100 | 8 | 82 |
| 149 | 100 | 12 | 60 |
| 150 | 100 | 13 | 85 |
| 151 | 35 | 16 | 42 |
| 152 | 31 | 13 | 38 |
| 153 | 100 | 6 | 52 |
| 154 | 100 | 11 | 54 |
| 155 | 100 | 14 | 54 |
| 156 | 96 | −1 | 8 |
| 157 | 96 | −2 | 15 |
| 158 | 99 | 4 | 34 |
| 159 | 98 | 5 | 39 |
| 160 | 99 | 11 | 38 |
| 161 | 76 | 1 | 20 |
| 162 | 99 | 5 | 34 |
| 163 | 95 | 1 | 32 |
| 164 | 97 | 1 | 18 |
| 165 | 96 | 6 | 43 |
| 166 | 100 | 12 | 36 |
| 167 | 101 | 7 | 34 |
| 168 | 96 | 5 | 23 |
| 169 | 98 | 10 | 40 |
| 170 | 100 | 16 | 64 |
| 171 | 98 | 9 | 67 |
| 172 | 99 | 7 | 49 |
| 173 | 100 | 5 | 42 |
| 174 | 90 | 8 | 60 |
| 175 | 100 | 5 | 57 |
| 177 | 98 | 8 | 64 |
| 178 | 99 | 8 | 61 |
| 179 | 90 | 11 | 84 |
| 180 | 99 | 13 | 72 |
| 181 | 74 | 2 | 41 |
| 182 | 98 | 10 | 71 |
| 183 | 77 | 1 | 47 |
| 184 | 98 | 7 | 56 |
| 185 | 97 | 5 | 41 |
| 186 | 97 | 26 | 95 |
| 187 | 99 | 9 | 29 |
| 188 | 95 | 10 | 45 |
| 190 | 100 | 19 | 84 |
| 191 | 99 | 20 | 66 |
| 192 | 99 | 6 | 40 |
| 193 | 43 | 4 | 32 |
| 194 | 100 | 3 | 26 |
| 195 | 98 | 1 | 57 |
| 196 | 101 | 4 | 22 |
| 197 | 100 | 6 | 48 |
| 198 | 95 | 26 | 66 |
| 199 | 68 | 5 | 75 |
| 200 | 96 | 35 | 85 |

TABLE 2-continued

| Ex. No. | HDAC6 inhibitory rate (%) (1 μM) | HDAC1 inhibitory rate (%) (1 μM) | HDAC9 inhibitory rate (%) (1 μM) |
|---|---|---|---|
| 201 | 98 | 16 | 86 |
| 202 | 99 | 13 | 59 |
| 203 | 100 | 8 | 69 |
| 204 | 99 | 7 | 71 |
| 205 | 99 | 5 | 52 |
| 206 | 97 | 5 | 52 |
| 208 | 98 | 4 | 53 |
| 209 | 48 | 13 | 51 |
| 210 | 55 | 10 | 56 |
| 211 | 43 | −1 | 33 |
| 212 | 82 | 12 | 58 |
| 213 | 96 | 31 | 77 |
| 214 | 98 | 68 | 97 |
| 217 | 82 | 21 | 53 |
| 218 | 44 | 5 | 29 |
| 219 | 40 | 5 | 50 |
| 220 | 84 | 23 | 65 |
| 221 | 90 | 34 | 86 |

Experimental Example 2

Increase in Acetylated Tubulin in Mice In Vivo administration and recovery of sample: BALB/c mice (female, Charles River Japan, 8-weeks old when used) were used. The compound was suspended in 0.5% methyl cellulose (hereinafter to be referred to as MC)/distilled water (hereinafter to be referred to as DW), and the suspension was orally administered at 30 mg/kg (10 mL/kg). After 1, 4, 8 and 24 hrs, the cervical spine was dislocated under isoflurane anesthesia, and after confirmation of the death, the spleen was removed by laparotomy. About 30 mg of the spleen was cut, recovered into tube containing beads (Lysing Matrix I), immediately freezed by immersion in liquid nitrogen, and cryopreserved at −80° C. until used. 0.5 mL RIPA buffer containing protease inhibitor (Nacalai tesque) was added to the spleen placed in Lysing Matrix I tube, and the spleen was crushed by the dedicated machine. The sample tube was centrifuged (15,000 rpm, 4° C., 5 min), and the supernatant was transferred to another tube. The tube was centrifuge again, and the supernatant was dispensed to a 96-well plate, and preserved at −80° C. until Western blotting measurement. The protein amount of the sample was measured using Pierce BCA protein assay kit. For each administration group, three examples were performed per one group, and data was shown as the mean±standard error. Western blotting: 0.1 M DTT/sample buffer solution prepared by ten-fold diluting 1 M DTT solution (Sigma) with sample buffer (BioRAD) was mixed with the spleen sample in the proportion of 1:1, and the sample was boiled at 100° C. for 3 min. The sample was applied to 15% 28 well gel (DRC) so that the protein amount was 5 to 10 μg/lane, and electrophoresed at 42 mA/gel for 40 min. After electrophoresed, the protein in the gel was transferred to PVDF membrane by semidryblotting (2 mA/cm$^2$, 60 min). The membrane was immersed in blocking reagent (Can Get Signal) at room temperature for 1 hr, washed, and reacted with primary antibody (Anti-mouse Ac-tubulin mAb, Cat#T7451, Sigma) against Ac-tubulin overnight at 4° C. After washed, the membrane was reacted with secondary antibody (Anti-mouse IgG-HRP, Cat#7076, CST) at room temperature for 1 hr, and immersed in ECL prime detecting solution (GE), and the chemiluminescence was detected by luminoimage analyzer (LAS3000, Fuji Photo Film) The strength of band detected around 52 kDa was quantified by LAS3000, and the protein expression level of Ac-tubulin was evaluated as fold increase relative to vehicle administration group. The results are shown in FIG. 1.

Experimental Example 3

Figure 2:
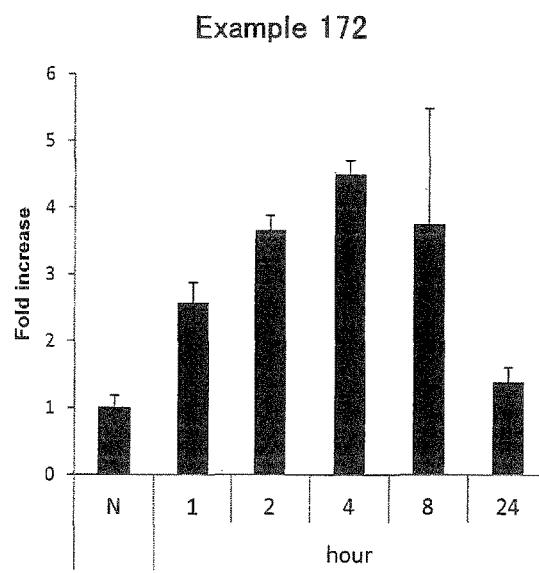
FIG. 2 shows increase in acetylated tubulin in mice in vivo in Experimental Example 3.

Increase in Acetylated Tubulin in Mice In Vivo administration and recovery of sample: C57BL/6 mice (male, Charles River Japan, 9-weeks old when used) were used. The compound was suspended in 0.5% MC/DW, and the suspension was orally administered at 30 mg/kg (10 mL/kg). After 1, 2, 4, 8 and 24 hrs, the cervical spine was dislocated under isoflurane anesthesia, and after confirmation of the death, the spleen was removed by laparotomy. About 20 mg of the spleen was cut, recovered into tube containing beads, immediately freezed by immersion in liquid nitrogen, and cryopreserved at −80° C. until used. 0.5 mL RIPA buffer containing protease inhibitor was added to the spleen placed in the tube containing beads, and the spleen was crushed by the dedicated machine. The sample tube was centrifuged (15,000 rpm, 4° C., 5 min), and the supernatant was transferred to another tube. The tube was centrifuge again, and the supernatant was dispensed to a 96-well plate, and preserved at −80° C. until Western blotting measurement. The protein amount of the sample was measured using Pierce BCA protein assay kit. For each administration group, four examples were performed per one group, and data was shown as the mean±standard error. Western blotting: Western blot was performed by a method similar to Experimental Example 2. The results are shown in FIG. 2.

Experimental Example 4

Increase in Acetylated Tubulin in Human Whole Blood

Human whole blood was collected from healthy volunteers (3 to 6) after informed consent in the company. Human whole blood was added to round-bottom 96-well plate by each 25 μL, and the compound 100-fold diluted with RPMI1640 medium (GIBCO) containing 10% FBS was added thereto by each 10 μL, in which the compound has been dissolved in 100% dimethyl sulfoxide (DMSO, Wako) in advance. For control group, DMSO was added to the plate so that the final concentration was 0.1%. After addition of the compound, the plate was left standing at 37° C. for 30 min. Then, 65 μL of PRMI1640 medium was added thereto, and the plate was left standing at 37° C. for 3.5 hr.

Figure 3:
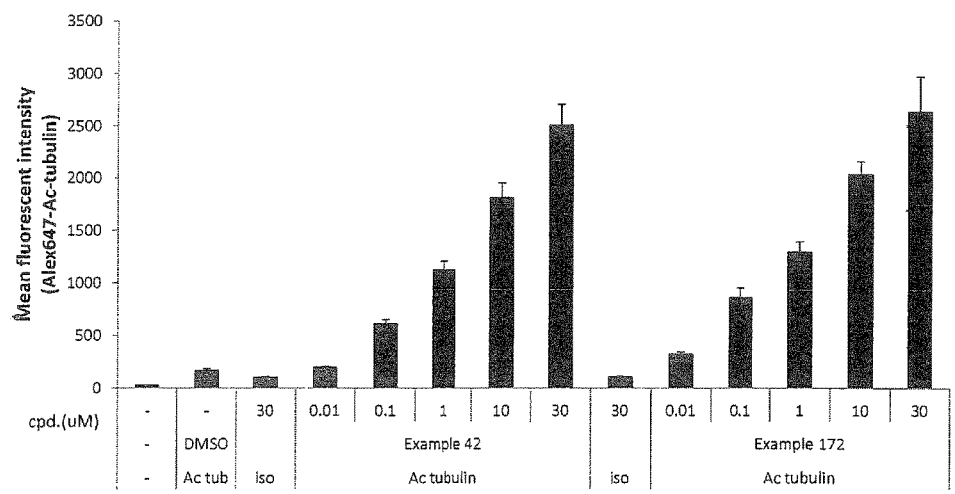
FIG. 3 shows increase in acetylated tubulin in human whole blood in Experimental Example 4.
Figure 4:
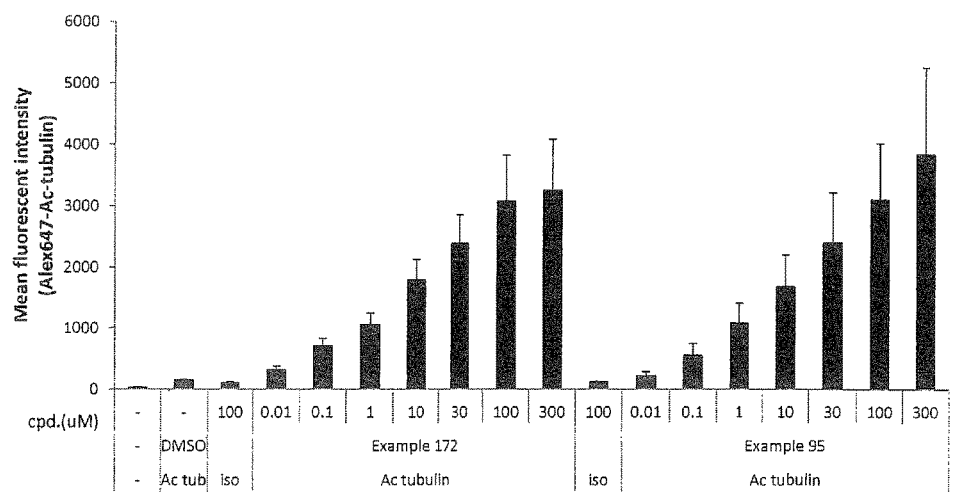
FIG. 4 shows increase in acetylated tubulin in human whole blood in Experimental Example 4.

The human whole blood treated with the compound was transferred to assay block (Costar), and Lyse/Fix buffer (BD Biosciences) diluted with DW was added thereto, and fully pipetted. The sample was left standing for 10 min at room temperature, and centrifuged at 400×g for 5 min. After centrifuged, the supernatant was removed, and 250 μL of Perm/Wash buffer I (BD Biosciences) was added thereto. The sample was transferred to V-bottom 96-well plate, and the plate was left standing for 20 min on ice. These samples were centrifuged at 400×g at room temperature for 5 min, and the supernatant was removed. The sample was stained using Zenon AF647 conjugated Ac-tubulin (Cat#ab179484, Abcam) or isotype control (Cat#ab172730, Abcam) for about 20-30 min on ice. Zenon Rabbit IgG Labeling Kit, AF647 (Molecular Probes) was used according to the attached protocol. The sample was centrifuged at 400×g for 5 min, the supernatant was removed, and the residue was washed with 200 μL of Perm/Wash buffer I. After centrifuged again, the supernatant was removed, and the residue was suspended in 200 μL of FACS stain buffer (1% FBS/PBS). The cell was analyzed by flow cytometer (BD Fortessa), and the results were analyzed by FlowJo software. The data was shown as the mean±standard error data. The results are shown in FIG. 3 and FIG. 4.

Formulation Example 1

Production of Capsule

| 1) compound of Example 1 | 30 mg |
|---|---|
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin

Formulation Example 2

Production of Tablet

| 1) compound of Example 1 | 30 g |
|---|---|
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention has a HDAC inhibitory action, and may be useful for the treatment of autoimmune diseases and/or inflammatory diseases (inflammatory bowel disease, rheumatoid arthritis, psoriasis, multiple sclerosis, Sjogren's syndrome, Behcet's disease, systemic lupus erythematosus, etc.), graft versus host disease (GvHD), cancers (multiple myeloma, leukemia, uterine leiomyosarcoma, prostate cancer, cachexia, myelofibrosis, etc.), central nervous diseases including neurodegenerative diseases (Alzheimer's disease, frontotemporal lobar degeneration, progressive supranuclea palsy, Parkinson's disease, Huntington's disease, etc.), Charcot-Marie-Tooth disease and the like.

This application is based on patent application No. 2015-143354 filed on Jul. 17, 2015 and No. 2016-029020 filed on Feb. 18, 2016 in Japan, the contents of which are encompassed in full herein.

The invention claimed is:
1. A compound represented by the formula:

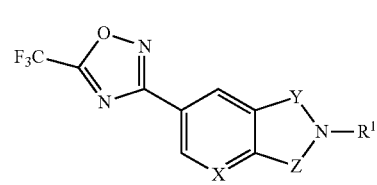

wherein
X is CH or N,
one of Y and Z is C(O), and the other is C($R^2$)($R^3$),
$R^2$ and $R^3$ are both hydrogen atoms;
the atom on $R^1$ bonded to N of the Y—N—Z is C; and
$R^1$ is
(1) a $C_{3-6}$ cycloalkyl group optionally substituted by 1 to 3 substituents selected from
  (a) a halogen atom,
  (b) a $C_{6-14}$ aryl group,
  (c) a 3- to 8-membered non-aromatic heterocyclic group optionally substituted by 1 to 3 oxo groups,
  (d) a $C_{1-6}$ alkyl-carbonylamino group optionally substituted by 1 to 3 hydroxy groups,
  (e) a $C_{1-6}$ alkoxy-carbonylamino group,
  (f) a $C_{3-6}$ cycloalkyl-carbonylamino group optionally substituted by 1 to 3 substituents selected from
    (i) a halogen atom,
    (ii) a cyano group,
    (iii) a hydroxy group,
    (iv) a $C_{1-6}$ alkyl group optionally substituted by 1 to 3 hydroxy groups, and
    (v) a $C_{1-6}$ alkoxy group,
  (g) a $C_{6-14}$ aryl-carbonylamino group,
  (h) a 4- to 10-membered non-aromatic heterocyclylcarbonylamino group optionally substituted by 1 to 3 substituents selected from
    (i) a halogen atom,
    (ii) a $C_{1-6}$ alkyl group, and
    (iii) a $C_{6-14}$ aryl group,
  (i) a mono- or di-$C_{1-6}$ alkyl-carbamoylamino group,
  (j) a $C_{3-6}$ cycloalkyl-carbamoylamino group,
  (k) a ($C_{1-6}$ alkyl)($C_{3-6}$ cycloalkyl)carbamoylamino group,
  (l) a 3- to 8-membered non-aromatic heterocyclylcarbamoylamino group, and
  (m) a $C_{3-6}$ cycloalkylsulfonylamino group, or
(2) a 3- to 8-membered non-aromatic heterocyclic group optionally substituted by 1 to 3 substituents selected from
  (a) a $C_{6-14}$ aryl group,
  (b) a $C_{1-6}$ alkyl-carbonyl group,
  (c) a $C_{1-6}$ alkoxy-carbonyl group,
  (d) a $C_{3-6}$ cycloalkyl-carbonyl group,
  (e) a $C_{6-14}$ aryl-carbonyl group,
  (f) a carbamoyl group,
  (g) a $C_{1-6}$ alkyl-carbamoyl group,
  (h) a $C_{1-6}$ alkoxy-carbonylamino group,
  (i) a $C_{3-6}$ cycloalkyl-carbonylamino group optionally substituted by 1 to 3 halogen atoms,
  (j) a 3- to 8-membered non-aromatic heterocyclylcarbonylamino group optionally substituted by 1 to 3 $C_{1-6}$ alkyl groups, and (k) a 3- to 8-membered non-aromatic heterocyclic group optionally substituted by 1 to 3 oxo groups or a salt thereof.

2. The compound or salt according to claim 1, wherein
Y is C(O); and
Z is C($R^2$)($R^3$).

3. The compound or salt according to claim 1, wherein
X is CH;
Y is C(O); and
Z is ($R^2$)($R^3$).

4. 3-Methyl-N-((1R,2R)-2-(1-oxo-6-(5-(trifluoromethyl)-1,2,4-oxadiazol-3-yl)-1,3-dihydro-2H-isoindol-2-yl)cyclohexyl)oxetane-3-carboxamide, or a salt thereof.

5. (2S)-N-((1R,2R)-2-(1-Oxo-6-(5-(trifluoromethyl)-1,2,4-oxadiazol-3-yl)-1,3-dihydro-2H-isoindol-2-yl)cyclohexyl)tetrahydrofuran-2-carboxamide, or a salt thereof.

6. 2-Hydroxy-2-methyl-N-((1R,2R)-2-(1-oxo-6-(5-(trifluoromethyl)-1,2,4-oxadiazol-3-yl)-1,3-dihydro-2H-isoindol-2-yl)cyclohexyl)propanamide, or a salt thereof.

7. (1S)-2,2-Difluoro-N-((3S,4R)-4-(1-oxo-6-(5-(trifluoromethyl)-1,2,4-oxadiazol-3-yl)-1,3-dihydro-2H-isoindol-2-yl)tetrahydro-2H-pyran-3-yl)cyclopropanecarboxamide, or a salt thereof.

8. (1S)-2,2-Difluoro-N-((3S,4R)-3-(1-oxo-6-(5-(trifluoromethyl)-1,2,4-oxadiazol-3-yl)-1,3-dihydro-2H-isoindol-2-yl)tetrahydro-2H-pyran-4-yl)cyclopropanecarboxamide, or a salt thereof.

9. A medicament comprising the compound or salt according to claim 1.

10. A method of inhibiting histone deacetylase in a mammal, which comprises administering an effective amount of the compound or salt according to claim 1 to the mammal.

11. A method for the prophylaxis or treatment of neurodegenerative diseases in a mammal, which comprises administering an effective amount of the compound or salt according to claim 1 to the mammal.

12. A method for the prophylaxis or treatment of Charcot-Marie-Tooth disease in a mammal, which comprises administering an effective amount of the compound or salt according to claim 1 to the mammal.

* * * * *